(12) United States Patent
Wang et al.

(10) Patent No.: US 8,445,490 B2
(45) Date of Patent: *May 21, 2013

(54) COMPOUNDS FOR THE TREATMENT OF HEPATITIS C

(75) Inventors: Tao Wang, Farmington, CT (US);
Annapurna Pendri, South Glastonbury, CT (US); Zhongxing Zhang, Madison, CT (US); Weixu Zhai, Middletown, CT (US); Guo Li, Wallingford, CT (US); Samuel Gerritz, Guilford, CT (US); Paul Michael Scola, Glastonbury, CT (US); Li-Qiang Sun, Glastonbury, CT (US); Qian Zhao, Wallingford, CT (US); Eric Mull, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/086,036

(22) Filed: Apr. 13, 2011

(65) Prior Publication Data

US 2012/0093766 A1 Apr. 19, 2012

Related U.S. Application Data

(63) Continuation-in-part of application No. 12/904,264, filed on Oct. 14, 2010.

(60) Provisional application No. 61/251,466, filed on Oct. 14, 2009.

(51) Int. Cl.
*A61K 31/53* (2006.01)
*C07D 251/18* (2006.01)

(52) U.S. Cl.
USPC ........... 514/245; 544/180; 544/194; 544/204; 544/208; 514/241

(58) Field of Classification Search
USPC .................. 544/180, 194, 204, 208; 514/241, 514/245
See application file for complete search history.

(56) References Cited

U.S. PATENT DOCUMENTS

| 4,816,064 | A | 3/1989 | Konno et al. |
| 7,163,943 | B2 | 1/2007 | Timmer et al. |
| 7,169,785 | B2 | 1/2007 | Timmer et al. |
| 8,067,588 | B2 * | 11/2011 | Niyaz et al. .................. 544/197 |
| 8,188,273 | B2 * | 5/2012 | Niyaz et al. .................. 544/197 |
| 2009/0286778 | A1 | 11/2009 | Combs et al. |
| 2011/0086858 | A1 | 4/2011 | Wang et al. |

FOREIGN PATENT DOCUMENTS

| KR | 2004/0033100 A | 4/2004 |
| WO | WO02/079187 A1 | 10/2002 |
| WO | WO 2004/026881 | 4/2004 |
| WO | WO 2004/089286 | 10/2004 |
| WO | WO 2008/057209 | 5/2008 |
| WO | WO 2009/091388 | 7/2009 |
| WO | WO 2009/132202 | 10/2009 |
| WO | WO2010/036896 A1 | 4/2010 |
| WO | WO 2010/118367 | 10/2010 |

OTHER PUBLICATIONS

U.S. Appl. No. 13/086,704, filed Apr. 14, 2011, Wang et al.

* cited by examiner

*Primary Examiner* — Golam M M Shameem
(74) *Attorney, Agent, or Firm* — James Epperson

(57) ABSTRACT

The disclosure provides compounds of formula I, including pharmaceutically acceptable salts, as well as compositions and methods of using the compounds. The compounds have activity against hepatitis C virus (HCV) and may be useful in treating those infected with HCV.

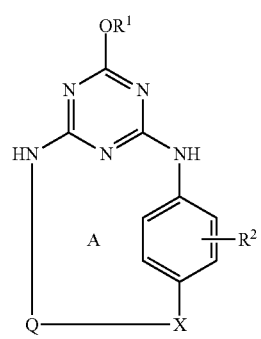

2 Claims, No Drawings

COMPOUNDS FOR THE TREATMENT OF HEPATITIS C

CROSS REFERENCE TO RELATED APPLICATIONS

This patent application claims the benefit of U.S. provisional patent application No. 61/251,466 filed Oct. 14, 2009 and to U.S. nonprovisional patent application Ser. No. 12/904,264 filed Oct. 14, 2010.

BACKGROUND OF THE INVENTION

The disclosure generally relates to the novel compounds of formula I including pharmaceutically acceptable salts, which have activity against hepatitis C virus (HCV) and are useful in treating those infected with HCV. The disclosure also relates to compositions and methods of using these compounds.

Hepatitis C virus (HCV) chronically infects an estimated 170 million people worldwide, with 3 to 4 million infected individuals in the United States alone (Boyer, N. and Marcellin, P. *J. Hepatology.* 2000, 32:98-112; Alter, M. J., et al. *Engl. J. Med.* 1999, 341:556-562). Prior to the mid 1990s, transfusion with infected blood products was the main route of HCV transmission. Following the introduction of blood screening methods, transmission via injection drug use became the primary risk factor. Chronic infection often leads to the development of severe liver complications, including fibrosis, cirrhosis, and hepatocellular carcinoma. HCV infection is also the leading cause of orthotopic liver transplantation in the United States. The degree to which disease progression is related to viral and cellular factors is not completely understood.

Considerable heterogeneity is found within the nucleotide and encoded amino acid sequence of the HCV genome (Simmonds, P. *J. Gen. Virology.* 2004, 85:3173-3188). Based on this sequence diversity, six major genotypes and multiple associated subtypes have been described. The genotypes of HCV differ in their worldwide distribution, and the clinical significance of the genetic heterogeneity of HCV remains elusive despite numerous studies of the possible effect of genotypes on pathogenesis and therapy.

Medical treatment for HCV is limited by the lack of a vaccine or approved therapies that specifically target the virus. Currently, patients undergo treatment with a combination of parenterally administered pegylated alpha-interferon and oral ribavirin. Genotype 1 HCV is the most difficult to treat and elimination of the virus (sustained virologic response) is achieved for only approximately 50% of patients (Fried, M. W. et al. *N. Engl. J. Med.* 2002, 347:975-982; Zeumzem, S. *Nature Clinical Practice.* 2008, 5:610-622). This poor treatment response, combined with often severe side effects induced by therapy, highlight a need for improved antiviral drugs with better efficacy and safety profiles.

HCV is a member of the Flaviviridae family of viruses with a single-stranded positive-sense RNA genome. Following infection of host cells, the 9.6 Kb genome is translated into a polyprotein precursor of approximately 3,000 amino acids (reviewed in Lindenbach, B. D. and Rice, C. M. *Nature.* 2005, 436:933-938; Moradpour, D, Penin, F., and Rice, C. M. *Nature Reviews.* 2007, 5:453-463). Post-translational processing by both cellular and viral proteases results in the generation of at least 10 separate viral proteins. The structural proteins (which by definition are found in mature virions) include core, E1, E2, and possibly p7, and originate from the amino-terminal region of the polyprotein. The core protein assembles into the viral nucleocapsid. The E1 and E2 glycoproteins form heterodimers that are found within the lipid envelope surrounding the viral particles, and mediate host cell receptor binding and entry of the virus into cells. It is unclear if p7 is a structural protein, and its role in replication has yet to be defined. However p7 is believed to form an ion channel in cellular membranes, preventing acidification of intracellular compartments in which virions are assembled, and it has been shown to be essential for viral replication and assembly. The nonstructural proteins NS2, NS3, NS4A, NS4B, NS5A, and NS5B are produced through maturational cleavages of the carboxy-terminal region of the polyprotein. NS2 along with the amino terminus of NS3 form the NS2-3 metalloprotease which cleaves at the NS2-NS3 junction. Additionally, NS2 is involved in assembly and egress of nascent virions. The NS3 protein contains both a serine protease in its amino-terminal region, and a nucleotide-dependent RNA helicase in its carboxy-terminal region. NS3 forms a heterodimer with the NS4A protein, constituting the active protease which mediates cleavages of the polyprotein downstream of NS3, both in cis, at the NS3-NS4A cleavage site, and in trans, for the remaining NS4A-NS4B, NS4B-NS5A, NS5A-NS5B sites. The complex formation of the NS3 protein with NS4A seems necessary to the processing events, enhancing the proteolytic efficiency at all of the sites. The NS3 protein also exhibits nucleoside triphosphatase and RNA helicase activities. The NS4B protein has been shown to be important for localization of HCV proteins into replication complexes in altered membranous structures within the cell. NS5B encodes an RNA-dependent RNA polymerase that is involved in the replication of HCV.

Subgenomic HCV replicons, containing the untranslated regions 5' and 3' to the coding sequence fused to the nonstructural proteins or the full-length polyprotein, are competent for translation, viral protein expression, and replication within cultured cells (Lohmann, V. et al. *Science.* 1999, 285:110-113; Moradpour, D, Penin, F., and Rice, C. M. *Nature Reviews.* 2007, 5:453-463). The replicon system has proven valuable for the identification of inhibitors targeting the nonstructural proteins associated with these functions. However, only limited subsets of HCV genotypes have been used to generate functional replicons.

Other systems have been used to study the biology of the HCV structural proteins that mediate the entry into host cells. For example, virus-like-particles made in recombinant baculovirus-infected cells with the HCV core, E1 and E2 proteins have also been used to study the function of the HCV E1 and E2 proteins (Barth, H., et al. *J. Biol. Chem.* 2003, 278:41003-41012). In addition, pseudotyping systems where the E1 and E2 glycoproteins are used to functionally replace the glycoproteins of retroviruses have been developed (Bartosch, B., Dubuisson, J. and Cosset, F.-L. *J. Exp. Med.* 2003, 197:633-642; Hsu, M. et al. *Proc. Natl. Acad. Sci. USA.* 2003, 100: 7271-7276). These systems yield HCV pseudoparticles that bind to and enter host cells in a manner which is believed to be analogous to the natural virus, thus making them a convenient tool to study the viral entry steps as well as to identify inhibitors block this process.

Recently, a full-length genotype 2a HCV clone, JFH1, was isolated and demonstrated the ability to replicate in vitro. Through repeated passage and adaptation in cell culture increased titers of infectious virus were produced (Lindenbach, B. D., et al. *Science.* 2005, 309:623-626; Wakita, T. et al. *Nature Med.* 2005, 11:791-796). In contrast to the HCV replicon or pseudotyping systems, the infectious virus is useful for studying the complete HCV replication cycle, including identifying inhibitors of not only the replication proteins, but those involved in early steps in virus infection (entry and uncoating) and production of progeny viruses (genome packaging, nucleocapsid assembly, virion envelopment and egress).

The invention provides technical advantages, for example, the compounds are novel and are effective against hepatitis C. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

One aspect of the invention is a compound of formula I

I where
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
$R^2$ is cyano, hydrogen, halo, alkyl, haloalkyl, alkoxy, or haloalkoxy;
$R^3$ is hydrogen, alkyl, (amino)alkyl, (alkylamino)alkyl, (dialkylamino)alkyl ((alkylcarbonyl)amino)alkyl, ((haloalkylcarbonyl)amino)alkyl, ((alkoxycarbonyl)amino)alkyl, ((benzyloxycarbonyl)amino)alkyl, alkylcarbonyl, alkoxycarbonyl, benzyloxycarbonyl, aminocarbonyl, alkylaminocarbonyl, or dialkyaminocarbonyl;
$R^4$ is hydrogen, alkyl, (amino)alkyl, (alkylamino)alkyl, or (dialkylamino)alkyl;
$R^5$ is hydrogen, alkyl, (amino)alkyl, (alkylamino)alkyl, or (dialkylamino)alkyl;
$R^6$ is pyrollidinyl, piperidinyl, or piperazinyl and is substituted with 0-3 substituents selected from alkyl, alkylcarbonyl, alkoxycarbonyl, and benzyloxycarbonyl;
Q is an alkylene or alkenylene chain containing 0-6 groups selected from the group consisting of O, $NR^3$, S, S(O), S($O_2$), C(O)O, C(O)$NR^4$, OC(O)$NR^4$, $NR^4$C(O)$NR^4$, and Z, provided that any O or S atom does not directly bond to another O or S atom, such that ring A is 13-24 membered; and where the alkylene or alkenylene chain is substituted with 0-6 substituents selected from the group consisting of alkyl, hydroxy, alkoxy, $R^6$, ($R^6$)alkyl, and phenyl where the phenyl substituent is further substituted with 0-4 cyano, halo, alkyl, haloalkyl, alkoxy, or haloalkoxy substituents;
X is O, $CH_2$, CO, $CO_2$, or C(O)$NR^5$; and
Z is $C_{3-7}$ cycloalkylene, phenylene, pyrrolidindiyl, piperidindiyl, or piperazindiyl;
or a pharmaceutically acceptable salt thereof
Another aspect of the invention is a compound of formula I where:
$R^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;

$R^2$ is cyano, hydrogen, halo, alkyl, haloalkyl, alkoxy, or haloalkoxy;
$R^3$ is hydrogen, alkyl, alkylcarbonyl, alkoxycarbonyl, aminocarbonyl, alkylaminocarbonyl, or dialkyaminocarbonyl;
$R^4$ is hydrogen or alkyl;
$R^5$ is hydrogen, alkyl, (amino)alkyl, (alkylamino)alkyl, or (dialkylamino)alkyl;
Q is an alkylene or alkenylene chain containing 0-3 groups selected from the group consisting of O, $NR^3$, S, S(O), S($O_2$), C(O)O, C(O)$NR^4$, OC(O)$NR^4$, $NR^4$C(O)$NR^4$, and Z, provided that O, $NR^3$, S, S(O), S($O_2$), C(O)O, C(O)$NR^4$, OC(O)$NR^4$, and $NR^4$C(O)$NR^4$ do not directly bond to each other or to NH or X, such that ring A is 13-24 membered; and where the alkylene or alkenylene chain is substituted with 0-3 substituents selected from the group consisting of alkyl, hydroxy, alkoxy, and phenyl where the phenyl substituent is further substituted with 0-4 cyano, halo, alkyl, haloalkyl, alkoxy, or haloalkoxy substituents;
X is O, $CO_2$, or C(O)$NR^5$; and
Z is $C_{3-7}$ cycloalkylene or phenylene;
or a pharmaceutically acceptable salt thereof.

Another aspect of the invention is a compound of formula I where $R^1$ is haloalkyl; $R^2$ is hydrogen; $R^3$ is hydrogen or alkylcarbonyl; $R^5$ is hydrogen; Q is an alkylene or alkeneylene chain containing 0-2 groups selected from the group consisting of O, $NR^3$, and Z, such that ring A is 16-23 membered; X is O or CONR$^5$; and Z is phenylene; or a pharmaceutically acceptable salt thereof.

Another aspect of the invention is a compound of formula I where $R^1$ is trifluoroethyl; $R^2$ is hydrogen; Q is (p-$C_6H_6$)O$CH_2$CH=CH$CH_2$, $CH_2$(p-$C_6H_6$)O$CH_2$$CH_2$$CH_2$, $CH_2$(p-$C_6H_6$)O$CH_2$$CH_2$$CH_2$$CH_2$, $CH_2$(p-$C_6H_6$)O$CH_2$$CH_2$$CH_2$$CH_2$$CH_2$, $CH_2$(p-$C_6H_6$)O$CH_2$CH=CH$CH_2$, $CH_2$$CH_2$$CH_2$$CH_2$$CH_2$$CH_2$$CH_2$$CH_2$, $CH_2$$CH_2$$CH_2$$CH_2$$CH_2$$CH_2$$CH_2$$CH_2$$CH_2$$CH_2$, $CH_2$$CH_2$$CH_2$O$CH_2$$CH_2$$CH_2$$CH_2$O$CH_2$$CH_2$$CH_2$, $CH_2$$CH_2$NH$CH_2$$CH_2$, $CH_2$$CH_2$N(Ac)$CH_2$$CH_2$, or

*—⟨⟩—CONH$CH_2$$CH_2$$CH_2$$CH_2$—;

and X is O or CONH; or a pharmaceutically acceptable salt thereof.

Another aspect of the invention is a compound of formula I where $R^1$ is trifluoroethyl.

Another aspect of the invention is a compound of formula I where Q is (p-$C_6H_6$)O$CH_2$CH=CH$CH_2$, $CH_2$(p-$C_6H_6$)O$CH_2$$CH_2$$CH_2$, $CH_2$(p-$C_6H_6$)O$CH_2$$CH_2$$CH_2$$CH_2$, $CH_2$(p-$C_6H_6$)O$CH_2$$CH_2$$CH_2$$CH_2$$CH_2$, $CH_2$(p-$C_6H_6$)O$CH_2$CH=CH$CH_2$, $CH_2$$CH_2$$CH_2$$CH_2$$CH_2$$CH_2$$CH_2$$CH_2$, $CH_2$$CH_2$$CH_2$$CH_2$$CH_2$$CH_2$$CH_2$$CH_2$$CH_2$$CH_2$, $CH_2$$CH_2$$CH_2$O$CH_2$$CH_2$$CH_2$$CH_2$O$CH_2$$CH_2$$CH_2$, $CH_2$$CH_2$NH$CH_2$$CH_2$, $CH_2$$CH_2$N(Ac)$CH_2$$CH_2$, or

*—⟨⟩—CONH$CH_2$$CH_2$$CH_2$$CH_2$—.

Another aspect of the invention is a compound of formula I where X is CONH.
Another aspect of the invention is a compound of formula I where X is O.

Another aspect of the invention is a compound of formula I where Z is phenylene.

Another aspect of the invention is a compound of formula I where Z is cyclopropanediyl or cyclohexanediyl.

Another aspect of the invention is a compound of formula I where Z is pyrrolidindiyl or piperazindiyl.

Any scope of any variable, including $R^1$, $R^2$, $R^3$, $R^4$, $R^5$, Q, X and Z, can be used independently with the scope of any other instance of a variable.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Alkylene" means a straight or branched divalent alkyl group composed of 1 to 6 carbons. "Alkenylene" means a straight or branched divalent alkyl group composed of 2 to 6 carbons with at least one double bond. For ring A, Q is an alkylene or alkenylene chain with sufficient carbons and optionally other defined groups to form a 13-24 membered ring. "Cycloalkylene" means a divalent cycloalkane moiety composed of 3 to 7 carbons and includes gem-divalency (for example 1,1-cyclopropanediyl) as well as non-gem-divalency (for example, 1,4-cyclohexanediyl). Phenylene is a divalent benzene ring. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The substituents described above may be attached at any suitable point of attachment unless otherwise specified. However, it is understood that the compounds encompassed by the present invention are those that are chemically stable as understood by those skilled in the art. Additionally, the compounds encompassed by the present disclosure are those that are suitably stable for use as a pharmaceutical agent.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, camsylate, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention possess asymmetric carbon atoms (see, for example, the structures below). The invention includes all stereoisomeric forms, including enantiomers and diastereomers as well as mixtures of stereoisomers such as racemates. Some stereoisomers can be made using methods known in the art. Stereoisomeric mixtures of the compounds and related intermediates can be separated into individual isomers according to methods commonly known in the art. The use of wedges or hashes in the depictions of molecular structures in the following schemes and tables is intended only to indicate relative stereochemistry, and should not be interpreted as implying absolute stereochemical assignments.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Infection assays. HCV pseudoparticles, produced using standardized methodology (Bartosch, B., Dubuisson, J. and Cosset, F.- L. *J. Exp. Med.* 2003, 197:633-642) were made via a liposome-based transfection procedure of 293T cells with plasmids expressing the murine leukemia virus capsid and polymerase proteins, an MLV genome encoding the luciferase reporter gene, and envelope glycoproteins from either HCV or vesicular stomatitis virus (VSV). The genotype 1a HCV E1 and E2 envelope coding sequences were derived from the H77C isolate (GenBank accession number AF009606). Media containing pseudoparticles was collected 3 days following transfection, filtered, and stored at −20° C. as a viral stock. Infections were performed in 384-well plates by mixing pseudovirus with $1 \times 10^4$ Huh7 cells/well in the presence or absence of test inhibitors, followed by incubation at 37° C. Luciferase activity, reflecting the degree of entry of the pseudoparticles into host cells, was measured 2 days after infection. The specificity of the compounds for inhibiting HCV was determined by evaluating inhibition of VSV pseudoparticle infection.

Compounds and data analysis. Test compounds were serially diluted 3-fold in dimethyl sulfoxide (DMSO) to give a final concentration range in the assay of 50.0 µM to 0.04 µM. Maximum activity (100% of control) and background were derived from control wells containing DMSO but no inhibitor or from uninfected wells, respectively. The individual signals in each of the compound test wells were then divided by the averaged control values after background subtraction and multiplied by 100% to determine percent activity. Assays were performed in duplicate and average $EC_{50}$ values (reflecting the concentration at which 50% inhibition of virus replication was achieved) were calculated. Compound $EC_{50}$ data is expressed as: A=0.1-100 nM; B=100-1000 nM; C=1000-5000 nM). Representative data for compounds are reported in Tables 1a and 1b.

TABLE 1a

| Example | $EC_{50}$ (nM) 1a (H77C) | $EC_{50}$ (nM) 1a (H77C) |
|---|---|---|
| 0001 | C | 4201 |
| 0002 | A | |
| 0003 | B | 100.6 |

TABLE 1a-continued

| Example | EC$_{50}$ (nM) 1a (H77C) | EC$_{50}$ (nM) 1a (H77C) |
|---|---|---|
| 0004 | A | 48.36 |
| 0005 | C | |
| 0006 | C | |
| 0007 | A | 8.31 |
| 0008 | A | |
| 0009 | B | |
| 0010 | C | |
| 0011 | A | 62.78 |
| 0021 | B | |
| 0022 | B | |
| 0023 | B | |
| 0024 | C | 16290.00 |
| 0031 | B | |
| 0032 | B | |
| 0033 | B | |
| 0034 | C | |
| 0035 | C | |
| 0036 | C | |
| 0037 | B | |
| 0038 | B | 840.30 |
| 0039 | B | |
| 0041 | C | 21610.00 |
| 0042 | B | |
| 0051 | B | |
| 0052 | B | |
| 0053 | B | |
| 0054 | C | 5209.00 |
| 0055 | B | |
| 0056 | B | |
| 0057 | B | |
| 0058 | B | |
| 0059 | A | |
| 0060 | B | |
| 0061 | B | |
| 0062 | B | |
| 0063 | B | |
| 0064 | B | 407.40 |
| 0065 | B | |
| 0067 | B | |
| 0068 | B | |
| 0069 | A | 78.81 |
| 0070 | A | |
| 0071 | B | |
| 0072 | A | |
| 2001 | A | 2.30 |
| 2002 | A | |
| 2003 | A | |
| 2004 | A | |
| 2005 | A | |
| 2006 | A | |
| 2007 | A | |
| 2008 | A | |
| 2009 | B | 159.30 |
| 2010 | A | |
| 2011 | A | |
| 2012 | A | |
| 2013 | A | |
| 2014 | A | |
| 2015 | A | |
| 2016 | A | |
| 2017 | B | |
| 2018 | A | 33.60 |
| 2019 | A | |
| 2020 | A | |
| 2021 | B | 417.00 |
| 2022 | A | |
| 2023 | A | |
| 3001 | A | |
| 3002 | B | |
| 3003 | B | |
| 3004 | C | 2937.00 |
| 3005 | C | |
| 3006 | C | |
| 3007 | B | 556.80 |
| 3008 | B | |
| 3009 | B | |
| 3010 | A | 20.32 |

TABLE 1a-continued

| Example | EC$_{50}$ (nM) 1a (H77C) | EC$_{50}$ (nM) 1a (H77C) |
|---|---|---|
| 3012 | B | 275.20 |

TABLE 1b

| Example | EC$_{50}$ (nM) 1a (H77C) | EC$_{50}$ (nM) 1a (H77C) |
|---|---|---|
| 4001 | A | |
| 4002 | B | 104.60 |
| 4003 | A | |
| 4004 | A | |
| 4005 | A | |
| 4006 | A | |
| 4007 | A | |
| 4008 | A | |
| 4009 | A | 8.47 |
| 4013 | A | |
| 4014 | A | |
| 4015 | A | |
| 4016 | A | |
| 4017 | A | |
| 4018 | A | |
| 4019 | A | |
| 4020 | A | |
| 4023 | A | |
| 4024 | A | |
| 4025 | A | |
| 4026 | A | |
| 4030 | A | |
| 4031 | A | |
| 4032 | A | |
| 4034 | A | |
| 4035 | A | 4.37 |
| 5001 | A | |
| 5002 | A | |
| 5003 | A | |
| 5004 | A | |
| 5005 | A | |
| 5006 | A | |
| 6001 | A | |
| 6002 | A | |
| 6003 | A | |
| 6004 | A | |
| 6005 | A | |
| 6006 | A | |
| 6007 | A | |
| 6008 | A | |
| 6011 | A | |
| 6012 | A | 6.10 |
| 6013 | A | |
| 6014 | A | 1.51 |
| 6015 | A | |
| 6016 | A | |
| 6017 | A | |
| 6018 | A | |
| 6019 | A | |
| 6020 | A | |
| 6021 | A | |
| 6022 | A | 11.82 |
| 6023 | A | |
| 6024 | A | |
| 6025 | A | |
| 6026 | A | |
| 6027 | A | |
| 6028 | A | |
| 6030 | A | |
| 6031 | A | |
| 6032 | A | |
| 6033 | A | |
| 6034 | A | |
| 6035 | A | |
| 6036 | A | |
| 6037 | A | |
| 6038 | A | |

TABLE 1b-continued

| Example | EC$_{50}$ (nM) 1a (H77C) | EC$_{50}$ (nM) 1a (H77C) |
|---|---|---|
| 6039 | A | |
| 6040 | A | |
| 6041 | A | |
| 7001 | C | |
| 8002 | C | >50000 |
| 9001 | B | 242.90 |
| 9002 | A | |
| 9003 | A | |
| 9004 | A | |
| 9006 | A | |
| 9008 | A | |
| 9009 | A | |

Pharmaceutical Compositions and Methods of Treatment

The compounds demonstrate activity against HCV and can be useful in treating HCV infection. Therefore, another aspect of the invention is a composition comprising a compound, or a pharmaceutically acceptable salt thereof, and a pharmaceutically acceptable carrier.

Another aspect of the invention is a composition further comprising a compound having anti-HCV activity.

Another aspect of the invention is a composition where the compound having anti-HCV activity is an interferon. Another aspect of the invention is where the interferon is selected from interferon alpha 2B, pegylated interferon alpha, consensus interferon, interferon alpha 2A, and lymphoblastoid interferon tau.

Another aspect of the invention is a composition where the compound having anti-HCV activity is a cyclosporin. Another aspect of the invention is where the cyclosporin is cyclosporin A.

Another aspect of the invention is a composition where the compound having anti-HCV activity is selected from the group consisting of interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is a composition where the compound having anti-HCV activity is effective to inhibit the function of a target selected from HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

Another aspect of the invention is a composition comprising a compound, or a pharmaceutically acceptable salt thereof, a pharmaceutically acceptable carrier, an interferon and ribavirin.

Another aspect of the invention is a method of inhibiting the function of the HCV replicon comprising contacting the HCV replicon with a compound or a pharmaceutically acceptable salt thereof.

Another aspect of the invention is a method of treating an HCV infection in a patient comprising administering to the patient a therapeutically effective amount of a compound or a pharmaceutically acceptable salt thereof. In another embodiment the compound is effective to inhibit the function of the HCV replicon. In another embodiment the compound is effective to inhibit the function of the HCV NS5B protein.

Another aspect of the invention is a method of treating an HCV infection in a patient comprising administering to the patient a therapeutically effective amount of a compound, or a pharmaceutically acceptable salt thereof, in conjunction with (prior to, after, or concurrently) another compound having anti-HCV activity.

Another aspect of the invention is the method where the other compound having anti-HCV activity is an interferon.

Another aspect of the invention is the method where the interferon is selected from interferon alpha 2B, pegylated interferon alpha, consensus interferon, interferon alpha 2A, and lymphoblastoid interferon tau.

Another aspect of the invention is the method where the other compound having anti-HCV activity is a cyclosporin.

Another aspect of the invention is the method where the cyclosporin is cyclosporin A.

Another aspect of the invention is the method where the other compound having anti-HCV activity is selected from interleukin 2, interleukin 6, interleukin 12, a compound that enhances the development of a type 1 helper T cell response, interfering RNA, anti-sense RNA, Imiqimod, ribavirin, an inosine 5'-monophospate dehydrogenase inhibitor, amantadine, and rimantadine.

Another aspect of the invention is the method where the other compound having anti-HCV activity is effective to inhibit the function of a target selected from the group consisting of HCV metalloprotease, HCV serine protease, HCV polymerase, HCV helicase, HCV NS4B protein, HCV entry, HCV assembly, HCV egress, HCV NS5A protein, IMPDH, and a nucleoside analog for the treatment of an HCV infection.

"Therapeutically effective" means the amount of agent required to provide a meaningful patient benefit as understood by practitioners in the field of hepatitis and HCV infection.

"Patient" means a person infected with the HCV virus and suitable for therapy as understood by practitioners in the field of hepatitis and HCV infection.

"Treatment," "therapy," "regimen," "HCV infection," and related terms are used as understood by practitioners in the field of hepatitis and HCV infection.

The compounds of this invention are generally given as pharmaceutical compositions comprised of a therapeutically effective amount of a compound or its pharmaceutically acceptable salt and a pharmaceutically acceptable carrier and may contain conventional excipients. Pharmaceutically acceptable carriers are those conventionally known carriers having acceptable safety profiles. Compositions encompass all common solid and liquid forms including for example capsules, tablets, losenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, Mack Publishing Company, Easton, Pa., 17th edition, 1985.

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other agents will be present in a unit range similar to agents of that class used clinically. Typically, this is 1-100 mg/mL.

The invention encompasses all conventional modes of administration; oral and parenteral methods are preferred. Generally, the dosing regimen will be similar to other agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating hepatitis and HCV infection. In these combination methods, the compound will generally be given in a daily dose of 1-100 mg/kg body weight daily in conjunction with other agents. The other agents generally will be given in the amounts used therapeutically. The specific dosing regime, however, will be determined by a physician using sound medical judgement.

Some examples of compounds suitable for compositions and methods are listed in Table 2.

TABLE 2

| Brand Name | Type of Inhibitor or Target | Source Company |
|---|---|---|
| Omega IFN | IFN-ω | Intarcia Therapeutics |
| BILN-2061 | serine protease inhibitor | Boehringer Ingelheim Pharma KG, Ingelheim, Germany |
| Summetrel | antiviral | Endo Pharmaceuticals Holdings Inc., Chadds Ford, PA |
| Roferon A | IFN-α2a | F. Hoffmann-La Roche LTD, Basel, Switzerland |
| Pegasys | PEGylated IFN-α2a | F. Hoffmann-La Roche LTD, Basel, Switzerland |
| Pegasys and Ribavirin | PEGylated IFN-α2a/ribavirin | F. Hoffmann-La Roche LTD, Basel, Switzerland |
| CellCept | HCV IgG immunosuppressant | F. Hoffmann-La Roche LTD, Basel, Switzerland |
| Wellferon | lymphoblastoid IFN-αn1 | GlaxoSmithKline plc, Uxbridge, UK |
| Albuferon-α | albumin IFN-α2b | Human Genome Sciences Inc., Rockville, MD |
| Levovirin | ribavirin | ICN Pharmaceuticals, Costa Mesa, CA |
| IDN-6556 | caspase inhibitor | Idun Pharmaceuticals Inc., San Diego, CA |
| IP-501 | antifibrotic | Indevus Pharmaceuticals Inc., Lexington, MA |
| Actimmune | INF-γ | InterMune Inc., Brisbane, CA |
| Infergen A | IFN alfacon-1 | InterMune Pharmaceuticals Inc., Brisbane, CA |
| ISIS 14803 | antisense | ISIS Pharmaceuticals Inc, Carlsbad, CA/Elan Phamaceuticals Inc., New York, NY |
| JTK-003 | RdRp inhibitor | Japan Tobacco Inc., Tokyo, Japan |
| Pegasys and Ceplene | PEGylated IFN-α2a/immune modulator | Maxim Pharmaceuticals Inc., San Diego, CA |
| Ceplene | immune modulator | Maxim Pharmaceuticals Inc., San Diego, CA |
| Civacir | HCV IgG immunosuppressant | Nabi Biopharmaceuticals Inc., Boca Raton, FL |
| Intron A and Zadaxin | IFN-α2b/α1-thymosin | RegeneRx Biopharmiceuticals Inc., Bethesda, MD/SciClone Pharmaceuticals Inc, San Mateo, CA |
| Levovirin | IMPDH inhibitor | Ribapharm Inc., Costa Mesa, CA |
| Viramidine | Ribavirin Prodrug | Ribapharm Inc., Costa Mesa, CA |
| Heptazyme | ribozyme | Ribozyme Pharmaceuticals Inc., Boulder, CO |
| Intron A | IFN-α2b | Schering-Plough Corporation, Kenilworth, NJ |
| PEG-Intron | PEGylated IFN-α2b | Schering-Plough Corporation, Kenilworth, NJ |
| Rebetron | IFN-α2b/ribavirin | Schering-Plough Corporation, Kenilworth, NJ |
| Ribavirin | ribavirin | Schering-Plough Corporation, Kenilworth, NJ |
| PEG-Intron/Ribavirin | PEGylated IFN-α2b/ribavirin | Schering-Plough Corporation, Kenilworth, NJ |
| Zadazim | Immune modulator | SciClone Pharmaceuticals Inc., San Mateo, CA |
| Rebif | IFN-β1a | Serono, Geneva, Switzerland |
| IFN-β and EMZ701 | IFN-β and EMZ701 | Transition Therapeutics Inc., Ontario, Canada |
| Batabulin (T67) | β-tubulin inhibitor | Tularik Inc., South San Francisco, CA |
| Merimepodib (VX-497) | IMPDH inhibitor | Vertex Pharmaceuticals Inc., Cambridge, MA |
| Telaprevir (VX-950, LY-570310) | NS3 serine protease inhibitor | Vertex Pharmaceuticals Inc., Cambridge, MA/ Eli Lilly and Co. Inc., Indianapolis, IN |
| Omniferon | natural IFN-α | Viragen Inc., Plantation, FL |
| XTL-6865 (XTL-002) | monoclonal antibody | XTL Biopharmaceuticals Ltd., Rehovot, Isreal |
| HCV-796 | NS5B Replicase Inhibitor | Wyeth/Viropharma |
| NM-283 | NS5B Replicase Inhibitor | Idenix/Novartis |
| GL-59728 | NS5B Replicase Inhibitor | Gene Labs/Novartis |
| GL-60667 | NS5B Replicase Inhibitor | Gene Labs/Novartis |
| 2'C MeA | NS5B Replicase Inhibitor | Gilead |
| PSI 6130 | NS5B Replicase Inhibitor | Roche |
| R1626 | NS5B Replicase Inhibitor | Roche |
| SCH 503034 | serine protease inhibitor | Schering Plough |
| NIM811 | Cyclophilin Inhibitor | Novartis |
| Suvus | Methylene blue | Bioenvision |
| Multiferon | Long lasting IFN | Viragen/Valentis |
| Actilon (CPG10101) | TLR9 agonist | Coley |
| Interferon-β | Interferon-β-1a | Serono |
| Zadaxin | Immunomodulator | Sciclone |
| Pyrazolopyrimidine compounds and salts From WO-2005047288 26 May 2005 | HCV Inhibitors | Arrow Therapeutics Ltd. |
| 2'C Methyl adenosine | NS5B Replicase Inhibitor | Merck |
| GS-9132 (ACH-806) | HCV Inhibitor | Achillion/Gilead |

Synthetic Methods

The compounds may be made by methods known in the art including those described below and including variations within the skill of the art. Some reagents and intermediates are known in the art. Other reagents and intermediates can be made by methods known in the art using readily available materials. The variables (e.g. numbered "R" substituents) used to describe the synthesis of the compounds are intended only to illustrate how to make the compounds and are not to be confused with variables used in the claims or in other sections of the specification. The following methods are for illustrative purposes and are not intended to limit the scope of the invention.

Abbreviations used in the schemes generally follow conventions used in the art. Chemical abbreviations used in the specification and examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

For the section of compounds in the 0000 series all Liquid Chromatography (LC) data were recorded on a Shimadzu LC-10AS or LC-20AS liquid chromatograph using a SPD-10AV or SPD-20A UV-Vis detector and Mass Spectrometry (MS) data were determined with a Micromass Platform for LC in electrospray mode.

HPLC Method (i.e., compound isolation). Compounds purified by preparative HPLC were diluted in methanol (1.2 mL) and purified using a Shimadzu LC-8A or LC-10A automated preparative HPLC system.

Synthesis of intermediate methyl 4-(4-chloro-6-(2,2,2-trifluoroethoxy)-1,3,5-triazin-2-ylamino)benzoate

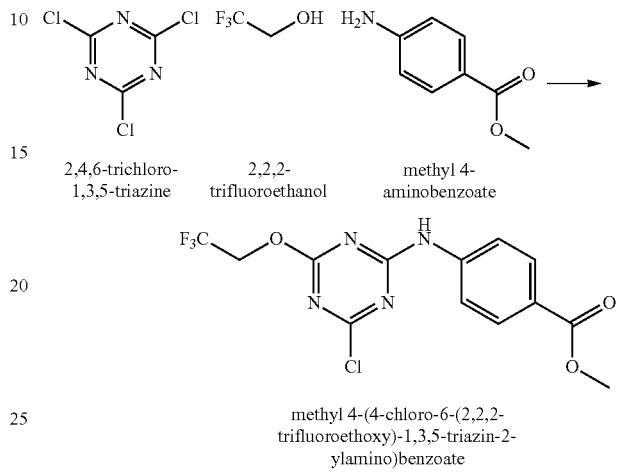

Step 1: To a soln. of 2,4,6-trichloro-1,3,5-triazine (10 g) in THF (200 mL) was added a mixture of 2,2,2-trifluoroethanol (5.42 g) and iPr$_2$NEt (20 mL) at room temperature. The resulting mixture was stirred at room temperature for 16 hours.

Step 2: Methyl 4-aminobenzoate (8.2 g) was added into the above solution and the reaction was carried out room temperature for 16 hours before adding water (200 mL). The aqueous layer was extracted with EtOAc (3×200 mL). The combined organic phase was dried over MgSO$_4$ and concentrated to give the crude product which was used in the further reactions without purification.

| Methyl 4-(4-chloro-6-(2,2,2-trifluoroethoxy)-1,3,5-triazin-2-ylamino)benzoate | |
|---|---|
| MS (M − H)$^+$ Calcd. | 361.0 |
| MS (M − H)$^+$ Observ. | 361.0 |
| Retention Time | 2.17 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 3 min |
| Flow Rate | 5 mL/min |
| Wavelength | 220 |
| Solvent Pair | ACN:Water:Ammonium Actetate |
| Column | Phenomenex Luna 4.6 × 50 mm S10 |

Synthesis of Compound 0001:

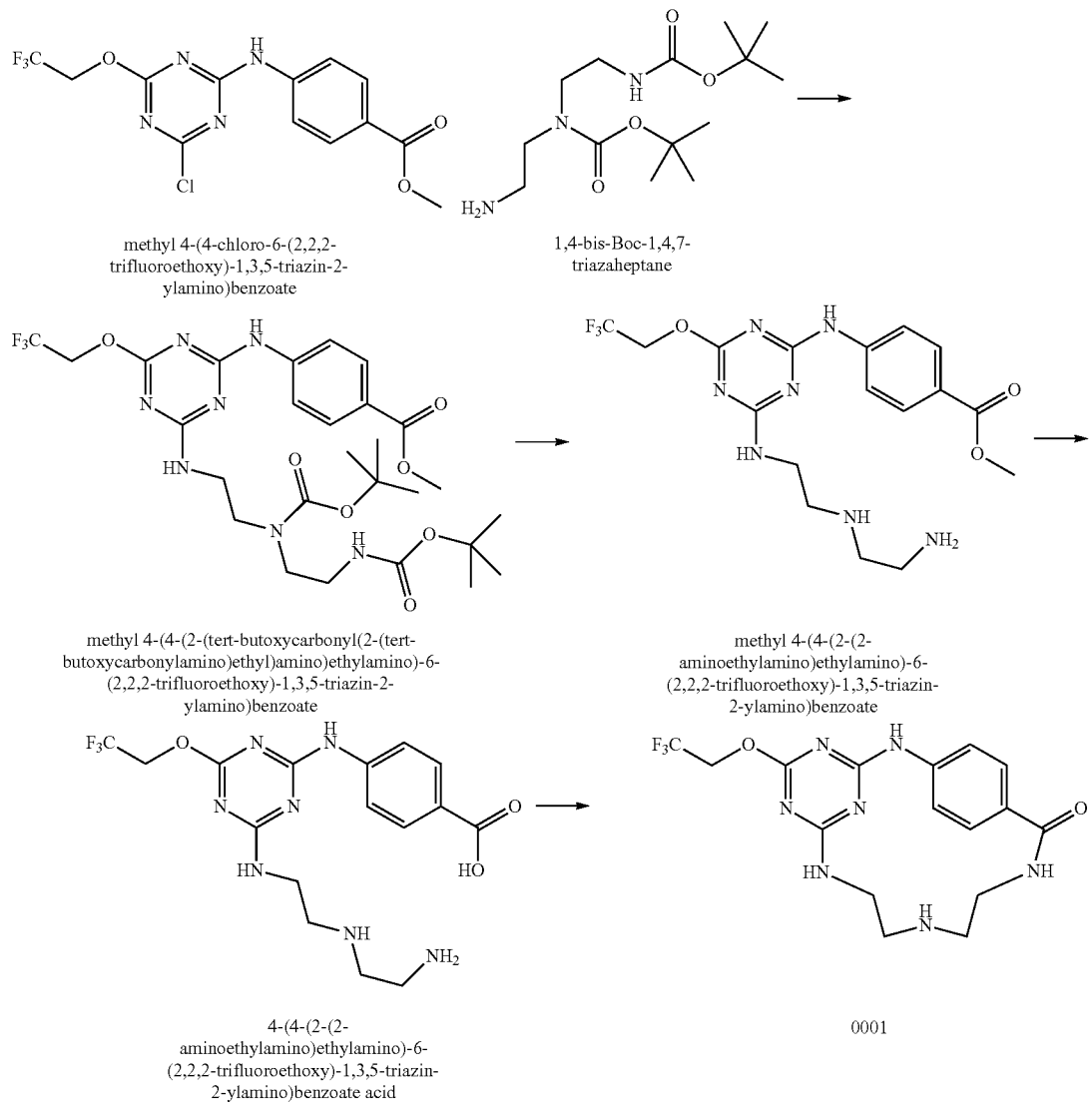

Step 1: To a suspension of methyl 4-(4-chloro-6-(2,2,2-trifluoroethoxy)-1,3,5-triazin-2-ylamino)benzoate (600 mg) in THF (8 mL) was added 1,4-1,4-bis-Boc-1,4,7-triazaheptane (502 mg) and iPr₂NEt (0.578 mL). The mixture was heated at 70° C. for 16 hours. The solvent was removed under vacuum. The residue was purified via silica gel column (EtOAC/Hexanes=4:1) to give methyl 4-(4-(2-(tert-butoxycarbonyl(2-(tert-butoxycarbonylamino)ethyl)amino)ethylamino)-6-(2,2,2-trifluoroethoxy)-1,3,5-triazin-2-ylamino)benzoate (0.69 g).

| Methyl 4-(4-(2-(tert-butoxycarbonyl(2-(tert-butoxycarbonylamino)ethyl)amino)ethylamino)-6-(2,2,2-trifluoroethoxy)-1,3,5-triazin-2-ylamino)benzoate | |
|---|---|
| MS (M + H)⁺ Calcd. | 630.3 |
| MS (M + H)⁺ Observ. | 630.2 |
| Retention Time | 1.99 min |
| | LC Condition |

| -continued | |
|---|---|
| Methyl 4-(4-(2-(tert-butoxycarbonyl(2-(tert-butoxycarbonylamino)ethyl)amino)ethylamino)-6-(2,2,2-trifluoroethoxy)-1,3,5-triazin-2-ylamino)benzoate | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a solution of methyl 4-(4-(2-(tert-butoxycarbonyl(2-(tert-butoxycarbonylamino)ethyl)amino)ethylamino)-6-(2,2,2-trifluoroethoxy)-1,3,5-triazin-2-ylamino)benzoate (200 mg) in dichloromethane (6 mL) was added TFA (0.734 mL). The mixture was stirred at r.t. for 4 hours. All solvents were removed under vacuum to afford the crude product which was used for next step without further purification.

| Methyl 4-(4-(2-(2-aminoethylamino)ethylamino)-6-(2,2,2-trifluoroethoxy)-1,3,5-triazin-2-ylamino)benzoate | |
|---|---|
| MS (M + H)$^+$ Calcd. | 430.2 |
| MS (M + H)$^+$ Observ. | 430.1 |
| Retention Time | 1.37 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a suspension of methyl 4-(4-(2-(2-aminoethylamino)ethylamino)-6-(2,2,2-trifluoroethoxy)-1,3,5-triazin-2-ylamino)benzoate (0.1 g) in acetone (6 mL) was added potassium carbonate (0.080 g) in water (6.00 mL). The mixture was heated to reflux for 16 hours. After cooling to room temperature, the reaction solution was acidified with 1N HCl to pH=3. All solvents were removed under vacuum. The residue was purified by prep. HPLC to give 4-(4-(2-(2-aminoethylamino)ethylamino)-6-(2,2,2-trifluoroethoxy)-1,3,5-triazin-2-ylamino)benzoic acid (40 mg).

| 4-(4-(2-(2-Aminoethylamino)ethylamino)-6-(2,2,2-trifluoroethoxy)-1,3,5-triazin-2-ylamino)benzoic acid | |
|---|---|
| MS (M + H)$^+$ Calcd. | 416.2 |
| MS (M + H)$^+$ Observ. | 416.1 |
| Retention Time | 1.17 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To a solution of 4-(4-(2-(2-aminoethylamino)ethylamino)-6-(2,2,2-trifluoroethoxy)-1,3,5-triazin-2-ylamino)benzoic acid (20 mg) in DMF (8 mL) was added 2-(1H-benzotriazol-1-yl)-1,1,3,3-tetramethyluronium tetrafluoroborate (TBTU) (17.01 mg) and iPr$_2$NEt (0.067 mL). The mixture was stirred at room temperature for 16 hours before all solvents were removed under vacuum. The residue was purified by prep. HPLC to give compound 0001.

| Compound 0001 | |
|---|---|
| MS (M + H)$^+$ Calcd. | 398.2 |
| MS (M + H)$^+$ Observ. | 398.1 |
| Retention Time | 1.20 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |
| NMR | |
| $^1$H (500 MHz, DMSO-D6) δ ppm | 2.45 (m, 2H), 2.64 (m, 2H), 2.92 (m, 2H), 3.06 (m, 2H), 4.91 (q, J = 10.0 Hz, 2H), 7.27 (d, J = 5.0 Hz, 2H), 7.42 (d, J = 5.0 Hz, 2H), 7.66 (t, J = 5.0 Hz, 1H), 7.86 (t, J = 5.0 Hz, 1H), 8.41 (b, 1H), 9.68 (s, 1H) |

Synthesis of Compound 0002:

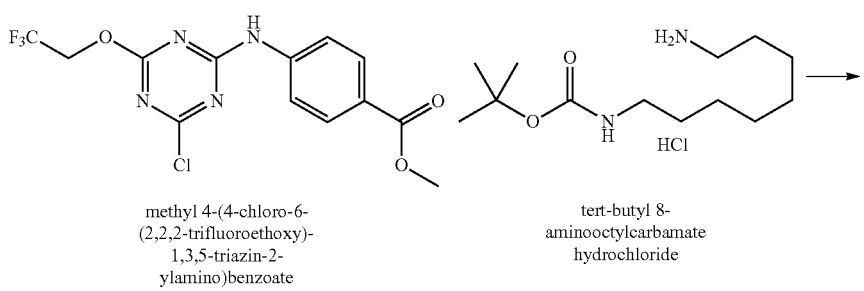

methyl 4-(4-chloro-6-(2,2,2-trifluoroethoxy)-1,3,5-triazin-2-ylamino)benzoate tert-butyl 8-aminooctylcarbamate hydrochloride

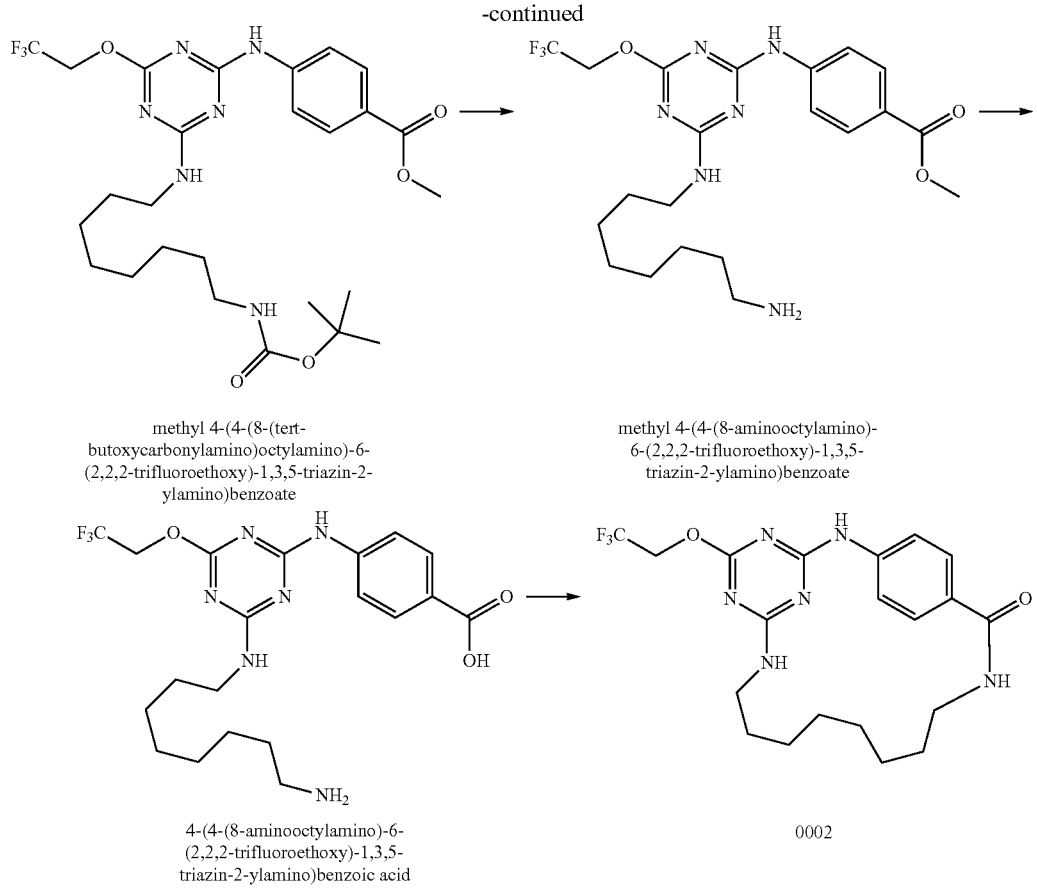

methyl 4-(4-(8-(tert-butoxycarbonylamino)octylamino)-6-(2,2,2-trifluoroethoxy)-1,3,5-triazin-2-ylamino)benzoate methyl 4-(4-(8-aminooctylamino)-6-(2,2,2-trifluoroethoxy)-1,3,5-triazin-2-ylamino)benzoate 4-(4-(8-aminooctylamino)-6-(2,2,2-trifluoroethoxy)-1,3,5-triazin-2-ylamino)benzoic acid

0002

Step 1: To a suspension of methyl 4-(4-chloro-6-(2,2,2-trifluoroethoxy)-1,3,5-triazin-2-ylamino)benzoate (600 mg) in THF (20 mL) was added tert-butyl 8-aminooctylcarbamate hydrochloride (465 mg) and iPr$_2$NEt (0.578 mL). The mixture was heated at 70° C. for 16 hours. The solvent was removed under vacuum. The residue was purified by silica gel column (EtOAC/Hexanes=4:1) to give methyl 4-(4-(8-(tert-butoxycarbonylamino)octylamino)-6-(2,2,2-trifluoroethoxy)-1,3,5-triazin-2-ylamino)benzoate (0.57 g).

| Methyl 4-(4-(8-(tert-butoxycarbonylamino)octylamino)-6-(2,2,2-trifluoroethoxy)-1,3,5-triazin-2-ylamino)benzoate | |
|---|---|
| MS (M + H)$^+$ Calcd. | 571.3 |
| MS (M + H)$^+$ Observ. | 571.2 |
| Retention Time | 2.14 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a solution of methyl 4-(4-(8-(tert-butoxycarbonylamino)octylamino)-6-(2,2,2-trifluoroethoxy)-1,3,5-triazin-2-ylamino)benzoate (200 mg) in dichloromethane (6 mL) was added TFA (0.405 mL). The mixture was stirred at r.t. for 4 hours. All solvents were removed under vacuum. The crude product was used for next step without further purification.

| Methyl 4-(4-(8-aminooctylamino)-6-(2,2,2-trifluoroethoxy)-1,3,5-triazin-2-ylamino)benzoate | |
|---|---|
| MS (M + H)$^+$ Calcd. | 471.2 |
| MS (M + H)$^+$ Observ. | 471.2 |
| Retention Time | 1.59 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a suspension of methyl 4-(4-(8-aminooctylamino)-6-(2,2,2-trifluoroethoxy)-1,3,5-triazin-2-ylamino)benzoate (0.1 g) in acetone (6 mL) was added potassium carbonate (0.073 g) in water (6.00 mL). The mixture was heated to reflux overnight. After cooling to r.t., the reaction solution was acidified with 1N HCl to pH=3. All solvents were removed under vacuum. The residue was purified by prep. HPLC to give 4-(4-(8-aminooctylamino)-6-(2,2,2-trifluoroethoxy)-1,3,5-triazin-2-ylamino)benzoic acid (38 mg).

| 4-(4-(8-Aminooctylamino)-6-(2,2,2-trifluoroethoxy)-1,3,5-triazin-2-ylamino)benzoic acid | |
|---|---|
| MS (M + H)$^+$ Calcd. | 457.2 |
| MS (M + H)$^+$ Observ. | 457.2 |
| Retention Time | 1.32 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To a solution of 4-(4-(8-aminooctylamino)-6-(2,2,2-trifluoroethoxy)-1,3,5-triazin-2-ylamino)benzoic acid (20 mg) in DMF (8 mL) was added TBTU (15.48 mg) and iPr$_2$NEt (0.061 mL). The mixture was stirred at r.t. for 16 hours. All solvents were removed under vacuum. The residue was purified via prep. HPLC to give compound 0002.

| Compound 0002 | |
|---|---|
| MS (M + H)$^+$ Calcd. | 439.2 |
| MS (M + H)$^+$ Observ. | 439.1 |
| Retention Time | 1.64 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Synthesis of Compound 0003:

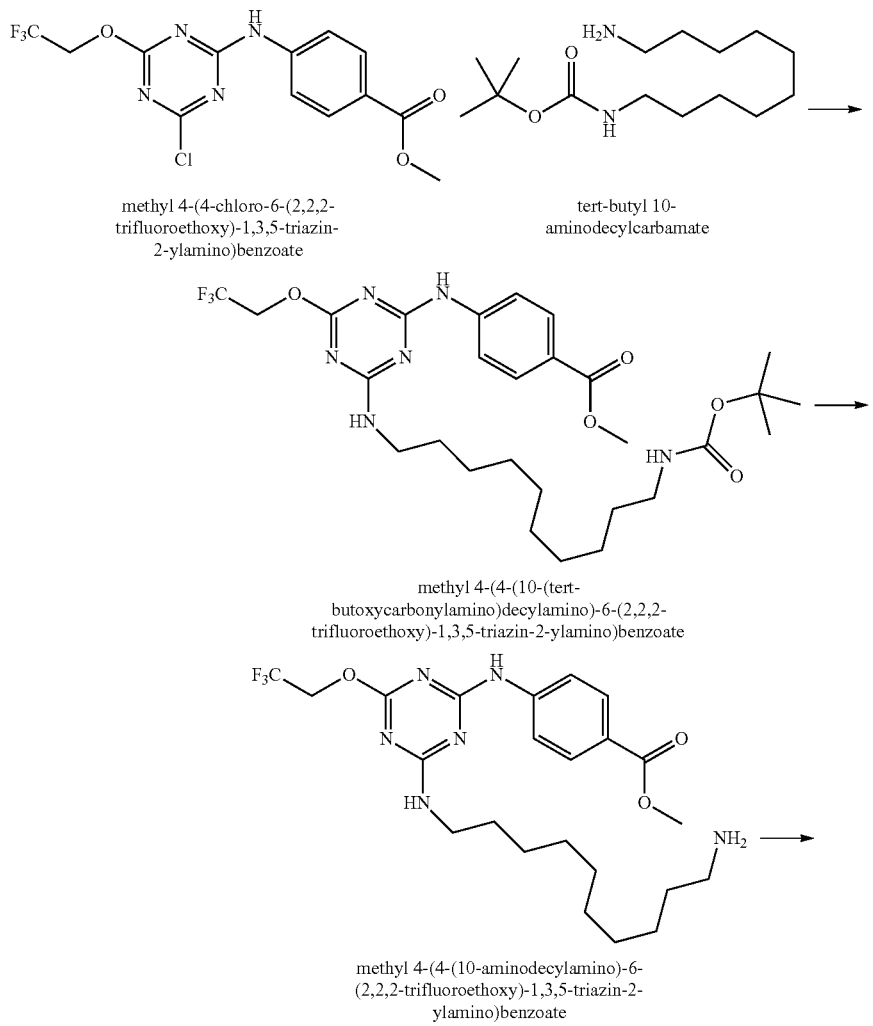

methyl 4-(4-chloro-6-(2,2,2-trifluoroethoxy)-1,3,5-triazin-2-ylamino)benzoate tert-butyl 10-aminodecylcarbamate methyl 4-(4-(10-(tert-butoxycarbonylamino)decylamino)-6-(2,2,2-trifluoroethoxy)-1,3,5-triazin-2-ylamino)benzoate methyl 4-(4-(10-aminodecylamino)-6-(2,2,2-trifluoroethoxy)-1,3,5-triazin-2-ylamino)benzoate

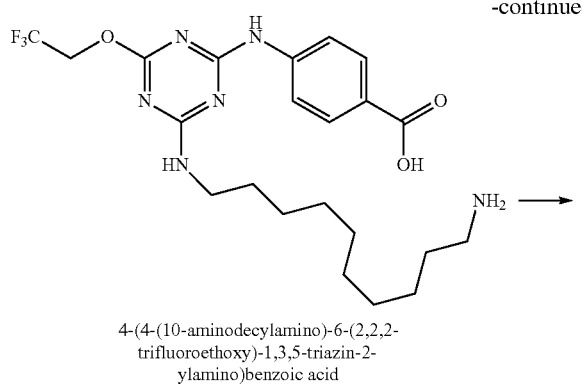

4-(4-(10-aminodecylamino)-6-(2,2,2-trifluoroethoxy)-1,3,5-triazin-2-ylamino)benzoic acid

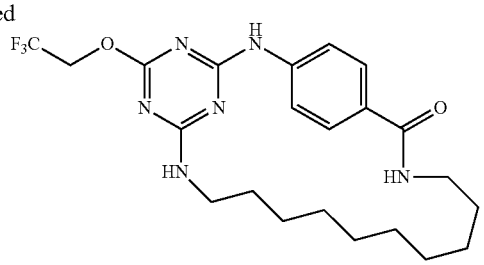

0003

Step 1: To a suspension of methyl 4-(4-chloro-6-(2,2,2-trifluoroethoxy)-1,3,5-triazin-2-ylamino)benzoate (600 mg) in THF (20 mL) was added tert-butyl 10-aminodecylcarbamate (451 mg) and iPr₂NEt (0.578 mL). The mixture was heated at 70° C. for 16 hours. The solvent was removed under vacuum. The residue was purified by silica gel column (EtOAC/Hexanes=4:1) to give methyl 4-(4-(10-(tert-butoxycarbonylamino)decylamino)-6-(2,2,2-trifluoroethoxy)-1,3,5-triazin-2-ylamino)benzoate (0.67 g).

| Methyl 4-(4-(10-(tert-butoxycarbonylamino)decylamino)-6-(2,2,2-trifluoroethoxy)-1,3,5-triazin-2-ylamino)benzoate | |
|---|---|
| MS (M + H)⁺ Calcd. | 599.3 |
| MS (M + H)⁺ Observ. | 599.3 |
| Retention Time | 2.26 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a solution of methyl 4-(4-(10-(tert-butoxycarbonylamino)decylamino)-6-(2,2,2-trifluoroethoxy)-1,3,5-triazin-2-ylamino)benzoate (200 mg) in dichloromethane (6 mL) was added TFA (0.386 mL). The mixture was stirred at r.t. for 4 hours before all solvents were removed under vacuum. The crude product was used for next step without further purification.

| Methyl 4-(4-(10-aminodecylamino)-6-(2,2,2-trifluoroethoxy)-1,3,5-triazin-2-ylamino)benzoate | |
|---|---|
| MS (M + H)⁺ Calcd. | 499.3 |
| MS (M + H)⁺ Observ. | 499.2 |
| Retention Time | 1.70 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a suspension of methyl 4-(4-(10-aminodecylamino)-6-(2,2,2-trifluoroethoxy)-1,3,5-triazin-2-ylamino)benzoate (0.1 g) in acetone (6 mL) was added potassium carbonate in water (6.00 mL). The mixture was heated to reflux overnight. After cooling to r.t., the reaction solution was acidified with 1N HCl to pH=3. All solvents were removed under vacuum. The residue was purified by prep. HPLC to give 4-(4-(10-aminodecylamino)-6-(2,2,2-trifluoroethoxy)-1,3,5-triazin-2-ylamino)benzoic acid (25 mg).

| 4-(4-(10-Aminodecylamino)-6-(2,2,2-trifluoroethoxy)-1,3,5-triazin-2-ylamino)benzoic acid | |
|---|---|
| MS (M + H)⁺ Calcd. | 485.3 |
| MS (M + H)⁺ Observ. | 485.1 |
| Retention Time | 1.39 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To a solution of 4-(4-(10-aminodecylamino)-6-(2,2,2-trifluoroethoxy)-1,3,5-triazin-2-ylamino)benzoic acid (15 mg) in DMF (8 mL) was added TBTU (10.93 mg) and iPr2NEt (0.043 mL). The mixture was stirred at r.t. for 16 hours before all the solvents were removed under vacuum. The residue was purified via prep. HPLC to give compound 0003.

| Compound 0003 | |
|---|---|
| MS (M + H)+ Calcd. | 467.2 |
| MS (M + H)+ Observ. | 467.2 |
| Retention Time | 1.82 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |

-continued

| Compound 0003 | |
|---|---|
| Flow Rate | 1 mL/min |
| Wavelength | 220 |
| Solvent Pair | ACN:Water:Ammonium Actetate |
| Column | Phenomenex LUNA C18, 30 × 2, 3 u |
| NMR | |
| $^1$H (500 MHz, DMSO-D6) δ ppm | 1.18-1.26 (m, 10H), 1.37 (m, 2H), 1.51 (m, 4H), 3.16 (m, 2H), 3.25 (m, 2H), 4.93 (q, J = 10.0 Hz, 2H), 7.69 (d, J = 5.0 Hz, 2H), 7.76 (d, J = 5.0 Hz, 2H), 7.92 (t, J = 5.0 Hz, 1H), 8.30 (t, J = 5.0 Hz, 1H), 9.88 (s, 1H) |

Synthesis of Compound 0004:

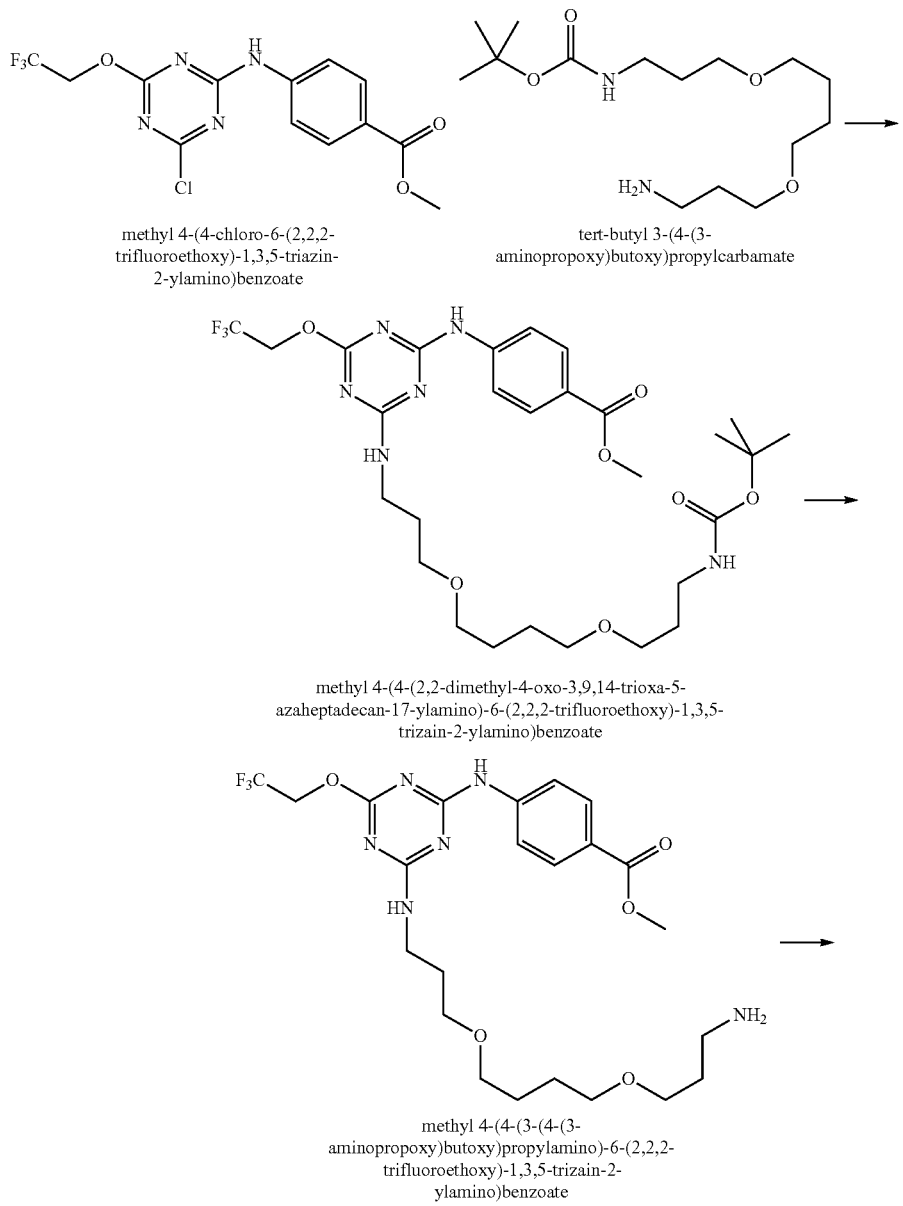

methyl 4-(4-chloro-6-(2,2,2-trifluoroethoxy)-1,3,5-triazin-2-ylamino)benzoate tert-butyl 3-(4-(3-aminopropoxy)butoxy)propylcarbamate methyl 4-(4-(2,2-dimethyl-4-oxo-3,9,14-trioxa-5-azaheptadecan-17-ylamino)-6-(2,2,2-trifluoroethoxy)-1,3,5-trizain-2-ylamino)benzoate methyl 4-(4-(3-(4-(3-aminopropoxy)butoxy)propylamino)-6-(2,2,2-trifluoroethoxy)-1,3,5-trizain-2-ylamino)benzoate

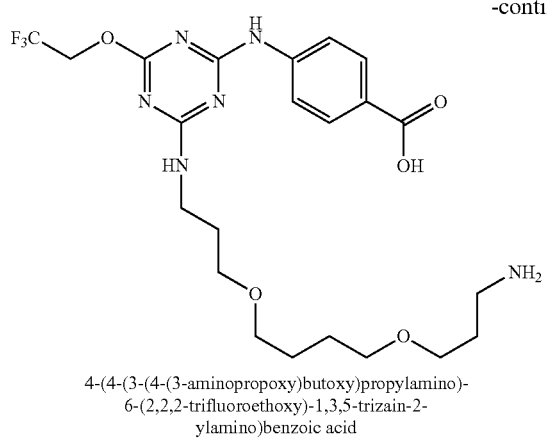

4-(4-(3-(4-(3-aminopropoxy)butoxy)propylamino)-
6-(2,2,2-trifluoroethoxy)-1,3,5-trizain-2-
ylamino)benzoic acid

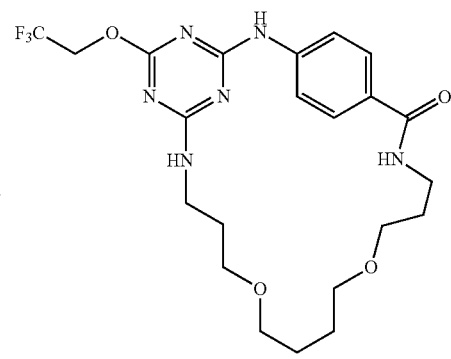

0004

Step 1: To a suspension of methyl 4-(4-chloro-6-(2,2,2-trifluoroethoxy)-1,3,5-triazin-2-ylamino)benzoate (600 mg) in THF (20 mL) was added tert-butyl 34443-aminopropoxy)butoxy)propylcarbamate (504 mg) and iPr$_2$NEt (0.578 mL). The mixture was heated at 70° C. for 16 hours. The solvent was removed under vacuum. The residue was purified by silica gel column (EtOAC/Hexanes=4:1) to give methyl 4-(4-(2,2-dimethyl-4-oxo-3,9,14-trioxa-5-azaheptadecan-17-ylamino)-6-(2,2,2-trifluoroethoxy)-1,3,5-triazin-2-ylamino)benzoate (601 mg).

| Methyl 4-(4-(2,2-dimethyl-4-oxo-3,9,14-trioxa-5-azaheptadecan-17-ylamino)-6-(2,2,2-trifluoroethoxy)-1,3,5-triazin-2-ylamino)benzoate | |
|---|---|
| MS (M + H)$^+$ Calcd. | 631.3 |
| MS (M + H)$^+$ Observ. | 631.3 |
| Retention Time | 3.61 min |
| | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |

Step 2: To a solution of methyl 4-(4-(2,2-dimethyl-4-oxo-3,9,14-trioxa-5-azaheptadecan-17-ylamino)-6-(2,2,2-trifluoroethoxy)-1,3,5-triazin-2-ylamino)benzoate (200 mg) in dichloromethane (6 mL) was added TFA (0.366 mL). The mixture was stirred at r.t. for 4 hours before all solvents were removed under vacuum. The crude product was used for next step without further purification.

| Methyl 4-(4-(3-(4-(3-aminopropoxy)butoxy)propylamino)-6-(2,2,2-trifluoroethoxy)-1,3,5-triazin-2-ylamino)benzoate | |
|---|---|
| MS (M + H)$^+$ Calcd. | 531.3 |
| MS (M + H)$^+$ Observ. | 531.2 |
| Retention Time | 1.55 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a suspension of methyl 4-(4-(3-(4-(3-aminopropoxy)butoxy)propylamino)-6-(2,2,2-trifluoroethoxy)-1,3,5-triazin-2-ylamino)benzoate (0.1 g) in acetone (6 mL) was added potassium carbonate in water (6.00 mL). The mixture was heated to reflux for 16 hours. After cooling to r.t., the reaction solution was acidified with 1N HCl to pH=3. All the solvents were removed under vacuum. The residue was purified by prep. HPLC to give 4-(4-(3-(4-(3-aminopropoxy)butoxy)propylamino)-6-(2,2,2-trifluoroethoxy)-1,3,5-triazin-2-ylamino)benzoic acid (28 mg, 0.054 mmol).

| 4-(4-(3-(4-(3-Aminopropoxy)butoxy)propylamino)-6-(2,2,2-trifluoroethoxy)-1,3,5-triazin-2-ylamino)benzoic acid | |
|---|---|
| MS (M + H)$^+$ Calcd. | 517.2 |
| MS (M + H)$^+$ Observ. | 517.2 |
| Retention Time | 1.23 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To a solution of 4-(4-(3-(4-(3-aminopropoxy)butoxy)propylamino)-6-(2,2,2-trifluoroethoxy)-1,3,5-triazin-2-ylamino)benzoic acid (30 mg) in DMF (8 mL) was added TBTU (20.51 mg) and iPr$_2$NEt (0.081 mL). The mixture was stirred at r.t. for 16 hours before all solvents were removed under vacuum. The residue was purified via prep. HPLC to give compound 0004.

|  | Compound 0004 |
|---|---|
| MS (M + H)+ Calcd. | 499.2 |
| MS (M + H)+ Observ. | 499.2 |
| Retention Time | 1.71 min |
|  | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Synthesis of Compound 0005:

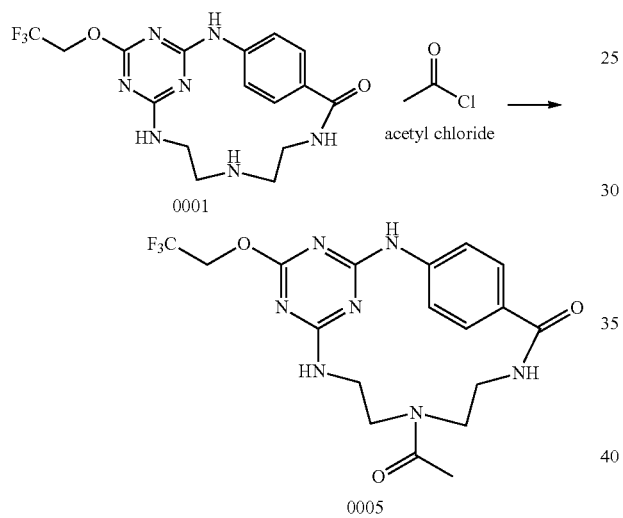

Acetyl chloride (0.02 g) and iPr2Net (0.033 g) were added into the solution of compound 0001 (0.05 g) in THF (2 mL). The mixture was stirred at r.t. for 2 hours before all the solvents were removed under vacuum. The residue was purified via prep. HPLC to give compound 0005 (0.003 g).

|  | Compound 0005 |
|---|---|
| MS (M + H)+ Calcd. | 440.2 |
| MS (M + H)+ Observ. | 440.2 |
| Retention Time | 1.75 min |
|  | LC Condition |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |

Synthesis of Compound 0006:

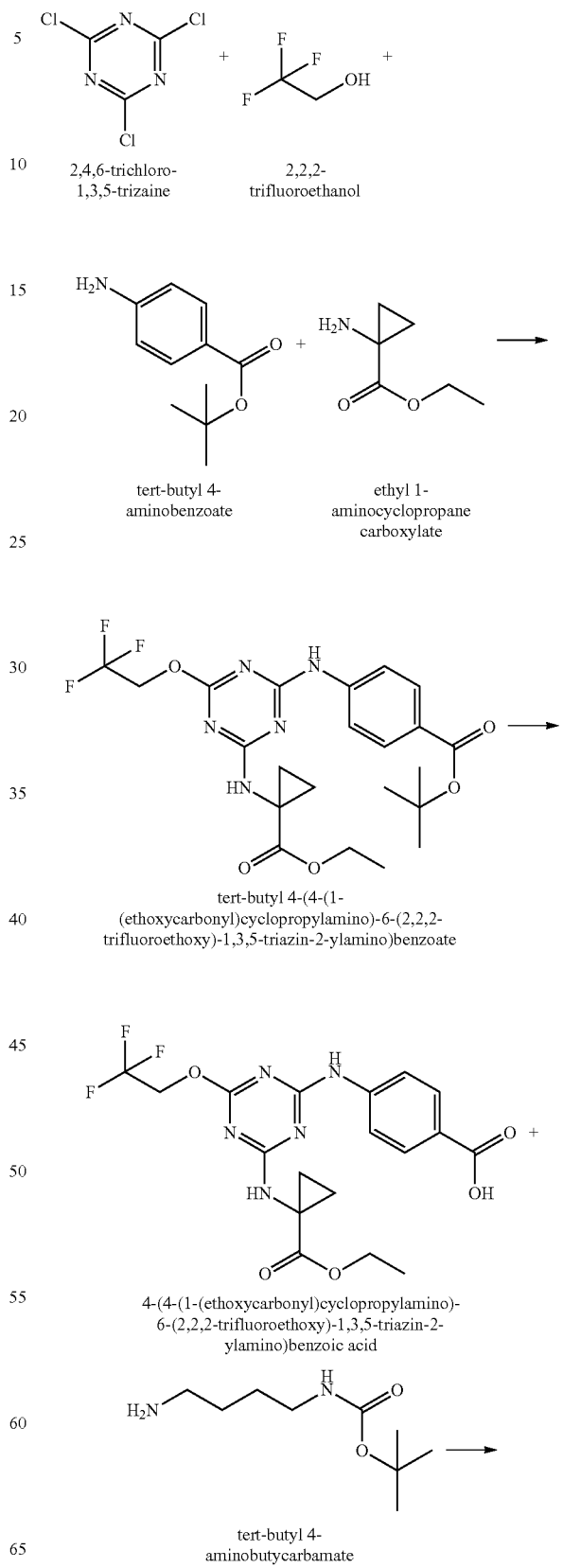

-continued

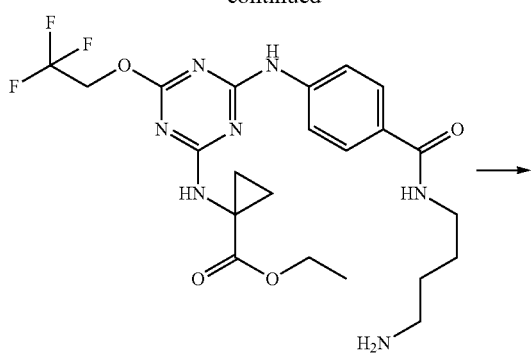

ethyl 1-(4-(4-(4-aminobutylcarbarmoyl)phenylamino)-6-(2,2,2-trifluoroethoxy)-1,3,5-triazin-2-ylamino)cyclopropanecarboxylate

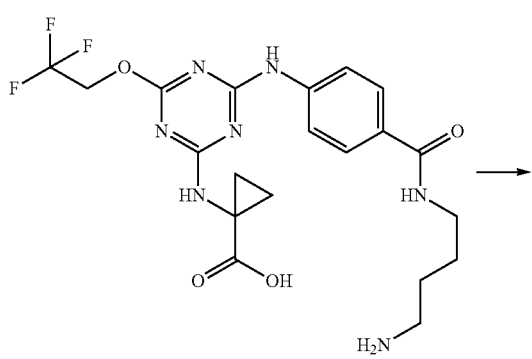

1-(4-(4-(4-aminobutylcarbamoyl)phenylamino)-6-(2,2,2-trifluoroethoxy)-1,3,5-triazin-2-ylamino)cyclopropanecarboxylic acid

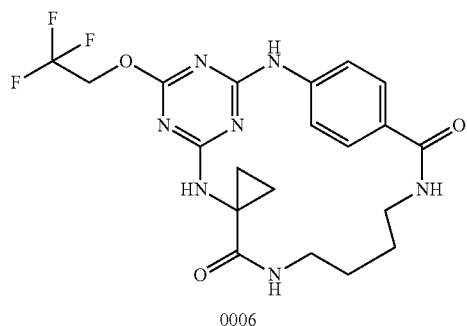

0006

Step 1: iPr2NEt (10 mL) was added into the solution of 2,4,6-trichloro-1,3,5-triazine (2.5 g) and 2,2,2-trifluoroethanol (1.36 g) in THF (100 mL). The reaction was stirred at room temperature for 16 hours before tert-butyl 4-aminobenzoate (2.62 g) was added. The resulting mixture was stirred at room temperature for 40 hours. Then, ethyl 1-aminocyclopropanecarboxylate hydrochloride (2.25 g) was added into the mixture. The reaction was carried out at r.t. for 16 hours, then 115° C. for 16 hours. The reaction was quenched with water. The aqueous layer was extracted with EtOAc (3×100 mL). The combined organic layer was dried over $Mg_2SO_4$ and concentrated to offer a residue which will be purified by silica gel chromatography.

| tert-Butyl 4-(4-(1-(ethoxycarbonyl)cyclopropylamino)-6-(2,2,2-trifluoroethoxy)-1,3,5-triazin-2-ylamino)benzoate | |
|---|---|
| MS (M + H)⁺ Calcd. | 498.2 |
| MS (M + H)⁺ Observ. | 498.3 |
| Retention Time | 2.05 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a suspension of tert-butyl 4-(4-(1-(ethoxycarbonyl)cyclopropylamino)-6-(2,2,2-trifluoroethoxy)-1,3,5-triazin-2-ylamino)benzoate (1.6 g) in dichloromethane (15 mL) was added TFA (4.96 mL). The mixture was stirred at r.t. for 16 hours. All solvents were removed under vacuum to give product 4-(4-(1-(ethoxycarbonyl)cyclopropylamino)-6-(2,2,2-trifluoroethoxy)-1,3,5-triazin-2-ylamino)benzoic acid (1.35 g).

| 4-(4-(1-(Ethoxycarbonyl)cyclopropylamino)-6-(2,2,2-trifluoroethoxy)-1,3,5-triazin-2-ylamino)benzoic acid | |
|---|---|
| MS (M + H)⁺ Calcd. | 442.1 |
| MS (M + H)⁺ Observ. | 442.3 |
| Retention Time | 1.29 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a solution of 4-(4-(1-(ethoxycarbonyl)cyclopropylamino)-6-(2,2,2-trifluoroethoxy)-1,3,5-triazin-2-ylamino)benzoic acid (100 mg) in DMF (5 mL) was added tert-butyl 4-aminobutylcarbamate (64.0 mg), 2-(1H-benzotriazol-1-yl)-1,1,3,3-tetramethyluronium tetrafluoroborate (109 mg) and iPr₂NEt (0.119 mL). The mixture was stirred at r.t. for 16 hours before all the solvents were removed under vacuum. The residue was dissolved in dichloromethane (5.00 mL) and 2 mL of TFA. The mixture was stirred at r.t. for 3 hours. All solvents were removed under vacuum and the residue was purified by prep. HPLC to give ethyl 1-(4-(4-(4-aminobutylcarbamoyl)phenylamino)-6-(2,2,2-trifluoroethoxy)-1,3,5-triazin-2-ylamino)cyclopropanecarboxylate (80 mg).

| Ethyl 1-(4-(4-(4-aminobutylcarbamoyl)phenylamino)-6-(2,2,2-trifluoroethoxy)-1,3,5-triazin-2-ylamino)cyclopropanecarboxylate | |
|---|---|
| MS (M + H)⁺ Calcd. | 512.2 |
| MS (M + H)⁺ Observ. | 512.1 |

-continued

| Ethyl 1-(4-(4-(4-aminobutylcarbamoyl)phenylamino)-6-(2,2,2-trifluoroethoxy)-1,3,5-triazin-2-ylamino)cyclopropanecarboxylate | |
|---|---|
| Retention Time | 2.18 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |

Step 4: Ethyl 1-(4-(4-(4-aminobutylcarbamoyl)phenylamino)-6-(2,2,2-trifluoroethoxy)-1,3,5-triazin-2-ylamino)cyclopropanecarboxylate (80 mg) and potassium carbonate (64.8 mg) were dissolved in acetone (3 mL)/water (2 mL). After stirring at r.t. for 16 hours and then heated to 90° C. for 2 hours, the mixture was acidified with 1N HCl to pH=3. All the solvents were then removed under vacuum. The residue was purified by perp. HPLC to give 1-(4-(4-(4-aminobutylcarbamoyl)phenylamino)-6-(2,2,2-trifluoroethoxy)-1,3,5-triazin-2-ylamino)cyclopropanecarboxylic acid (20 mg).

| 1-(4-(4-(4-Aminobutylcarbamoyl)phenylamino)-6-(2,2,2-trifluoroethoxy)-1,3,5-triazin-2-ylamino)cyclopropanecarboxylic acid | |
|---|---|
| MS (M + H)$^+$ Calcd. | 484.2 |
| MS (M + H)$^+$ Observ. | 484.3 |
| Retention Time | 1.21 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 5: To a solution of 1-(4-(4-(4-aminobutylcarbamoyl)phenylamino)-6-(2,2,2-trifluoroethoxy)-1,3,5-triazin-2-ylamino)cyclopropanecarboxylic acid (20 mg) in THF (80 mL) was added TBTU (19.92 mg) and iPr$_2$NEt (0.022 mL). The mixture was stirred at r.t. for 16 hours before all the solvents were removed under vacuum. All solvents were removed nuder vacuum and the residue was purified by prep. HPLC to give compound 0006 (5.8 mg).

| Compound 0006 | |
|---|---|
| MS (M + H)$^+$ Calcd. | 466.2 |
| MS (M + H)$^+$ Observ. | 466.2 |
| Retention Time | 2.94 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |

Syntheses of Compounds 0007:

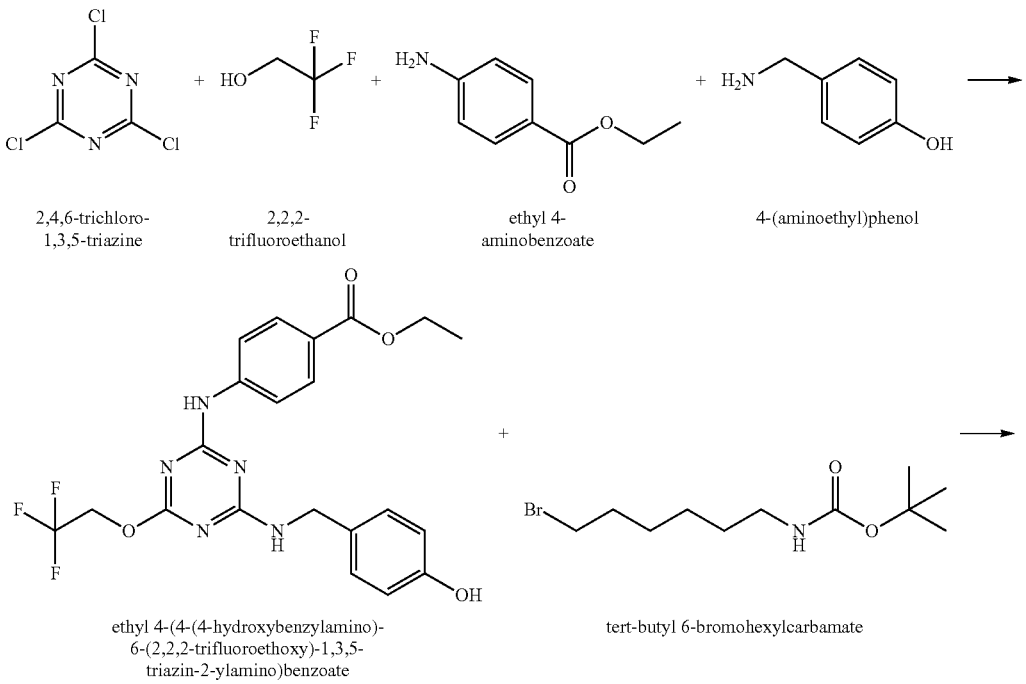

2,4,6-trichloro-1,3,5-triazine 2,2,2-trifluoroethanol ethyl 4-aminobenzoate 4-(aminoethyl)phenol ethyl 4-(4-(4-hydroxybenzylamino)-6-(2,2,2-trifluoroethoxy)-1,3,5-triazin-2-ylamino)benzoate tert-butyl 6-bromohexylcarbamate -continued
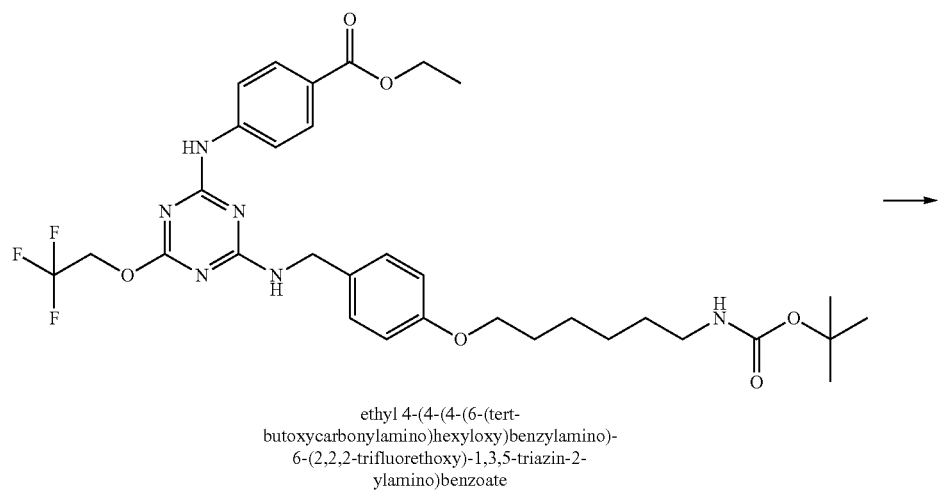
ethyl 4-(4-(4-(6-(tert-butoxycarbonylamino)hexyloxy)benzylamino)-6-(2,2,2-trifluorethoxy)-1,3,5-triazin-2-ylamino)benzoate
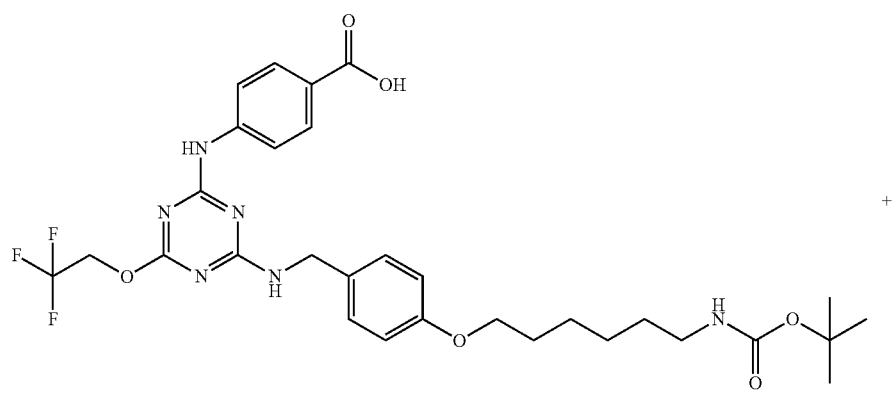
4-(4-(4-(6-(tert-butoxycarbonylamino)hexyloxy)benzylamino)-6-(2,2,2-trifluoroethoxy)-1,3,5-triazin-2-ylamino)benzoic acid
+
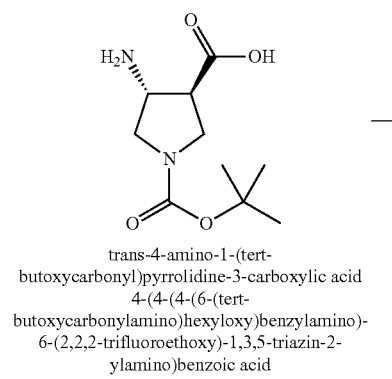
trans-4-amino-1-(tert-butoxycarbonyl)pyrrolidine-3-carboxylic acid -continued

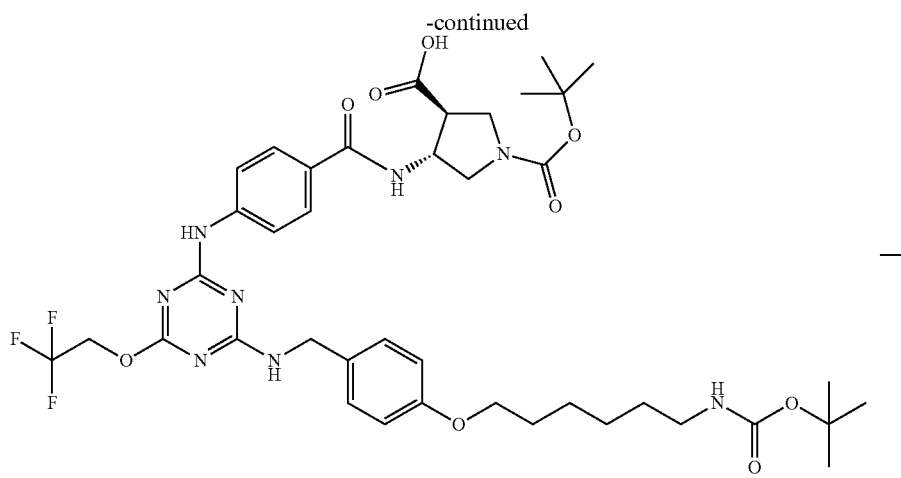

trans-1-(tert-butoxycarbonyl)-4-(4-(4-(4-(6-(tert-butoxycarbonylamino)hexyloxy)benzylamino)-6-(2,2,2-trifluoroethoxy)-1,3,5-triazin-2-ylamino)benzamido)pyrrolidine-3-carboxylic acid

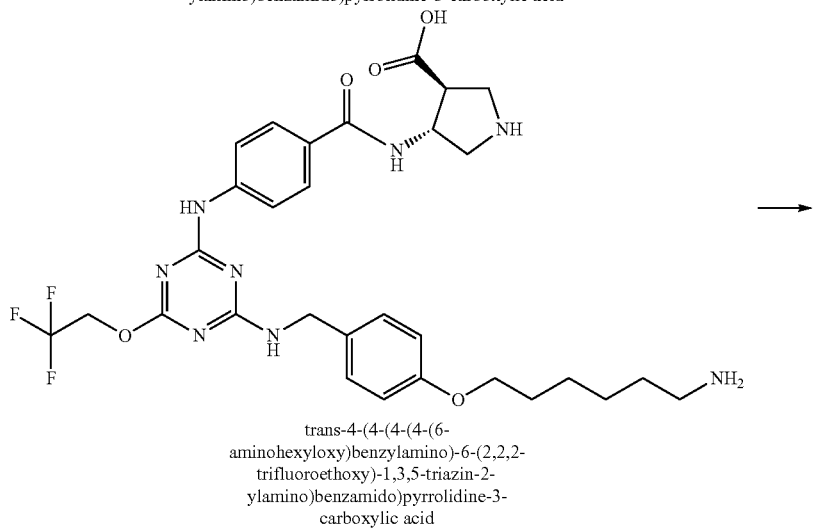

trans-4-(4-(4-(4-(6-aminohexyloxy)benzylamino)-6-(2,2,2-trifluoroethoxy)-1,3,5-triazin-2-ylamino)benzamido)pyrrolidine-3-carboxylic acid

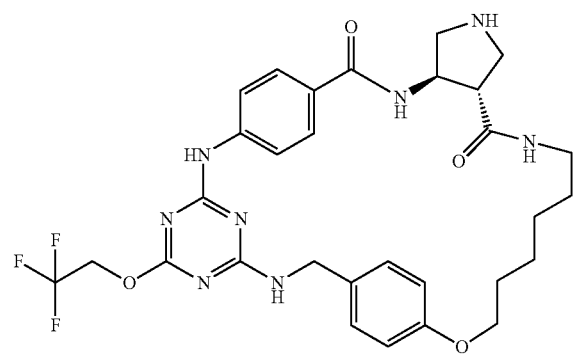

0007

Step 1: To a solution of 2,4,6-trichloro-1,3,5-triazine (10 g) in acetone (210 mL) was added a solution of 2,2,2-trifluoroethanol (5.97 g) and 2,4,6-collidine (7.88 mL) in acetone (210 mL) dropwise over 1 hour. The resulting mixture was stirred at room temperature for 16 hours. All the solvents were removed under vacuum to give a residue which was diluted with NMP (100 mL) and ethyl 4-aminobenzoate (9.85 g), iPr$_2$NEt (28.4 mL) were added. After stirring at room temperature for 6 hours, 4-(aminomethyl)phenol (7.35 g) was added. The resulting mixture was stirred for 16 hours at room temperature. The mixture was diluted with 300 mL of water and extracted with EtOAc (2×500 mL). The organic layers were combined, washed with brine (300 mL), dried over MgSO$_4$ and concentrated. The residue was purified by recrystallization in MeOH to give ethyl 4-(4-(4-hydroxybenzylamino)-6-(2,2,2-trifluoroethoxy)-1,3,5-triazin-2-ylamino)benzoate (13.6 g).

| ethyl 4-(4-(4-hydroxybenzylamino)-6-(2,2,2-trifluoroethoxy)-1,3,5-triazin-2-ylamino)benzoate | |
|---|---|
| MS (M + H)+ Calcd. | 464.1 |
| MS (M + H)+ Observ. | 464.3 |
| Retention Time | 1.75 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a solution of ethyl 4-(4-(4-hydroxybenzylamino)-6-(2,2,2-trifluoroethoxy)-1,3,5-triazin-2-ylamino)benzoate (1.5 g) in DMF (8 mL) was added tert-butyl 6-bromohexylcarbamate (1.1 g) and K$_2$CO$_3$ (0.9 g). The mixture was heated to 65° C. for 16 hours. After cooling to room temperature, the mixture was diluted with EtOAc (250 mL) and washed with water (50 mL) and brine (50 mL). The organic layer was dried over MgSO$_4$ and concentrated. The residue was purified by recrystallization in MeOH to give ethyl 4-(4-(4-(6-(tert-butoxycarbonylamino)hexyloxy)benzylamino)-6-(2,2,2-trifluoroethoxy)-1,3,5-triazin-2-ylamino)benzoate (1.2 g).

| ethyl 4-(4-(4-(6-(tert-butoxycarbonylamino)hexyloxy)benzylamino)-6-(2,2,2-trifluoroethoxy)-1,3,5-triazin-2-ylamino)benzoate | |
|---|---|
| MS (M + H)+ Calcd. | 663.3 |
| MS (M + H)+ Observ. | 663.2 |
| Retention Time | 3.98 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |

Step 3: A mixture of ethyl 4-(4-(4-(6-(tert-butoxycarbonylamino)hexyloxy)benzylamino)-6-(2,2,2-trifluoroethoxy)-1,3,5-triazin-2-ylamino)benzoate (1.0 g) and K$_2$CO$_3$ (1.25 g) in acetone (12 mL)/water (12 mL) was heated at 110° C. for 24 hours. After cooling to room temperature, the mixture was acidified with 1N HCl to pH=3. The white precipitate was collected, washed with water (20 mL) and dried under vacuum to give 4-(4-(4-(6-(tert-butoxycarbonylamino)hexyloxy)benzylamino)-6-(2,2,2-trifluoroethoxy)-1,3,5-triazin-2-ylamino)benzoic acid (0.72 g).

| 4-(4-(4-(6-(tert-butoxycarbonylamino)hexyloxy)benzylamino)-6-(2,2,2-trifluoroethoxy)-1,3,5-triazin-2-ylamino)benzoic acid | |
|---|---|
| MS (M + H)+ Calcd. | 635.3 |
| MS (M + H)+ Observ. | 635.1 |
| Retention Time | 3.73 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |

Step 4: To a solution of 4-(4-(4-(6-(tert-butoxycarbonylamino)hexyloxy)benzylamino)-6-(2,2,2-trifluoroethoxy)-1,3,5-triazin-2-ylamino)benzoic acid (200 mg), trans-4-amino-1-Boc-pyrrolidine-3-carboxylic acid (72.6 mg) and O-benzotriazol-1-yl-N,N,N',N'-tetra-methyluronium tetrafluoroborate (121 mg) was added iPr$_2$NEt (0.22 mL). The mixture was stirred at room temperature for 4 hours. The mixture was purified by preparative HPLC to give trans-1-(tert-butoxycarbonyl)-4-(4-(4-(6-(tert-butoxycarbonylamino)hexyloxy)benzylamino)-6-(2,2,2-trifluoroethoxy)-1,3,5-triazin-2-ylamino)benzamido)pyrrolidine-3-carboxylic acid (32 mg).

| trans-1-(tert-butoxycarbonyl)-4-(4-(4-(6-(tert-butoxycarbonylamino)hexyloxy)benzylamino)-6-(2,2,2-trifluoroethoxy)-1,3,5-triazin-2-ylamino)benzamido)pyrrolidine-3-carboxylic acid | |
|---|---|
| MS (M + H)+ Calcd. | 847.4 |
| MS (M + H)+ Observ. | 847.4 |
| Retention Time | 1.70 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 5: To a suspension of trans-1-(tert-butoxycarbonyl)-4-(4-(4-(6-(tert-butoxycarbonylamino)hexyloxy)benzylamino)-6-(2,2,2-trifluoroethoxy)-1,3,5-triazin-2-ylamino)benzamido)pyrrolidine-3-carboxylic acid (32 mg) was added TFA (0.2 mL). The mixture was heated at 60° C. for 3 hours. All solvents were removed under vacuum. The residue was used for next step reaction without further purification.

| trans-4-(4-(4-(6-aminohexyloxy)benzylamino)-6-(2,2,2-trifluoroethoxy)-1,3,5-triazin-2-ylamino)benzamido)pyrrolidine-3-carboxylic acid | |
|---|---|
| MS (M + H)+ Calcd. | 647.3 |
| MS (M + H)+ Observ. | 647.4 |

| trans-4-(4-(4-(4-(6-aminohexyloxy)benzylamino)-6-(2,2,2-trifluoroethoxy)-1,3,5-triazin-2-ylamino)benzamido)pyrrolidine-3-carboxylic acid | |
|---|---|
| Retention Time | 1.21 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 6: To a solution of trans-4-(4-(4-(4-(6-aminohexyloxy)benzylamino)-6-(2,2,2-trifluoroethoxy)-1,3,5-triazin-2-ylamino)benzamido)pyrrolidine-3-carboxylic acid (23 mg) and O-benzotriazol-1-yl-N,N,N',N'-tetra-methyluronium tetrafluoroborate (13.7 mg) was added iPr$_2$NEt (0.012 mL). The mixture was stirred at room temperature for 2 hours. DMF was removed under vacuum. The residue was purified by preparative HPLC to give Compound 0007 (6.3 mg).

| Compound 0007 | |
|---|---|
| MS (M + H)$^+$ Calcd. | 629.3 |
| MS (M + H)$^+$ Observ. | 629.4 |
| Retention Time | 1.43 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Syntheses of Compounds 0008:

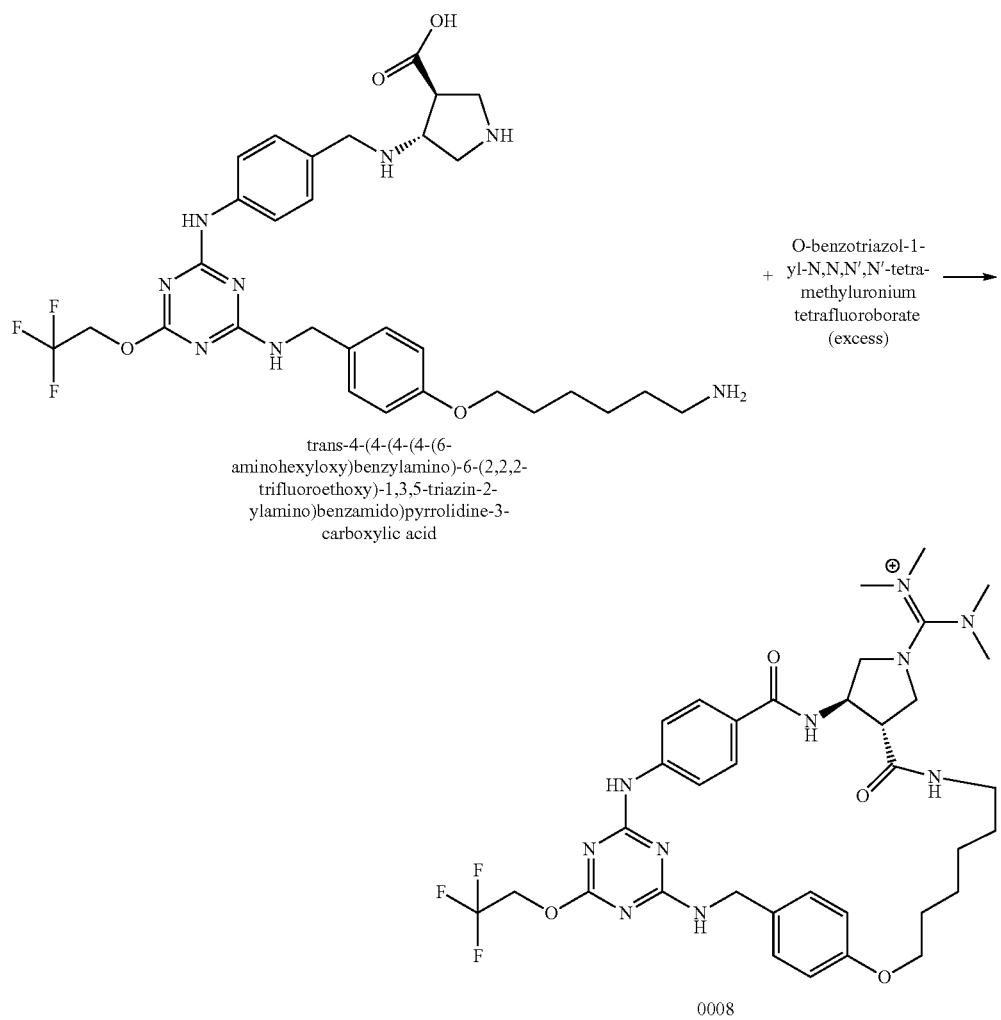

To a solution of 4-(4-(4-(4-(6-aminohexyloxy)benzylamino)-6-(2,2,2-trifluoroethoxy)-1,3,5-triazin-2-ylamino)benzamido)pyrrolidine-3-carboxylic acid (83 mg) in DMF (5 mL) was added O-benzotriazol-1-yl-N,N,N',N'-tetra-methyluronium tetrafluoroborate (103 mg) and iPr$_2$NEt (0.067 mL). After stirring at room temperature for 4 hours, the mixture was purified by preparative HPLC to give Compound 0008 (15 mg).

|  | Compound 0008 |
| --- | --- |
| MS M$^+$ Calcd. | 727.4 |
| MS M$^+$ Observ. | 727.5 |
| Retention Time | 1.62 min |
|  | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Syntheses of Compounds 0009 and 0010:

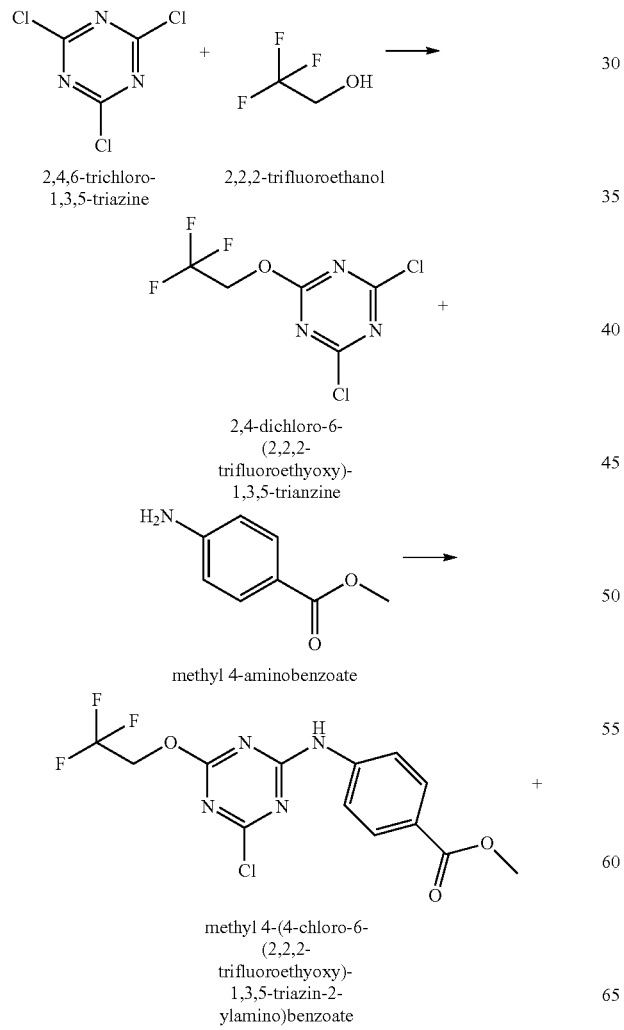

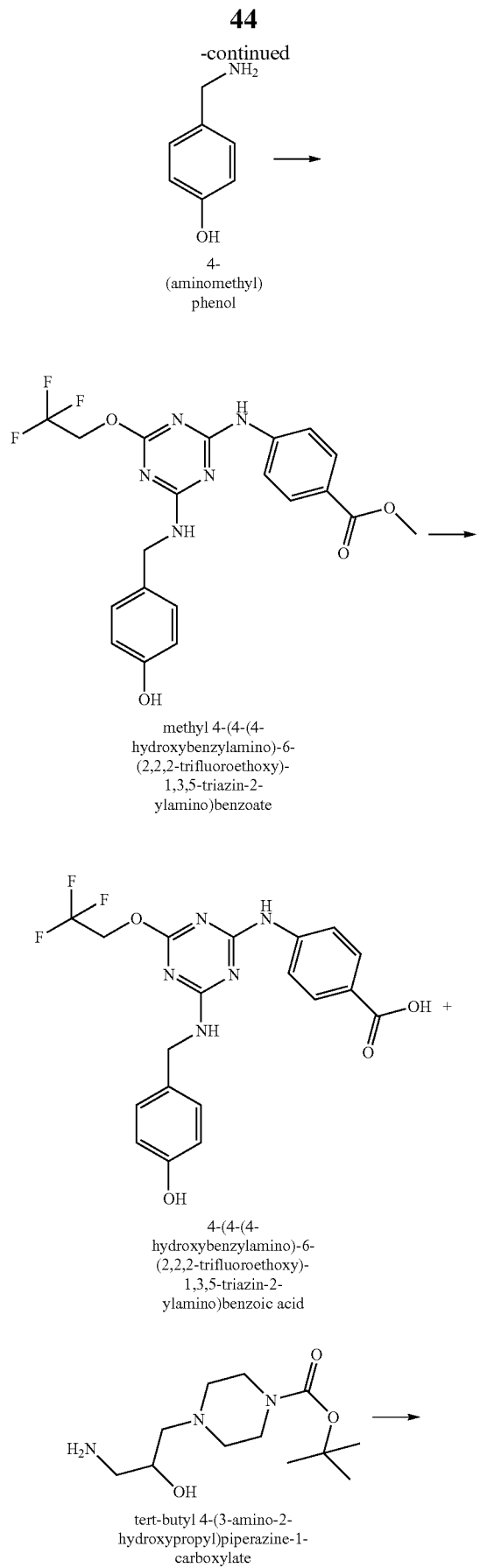

-continued

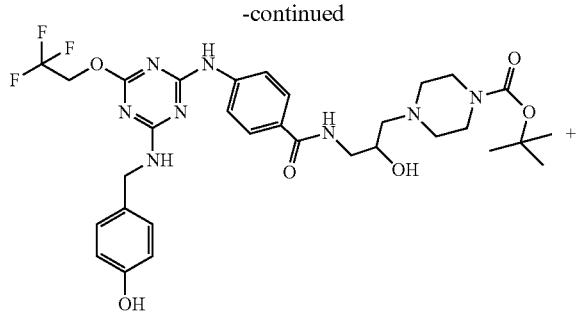

tert-butyl 4-(2-hydroxy-3-(4-(4-(4-hydroxybenzylamino)-6-(2,2,2-trifluoroethy)-1,3,5-triazin-2-ylamino)benzamido)propyl)piperzaine-1-carboxylate

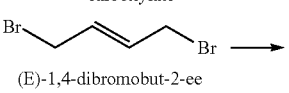

(E)-1,4-dibromobut-2-ee

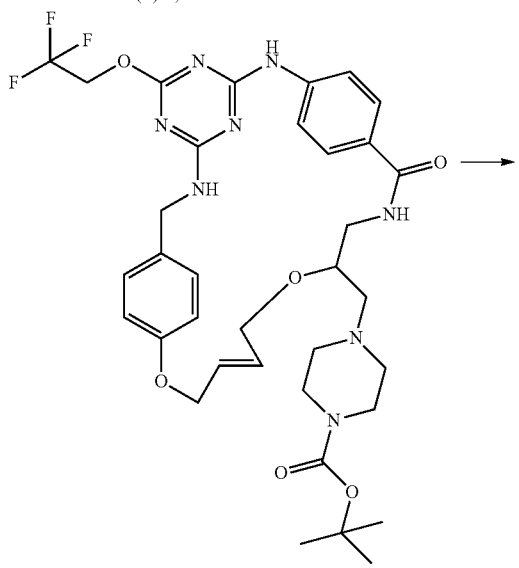

0009

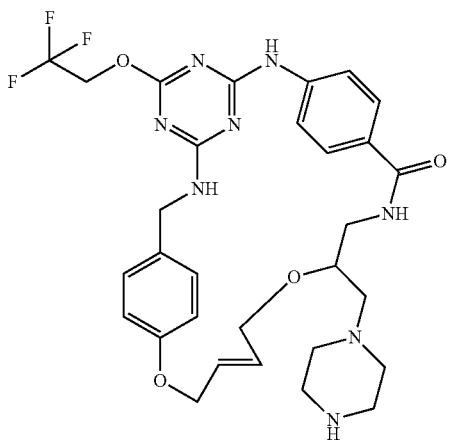

0010

Step 1: 2,2,2-Trifluoroethanol (4.9 g) and iPr₂NEt (6.3 g) were added into a solution of 2,4,6-trichloro-1,3,5-triazine (9.0 g) in THF (500 mL). The mixture was stirred at room temperature for 16 hours before being carried to the Step 2 directly.

Step 2: Methyl 4-aminobenzoate (7.26 g) and iPr₂NEt (6.20 g) were added into the reaction mixture from Step 1. The reaction was stirred at room temperature for 16 hours before solvents were removed under vacuum. The residue was partitioned with 25 mL of water and 100 mL of EtOAc, and the suspension mixture was stirred at room temperature for 16 hours. Filtration offered 12.0 g of methyl 4-(4-chloro-6-(2,2,2-trifluoroethoxy)-1,3,5-triazin-2-ylamino)benzoate as white solid.

| methyl 4-(4-chloro-6-(2,2,2-trifluoroethoxy)-1,3,5-triazin-2-ylamino)benzoate | |
|---|---|
| MS (M + H)⁺ Calcd. | 363.0 |
| MS (M + H)⁺ Observ. | 363.1 |
| Retention Time | 3.05 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Step 3: 4-(aminomethyl)phenol (2.4 g) white solid and iPr₂NEt (5.0 g) were added into a solution of methyl 4-(4-chloro-6-(2,2,2-trifluoroethoxy)-1,3,5-triazin-2-ylamino)benzoate (7.0 g) in THF (150 mL). The mixture was heated at 70° C. for 16 hours. After cooling, the mixture was charged with 250 mL of EtOAc. The resulting solution was washed with water (2×50 mL) and brine (30 mL). The organic layer was dried over MgSO₄ and concentrated under vacuum to give a residue which was recrystallized in EtOAc to give 6.54 g of methyl 4-(4-(4-hydroxybenzylamino)-6-(2,2,2-trifluoroethoxy)-1,3,5-triazin-2-ylamino)benzoate.

| methyl 4-(4-(4-hydroxybenzylamino)-6-(2,2,2-trifluoroethoxy)-1,3,5-triazin-2-ylamino)benzoate | |
|---|---|
| MS (M + H)⁺ Calcd. | 450.1 |
| MS (M + H)⁺ Observ. | 450.3 |
| Retention Time | 2.86 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Step 4: A solution of methyl 4-(4-(4-hydroxybenzylamino)-6-(2,2,2-trifluoroethoxy)-1,3,5-triazin-2-ylamino)benzoate (0.5 g) and potassium carbonate (0.461 g) in dioxane (9 mL) and water (9 mL) in sealed tube was heated at 105° C. for 16 hours. After cooling, the mixture was charged with 1N HCl solution to pH=1. Solvents were removed under vacuum to give a residue which was washed with water (2 mL). White solid, 4-(4-(4-hydroxybenzylamino)-6-(2,2,2- trifluoroethoxy)-1,3,5-triazin-2-ylamino)benzoic acid, was collected and dried at 78° C. under vacuum for 16 hours to weigh 0.35 g.

| 4-(4-(4-hydroxybenzylamino)-6-(2,2,2-trifluoroethoxy)-1,3,5-triazin-2-ylamino)benzoic acid | |
|---|---|
| MS (M + H)+ Calcd. | 436.1 |
| MS (M + H)+ Observ. | 436.0 |
| Retention Time | 1.69 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |

Step 5: N,N-diisopropylethylamine (0.30 g) and O-benzotriazol-1-yl-N,N,N',N'-tetra-methyluronium tetrafluoroborate (0.44 g) were added into a solution of 4-(4-(4-hydroxybenzylamino)-6-(2,2,2-trifluoroethoxy)-1,3,5-triazin-2-ylamino)benzoic acid (0.5 g) and tert-butyl 4-(3-amino-2-hydroxypropyl)piperazine-1-carboxylate (0.33 g) in DMF (2 mL). The mixture was stirred at room temperature for 16 hours. Then, 50 mL of EtOAc was added into the reaction mixture which was sequentially washed with water (2×20 mL) and brine (15 mL). The organic layer was dried over MgSO$_4$ and concentrated under vacuum to give a residue which was purified by silica gel chromatography to provide tert-butyl 4-(2-hydroxy-3-(4-(4-(4-hydroxybenzylamino)-6-(2,2,2-trifluoroethoxy)-1,3,5-triazin-2-ylamino)benzamido)propyl)piperazine-1-carboxylate (0.20 g).

| tert-butyl 4-(2-hydroxy-3-(4-(4-(4-hydroxybenzylamino)-6-(2,2,2-trifluoroethoxy)-1,3,5-triazin-2-ylamino)benzamido)propyl)piperazine-1-carboxylate | |
|---|---|
| MS (M + H)+ Calcd. | 677.3 |
| MS (M + H)+ Observ. | 677.2 |
| Retention Time | 1.53 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 2 min |
| Flow Rate | 5 mL/min |
| Wavelength | 220 |
| Solvent Pair | Water-Methanol-TFA |
| Column | PHENOMENEX-LUNA 4.6 × 50 mm S10 |

Step 6: (E)-1,4-dibromobut-2-ene (25 mg) and potassium carbonate (49 mg) were added into a solution of tert-butyl 4-(2-hydroxy-3-(4-(4-(4-hydroxybenzylamino)-6-(2,2,2-trifluoroethoxy)-1,3,5-triazin-2-ylamino)benzamido)propyl) piperazine-1-carboxylate (80 mg) in DMF (3 mL). The mixture was stirred at room temperature for 16 hours. The Compound 0009 (10 mg) was isolated by preparative HPLC as white solid.

| Compound 0009 | |
|---|---|
| MS (M + H)+ Calcd. | 729.3 |
| MS (M + H)+ Observ. | 729.7 |
| Retention Time | 3.76 min |
| LC Condition | |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Step 7: TFA (6.34 µL) was added into a solution of Compound 0009 (4 mg) in dichloromethane (1 mL). The mixture was stirred at room temperature for 16 hours. Removal of solvents under vacuum offered a residue which was purified by preparative HPLC to give Compound 0010 (3 mg).

| Compound 0010 | |
|---|---|
| MS (M + H)+ Calcd. | 629.3 |
| MS (M + H)+ Observ. | 629.3 |
| Retention Time | 3.66 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 0.8 mL/min |
| Wavelength | 220 |
| Solvent Pair | Water-Methanol-TFA |
| Column | PHENOMENEX-LUNA 2.0 × 50 mm 3 um |

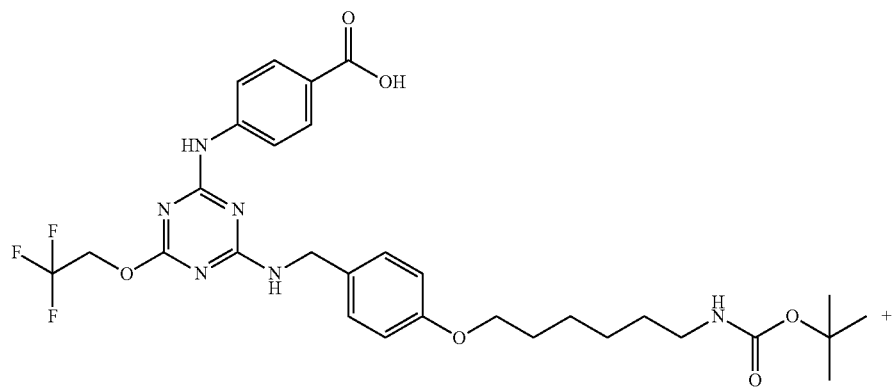
4-(4-(4-(6-(tert-butoxycarbonylamino)hexyloxy)benzylamino)-6-(2,2,2-trifluoroethoxy)-1,3,5-triazin-2-ylamino)benzoic acid
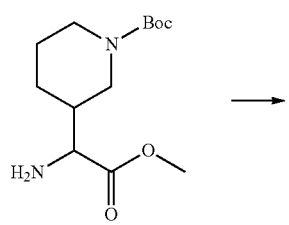
tert-butyl 3-(1-amino-2-methoxy-2-oxoethyl)piperidine-1-carboxylate
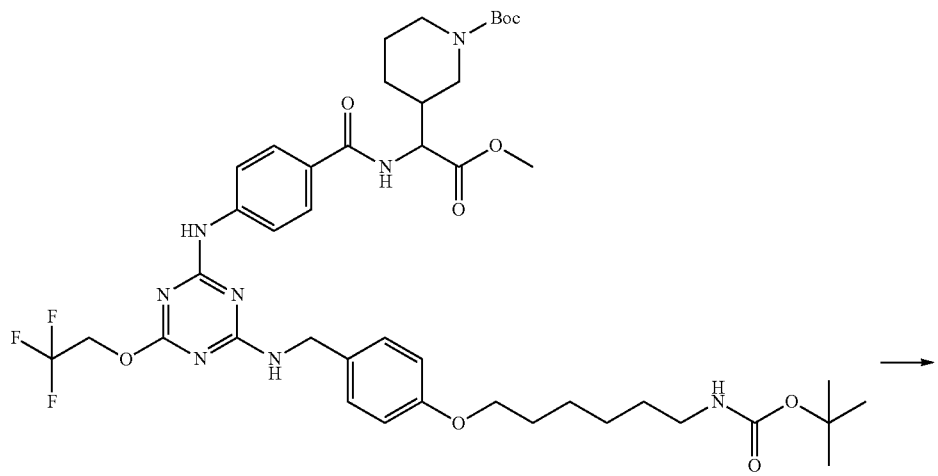
tert-butyl 3-(1-(4-(4-(6-(tert-butoxycarbonylamino)hexyloxy)benzylamino)-6-(2,2,2-trifluoroethoxy)-1,3,5-triazin-2-ylamino)benzamido)-2-methoxy-2-oxoethyl)piperidine-1-carboxylate -continued
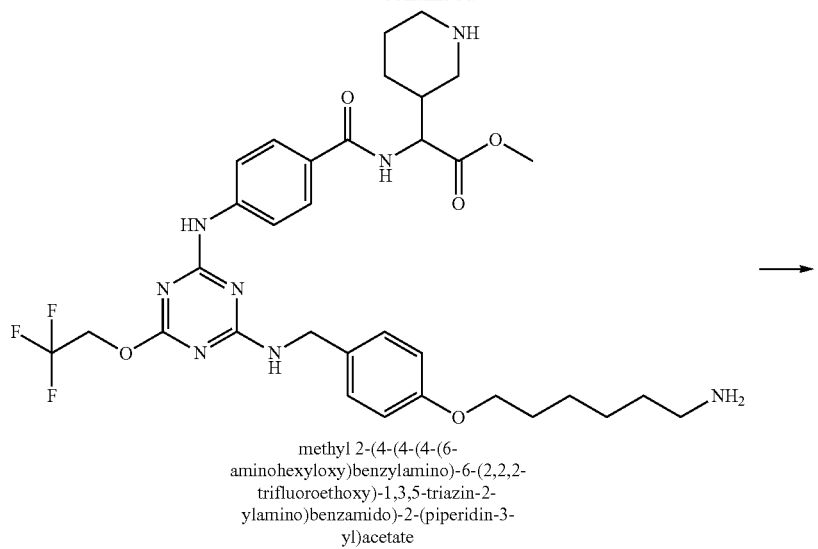
methyl 2-(4-(4-(4-(6-aminohexyloxy)benzylamino)-6-(2,2,2-trifluoroethoxy)-1,3,5-triazin-2-ylamino)benzamido)-2-(piperidin-3-yl)acetate
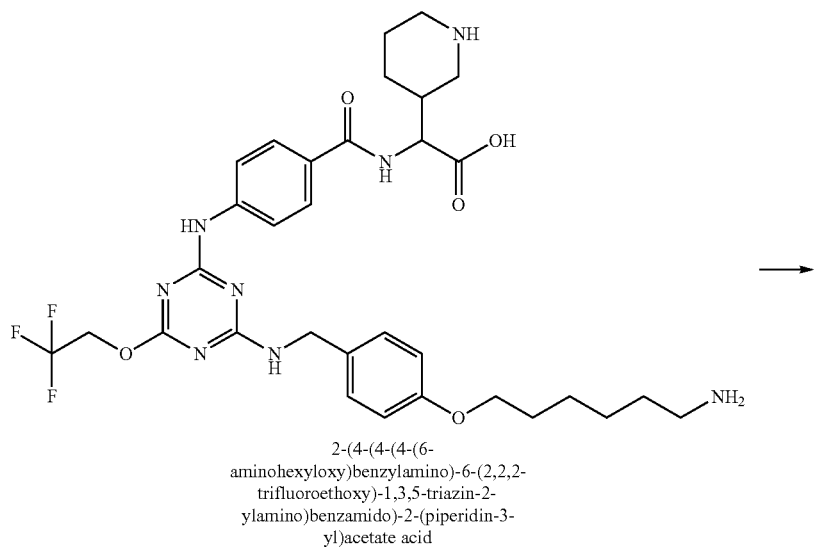
2-(4-(4-(4-(6-aminohexyloxy)benzylamino)-6-(2,2,2-trifluoroethoxy)-1,3,5-triazin-2-ylamino)benzamido)-2-(piperidin-3-yl)acetate acid
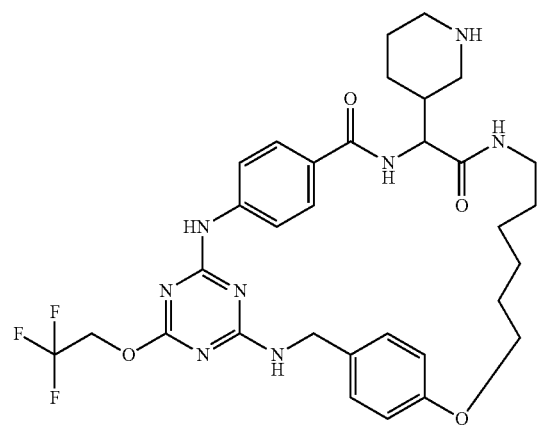
0011

Step 1: To a solution of 4-(4-(4-(6-(tert-butoxycarbonylamino)hexyloxy)benzylamino)-6-(2,2,2-trifluoroethoxy)-1,3,5-triazin-2-ylamino)benzoic acid (100 mg), tert-butyl 3-(1-amino-2-methoxy-2-oxoethyl)piperidine-1-carboxylate (51.5 mg) and O-benzotriazol-1-yl-N,N,N',N'-tetra-methyluronium tetrafluoroborate (60.7 mg) was added iPr$_2$NEt (0.055 mL). The mixture was stirred at room temperature for 4 hours. The mixture was purified by preparative HPLC to give tert-butyl 3-(1-(4-(4-(4-(6-(tert-butoxycarbonylamino)hexyloxy)benzylamino)-6-(2,2,2-trifluoroethoxy)-1,3,5-triazin-2-ylamino)benzamido)-2-methoxy-2-oxoethyl)piperidine-1-carboxylate (80 mg).

| tert-butyl 3-(1-(4-(4-(4-(6-(tert-butoxycarbonylamino)hexyloxy)-benzylamino)-6-(2,2,2-trifluoroethoxy)-1,3,5-triazin-2-ylamino)-benzamido)-2-methoxy-2-oxoethyl)piperidine-1-carboxylate | |
|---|---|
| MS (M + H)$^+$ Calcd. | 889.4 |
| MS (M + H)$^+$ Observ. | 889.5 |
| Retention Time | 2.16 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: To a solution of tert-butyl 3-(1-(4-(4-(4-(6-(tert-butoxycarbonylamino)hexyloxy)benzylamino)-6-(2,2,2-trifluoroethoxy)-1,3,5-triazin-2-ylamino)benzamido)-2-methoxy-2-oxoethyl)piperidine-1-carboxylate (80 mg) in CH$_2$Cl$_2$ (2 mL) was added TFA (0.4 mL). The mixture was stirred at room temperature for 3 hours. All the solvents were removed under vacuum. The residue was used for next step reaction without further purification.

| methyl 2-(4-(4-(4-(6-aminohexyloxy)benzylamino)-6-(2,2,2-trifluoroethoxy)-1,3,5-triazin-2-ylamino)benzamido)-2-(piperidin-3-yl)acetate | |
|---|---|
| MS (M + H)$^+$ Calcd. | 689.3 |
| MS (M + H)$^+$ Observ. | 689.5 |
| Retention Time | 2.45 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 4 min |
| Flow Rate | 0.8 mL/min |
| Wavelength | 220 |
| Solvent Pair | ACN:Water:Ammonium Actetate |
| Column | Phenomenex LUNA C18, 50 × 2, 3 u |

Step 3: A mixture of methyl 2-(4-(4-(4-(6-aminohexyloxy)benzylamino)-6-(2,2,2-trifluoroethoxy)-1,3,5-triazin-2-ylamino)benzamido)-2-(piperidin-3-yl)acetate (50 mg) and K$_2$CO$_3$ (50.2 mg) in acetone (2 mL)/water (2 mL) was heated at 85° C. for 4 hours. After cooling to room temperature, the mixture was acidified with 1N HCl to pH=3. All the solvents were removed under vacuum. The residue was purified by preparative HPLC to give 2-(4-(4-(4-(6-aminohexyloxy)benzylamino)-6-(2,2,2-trifluoroethoxy)-1,3,5-triazin-2-ylamino)benzamido)-2-(piperidin-3-yl)acetic acid (40 mg).

| 2-(4-(4-(4-(6-aminohexyloxy)benzylamino)-6-(2,2,2-trifluoroethoxy)-1,3,5-triazin-2-ylamino)benzamido)-2-(piperidin-3-yl)acetic acid | |
|---|---|
| MS (M + H)$^+$ Calcd. | 675.3 |
| MS (M + H)$^+$ Observ. | 675.5 |
| Retention Time | 1.33 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To a solution of 2-(4-(4-(4-(6-aminohexyloxy)benzylamino)-6-(2,2,2-trifluoroethoxy)-1,3,5-triazin-2-ylamino)benzamido)-2-(piperidin-3-yl)acetic acid (35 mg) in DMF (5 mL) was added TBTU (20.0 mg) and iPr$_2$NEt (0.027 mL). After stirring at room temperature for 4 hours, the mixture was directly purified by preparative HPLC to give Compound 0011 (7.8 mg).

| Compound 0011 | |
|---|---|
| MS (M + H)$^+$ Calcd. | 657.3 |
| MS (M + H)$^+$ Observ. | 657.4 |
| Retention Time | 1.53 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Synthesis Compounds 0021-0024:

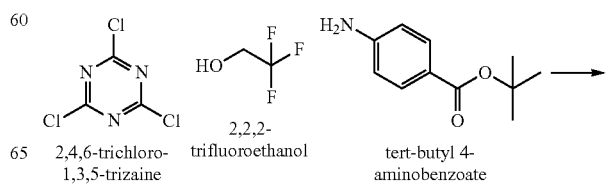

2,4,6-trichloro-1,3,5-trizaine    2,2,2-trifluoroethanol    tert-butyl 4-aminobenzoate

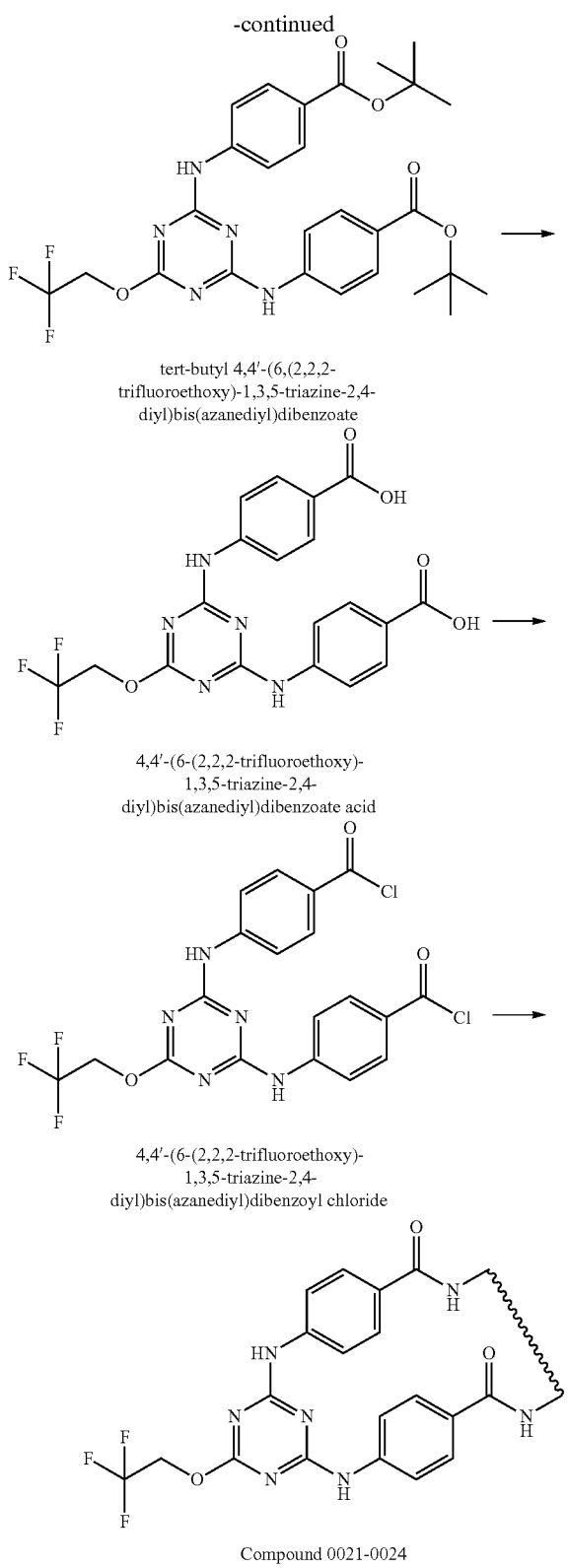

tert-butyl 4,4'-(6,(2,2,2-trifluoroethoxy)-1,3,5-triazine-2,4-diyl)bis(azanediyl)dibenzoate 4,4'-(6-(2,2,2-trifluoroethoxy)-1,3,5-triazine-2,4-diyl)bis(azanediyl)dibenzoate acid 4,4'-(6-(2,2,2-trifluoroethoxy)-1,3,5-triazine-2,4-diyl)bis(azanediyl)dibenzoyl chloride Compound 0021-0024

Step 1: To a solution of 2,4,6-trichloro-1,3,5-triazine (1.2 g) in acetone (30 mL) was added a solution of 2,2,2-trifluoroethanol (0.716 g) and 2,4,6-collidine (0.946 mL) in acetone (30.0 mL) dropwise over 15 minutes. The resulting mixture was stirred at room temperature for 16 hours. All solvents were removed under vacuum to give a residue which was diluted with NMP (10 mL) and tert-butyl 4-aminobenzoate (2.77 g), iPr$_2$NEt (3.41 mL) were added. The resulting mixture was stirred for 16 hours at room temperature and 16 hours at 65° C. The mixture was diluted with 100 mL of water and extracted with EtOAc (2×150 mL). The organic layers were combined, washed with brine (100 mL), dried over MgSO$_4$ and concentrated under vacuum to give the crude tert-butyl 4,4'-(6-(2,2,2-trifluoroethoxy)-1,3,5-triazine-2,4-diyl)bis(azanediyl)dibenzoate which was used in Step 2 without purification.

| tert-butyl 4,4'-(6-(2,2,2-trifluoroethoxy)-1,3,5-triazine-2,4-diyl)bis(azanediyl)dibenzoate | |
|---|---|
| MS (M + H)$^+$ Calcd. | 562.2 |
| MS (M + H)$^+$ Observ. | 562.1 |
| Retention Time | 4.17 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |

Step 2: To a solution of crude tert-butyl 4,4'-(6-(2,2,2-trifluoroethoxy)-1,3,5-triazine-2,4-diyl)bis(azanediyl) dibenzoate (562 mg) in CH$_2$Cl$_2$ (10 mL) was added TFA (3 mL). The mixture was stirred at room temperature for 16 hours. All solvents were removed under vacuum. The residue was purified by preparative HPLC to give 4,4'-(6-(2,2,2-trifluoroethoxy)-1,3,5-triazine-2,4-diyl)bis(azanediyl)dibenzoic acid (110 mg).

| 4,4'-(6-(2,2,2-trifluoroethoxy)-1,3,5-triazine-2,4-diyl)bis(azanediyl)dibenzoic acid | |
|---|---|
| MS (M + H)$^+$ Calcd. | 450.1 |
| MS (M + H)$^+$ Observ. | 449.9 |
| Retention Time | 3.19 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |

Step 3: To a suspension of 4,4'-(6-(2,2,2-trifluoroethoxy)-1,3,5-triazine-2,4-diyl)bis(azanediyl)dibenzoic acid (100 mg) in CH$_2$Cl$_2$ (4 mL) was added thionyl chloride (2 mL). The mixture was heated at 80° C. for 1 hour. All solvents were removed under vacuum. The residue, crude 4,4'-(6-(2,2,2-trifluoroethoxy)-1,3,5-triazine-2,4-diyl)bis(azanediyl) dibenzoyl chloride, was used in Step 4 without further purification.

Step 4: To a solution of 4,4'-(6-(2,2,2-trifluoroethoxy)-1,3,5-triazine-2,4-diyl)bis(azanediyl)dibenzoyl chloride (1. eq.) in CH$_2$Cl$_2$ was added a mixture of diamine (1 eq.) and iPr$_2$NEt (10 eq.) in CH$_2$Cl$_2$ dropwise. The mixture was stirred at room temperature for 1 hour. All solvents were removed and the residue was purified by preparative HPLC to give compounds 0021-0024.

LC-MS Condition

| LC Condition | |
|---|---|
| Solvent A | 90% Water-10% Methanol-0.1% TFA |
| Solvent B | 10% Water-90% Methanol-0.1% TFA |
| Start % B | 0 |
| Final % B | 100 |
| Gradient Time | 4 min |
| Flow Rate | 5 mL/min |
| Wavelength | 220 |
| Solvent Pair | Water-Methanol-TFA |
| Column | PHENOMENEX-LUNA 3.0 × 50 mm S10 |

| Compd. Number | Structure | MS (M + H)$^+$ Calcd. | MS (M + H)$^+$ Observ. | Rt (min) |
|---|---|---|---|---|
| 0021 | 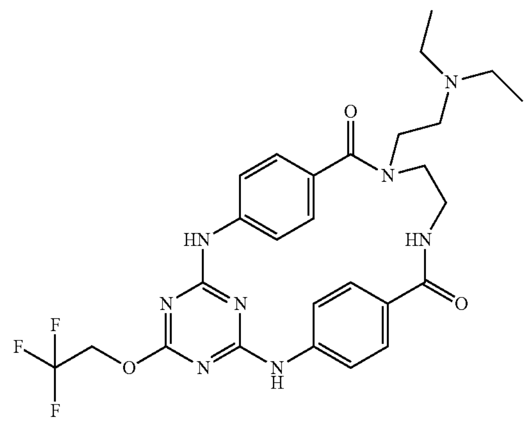 [SMILES: CCN(CC)CCN1CCNC(=O)c2ccc(cc2)Nc2nc(nc(OCC(F)(F)F)n2)Nc2ccc(cc2)C1=O] | 573.2 | 573.2 | 2.21 |
| 0022 | 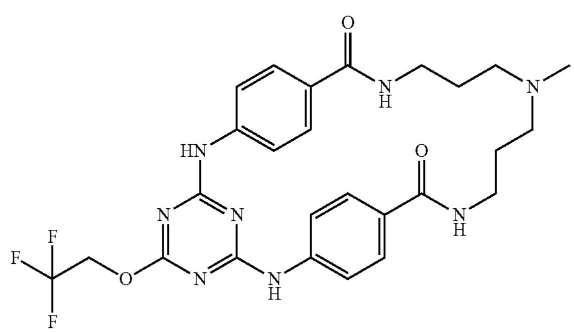 [SMILES: CN1CCCNC(=O)c2ccc(cc2)Nc2nc(nc(OCC(F)(F)F)n2)Nc2ccc(cc2)C(=O)NCCC1] | 559.2 | 559.2 | 2.29 |
| 0023 | 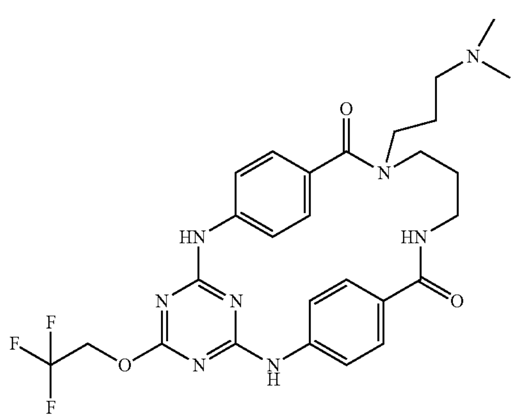 [SMILES: CN(C)CCCN1CCCNC(=O)c2ccc(cc2)Nc2nc(nc(OCC(F)(F)F)n2)Nc2ccc(cc2)C1=O] | 573.2 | 573.2 | 1.91 |

| Compd. Number | Structure | MS (M + H)+ Calcd. | MS (M + H)+ Observ. | Rt (min) |
|---|---|---|---|---|
| 0024 | 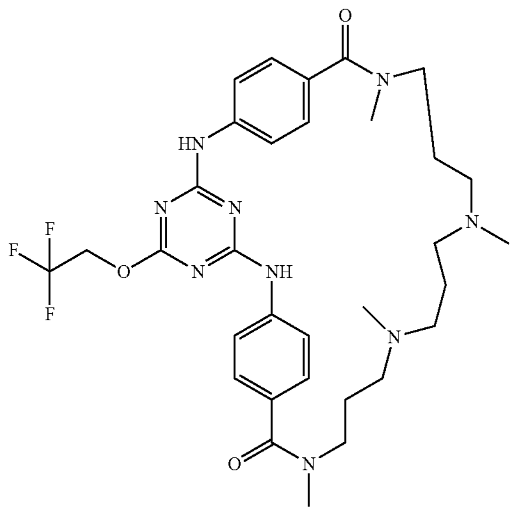 [SMILES: CN1CCCN(C)CCCN(C)C(=O)c2ccc(cc2)Nc2nc(nc(OCC(F)(F)F)n2)Nc2ccc(cc2)C(=O)N(C)CCC1] | 658.3 | 658.3 | 2.00 |

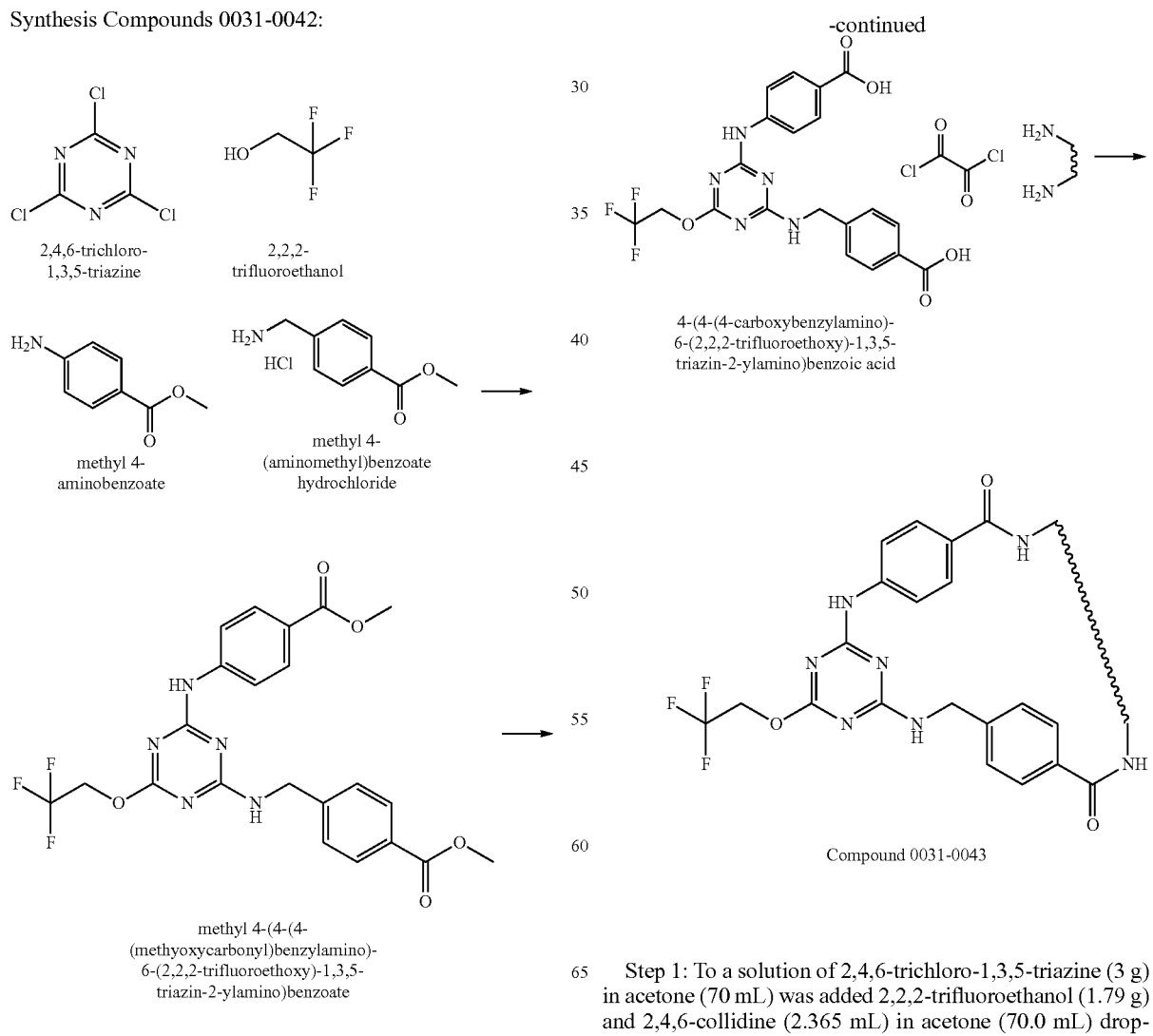

Synthesis Compounds 0031-0042:

2,4,6-trichloro-1,3,5-triazine 2,2,2-trifluoroethanol methyl 4-aminobenzoate methyl 4-(aminomethyl)benzoate hydrochloride methyl 4-(4-(4-(methyoxycarbonyl)benzylamino)-6-(2,2,2-trifluoroethoxy)-1,3,5-triazin-2-ylamino)benzoate 4-(4-(4-carboxybenzylamino)-6-(2,2,2-trifluoroethoxy)-1,3,5-triazin-2-ylamino)benzoic acid Compound 0031-0043

Step 1: To a solution of 2,4,6-trichloro-1,3,5-triazine (3 g) in acetone (70 mL) was added 2,2,2-trifluoroethanol (1.79 g) and 2,4,6-collidine (2.365 mL) in acetone (70.0 mL) dropwise over 1 hour. The resulting mixture was stirred at room temperature for 16 hours. All solvents were removed under vacuum to give a residue which was diluted with NMP (25 mL) and combined with methyl 4-aminobenzoate (2.71 g) and iPr$_2$NEt (8.52 mL). After stirring at room temperature for 6 hours, methyl 4-(aminomethyl)benzoate hydrochloride (3.28 g) was added and the resulting mixture was stirred at room temperature for 16 hours. The mixture was diluted with water (300 mL) and extracted with EtOAc (2×400 mL). The organic layers were combined, washed with water (200 mL), brine (300 mL), dried over MgSO$_4$ and concentrated. The residue was purified by recrystallization with MeOH to give methyl 4-(4-(4-(methoxycarbonyl)benzylamino)-6-(2,2,2-trifluoroethoxy)-1,3,5-triazin-2-ylamino)benzoate (5 g).

| methyl 4-(4-(4-(methoxycarbonyl)benzylamino)-6-(2,2,2-trifluoroethoxy)-1,3,5-triazin-2-ylamino)benzoate | |
|---|---|
| MS (M + H)$^+$ Calcd. | 492.1 |
| MS (M + H)$^+$ Observ. | 492.2 |
| Retention Time | 1.76 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 2: A mixture of methyl 4-(4-(4-(methoxycarbonyl)benzylamino)-6-(2,2,2-trifluoroethoxy)-1,3,5-triazin-2-ylamino)benzoate (2.9 g) and K$_2$CO$_3$ (3.26 g) in acetone (20 mL)/water (20.00 mL) was heated at 115° C. for 24 hours. After cooling to room temperature, the mixture was acidified with 1 N HCl to pH=3. The white precipitate was collected, washed with water and dried under vacuum to give 4-(4-(4-carboxybenzylamino)-6-(2,2,2-trifluoroethoxy)-1,3,5-triazin-2-ylamino)benzoic acid (2.6 g).

| 4-(4-(4-carboxybenzylamino)-6-(2,2,2-trifluoroethoxy)-1,3,5-triazin-2-ylamino)benzoic acid | |
|---|---|
| MS (M + H)$^+$ Calcd. | 464.1 |
| MS (M + H)$^+$ Observ. | 464.2 |
| Retention Time | 1.09 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 3: To a solution of 4-(4-(4-carboxybenzylamino)-6-(2,2,2-trifluoroethoxy)-1,3,5-triazin-2-ylamino)benzoic acid (1 eq.) in CH$_2$Cl$_2$ (30 mL) was added oxalyl dichloride (2 eq.) and a drop of DMF. After stirring for 1 hour, a solution of diamine (1 eq.) and iPr$_2$NEt (3 eq.) in CH$_2$Cl$_2$ (5 mL) was added dropwise. The resulting solution was stirred at room temperature for 16 hours. All solvents were removed under vacuum and the residue was purified by preparative HPLC to give compounds 0031-0043.

| Compound 0031 | |
|---|---|
| MS (M + H)$^+$ Calcd. | 600.3 |
| MS (M + H)$^+$ Observ. | 600.3 |
| Retention Time | 1.73 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

LC-MS Condition for Compounds 0032-0035:

Start % B=30, Final % B=95 over 13.00° minute gradient

Wavelength=220 nm

Flow Rate=1 mL/min

Solvent A=water

Solvent B=ACN; Modifier=10 mm Ammonium Acetate

Column: Cosmosil PYE 4.6×150 mm

| Compd. Number | Structure | LC Rt (min) | Calcd. Ms Ion | Obs. Ms Ion |
|---|---|---|---|---|
| 0032 | 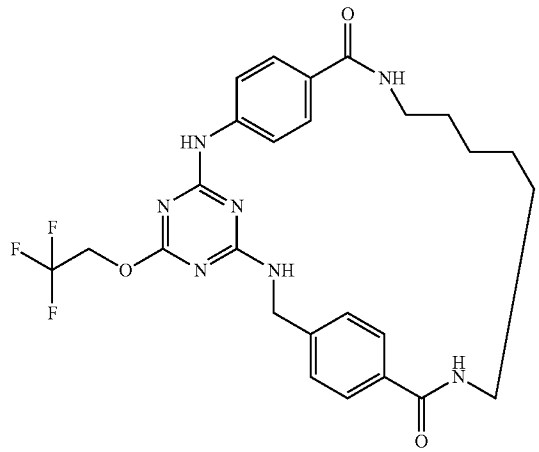 [SMILES: O=C1NCCCCCCNC(=O)c2ccc(cc2)Nc2nc(nc(OCC(F)(F)F)n2)NCc2ccc1cc2] | 8.47 | 544.2 | 544.3 |
| 0033 | 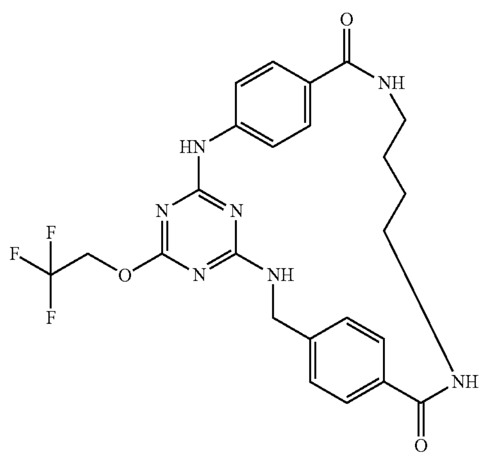 [SMILES: O=C1NCCCCNC(=O)c2ccc(cc2)Nc2nc(nc(OCC(F)(F)F)n2)NCc2ccc1cc2] | 5.08 | 516.2 | 516.2 |
| 0034 | 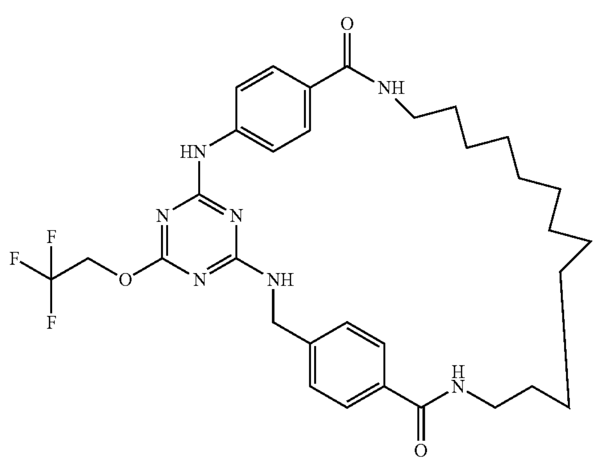 [SMILES: O=C1NCCCCCCCCCCCCNC(=O)c2ccc(cc2)Nc2nc(nc(OCC(F)(F)F)n2)NCc2ccc1cc2] | 9.54 | 628.3 | 628.5 |

-continued

| Compd. Number | Structure | LC Rt (min) | Calcd. Ms Ion | Obs. Ms Ion |
|---|---|---|---|---|
| 0035 | 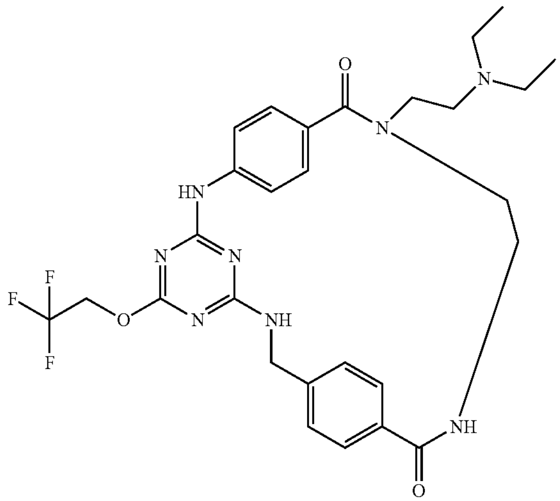 [SMILES: CCN(CC)CCN1CCNC(=O)c2ccc(cc2)CNc2nc(nc(OCC(F)(F)F)n2)Nc2ccc(cc2)C1=O] | 3.74 | 587.3 | 587.5 |

LC-MS Condition for Compounds 0036-0042:
  Start % B=10, Final % B=95 over 8.30° minute gradient
  Wavelength=220 nm
  Solvent A=water Solvent B=ACN; Modifier=10 mm Ammonium Acetate
Flow Rate=1 mL/min
Column: Waters Xbridge 4.6×100 mm 5 um C18

| Compd. Number | Structure | LC Rt (min) | Calcd. Ms Ion | Obs. Ms Ion |
|---|---|---|---|---|
| 0036 | 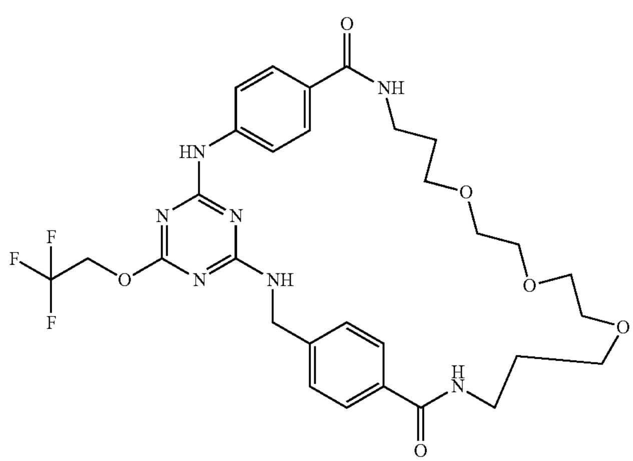 [SMILES: O=C1NCCCOCCOCCOCCCNC(=O)c2ccc(cc2)Nc2nc(nc(OCC(F)(F)F)n2)NCc2ccc1cc2] | 4.27 | 648.3 | 648.4 |

| Compd. Number | Structure | LC Rt (min) | Calcd. Ms Ion | Obs. Ms Ion |
| --- | --- | --- | --- | --- |
| 0037 | 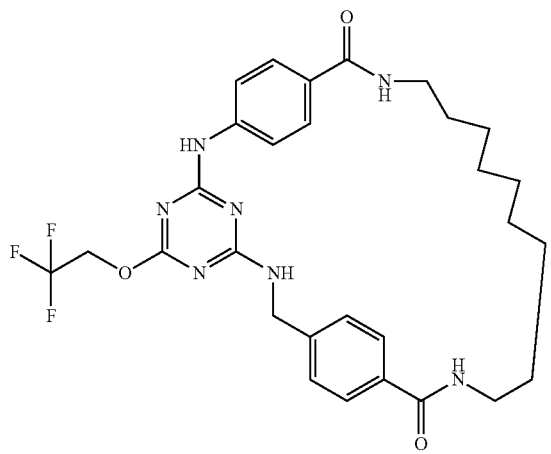 [SMILES: O=C1NCCCCCCCCCNC(=O)c2ccc(cc2)Nc2nc(nc(OCC(F)(F)F)n2)NCc2ccc1cc2] | 5.25 | 586.3 | 586.4 |
| 0038 | 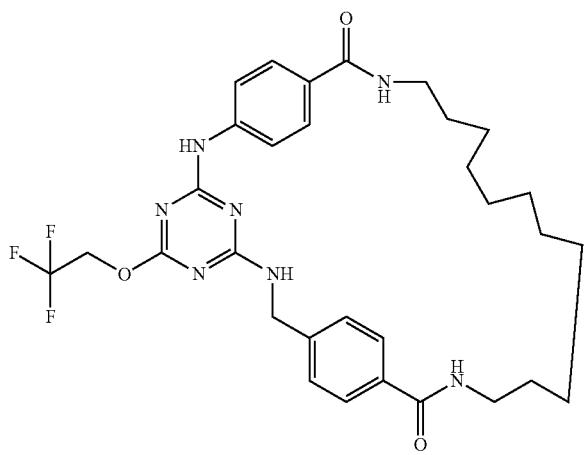 [SMILES: O=C1NCCCCCCCCCCCNC(=O)c2ccc(cc2)Nc2nc(nc(OCC(F)(F)F)n2)NCc2ccc1cc2] | 5.81 | 614.3 | 614.5 |
| 0039 | 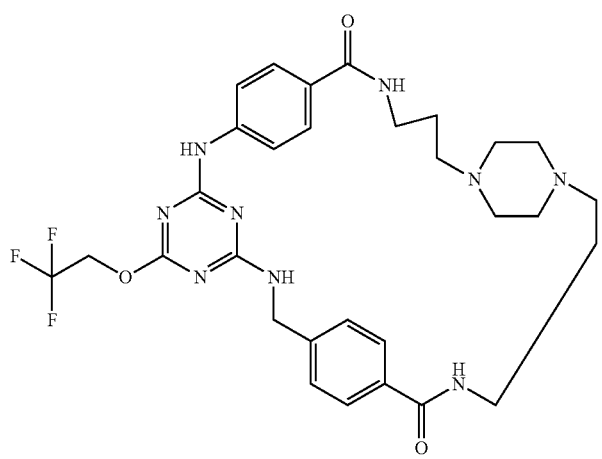 [SMILES: O=C1NCCCN2CCN(CCCNC(=O)c3ccc(cc3)Nc3nc(nc(OCC(F)(F)F)n3)NCc3ccc1cc3)CC2] | 3.65 | 628.3 | 628.5 |

| Compd. Number | Structure | LC Rt (min) | Calcd. Ms Ion | Obs. Ms Ion |
|---|---|---|---|---|
| 0041 | 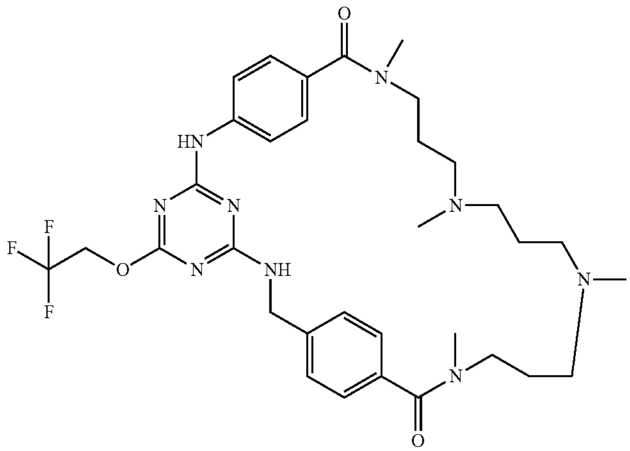 [SMILES: CN1CCCN(C)CCCN(C)C(=O)c2ccc(cc2)Nc2nc(nc(OCC(F)(F)F)n2)NCc2ccc(cc2)C(=O)N(C)CCC1] | 3.68 | 672.4 | 672.6 |
| 0042 | 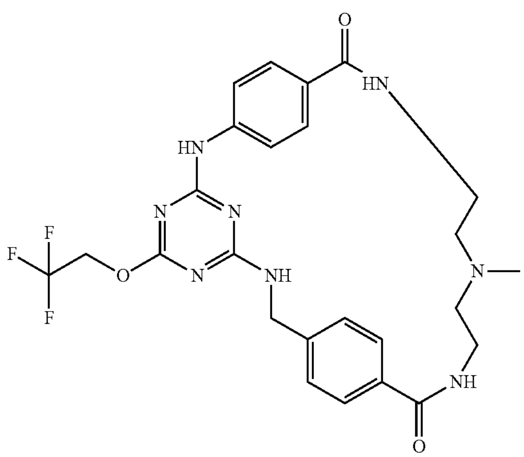 [SMILES: CN1CCNC(=O)c2ccc(cc2)CNc2nc(nc(OCC(F)(F)F)n2)Nc2ccc(cc2)C(=O)NCC1] | 4.20 | 545.2 | 545.3 |

Syntheses of Compounds 0051-0072:

Step 1 to Step 4: Preparation of Intermediates N2-(3-(aminomethyl)benzyl)-N4-(4-(aminomethyl)phenyl)-6-(2,2,2-trifluoroethoxy)-1,3,5-triazine-2,4-diamine and N2-(4-(aminomethyl)benzyl)-N4-(4-(aminomethyl)phenyl)-6-(2,2,2-trifluoroethoxy)-1,3,5-triazine-2,4-diamine:

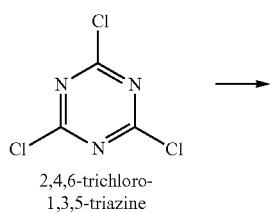

2,4,6-trichloro-1,3,5-triazine

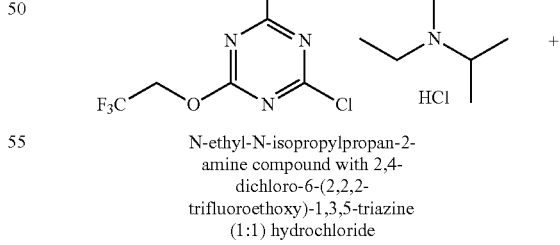

N-ethyl-N-isopropylpropan-2-amine compound with 2,4-dichloro-6-(2,2,2-trifluoroethoxy)-1,3,5-triazine (1:1) hydrochloride

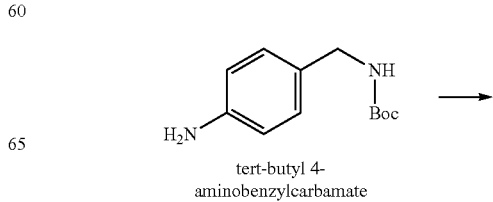

tert-butyl 4-aminobenzylcarbamate

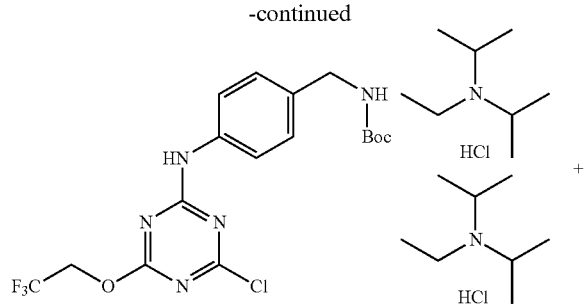

tert-butyl 4-(4-chloro-6-(2,2,2-trifluoroethoxy)-1,3,5-triazin-2-ylamino)benzylcarbamate compound with N-ethyl-N-isopropylpropan-2-amine (1:2) dihydrochloride

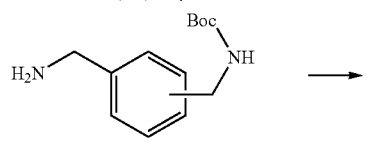

Meta derivative: tert-butyl 3-(aminomethyl)benzylcarbamate

Para derivative: tert-butyl 4-(aminomethyl)benzylcarbamate

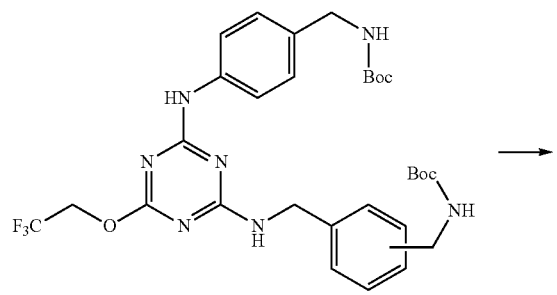

Meta derivate: Interm-0051-Meta

Para derivate: Interm-0051-Para

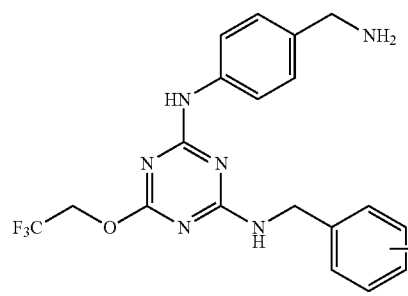

Meta derivative: N²-(3-(aminomethyl)benzyl)-N⁴-(4-(aminomethyl)phenyl)-6-(2,2,2-trifluoroethoxy)-1,3,5-triazine-2,4-diamine Para derivative: N²-(4-(aminomethyl)benzyl)-N⁴-(4-(aminomethyl)phenyl)-6-(2,2,2-trifluoroethoxy)-1,3,5-triazine-2,4-diamine Step 1: To a soln. of 2,4,6-trichloro-1,3,5-triazine (3.32 g) in THF (100 mL) was added a mixture of 2,2,2-trifluoroethanol (1.8 g) and iPr$_2$NEt (10 mL) at room temperature. The resulting mixture was stirred at room temperature for 24 hours.

Step 2: To above mixture was added tert-butyl 4-aminobenzylcarbamate (4 g) and iPr$_2$NEt. The mixture was then stirred for 24 hours to show formation of the desired product. After removal of solvents, the crude tert-butyl 4-(4-chloro-6-(2,2,2-trifluoroethoxy)-1,3,5-triazin-2-ylamino)benzylcarbamate compound with N-ethyl-N-isopropylpropan-2-amine (1:2) dihydrochloride was used in the further step without purification.

Step 3: iPr$_2$NEt was added into the solution of tert-butyl 4-(4-chloro-6-(2,2,2-trifluoroethoxy)-1,3,5-triazin-2-ylamino)benzylcarbamate compound with N-ethyl-N-isopropylpropan-2-amine (1:2) dihydrochloride (5 g) and 1.54 g of tert-butyl 3-(aminomethyl)benzylcarbamate or tert-butyl 4-(aminomethyl)benzylcarbamate in THF (100 mL). The reaction was stirred at room temperature for 16 hours before being quenched with water (100 mL). The aqueous layer was extracted with EtOAc (3×100 mL). The combined organic phase was dried over MgSO$_4$ and concentrated to give the desired product which was purified by silica gel chromatography.

| Meta derivative: Interm-0051-Meta | |
|---|---|
| MS (M + H)⁺ Calcd. | 634.3 |
| MS (M + H)⁺ Observ. | 634.4 |
| Retention Time | 2.08 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

| Meta derivative: Interm-0051-Para | |
|---|---|
| MS (M + H)⁺ Calcd. | 634.3 |
| MS (M + H)⁺ Observ. | 634.4 |
| Retention Time | 2.07 min |
| | LC Condition |
| Solvent A | 5% ACN:95% Water:10 mM Ammonium Actetate |
| Solvent B | 95% ACN:5% Water:10 mM Ammonium Actetate |
| Start % B | 0 |
| Final % B | 100 |
| Gradient Time | 2 min |
| Flow Rate | 1 mL/min |
| Wavelength | 220 |
| Solvent Pair | ACN:Water:Ammonium Actetate |
| Column | Phenomenex LUNA C18, 30 × 2, 3 u |

Step 4: To Interm-0051-Meta or Interm-0051-Para (0.38 g) in a 16×100 mm Wheaton vial was added TFA (3 mL). Vial was capped and agitated at 350 rpm on an Innova platform shaker at room temperature for 18 hours. Solvents were blown away in the Zymark tabletop dryer at 40° C. for 3 hours. After being dried under reduced pressure, the residue was used in the further reactions without purification.

Step 5: General Procedure for Preparation of Cyclic Di-Ureas

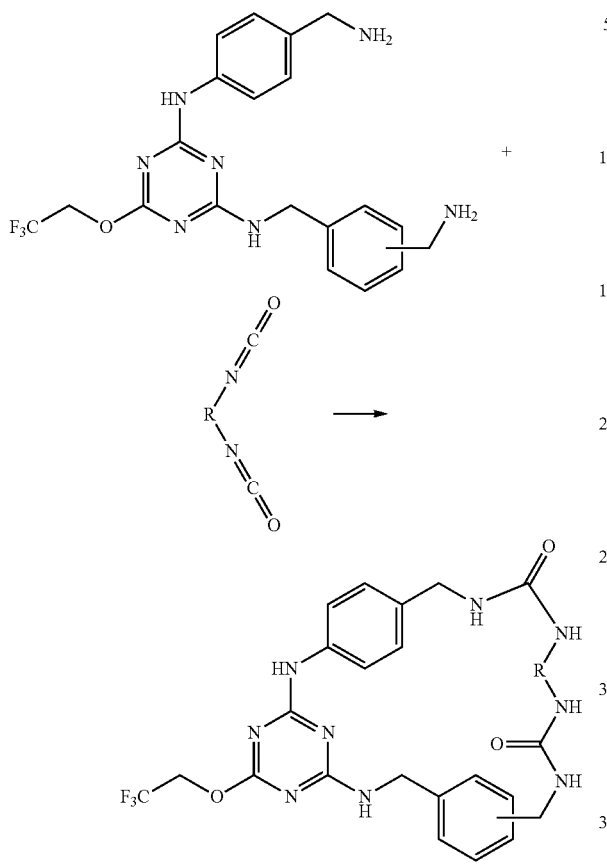

Stock solutions of the diamine cores (173 mg, 400 μmol each) in DMF (8.0 mL each) were prepared. To each of these stock solutions was added iPr$_2$NEt (352 μL, 2.0 mmol). To each of the isocyanates (pre-weighed into 16×100 mm Wheaton vials) was added 2 mL of dichloroethane. 1 mL of each of these solutions was transferred to seperate Wheaton vials and 4 mL of dichloroethane was added to each of these solutions. To each of the vials containing the isocyanates was added the 1 mL of the appropriate diamine solution. Vials were capped and agitated at 350 rpm on an Innova platform shaker at room temperature for 18 hours. Samples were blown down in the Zymark tabletop dryer at 40° C. for 3 hours, before 1 mL of DMF was added to each vial. Suspend contents were vortexed well and suspensions were applied to 6-mL silica SPE cartridges, eluted w/4 mL of MeOH each, collected into 16×100 mm culture tubes. Samples were blown down in the Zymark tabletop dryer at 40° C. for 3 hours. Then, 1 mL of DMF was added into each vial. Contents were transferred to 96 well deep-well plate, filtered w/0.45 μm syringe filters. Reaction vials were rinsed and transferred w/filtering. 25 μL of solution was removed from each well and diluted w/225 μL of DMF for LC/MS analysis. Purification via preparative HPLC offered products.

Initial Analysis:
  WFD-446-LCMS2:
    MassLynx 4.0 SP4 LC-MS software
    CTC-Leap HTS-PAL autosampler
    Agilent 1100 quaternary pump
    Agilent 1100 photodiode array
    Polymer Lab 2100 ELS detector (Evap. Temp.=45° C., Neb. Temp.=35° C.)
    Waters ZQ mass spectrometer
    Column—Waters Xbridge 4.6×50 mm 5 um C18
    Mobile Phase—A=5:95 Acetonitrile or MeOH:Water; B=95:5
    Acetonitrile or MeOH:Water; Modifier=10 mM NH$_4$OAc
Method
  WFD-LCMS-003 MeOH (4.6×50 mm, 5um, 9 min):

| Time | B % | Flow |
|---|---|---|
| 0.00' | 0 | 2.0 |
| 8.00' | 100 | 2.0 |
| 9.00' | 100 | 2.0 |
| 9.10' | 0 | 2.0 |
| 10.00' | 0 | 2.0 |

Preparative HPLC
  WFD-445-PMS1 (Waters):
    Masslynx 4.0 SP2
    Waters 2767 Sample Manager (autosampler/fraction collector)
    Waters Column Fluidics Organizer
    Waters 2525 binary pump
    Waters 515 pumps for Makeup, At-Column-Dilution, and Dial-A-Mix flows (resp.)
    Waters 2787 UV detector
    Waters ZQ with ESCi mass spectrometer
    Column—a) Waters Xbridge 19×200 mm 5 um C18 or b) Waters
    Xbridge 19×200 mm 5 um Shield RP-18
    Guard Column—Waters Xbridge 19×10 mm 5 um C18
    Mobile Phase—A=Water; B=95:5 Acetonitrile; Water; Modifier=20 mM NH$_4$OAc
Method
  WFD-PMS1-Nwx14aA (19×200 mm): for B=ACN 25 mL/min, 0'=20% B, 0.5° (12.5 mL/min)=20% B, 2' (12.5 mL/min)=20% B, 2.5'=20% B, 23'=95% B, 30'=95% B
Sample Drying—GeneVac Program HT-24-ACN-H$_2$O-Buffer in 16×100 TT & AL blocks: Temp=45 C, 0.3 h @ 175 to 40 bar, 1.7 h @ 40 bar, defrost, 6 h @ 8 bar, 6 h @ Full Vac, defrost.
Final Analysis
  WFD-446-LCMS2:
    MassLynx 4.0 SP4 LC-MS software
    CTC-Leap HTS-PAL autosampler
    Agilent 1100 binary pump
    Agilent 1100 photodiode array (220 nm)
    Polymer Lab 2100 ELS detector (Evap. Temp.=45° C., Neb. Temp.=35° C.)
    Waters ZQ mass spectrometer
    Column—Supelco Ascentis Express 4.6×50 mm 2.7 um C18
    Mobile Phase—A=5:95 ACN:Water; B=95:5 ACN:Water; Modifier=10 mM NH$_4$OAc
Method
  WFD-MUX-004 (4.6×50 mm):

| Time | B % | Flow |
|---|---|---|
| 0.00' | 0 | 2.0 |
| 8.00' | 100 | 2.0 |
| 9.00' | 100 | 2.0 |
| 9.10' | 100 | 2.0 |
| 10.00' | 0 | 2.0 |

| Cpd. | Structure | HPLC Rt | Calcd. Ms Ion | Obs. Ms Ion | Prep Column |
|------|-----------|---------|---------------|-------------|-------------|
| 0051 | 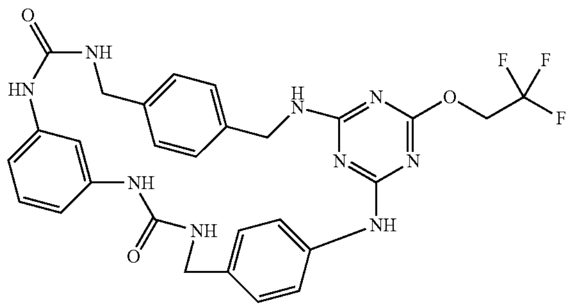 [SMILES: O=C1NCc2ccc(cc2)CNc2nc(nc(OCC(F)(F)F)n2)Nc2ccc(cc2)CNC(=O)Nc2cccc(c2)N1] | 3.99 | 594.2 | 594.2 | b |
| 0052 | 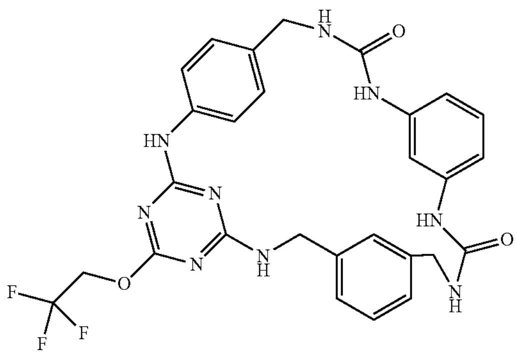 [SMILES: O=C1NCc2ccc(cc2)Nc2nc(nc(OCC(F)(F)F)n2)NCc2cccc(c2)CNC(=O)Nc2cccc(c2)N1] | 3.81 | 594.2 | 594.2 | a |
| 0053 | 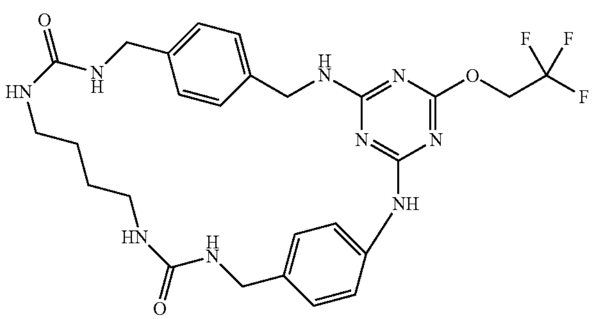 [SMILES: O=C1NCCCCNC(=O)NCc2ccc(cc2)Nc2nc(nc(OCC(F)(F)F)n2)NCc2ccc(cc2)CN1] | 3.53 | 574.3 | 574.3 | a |
| 0054 | 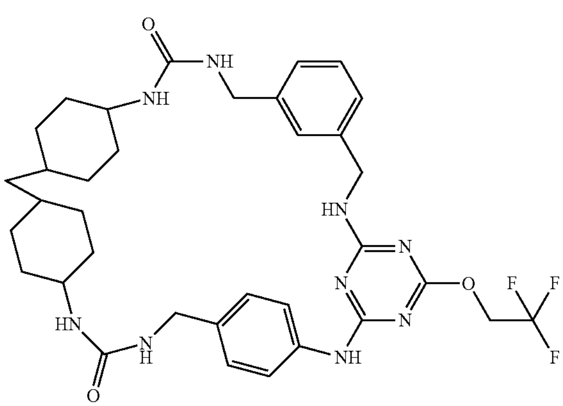 [SMILES: O=C1NCc2ccc(cc2)Nc2nc(nc(OCC(F)(F)F)n2)NCc2cccc(c2)CNC(=O)NC2CCC(CC2)CC2CCC(CC2)N1] | 4.34 | 696.4 | 696.4 | a |

-continued

| Cpd. | Structure | HPLC Rt | Calcd. Ms Ion | Obs. Ms Ion | Prep Column |
|---|---|---|---|---|---|
| 0055 | 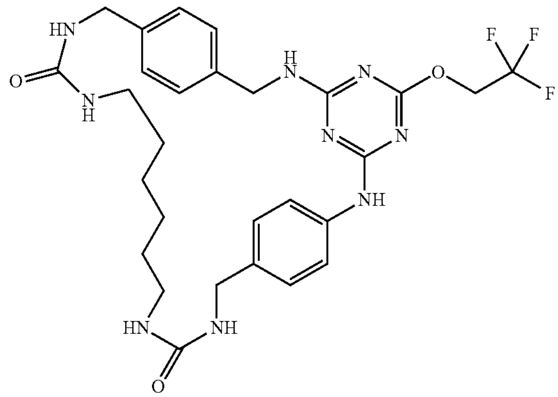 [SMILES: O=C1NCCCCCCNC(=O)NCc2ccc(cc2)Nc2nc(nc(OCC(F)(F)F)n2)NCc2ccc(cc2)CN1] | 3.85 | 602.3 | 602.3 | b |
| 0056 | 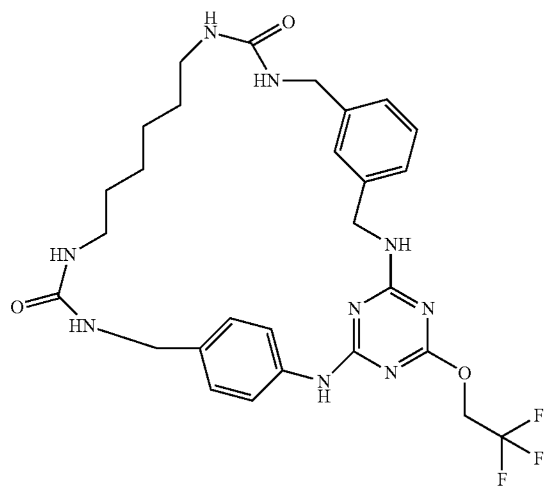 [SMILES: O=C1NCCCCCCNC(=O)NCc2cccc(c2)CNc2nc(nc(OCC(F)(F)F)n2)Nc2ccc(cc2)CN1] | 3.81 | 602.3 | 602.3 | b |
| 0057 | 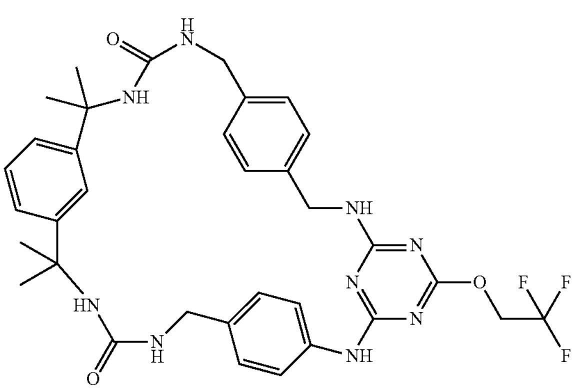 [SMILES: CC1(C)NC(=O)NCc2ccc(cc2)CNc2nc(nc(OCC(F)(F)F)n2)Nc2ccc(cc2)CNC(=O)NC(C)(C)c2cccc1c2] | 4.56 | 678.3 | 678.3 | a |

| Cpd. | Structure | HPLC Rt | Calcd. Ms Ion | Obs. Ms Ion | Prep Column |
|---|---|---|---|---|---|
| 0058 | 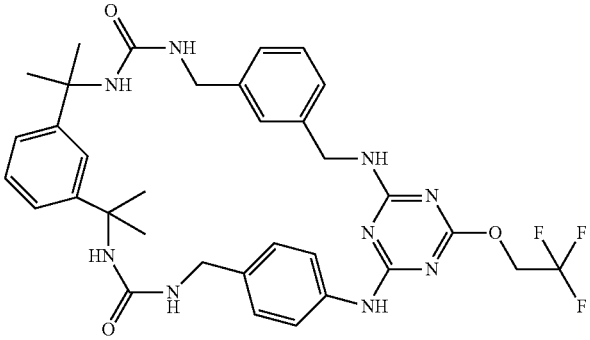 [SMILES: CC1(C)NC(=O)NCc2ccc(cc2)Nc2nc(nc(OCC(F)(F)F)n2)NCc2cccc(c2)CNC(=O)NC(C)(C)c2cccc1c2] | 4.42 | 678.3 | 678.3 | b |

Step 5: General Procedure for Preparation of Cyclic Di-Amides

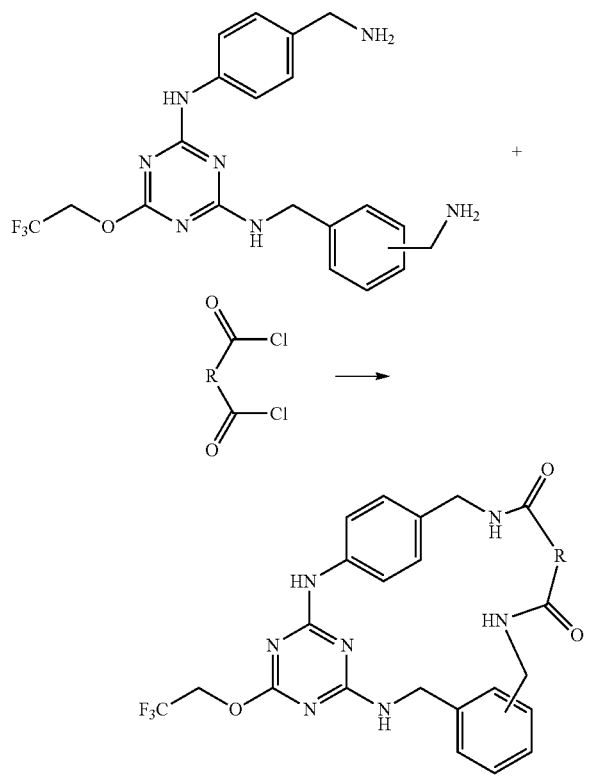

Stock solutions of the diamine cores (173 mg, 400 μmol each) in DMF were prepared (8.0 mL each). To each of these stock solutions was added iPr$_2$NEt (528 μL, 3.0 mmol). To each of the acid chlorides (pre-weighed into 16×100 mm Wheaton vials) was added 2 mL of dichloroethane. 1 ml of each of these solutions was transferred to seperate Wheaton vials. And 5 mL of dichloroethane was added to each of these solutions. To each of the vials containing the isocyanates was added the 1 mL of the appropriate diamine solution. Vials were capped and agitated at 350 rpm on an Innova platform shaker at room temperature for 18 hours. Samples were blown down in the Zymark tabletop dryer at 40° C. for 2 hours, before addition of 750 μL of DMF to each sample. Contents were transferred to a 96 well filter plate, collected into a 96 well deep-well plate. Reaction vials were rinsed w/250 μL of DMF and transferred rinses to the filter plate. 25 μL of solution was removed from each well and diluted to 325 μL for LC/MS analysis. Purification via preparative HPLC offered products.

Initial Analysis:
  WFD-446-UPLC4:
  MassLynx 4.1
  Waters 2777 Sample Manager (CTC MXY01-01B)
  Waters Acquity Binary UPLC pump
  Waters Acquity TUV detector (220 nm)
  Waters SD mass spectrometer with ESI probe
  Column—Waters Xbridge 2.1×50 mm 1.7 um C18 (BEH-C18 for UPLC)
  Mobile Phase—A=5:95 SS:Water; B=95:5 SS:Water; Modifier=10 mM NH$_4$OAc
  Methods
  WFD-UPLC-001 MeOH (2×50 mm, 1.7 um, 5 min):

| Time | B % | Flow |
|---|---|---|
| 0.00' | 0 | 0.5 |
| 4.00' | 100 | 0.5 |
| 5.00' | 100 | 0.5 |
| 5.10' | 0 | 0.5 |
| 5.50' | 0 | 0.5 |

WFD-UPLC-002 ACN (2×50 mm, 1.7 um, 5 min):

| Time | B % | Flow |
|---|---|---|
| 0.00' | 0 | 0.83 |
| 4.00' | 100 | 0.83 |
| 5.00' | 100 | 0.83 |
| 5.10' | 0 | 0.83 |
| 5.50' | 0 | 0.83 |

Preparative HPLC
  WFD-445-PMS3 (Dionex APS-3000):
  Chromeleon 6.70 sp1 LC software
  Dionex P680 binary pump for analytical
  Dionex PP 150 binary pump prep
  Dionex UVD340U UV spectrometer (220 nm)
  Sedex 75 ELS detector
  Thermo-Finnigen MSQ Surveyor Plus mass spectrometer Column—Waters Xbridge 19×150 mm 5 um C18
Guard Column—Waters Xbridge 19×10 mm 5 um C18
Mobile Phase—A=Water; B=95:5 Acetonitrile; Water; Modifier=20 mM NH$_4$OAc Method
WFD-PMS3_Methanol (19×150 mm): 30 mL/min, 0'=40% B, 0.5' (10 mL/min)=40% B, 2' (10 mL/min)=40% B, 2.5° (20 mL/min)=30% B, 20'=95% B, 20'=95% B Sample Drying—GeneVac Program HT-24-ACN-H$_2$O-Buffer in 16×100 TT & AL blocks: Temp=45 C, 0.3 h @ 175 to 40 bar, 1.7 h @ 40 bar, defrost, 6 h @ 8 bar, 6 h @ Full Vac, defrost.

Final Analysis
WFD-446-LCMS2:
MassLynx 4.0 SP4 LC-MS software
CTC-Leap HTS-PAL autosampler
Agilent 1100 binary pump
Agilent 1100 photodiode array (220 nm)
Polymer Lab 2100 ELS detector (Evap. Temp.=45° C., Neb. Temp.=35° C.)
Waters ZQ mass spectrometer
Column—Supelco Ascentis Express 4.6×50 mm 2.7 um C18
Mobile Phase—A=5:95 ACN:Water; B=95:5 ACN:Water; Modifier=10 mM NH$_4$OAc Method
WFD-MUX-004 (4.6×50 mm):

| Time | B % | Flow |
| --- | --- | --- |
| 0.00' | 0 | 2.0 |
| 8.00' | 100 | 2.0 |
| 9.00' | 100 | 2.0 |
| 9.10' | 100 | 2.0 |
| 10.00' | 0 | 2.0 |

| Compd. Number | Structure | HPLC Rt | Calcd. Ms Ion | Observed Ms Ion |
| --- | --- | --- | --- | --- |
| 0059 | 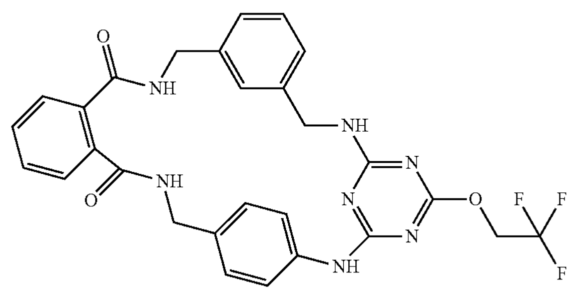 [SMILES: O=C1NCc2ccc(cc2)Nc2nc(nc(OCC(F)(F)F)n2)NCc2cccc(c2)CNC(=O)c2ccccc21] | 4.06 | 564.2 | 564.2 |
| 0060 | 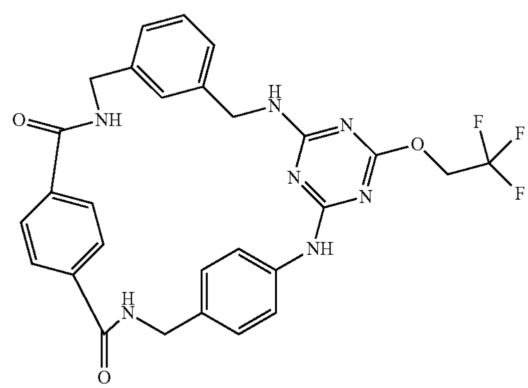 [SMILES: O=C1NCc2ccc(cc2)Nc2nc(nc(OCC(F)(F)F)n2)NCc2cccc(c2)CNC(=O)c2ccc1cc2] | 3.87 | 564.2 | 564.2 |
| 0061 | 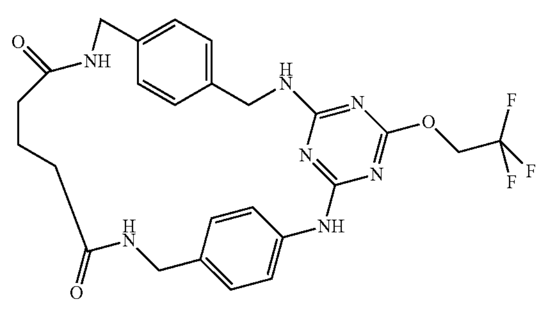 [SMILES: O=C1CCCC(=O)NCc2ccc(cc2)Nc2nc(nc(OCC(F)(F)F)n2)NCc2ccc(cc2)CN1] | 3.41 | 530.2 | 530.2 |

-continued

| Compd. Number | Structure | HPLC Rt | Calcd. Ms Ion | Observed Ms Ion |
|---|---|---|---|---|
| 0062 | 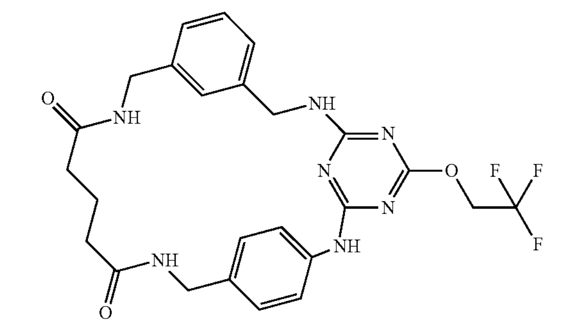 [SMILES: O=C1CCCC(=O)NCc2cccc(c2)CNc2nc(nc(OCC(F)(F)F)n2)Nc2ccc(cc2)CN1] | 3.47 | 530.2 | 530.2 |
| 0063 | 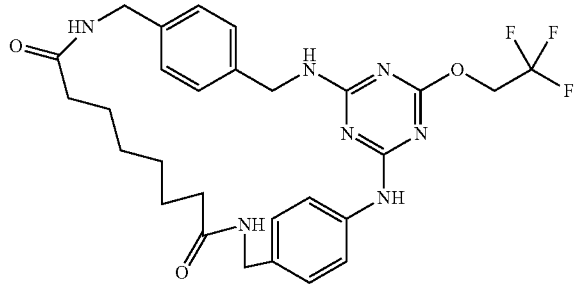 [SMILES: O=C1CCCCCCC(=O)NCc2ccc(cc2)Nc2nc(nc(OCC(F)(F)F)n2)NCc2ccc(cc2)CN1] | 3.77 | 572.3 | 572.2 |
| 0064 | 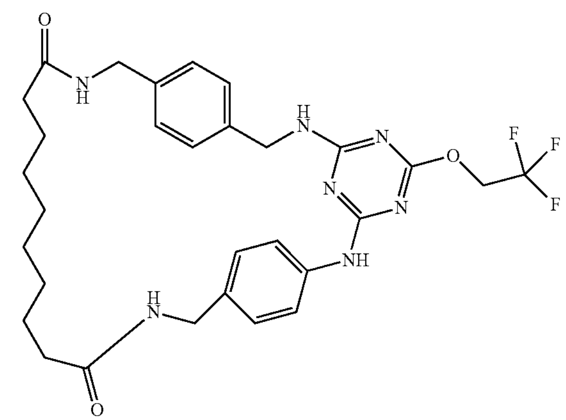 [SMILES: O=C1CCCCCCCCC(=O)NCc2ccc(cc2)Nc2nc(nc(OCC(F)(F)F)n2)NCc2ccc(cc2)CN1] | 4.22 | 600.3 | 600.3 |
| 0065 | 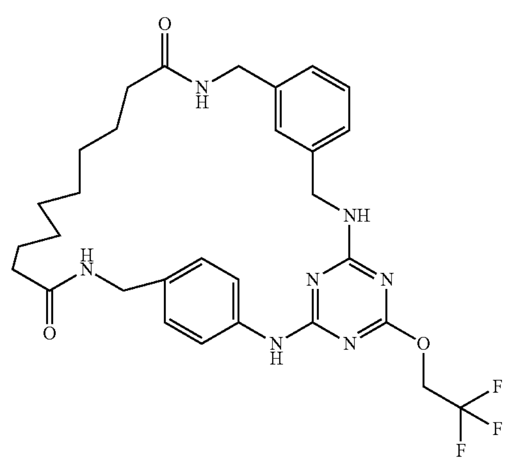 [SMILES: O=C1CCCCCCCCC(=O)NCc2cccc(c2)CNc2nc(nc(OCC(F)(F)F)n2)Nc2ccc(cc2)CN1] | 4.38 | 600.3 | 600.3 |

-continued

| Compd. Number | Structure | HPLC Rt | Calcd. Ms Ion | Observed Ms Ion |
|---|---|---|---|---|
| 0067 | 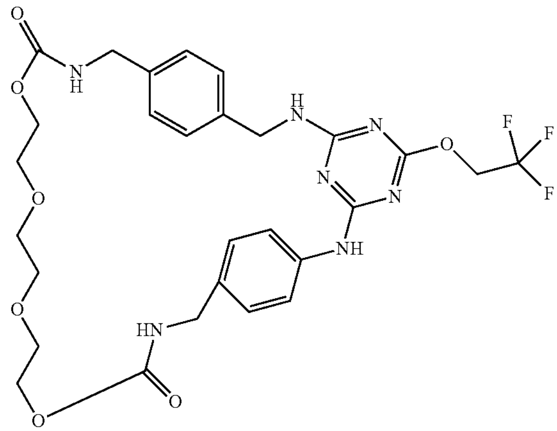 [SMILES: O=C1NCc2ccc(cc2)CNc2nc(nc(OCC(F)(F)F)n2)Nc2ccc(cc2)CNC(=O)OCCOCCOCCO1] | 4.12 | 636.2 | 636.2 |
| 0068 | 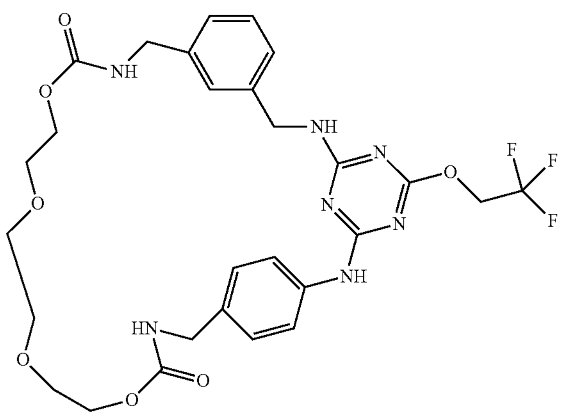 [SMILES: O=C1NCc2ccc(cc2)Nc2nc(nc(OCC(F)(F)F)n2)NCc2cccc(c2)CNC(=O)OCCOCCOCCO1] | 4.27 | 636.2 | 636.2 |
| 0069 | 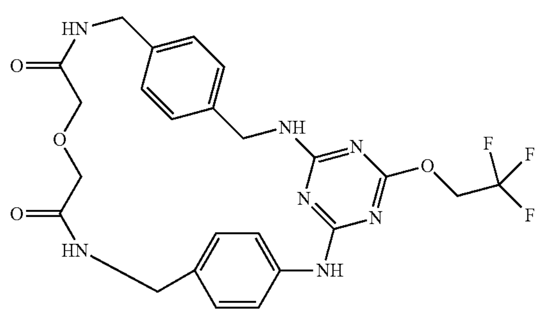 [SMILES: O=C1COCC(=O)NCc2ccc(cc2)Nc2nc(nc(OCC(F)(F)F)n2)NCc2ccc(cc2)CN1] | 3.54 | 532.2 | 532.2 |
| 0070 | 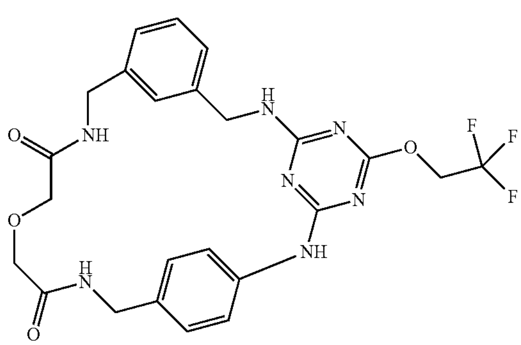 [SMILES: O=C1COCC(=O)NCc2cccc(c2)CNc2nc(nc(OCC(F)(F)F)n2)Nc2ccc(cc2)CN1] | 3.66 | 532.2 | 532.2 |

-continued
| Compd. Number | Structure | HPLC Rt | Calcd. Ms Ion | Observed Ms Ion |
|---|---|---|---|---|
| 0071 | 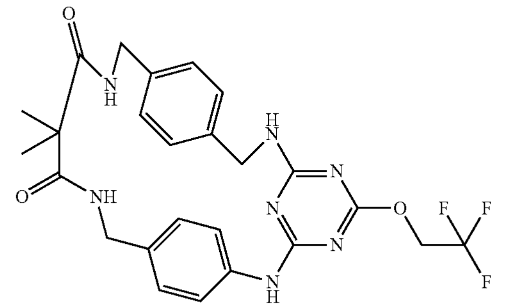 [SMILES: CC1(C)C(=O)NCc2ccc(cc2)CNc2nc(nc(OCC(F)(F)F)n2)Nc2ccc(cc2)CNC1=O] | 3.98 | 530.2 | 530.2 |
| 0072 | 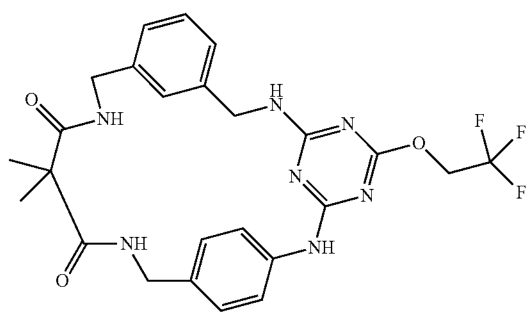 [SMILES: CC1(C)C(=O)NCc2ccc(cc2)Nc2nc(nc(OCC(F)(F)F)n2)NCc2cccc(c2)CNC1=O] | 4.1 | 530.2 | 530.2 |
Example 3001
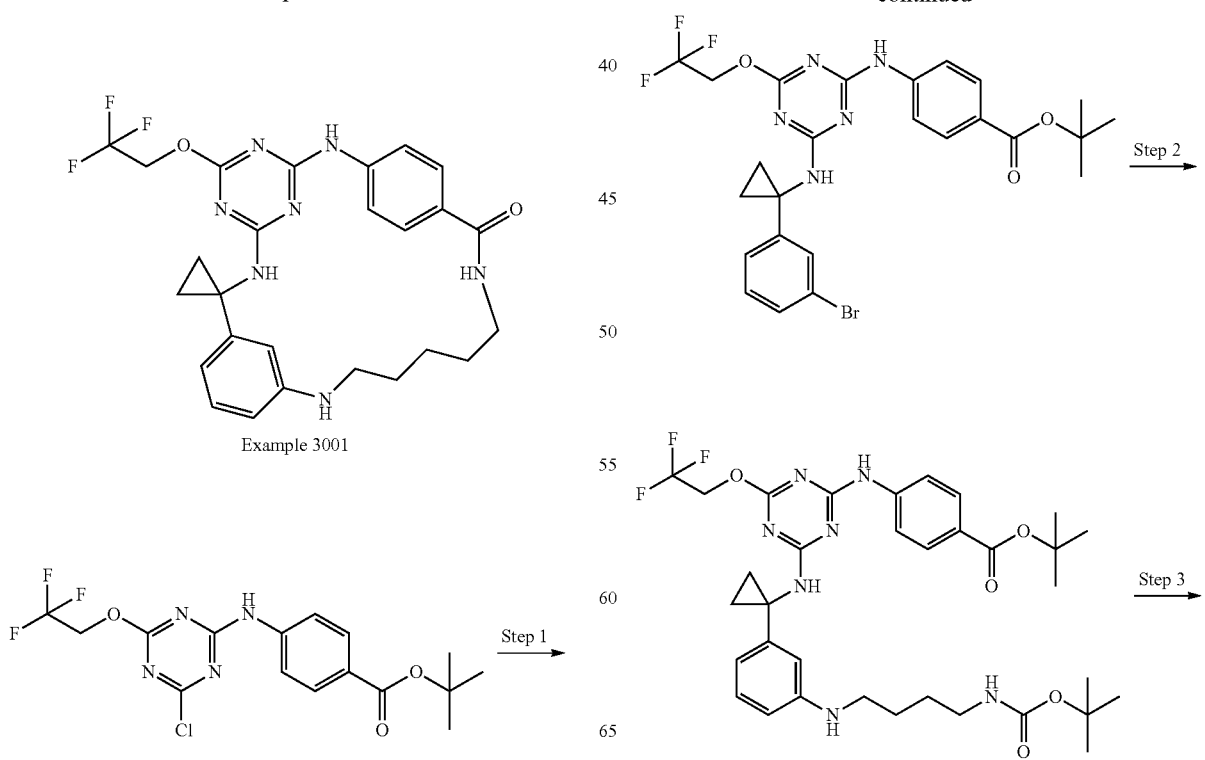
Example 3001

-continued

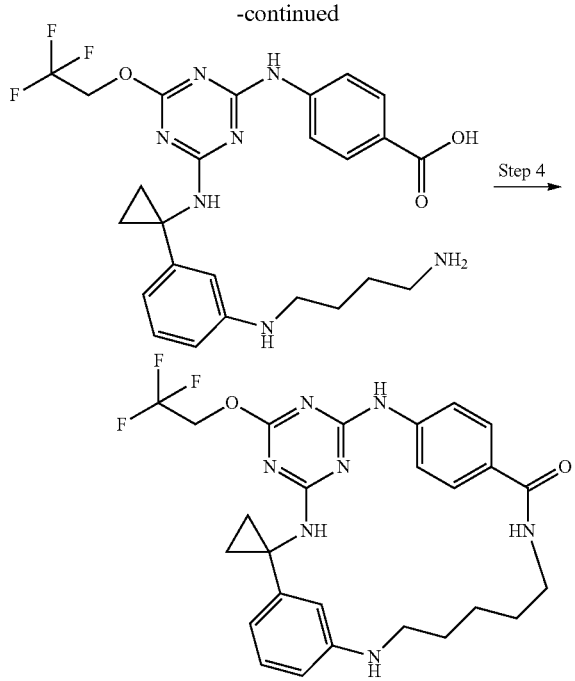

Step 1: tert-butyl 4-(4-(1-(3-bromophenyl)cyclopropylamino)-6-(2,2,2-trifluoroethoxy)-1,3,5-triazin-2-ylamino)benzoate. To a solution of tert-butyl 4-(4-chloro-6-(2,2,2-trifluoroethoxy)-1,3,5-triazin-2-ylamino)benzoate (1156 mg, 2 mmol) in THF (10 mL) was added 1-(3-bromophenyl)cyclopropanamine (424 mg, 2.000 mmol) and Hunig's Base (1.747 mL, 10.00 mmol). The resulting mixture was stirred for 16 h. After concentration, the residue was purified by Biotage eluting with 20% ethyl acetate in hexane to give 400 mg (35%) of the desired product as a solid.

| tert-butyl 4-(4-(1-(3-bromophenyl)cyclopropylamino)-6-(2,2,2-trifluoroethoxy)-1,3,5-triazin-2-ylamino)benzoate | |
|---|---|
| MS (M)$^+$ Calcd. | 687.34 |
| MS (M + H)$^+$ Observ. | 688.37 |
| Retention Time | 2.96 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient/Stop Time | 3 min/4 min |
| Flow Rate | 1 mL/min |
| Wavelength | 220 |
| Solvent Pair | methanol:Water:TFA |
| Column | PHENOMENEX-LUNA 2.0 × 30 mm 3 um |

Step 2: tert-butyl 4-(4-(1-(3-(4-(tert-butoxycarbonylamino)butylamino)phenyl)cyclopropylamino)-6-(2,2,2-trifluoroethoxy)-1,3,5-triazin-2-ylamino)benzoate. To a mixture of tert-butyl 4-(4-(1-(3-bromophenyl)cyclopropylamino)-6-(2,2,2-trifluoroethoxy)-1,3,5-triazin-2-ylamino)benzoate (116 mg, 0.2 mmol),tert-butyl 4-aminobutylcarbamate (37.7 mg, 0.200 mmol), 2-(Di-t-butylphosphino)biphenyl (0.020 mmol), Pd2(dba)$_3$ (18.31 mg, 0.020 mmol), K3PO4 (34.8 mg, 0.200 mmol) in a microwave tube in DME (Volume: 2 mL) was stirred for 3 h at 85° C. The reaction mixture was diluted with CH2Cl2, filtrated through a celite plug washing with CH2Cl2, concentrated to give a residue that was purified by Biotage eluting with 20%-50% ethyl acetate in hexane to give 38 mg (28%) of the desired product.

| tert-butyl 4-(4-(1-(3-(4-(tert-butoxycarbonylamino)butylamino)phenyl)cyclopropylamino)-6-(2,2,2-trifluoroethoxy)-1,3,5-triazin-2-ylamino)benzoate | |
|---|---|
| MS (M)$^+$ Calcd. | 579.11 |
| MS (M + H)$^+$ Observ. | 580.1 |
| Retention Time | 3.301 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient/Stop Time | 3 min/4 min |
| Flow Rate | 1 mL/min |
| Wavelength | 220 |
| Solvent Pair | methanol:Water:TFA |
| Column | PHENOMENEX-LUNA 2.0 × 30 mm 3 um |

Step 3: 4-(4-(1-(3-(4-aminobutylamino)phenyl)cyclopropylamino)-6-(2,2,2-trifluoroethoxy)-1,3,5-triazin-2-ylamino)benzoic acid, TFA salt. To a solution of tert-butyl 4-(4-(1-(3-(4-(tert-butoxycarbonylamino)butylamino)phenyl)cyclopropylamino)-6-(2,2,2-trifluoroethoxy)-1,3,5-triazin-2-ylamino)benzoate (38 mg, 0.055 mmol) in CH$_2$Cl$_2$ (Volume: 2 mL) was added TFA (0.017 mL, 0.221 mmol). The resulting mixture was stirred for 2 h. Concentration gave 35.7 mg (100%) of a crude product that will be used in the next step as it is.

| 4-(4-(1-(3-(4-aminobutylamino)phenyl)cyclopropylamino)-6-(2,2,2-trifluoroethoxy)-1,3,5-triazin-2-ylamino)benzoic acid, TFA salt | |
|---|---|
| MS (M)$^+$ Calcd. | 531.22 |
| MS (M + H)$^+$ Observ. | 532.17 |
| Retention Time | 2.30 min |
| LC Condition | |
| Solvent A | 10% methanol:90% Water:0.1% TFA |
| Solvent B | 90% methanol:10% Water:0.1% TFA |
| Start % B | 0 |
| Final % B | 100 |
| Gradient/Stop Time | 3 min/4 min |
| Flow Rate | 1 mL/min |
| Wavelength | 220 |
| Solvent Pair | methanol:Water:TFA |
| Column | PHENOMENEX-LUNA 2.0 × 30 mm 3 um |

Step 4: To a solution of 4-(4-(1-(3-(5-aminopentylamino)phenyl)cyclopropylamino)-6-(2,2,2-trifluoroethoxy)-1,3,5-triazin-2-ylamino)benzoic acid, HCl (100 mg, 0.172 mmol), Hunig's Base (0.150 mL, 0.859 mmol) in CH$_2$Cl$_2$ (2 mL) was added HATU (98 mg, 0.258 mmol) and then stirred for 16 h. After concentration, the residue was purified by prep HPLC to give 10 mg (91%) of the desired product.

| Example 3001 | |
|---|---|
| MS (M)$^+$ Calcd. | 527.23 |
| MS (M + H)$^+$ Observ. | 528.19 |
| Retention Time | 2.325 min |

Example 3001
LC Condition
| | |
|---|---|
| Solvent A | 10% methanol:90% Water:0.1% TFA |
| Solvent B | 90% methanol:10% Water:0.1% TFA |
| Start % B | 0 |
| Final % B | 100 |
| Gradient/Stop Time | 3 min/4 min |
Example 3001
| | |
|---|---|
| Flow Rate | 1 mL/min |
| Wavelength | 220 |
| Solvent Pair | methanol:Water:TFA |
| Column | PHENOMENEX-LUNA 2.0 × 30 mm 3 um |
Example 3002
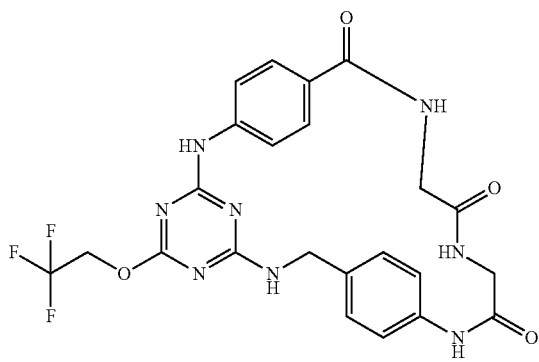
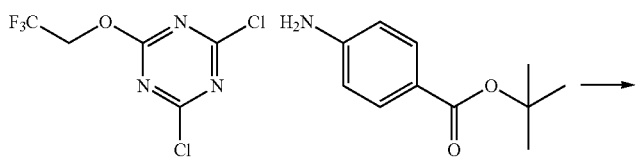
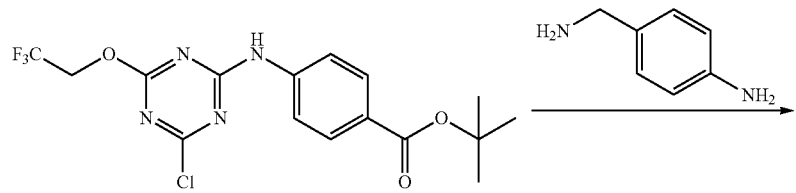
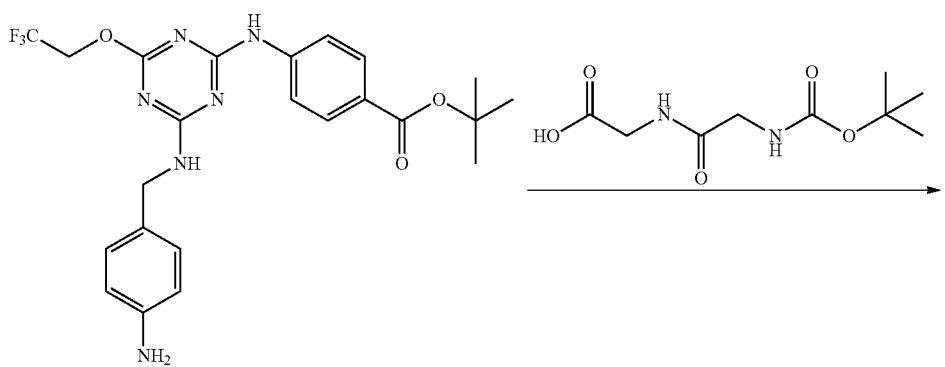

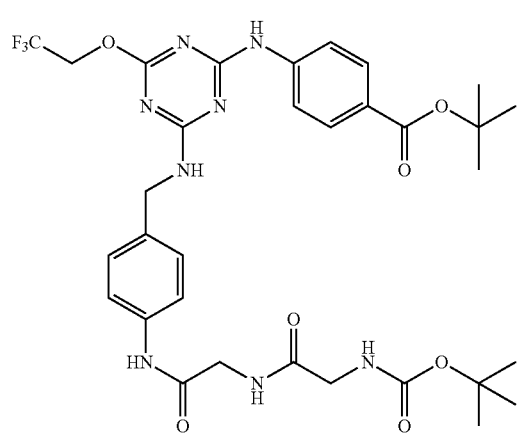

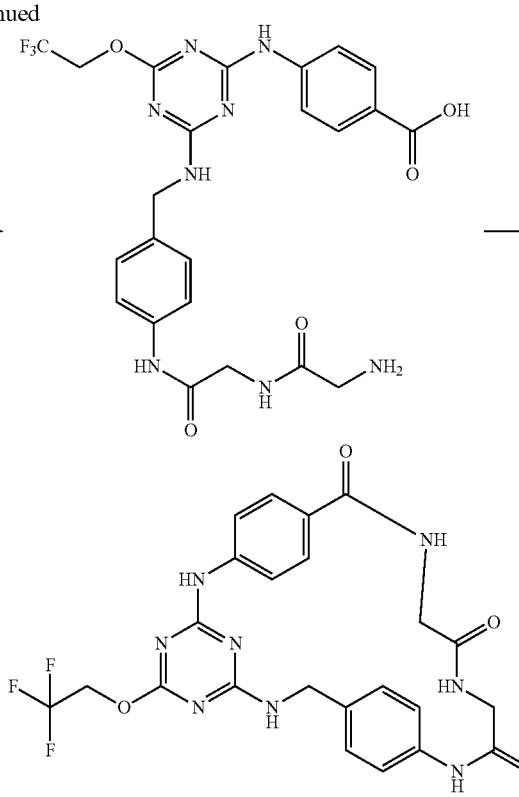

Step 1: To a solution of 2,4-dichloro-6-(2,2,2-trifluoroethoxy)-1,3,5-triazine (10 g, 40.3 mmol) in THF (100 mL) was added tert-butyl 4-aminobenzoate (7.79 g, 40.3 mmol) and Hunig's Base (7.04 mL, 40.3 mmol). The resulting mixture was stirred for 16 h. The precipitate was filtered and washed with $Et_2O$, dried, then washed with water and dried to give the tert-butyl 4-(4-chloro-6-(2,2,2-trifluoroethoxy)-1,3,5-triazin-2-ylamino)benzoate (10.6 g).

| tert-butyl 4-(4-chloro-6-(2,2,2-trifluoroethoxy)-1,3,5-triazin-2-ylamino)benzoate | |
|---|---|
| MS (M + H)$^+$ Calcd. | 405.1 |
| MS (M + H)$^+$ Observ. | 405.0 |
| Retention Time | 1.15 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 2: To a solution of the tert-butyl 4-(4-chloro-6-(2,2,2-trifluoroethoxy)-1,3,5-triazin-2-ylamino)benzoate (2 g, 4.94 mmol) in THF (10 mL) was added 4-(aminomethyl)aniline (0.616 mL, 5.44 mmol) and Hunig's Base (3.45 mL, 19.76 mmol). The resulting mixture was stirred for 16 h. The reaction was then warmed to 65° C. for 2 h at which point the reaction became a homogeneous solution. The reaction was cooled and diluted with DCM and washed with water and brine. The organic layer was collected, dried over sodium sulfate, and concentrated under vacuum to give an oily residue. The residue was purified by silica gel chromatography using 40% EtOAc/Hexanes to give tert-butyl 4-(4-(4-aminobenzylamino)-6-(2,2,2-trifluoroethoxy)-1,3,5-triazin-2-ylamino)benzoate (1.5 g).

| tert-butyl 4-(4-(4-aminobenzylamino)-6-(2,2,2-trifluoroethoxy)-1,3,5-triazin-2-ylamino)benzoate | |
|---|---|
| MS (M + H)$^+$ Calcd. | 491.2 |
| MS (M + H)$^+$ Observ. | 491.0 |
| Retention Time | 0.92 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: tert-butyl 4-(4-(4-aminobenzylamino)-6-(2,2,2-trifluoroethoxy)-1,3,5-triazin-2-ylamino)benzoate (100 mg, 0.204 mmol), 2-(2-(tert-butoxycarbonylamino)acetamido)acetic acid (56.8 mg, 0.245 mmol), HATU (116 mg, 0.306 mmol), and Hunig's Base (0.178 mL, 1.019 mmol) were stirred in DCM (3 mL) for 16 h. The solvent was removed and the crude material was purified by silica gel chromatography using EtOAc to give tert-butyl 4-(4-(4-(2-(2-(tert-butoxycarbonylamino)acetamido)acetamido)benzylamino)-6-(2,2,2-trifluoroethoxy)-1,3,5-triazin-2-ylamino)benzoate (144 mg).

| tert-butyl 4-(4-(4-(2-(2-(tert-butoxycarbonylamino)acetamido)acetamido)benzylamino)-6-(2,2,2-trifluoroethoxy)-1,3,5-triazin-2-ylamino)benzoate | |
|---|---|
| MS (M + H)+ Calcd. | 705.3 |
| MS (M + H)+ Observ. | 705.1 |
| Retention Time | 1.07 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: tert-butyl 4-(4-(4-(2-(2-(tert-butoxycarbonylamino)acetamido)acetamido)benzylamino)-6-(2,2,2-trifluoroethoxy)-1,3,5-triazin-2-ylamino)benzoate and 4 N HCl in Dioxane (2 mL, 8.00 mmol) were stirred for 1 h then concentrated under vacuum to give 4-(4-(4-(2-(2-aminoacetamido)acetamido)benzylamino)-6-(2,2,2-trifluoroethoxy)-1,3,5-triazin-2-ylamino)benzoic acid (112 mg) which was carried to the next step without purification.

| 4-(4-(4-(2-(2-aminoacetamido)acetamido)benzylamino)-6-(2,2,2-trifluoroethoxy)-1,3,5-triazin-2-ylamino)benzoic acid | |
|---|---|
| MS (M + H)+ Calcd. | 549.2 |
| MS (M + H)+ Observ. | 549.0 |
| Retention Time | 0.76 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: 4-(4-(4-(2-(2-aminoacetamido)acetamido)benzylamino)-6-(2,2,2-trifluoroethoxy)-1,3,5-triazin-2-ylamino) benzoic acid (112 mg, 0.263 mmol), HATU (150 mg, 0.394 mmol), and Hunig's Base (0.229 mL, 1.313 mmol) were stirred in DMF (3 mL) for 16 h. The solvent was removed and the crude material was purified by reverse phase preparative HPLC to give Example 5001 (10 mg). 1H NMR (400 MHz, DMSO-d$_6$) δ ppm 4.25-4.36 (m, 1H), 4.36-4.56 (m, 4H), 4.92-5.08 (m, 3H), 7.08-7.25 (m, 6H), 7.45 (d, J=8.5 Hz, 2H), 7.60 (d, J=8.3 Hz, 1H), 8.01 (d, J=8.3 Hz, 1H), 8.23 (dd, J=6.1, 3.9 Hz, 1H), 9.60 (s, 1H), 9.66 (s, 1H).

| Example 3002 | |
|---|---|
| MS (M + H)+ Calcd. | 531.2 |
| MS (M + H)+ Observ. | 531.0 |
| Retention Time | 0.79 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3003

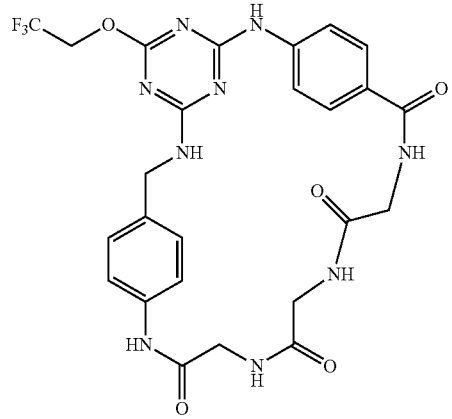 [SMILES: O=C1CNC(=O)CNC(=O)c2ccc(cc2)Nc2nc(nc(OCC(F)(F)F)n2)NCc2ccc(cc2)NC(=O)CN1]

The above compound was prepared by analogy to Example 3002. 1H NMR (400 MHz, DMSO-d$_6$) δ ppm 3.73 (d, 2H), 3.85 (d, J=5.5 Hz, 2H), 3.96 (d, J=5.3 Hz, 2 H), 4.40 (d, J=5.5 Hz, 2H), 4.98 (q, J=9.2 Hz, 2H), 7.25 (dd, J=16.2, 8.7 Hz, 4H), 7.52 (d, J=8.8 Hz, 2H), 7.69 (d, J=8.5 Hz, 2H), 8.28 (t, J=5.3 Hz, 1H), 8.35 (ddd, J=15.6, 5.7, 5.5 Hz, 2H), 8.77 (t, J=5.3 Hz, 1H), 9.29 (s, 1H), 9.77 (s, 1H).

| Example 3003 | |
|---|---|
| MS (M + H)+ Calcd. | 588.2 |
| MS (M + H)+ Observ. | 588.0 |
| Retention Time | 0.78 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3004
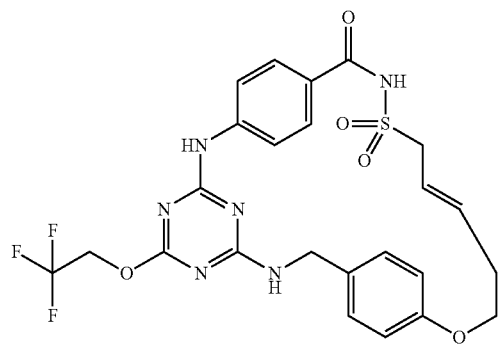
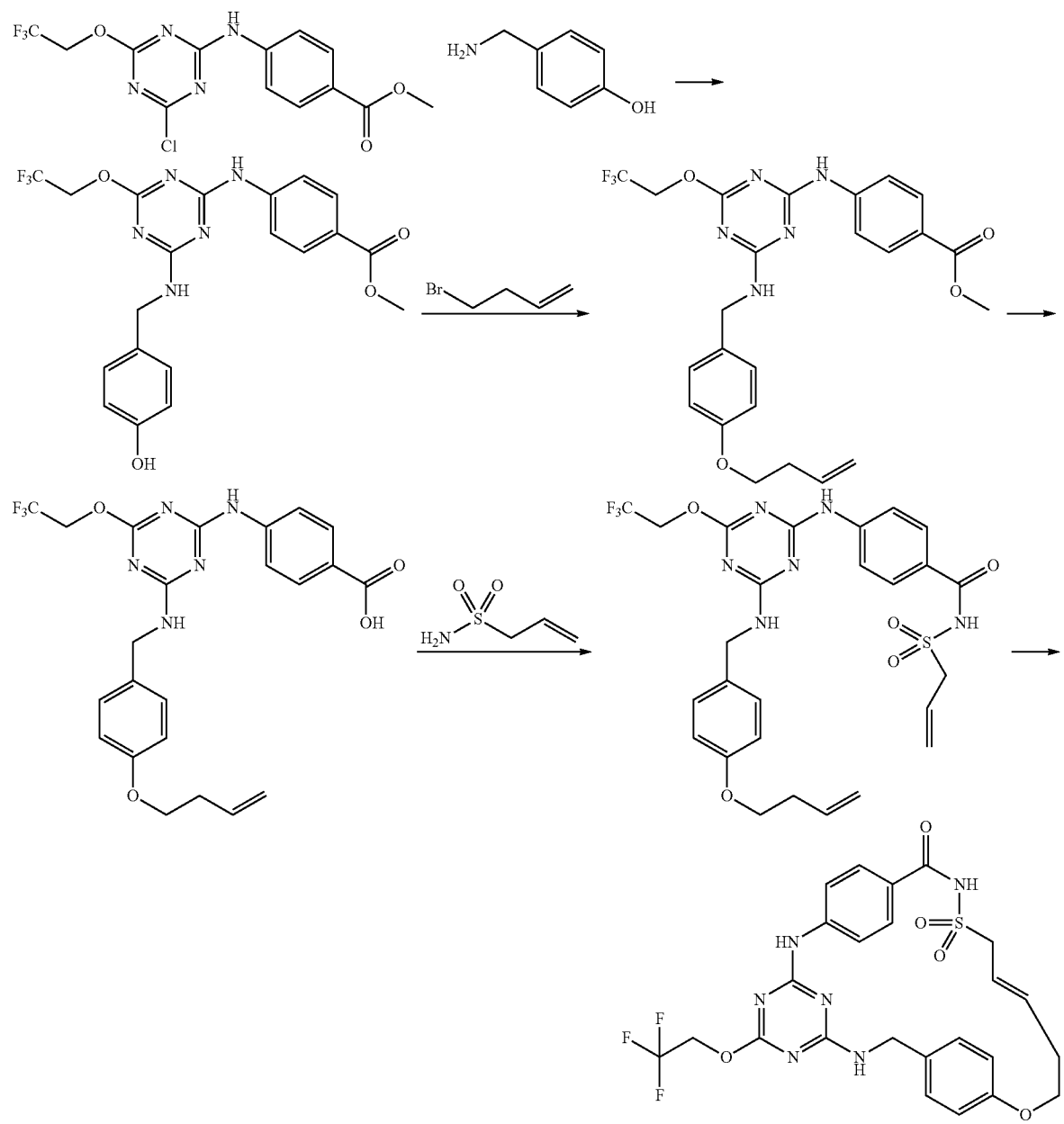

Step 1: To a solution of methyl 4-(4-chloro-6-(2,2,2-trifluoroethoxy)-1,3,5-triazin-2-ylamino)benzoate (intermediate from series 1000) (4 g, 5.07 mmol) in THF (30 mL) was added 4-(aminomethyl)phenol, HCl (0.891 g, 5.58 mmol) and Hunig's Base (3.54 mL, 20.29 mmol). The resulting mixture was stirred for 16 h. The reaction was then warmed to 65° C. for 2 h at which time the reaction became a homogeneous solution. The reaction was cooled and diluted with DCM and washed with water and brine. The organic layer was collected, dried over sodium sulfate, and concentrated under vacuum to give an oily residue. The residue was taken up in $Et_2O$ and a white solid ppt from the mixture which was filtered and dried to give methyl 4-(4-(4-hydroxybenzylamino)-6-(2,2,2-trifluoroethoxy)-1,3,5-triazin-2-ylamino)benzoate (1.2 g).

| methyl 4-(4-(4-hydroxybenzylamino)-6-(2,2,2-trifluoroethoxy)-1,3,5-triazin-2-ylamino)benzoate | |
|---|---|
| MS (M + H)+ Calcd. | 450.1 |
| MS (M + H)+ Observ. | 449.9 |
| Retention Time | 2.12 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient/Stop Time | 2 min/3 min |
| Flow Rate | 1 mL/min |
| Wavelength | 220 |
| Solvent Pair | Water-Methanol-TFA |
| Column | PHENOMENEX-LUNA 2.0 × 30 mm S10 3 μM |

Step 2: To a solution of methyl 4-(4-(4-hydroxybenzylamino)-6-(2,2,2-trifluoroethoxy)-1,3,5-triazin-2-ylamino)benzoate (100 mg, 0.223 mmol) in DMF (2 mL) was added 4-bromobut-1-ene (90 mg, 0.668 mmol) and Potassium Carbonate (154 mg, 1.113 mmol). The mixture was heated to 65° C. for 16 h. After cooling to rt, the mixture was diluted with EtOAc, washed with water, and brine. The organic layer was dried over $MgSO_4$ and concentrated. The crude product was purified by silica gel chromatography using 20-40% EtOAc/Hexanes to give methyl 4-(4-(4-(but-3-enyloxy)benzylamino)-6-(2,2,2-trifluoroethoxy)-1,3,5-triazin-2-ylamino)benzoate (45 mg).

| methyl 4-(4-(4-(but-3-enyloxy)benzylamino)-6-(2,2,2-trifluoroethoxy)-1,3,5-triazin-2-ylamino)benzoate | |
|---|---|
| MS (M + H)+ Calcd. | 504.2 |
| MS (M + H)+ Observ. | 504.0 |
| Retention Time | 1.14 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: methyl 4-(4-(4-(but-3-enyloxy)benzylamino)-6-(2,2,2-trifluoroethoxy)-1,3,5-triazin-2-ylamino)benzoate (46 mg, 0.091 mmol) was dissolved in THF (2 mL). LiOH (10.94 mg, 0.457 mmol) and Water (2 mL) were added to the solution and the reaction was warmed to 60° C. for 16 h. The reaction was diluted with DCM and acidified with 1N HCl. The organic layer was collected, dried over sodium sulfate, and concentrated under vacuum to give 4-(4-(4-(but-3-enyloxy)benzylamino)-6-(2,2,2-trifluoroethoxy)-1,3,5-triazin-2-ylamino)benzoic acid (45 mg).

| 4-(4-(4-(but-3-enyloxy)benzylamino)-6-(2,2,2-trifluoroethoxy)-1,3,5-triazin-2-ylamino)benzoic acid | |
|---|---|
| MS (M + H)+ Calcd. | 490.2 |
| MS (M + H)+ Observ. | 490.0 |
| Retention Time | 1.04 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: 4-(4-(4-(but-3-enyloxy)benzylamino)-6-(2,2,2-trifluoroethoxy)-1,3,5-triazin-2-ylamino)benzoic acid (44 mg, 0.090 mmol), prop-2-ene-1-sulfonamide (13.07 mg, 0.108 mmol), HATU (51.3 mg, 0.135 mmol), and Hunig's Base (0.079 mL, 0.449 mmol) were stirred in DCM (3 mL) for 16 h. The solvent was removed and the crude material was purified by silica gel chromatography using EtOAc to give N-(allylsulfonyl)-4-(4-(4-(but-3-enyloxy)benzylamino)-6-(2,2,2-trifluoroethoxy)-1,3,5-triazin-2-ylamino)benzamide (45 mg).

| N-(allylsulfonyl)-4-(4-(4-(but-3-enyloxy)benzylamino)-6-(2,2,2-trifluoroethoxy)-1,3,5-triazin-2-ylamino)benzamide | |
|---|---|
| MS (M + H)+ Calcd. | 593.2 |
| MS (M + H)+ Observ. | 593.0 |
| Retention Time | 1.07 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: A solution of N-(allylsulfonyl)-4-(4-(4-(but-3-enyloxy)benzylamino)-6-(2,2,2-trifluoroethoxy)-1,3,5-triazin-2-ylamino)benzamide (70 mg, 0.118 mmol) in DCE (20 ml) was sparged with nitrogen for 30 min. and then HOVEYDA-GRUBBS CATALYST 2ND GENERATION (14.80 mg, 0.024 mmol) was added and the reaction heated to 80° C. for 16 h. The solvent was removed under vacuum and the crude material was purified by rev phase preparative HPLC using a gradient of 20-100% MeOH/water w/0.1% TFA modifier to give Example 3004. 1H NMR (400 MHz, DMSO-d$_6$) δ ppm 2.28-2.41 (m, 2H), 3.81 (t, J=5.3 Hz, 2H), 4.19 (d, J=7.5 Hz, 2H), 4.48 (d, J=5.3 Hz, 2H), 5.01 (q, J=9.2 Hz, 2H), 5.50-5.84 (m, 2H), 6.93 (d, J=8.8 Hz, 2H), 7.15 (d, J=8.5 Hz, 2H), 7.19-7.37 (m, 4H), 8.36-8.48 (m, 1H), 9.90 (s, 1H), 11.73 (s, 1H).

| Example 3004 | |
|---|---|
| MS (M + H)$^+$ Calcd. | 565.1 |
| MS (M + H)$^+$ Observ. | 565.0 |
| Retention Time | 0.96 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3005

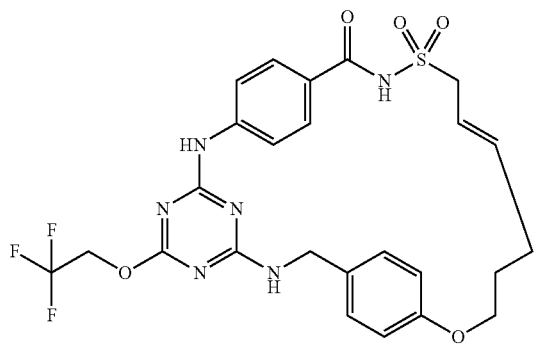 [SMILES: O=C1NS(=O)(=O)C/C=C/CCCOc2ccc(cc2)CNc2nc(nc(OCC(F)(F)F)n2)Nc2ccc1cc2]

The above compound was prepared by analogy to Example 3004. 1H NMR (400 MHz, DMSO-d$_6$) δ ppm 1.69-1.81 (m, 2H), 2.18 (q, J=5.8 Hz, 2H), 3.89 (t, J=7.4 Hz, 2H), 4.20 (d, J=7.0 Hz, 2H), 4.47 (d, J=5.5 Hz, 2H), 4.99 (q, J=9.0 Hz, 2H), 5.44-5.76 (m, 2H), 6.94-7.00 (m, 2H), 7.16-7.23 (m, 2H), 7.36 (d, J=9.0 Hz, 2H), 7.62 (d, J=8.8 Hz, 2H), 8.51 (t, J=5.5 Hz, 1H), 9.95 (s, 1H), 11.87 (s, 1H).

| Example 3005 | |
|---|---|
| MS (M + H)$^+$ Calcd. | 579.2 |
| MS (M + H)$^+$ Observ. | 579.0 |
| Retention Time | 0.98 min |
| LC Condition | |
| Solvent A | 100% Water:0.05% TFA |
| Solvent B | 100% ACN:0.05% TFA |
| Start % B | 2 |
| Final % B | 98 |

| Example 3005 | |
|---|---|
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3006

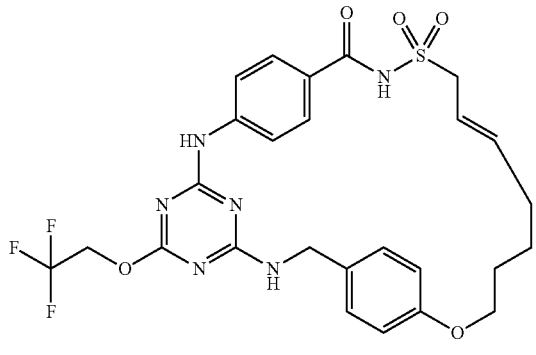 [SMILES: O=C1NS(=O)(=O)C/C=C/CCCCOc2ccc(cc2)CNc2nc(nc(OCC(F)(F)F)n2)Nc2ccc1cc2]

The above compound was prepared by analogy to Example 3004. 1H NMR (400 MHz, DMSO-d$_6$) δ ppm 1.27-1.41 (m, 2H), 1.53-1.65 (m, 2H), 1.90-2.00 (m, 2H), 3.97 (t, J=5.6 Hz, 2H), 4.18 (d, J=7.3 Hz, 2H), 4.45 (d, J=5.8 Hz, 2H), 5.00 (q, J=9.0 Hz, 2H), 5.37-5.76 (m, 2H), 6.94-7.01 (m, 2H), 7.17-7.25 (m, 2H), 7.39 (d, J=8.8 Hz, 2H), 7.58 (d, J=8.8 Hz, 2H), 8.53 (t, J=5.8 Hz, 1H), 9.98 (s, 1H), 11.79 (s, 1H).

| Example 3006 | |
|---|---|
| MS (M + H)$^+$ Calcd. | 593.0 |
| MS (M + H)$^+$ Observ. | 593.2 |
| Retention Time | 1.01 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 3007
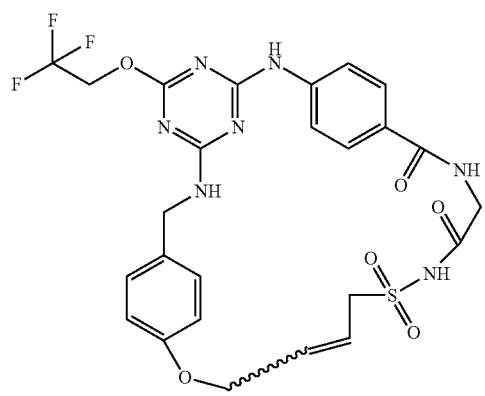
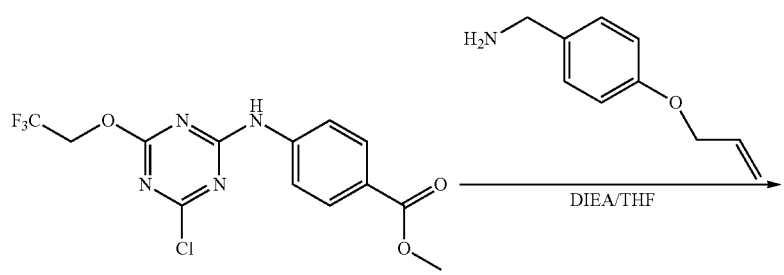
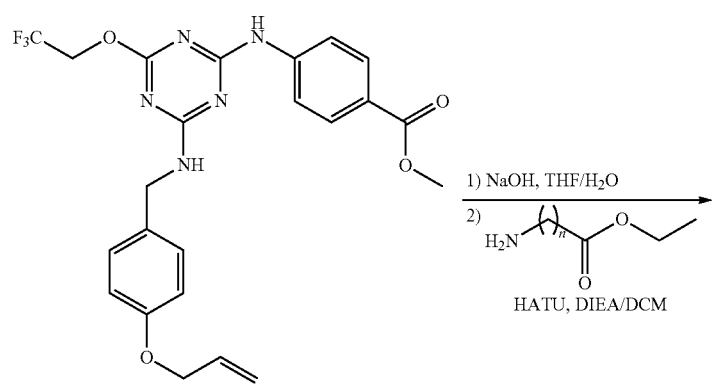
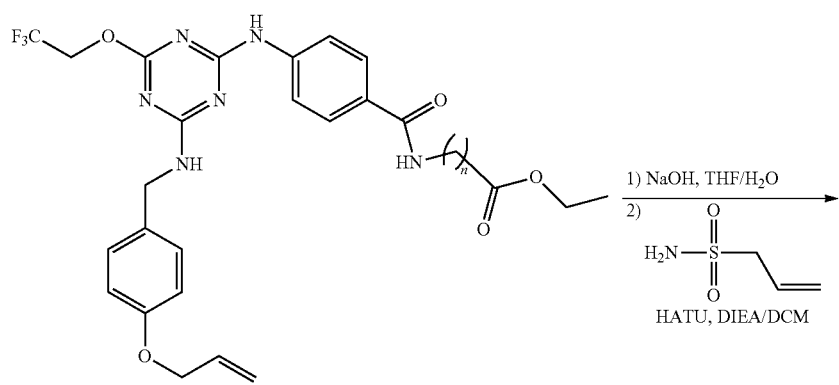
n = 0-4

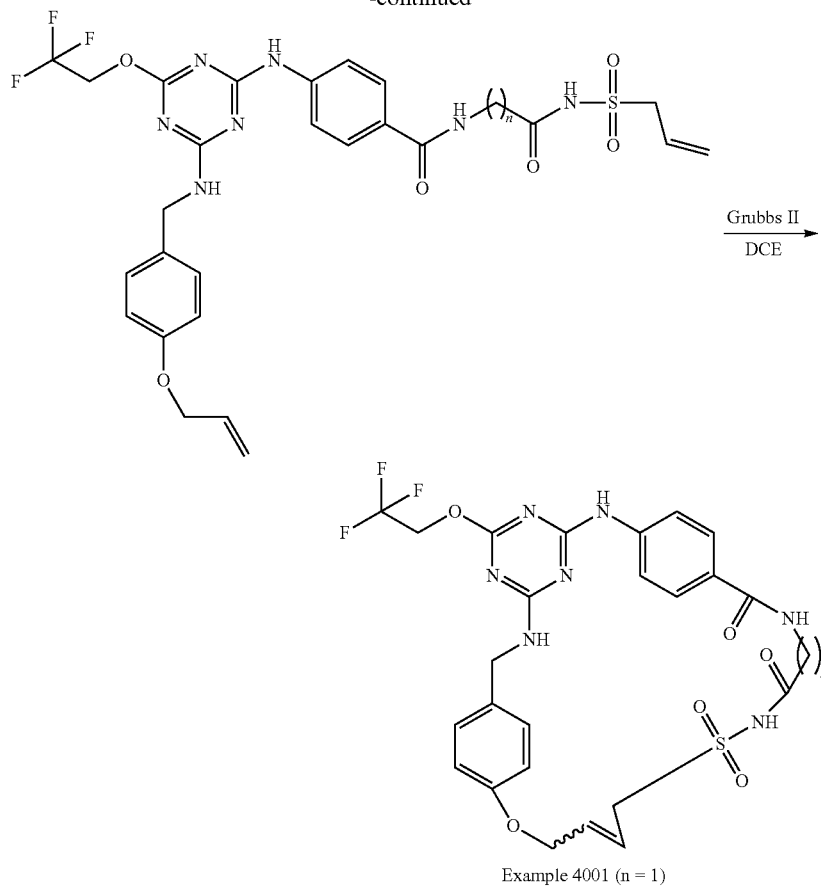

Example 4001 (n = 1)

Step 1: To a suspension of methyl 4-(4-chloro-6-(2,2,2-trifluoroethoxy)-1,3,5-triazin-2-ylamino)benzoate (500 mg, 1.38 mmol) in THF (5 mL) was added (4-(allyloxy)phenyl)methanamine (275 mg, 1.38 mmol) and iPr₂NEt (0.96 mL, 5.51 mmol). The mixture was stirred at room temperature for 16 hours. The solvent was removed under vacuum. The residue was purified via silica gel column (EtOAC/Hexanes=4:1) to give methyl 4-(4-(4-(allyloxy)benzylamino)-6-(2,2,2-trifluoroethoxy)-1,3,5-triazin-2-ylamino)benzoate (0.2 g, 30%) as a white solid.

| methyl 4-(4-(4-(allyloxy)benzylamino)-6-(2,2,2-trifluoroethoxy)-1,3,5-triazin-2-ylamino)benzoate | |
|---|---|
| MS (M + H)⁺ Calcd. | 490.5 |
| MS (M + H)⁺ Observ. | 490.1 |
| Retention Time | 1.09 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 2: To a suspension of methyl 4-(4-(2-(2-aminoethylamino)ethylamino)-6-(2,2,2-trifluoroethoxy)-1,3,5-triazin-2-ylamino)benzoate (200 mg, 0.41 mmol) in THF and water solution (6 mL, 1:1 ratio) was added NaOH (163 mg, 4.1 mmol). The mixture was heated to reflux for 16 hours. After cooling to room temperature, the reaction solution was acidified with 1N HCl. The product was extracted by EtOAc. The organic layer was washed with brine, dried over Na₂SO₄ and concentrated under vacuum. The crude product was used directly in the next step.

| 4-(4-(4-(allyloxy)benzylamino)-6-(2,2,2-trifluoroethoxy)-1,3,5-triazin-2-ylamino)benzoic acid | |
|---|---|
| MS (M + H)⁺ Calcd. | 476.42 |
| MS (M + H)⁺ Observ. | 475.99 |
| Retention Time | 2.21 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 2 min |
| Flow Rate | 1 mL/min |
| Wavelength | 220 |
| Solvent Pair | MeOH:Water:TFA |
| Column | Phenomenex 2.0 × 30 mm, 3 uM |

Step 3: To a solution of 4-(4-(4-(allyloxy)benzylamino)-6-(2,2,2-trifluoroethoxy)-1,3,5-triazin-2-ylamino)benzoic acid (100 mg, 0.21 mmol) in DCM (3 mL) was added glycine ethyl ester HCl (44 mg, 0.32 mmol), HATU (120 mg, 0.32 mol) and iPr₂NEt (0.11 mL, 0.63 mmol). The mixture was stirred at r.t. for 16 hours before all the solvents were removed under vacuum. All solvents were removed nuder vacuum and the residue was purified by silica gel column (EtOAC/Hexanes=40% to 60%) to give ethyl 2-(4-(4-(4-(allyloxy)benzylamino)-6-(2,2,2-trifluoroethoxy)-1,3,5-triazin-2-ylamino)benzamido)acetate (100 mg, 81%) as a white solid.

| ethyl 2-(4-(4-(4-(allyloxy)benzylamino)-6-(2,2,2-trifluoroethoxy)-1,3,5-triazin-2-ylamino)benzamido)acetate | |
|---|---|
| MS (M + H)+ Calcd. | 561.5 |
| MS (M + H)+ Observ. | 561.0 |
| Retention Time | 1.02 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 4: To a suspension of ethyl 2-(4-(4-(4-(allyloxy)benzylamino)-6-(2,2,2-trifluoroethoxy)-1,3,5-triazin-2-ylamino)benzamido)acetate (100 mg, 0.18 mmol) in THF and water solution (6 mL, 1:1 ratio) was added NaOH (29 mg, 0.71 mmol). The mixture was heated to reflux for 2 hours. After cooling to room temperature, the reaction solution was acidified with 1N HCl. The product was extracted by EtOAc. The organic layer was washed with brine, dried over Na$_2$SO$_4$ and concentrated under vacuum. The crude product was used directly in the next step.

| 2-(4-(4-(4-(allyloxy)benzylamino)-6-(2,2,2-trifluoroethoxy)-1,3,5-triazin-2-ylamino)benzamido)acetic acid | |
|---|---|
| MS (M + H)+ Calcd. | 533.5 |
| MS (M + H)+ Observ. | 533.0 |
| Retention Time | 0.95 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 5: To a solution of 2-(4-(4-(4-(allyloxy)benzylamino)-6-(2,2,2-trifluoroethoxy)-1,3,5-triazin-2-ylamino)benzamido)acetic acid (50 mg, 0.09 mmol) in DMF (2 mL) was added prop-2-ene-1-sulfonamide (17 mg, 0.14 mmol), HATU (71 mg, 0.19 mol) and iPr$_2$NEt (66 uL, 0.38 mmol). The mixture was stirred at r.t. for 16 hours before all the solvents were removed under vacuum. All solvents were removed nuder vacuum and the residue was purified by silica gel column (MeOH/DCM=5% to 10%) to give 4-(4-(4-(allyloxy)benzylamino)-6-(2,2,2-trifluoroethoxy)-1,3,5-triazin-2-ylamino)-N-(2-(allylsulfonamido)-2-oxoethyl)benzamide (53 mg, 89%) as a white solid.

| 4-(4-(4-(allyloxy)benzylamino)-6-(2,2,2-trifluoroethoxy)-1,3,5-triazin-2-ylamino)-N-(2-(allylsulfonamido)-2-oxoethyl)benzamide | |
|---|---|
| MS (M + H)+ Calcd. | 636.6 |
| MS (M + H)+ Observ. | 636.0 |
| Retention Time | 0.99 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 uM |

Step 6: To a solution of 4-(4-(4-(allyloxy)benzylamino)-6-(2,2,2-trifluoroethoxy)-1,3,5-triazin-2-ylamino)-N-(2-(allylsulfonamido)-2-oxoethyl)benzamide (30 mg, 0.05 mmol) in dichloroethane (15 ml) in a sealed tube, nitrogen was bubbled in for ½ hr. Under nitrogen GrubbsII catalyst (18 mg, 9.5 umol) was added. The sealed tube was sealed and the reaction mixture was stirred at 90° C. for 16 hrs. The solvent was evaporated and the residue was purified by preparative HPLC to afford 3.7 mg (12%) white solid as desired product. 1H NMR (400 MHz, DMSO-D6) δ ppm 3.88 (m, 2 H), 4.21 (m, 2H) 4.46 (m, 2H), 4.65 (m, 2H), 4.99 (m, 2H), 5.99-6.10 (m, 2H), 6.92 (d, J=8.78 Hz, 2H), 7.17-7.23 (m, 4H), 7.48 (d, J=8.53 Hz, 2H), 8.35 (s, broad, NH), 8.77 (s, broad, NH), 9.79 (s, broad, NH).

| Example 3007 | |
|---|---|
| MS (M + H)+ Calcd. | 608.6 |
| MS (M + H)+ Observ. | 608.1 |
| Retention Time | 2.51 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

Example 3008 and 3009

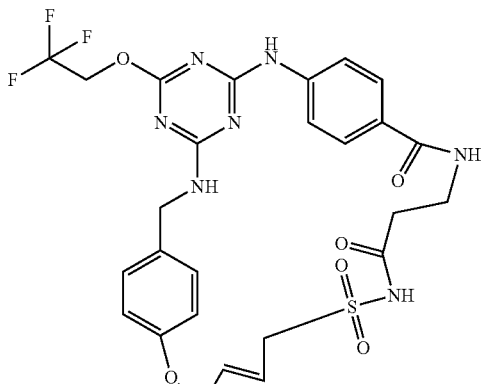

Example 3008

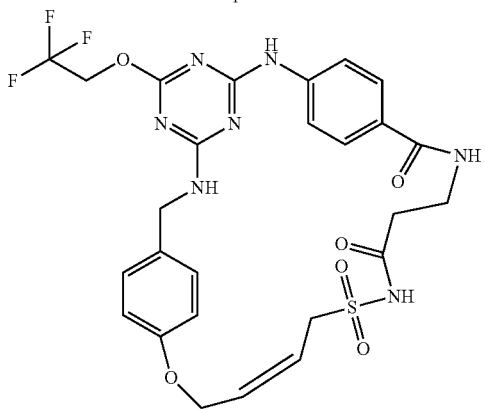

Example 3009

The Example 3008 and Example 3009 were synthesized following the procedure reported in Example 3007. ethyl 3-aminopropanoate HCl was used instead of glycine ethyl ester HCl in step 3.

Example 3008: 1H NMR (400 MHz, MeOD) δ ppm 2.63-2.71 (m, 2H), 3.72 (dd, J=6.02, 4.52 Hz, 2H), 4.13 (d, J=6.78 Hz, 2H), 4.54 (s, 2H), 4.61 (d, J=5.52 Hz, 2 H), 4.90 (m, 2H), 5.84-5.92 (m, 1H) 5.99 (m, 1H), 6.90-6.94 (d, J=8.78 Hz, 2H), 7.24 (d, J=8.78 Hz, 2H), 7.40 (ddd, J=9.29, 2.51, 2.26 Hz, 2H), 7.55-7.63 (d, J=9.04 Hz, 2H).

Example 3009: 1H NMR (400 MHz, MeOD) δ ppm 2.68 (m, 2H), 3.71 (m, 2H), 4.42 (d, J=6.78 Hz, 2), 4.52 (s, 2H), 4.90 (m, 2H), 4.70 (d, J=5.52 Hz, 2H), 5.75 (m, 1H), 6.11 (m, 1H), 7.03 (d, J=8.78 Hz, 2H), 7.32 (d, J=8.53 Hz, 2H), 7.33-7.39 (m, 2H), 7.62 (d, J=9.03 Hz, 2H).

| Example 3008 | |
|---|---|
| MS (M + H)+ Calcd. | 622.6 |
| MS (M + H)+ Observ. | 622.2 |
| Retention Time | 2.56 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

| Example 3009 | |
|---|---|
| MS (M + H)+ Calcd. | 622.6 |
| MS (M + H)+ Observ. | 622.2 |
| Retention Time | 2.64 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

Example 3010

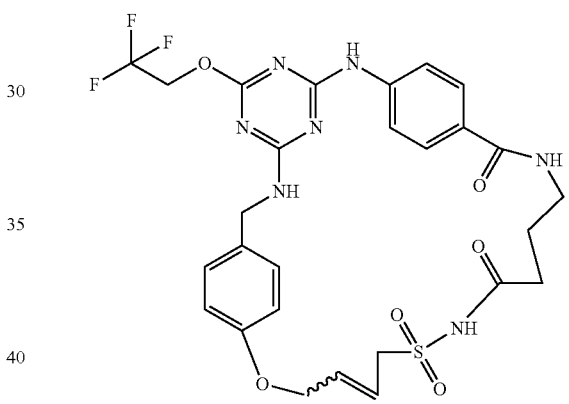

The Example 3010 was synthesized following the procedure reported in Example 3007. Ethyl 4-aminobutanoate HCl was used instead of glycine ethyl ester HCl in step 3. 1H NMR (400 MHz, MeOD) δ ppm 1.93 (m, 2H), 2.40 (m, 2H) 3.52 (m, 2 H), 4.09 (d, J=6.78 Hz, 2H), 4.53 (s, 2H), 4.58 (d, J=5.52 Hz, 2H), 4.90 (m, 2H) 5.99 (m, 1H) 6.04 (m, 1H), 6.97 (d, J=9.03 Hz, 2H), 7.26 (d, J=8.78 Hz, 2H), 7.32 (d, J=8.78 Hz, 2H), 7.55 (d, J=8.78 Hz, 2H).

| Example 3010 | |
|---|---|
| MS (M + H)+ Calcd. | 636.6 |
| MS (M + H)+ Observ. | 636.2 |
| Retention Time | 2.55 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

Example 3011

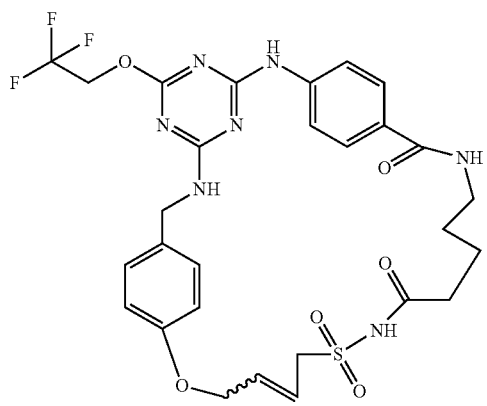 [SMILES: O=C1CCCCNC(=O)c2ccc(cc2)Nc2nc(nc(OCC(F)(F)F)n2)NCc2ccc(cc2)OCC=CCS(=O)(=O)N1]

The Example 3011 was synthesized following the procedure reported in Example 3007. Ethyl 5-aminopentanoate was used instead of glycine ethyl ester HCl in step 3.

1H NMR (400 MHz, DMSO-D6) δ ppm 1.53 (m, 4H), 2.34 (m, 2H), 3.50 (m, 2H), 4.19 (m, 2H), 4.41 (d, J=6.27 Hz, 2H), 4.57 (m, 2H), 4.98 (m, 2H), 5.78 (m, 1H), 6.02 (m, 1H) 6.52 (s, broad, NH), 6.97 (d, J=8.53 Hz, 2H), 7.24 (d, J=8.78 Hz, 2H), 7.33 (d, J=8.53 Hz, 2H), 7.57 (d, J=8.78 Hz, 2H), 8.28 (s, broad, NH), 8.44 (s, broad, NH).

| | Example 3011 |
|---|---|
| MS (M + H)$^+$ Calcd. | 650.6 |
| MS (M + H)$^+$ Observ. | 650.2 |
| Retention Time | 2.61 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

Example 1019

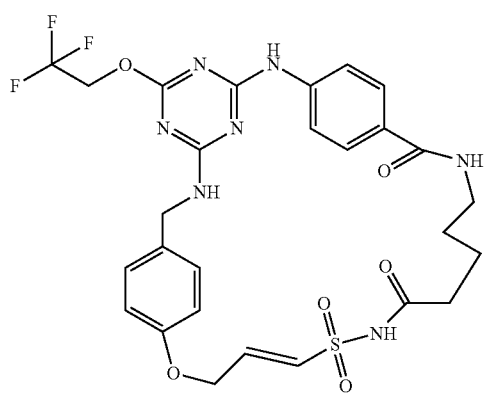 [SMILES: O=C1CCCCNC(=O)c2ccc(cc2)Nc2nc(nc(OCC(F)(F)F)n2)NCc2ccc(cc2)OC/C=C/S(=O)(=O)N1]

The Example 3012 was synthesized following the procedure reported in Example 3007. Ethyl 5-aminopentanoate and ethenesulfonamide were used instead of glycine ethyl ester HCl and prop-2-ene-1-sulfonamide in step 3 and step 5.

1H NMR (400 MHz, DMSO-D6) δ ppm 1.67 (m, 4H), 2.34 (m, 2H), 4.57 (s, 2H), 4.78 (m, 2H), 4.85 (m, 4H), 6.84 (m, 1H), 6.95 (m, 1H), 7.01 (d, J=8.53 Hz, 2H), 7.31 (d, J=8.78 Hz, 2H), 7.45 (d, J=8.53 Hz, 2H), 7.54 (d, J=8.78 Hz, 2H).

Example 4001

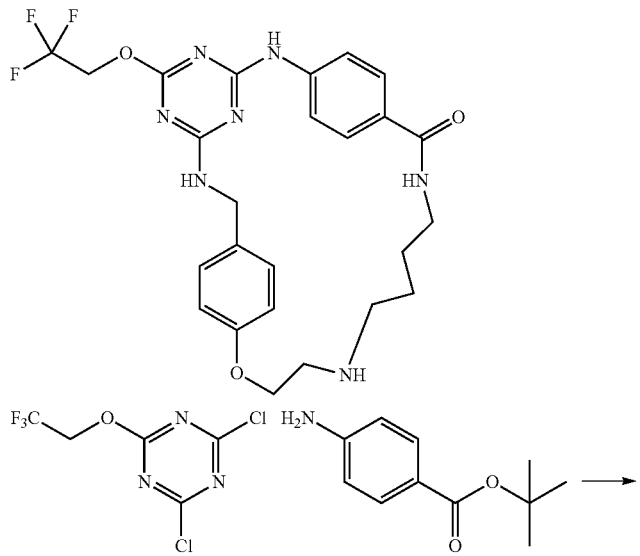

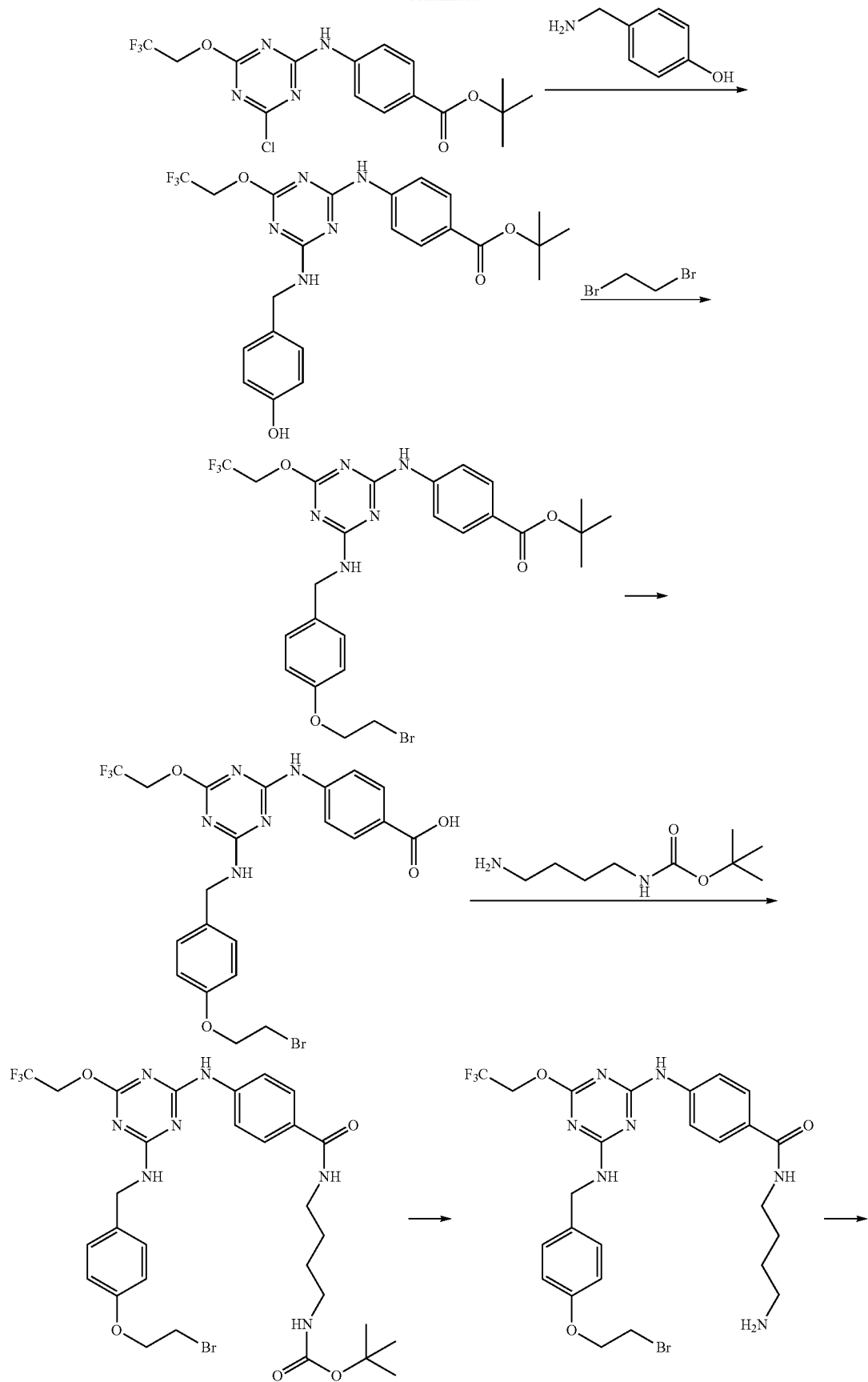

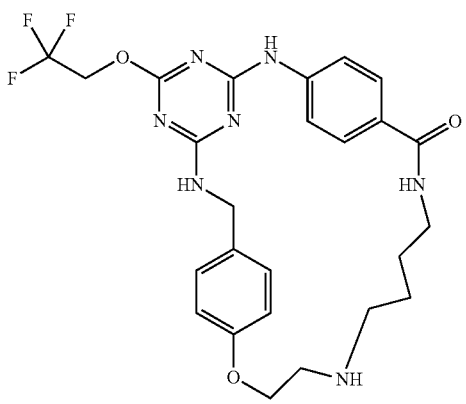

Step 1: To a solution of 2,4-dichloro-6-(2,2,2-trifluoroethoxy)-1,3,5-triazine (10 g, 40.3 mmol) in THF (100 mL) was added tert-butyl 4-aminobenzoate (7.79 g, 40.3 mmol) and Hunig's Base (7.04 mL, 40.3 mmol). The resulting mixture was stirred for 16 h. After removal of most THF, the precipitate was filtered and washed with THF, then washed with water and dried to give the product tert-butyl 4-(4-chloro-6-(2,2,2-trifluoroethoxy)-1,3,5-triazin-2-ylamino)benzoate (10.6 g) as white solid.

| tert-butyl 4-(4-chloro-6-(2,2,2-trifluoroethoxy)-1,3,5-triazin-2-ylamino)benzoate | |
|---|---|
| MS (M + H)+ Calcd. | 405.1 |
| MS (M + H)+ Observ. | 405.0 |
| Retention Time | 1.15 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 2: To a suspension of tert-butyl 4-(4-chloro-6-(2,2,2-trifluoroethoxy)-1,3,5-triazin-2-ylamino)benzoate (10 g, 24.71 mmol) and Hunig's Base (8.63 mL, 49.4 mmol) in THF (100 mL) was added 4-(aminomethyl)phenol (3.19 g, 25.9 mmol). The resulting mixture was refluxed for 1 hour. After cooling to rt, the solvent was removed and the crude product was purified by silica gel chromatography using 20-40-100% EtOAc/Hexanes to give tert-butyl 4-((4-((4-hydroxybenzyl)amino)-6-(2,2,2-trifluoroethoxy)-1,3,5-triazin-2-yl)amino)benzoate (10.3 g, 85%) as white solid.

| tert-butyl 4-((4-((4-hydroxybenzyl)amino)-6-(2,2,2-trifluoroethoxy)-1,3,5-triazin-2-yl)amino)benzoate | |
|---|---|
| MS (M + H)+ Calcd. | 492.46 |
| MS (M + H)+ Observ. | 492.04 |
| Retention Time | 3.02 min |
| LC Condition | |
| Solvent A | 90% Water-10% Methanol-0.1% TFA |
| Solvent B | 10% Water-90% Methanol-0.1% TFA |
| Start % B | 0 |
| Final % B | 100 |
| Gradient/Stop Time | 3 min/4 min |
| Flow Rate | 1 mL/min |
| Wavelength | 220 |
| Solvent Pair | Water-Methanol-TFA |
| Column | PHENOMENEX-LUNA 2.0 × 30 mm S10 3 μM |

Step 3: To a solution of tert-butyl 4-((4-((4-hydroxybenzyl)amino)-6-(2,2,2-trifluoroethoxy)-1,3,5-triazin-2-yl)amino)benzoate (4 g, 8.14 mmol), 1,2-dibromoethane (2.1 mL, 24.42 mmol) in acetone (20 mL) was added potassium carbonate (4.50 g, 32.6 mmol). The resulting solution was stirred for 16 h at reflux. Add another 4 eq of potassium carbonate and 3 eq of 1,2-dibromoethane. The mixture was refluxed for another 7 hs. After cooling to rt, the white solid was filtered and washed with actone. The filtrate was concentrated and purified by Biotage eluting with 20-33% ethyl acetate in hexane to give tert-butyl 4-((4-((4-(2-bromoethoxy)benzyl)amino)-6-(2,2,2-trifluoroethoxy)-1,3,5-triazin-2-yl)amino)benzoate (2.91 g, 60%) as white solid.

| tert-butyl 4-((4-((4-(2-bromoethoxy)benzyl)amino)-6-(2,2,2-trifluoroethoxy)-1,3,5-triazin-2-yl)amino)benzoate | |
|---|---|
| MS (M + H)+ Calcd. | 598.4 |
| MS (M + H)+ Observ. | 598.2 |
| Retention Time | 2.43 min |
| LC Condition | |
| Solvent A | 95% Water-5% Methanol-10 mM Ammonium Actetate |
| Solvent B | 5% Water-95% Methanol-10 mM ammonium actetate |
| Start % B | 0 |
| Final % B | 100 |
| Gradient/Stop Time | 2 min/3 min |
| Flow Rate | 1 mL/min |
| Wavelength | 220 |
| Solvent Pair | Water-Methanol-Ammonium Actetate |
| Column | PHENOMENEX-LUNA C18 30 × 2 mm 3 μM |

Step 4: Tert-butyl 4-((4-((4-(2-bromoethoxy)benzyl)amino)-6-(2,2,2-trifluoroethoxy)-1,3,5-triazin-2-yl)amino)benzoate (2.91 g, 4.85 mmol) and 4 N HCl in Dioxane (20 mL) were stirred for 16 hs then concentrated under vacuum to give 4-((4-((4-(2-bromoethoxy)benzyl)amino)-6-(2,2,2-trifluoroethoxy)-1,3,5-triazin-2-yl)amino)benzoic acid which was carried to the next step without purification.

| 4-((4-((4-(2-bromoethoxy)benzyl)amino)-6-(2,2,2-trifluoroethoxy)-1,3,5-triazin-2-yl)amino)benzoic acid | |
|---|---|
| MS (M + H)+ Calcd. | 542.0 |
| MS (M + H)+ Observ. | 544.1 |
| Retention Time | 1.99 min |
| LC Condition | |
| Solvent A | 95% Water-5% Methanol-10 mM Ammonium Actetate |
| Solvent B | 5% Water-95% Methanol-10 mM ammonium actetate |
| Start % B | 0 |
| Final % B | 100 |
| Gradient/Stop Time | 2 min/3 min |
| Flow Rate | 1 mL/min |
| Wavelength | 220 |
| Solvent Pair | Water-Methanol-Ammonium Actetate |
| Column | PHENOMENEX-LUNA C18 30 × 2 mm 3 µM |

Step 5: 4-((4-((4-(2-bromoethoxy)benzyl)amino)-6-(2,2,2-trifluoroethoxy)-1,3,5-triazin-2-yl)amino)benzoic acid (2.63 g, 4.85 mmol), tert-butyl (4-aminobutyl)carbamate (1.37 g, 7.27 mmol), HATU (5.53 g, 14.55 mmol), and Hunig's Base (4.24 mL, 24.25 mmol) were stirred in DCM (20 mL) for 3 h. The solvent was removed and the crude material was purified by silica gel chromatography eluting with 20-40-80% ethyl acetate in hexane to give tert-butyl (4-(4-((4-((4-(2-bromoethoxy)benzyl)amino)-6-(2,2,2-trifluoroethoxy)-1,3,5-triazin-2-yl)amino)benzamido)butyl)carbamate (3.0 g, 87%) as product.

| tert-butyl (4-(4-((4-((4-(2-bromoethoxy)benzyl)amino)-6-(2,2,2-trifluoroethoxy)-1,3,5-triazin-2-yl)amino)benzamido)butyl)carbamate | |
|---|---|
| MS (M + H)+ Calcd. | 713.6 |
| MS (M + H)+ Observ. | 714.2 |
| Retention Time | 1.05 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 µm |

Step 6: Tert-butyl (4-(4-((4-((4-(2-bromoethoxy)benzyl)amino)-6-(2,2,2-trifluoroethoxy)-1,3,5-triazin-2-yl)amino)benzamido)butyl)carbamate (3.0 g, 4.21 mmol) was stirred in TFA/DCM (1:1) solution (20 mL) for 1 h. The solution was concentrated under vacuum to give N-(4-aminobutyl)-4-((4-((4-(2-bromoethoxy)benzyl)amino)-6-(2,2,2-trifluoroethoxy)-1,3,5-triazin-2-yl)amino)benzamide which was carried to the next step without purification.

| N-(4-aminobutyl)-4-((4-((4-(2-bromoethoxy)benzyl)amino)-6-(2,2,2-trifluoroethoxy)-1,3,5-triazin-2-yl)amino)benzamide | |
|---|---|
| MS (M + H)+ Calcd. | 613.4 |
| MS (M + H)+ Observ. | 614.1 |
| Retention Time | 0.88 min |

| N-(4-aminobutyl)-4-((4-((4-(2-bromoethoxy)benzyl)amino)-6-(2,2,2-trifluoroethoxy)-1,3,5-triazin-2-yl)amino)benzamide | |
|---|---|
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 µm |

Step 7: To a solution of N-(4-aminobutyl)-4-((4-((4-(2-bromoethoxy)benzyl)amino)-6-(2,2,2-trifluoroethoxy)-1,3,5-triazin-2-yl)amino)benzamide (500 mg, 0.82 mmol) in ACN (10 mL) was added potassium carbonate (451 mg, 3.27 mmol). The mixture was heated in microwave reactor at 130° C. for 1 h. After cooling to rt, the mixture was filtered and white solid was washed with ACN. Took small amount of filtrate and run pre-HPLC separation to give Compound 4001 (2E)-5-(2,2,2-trifluoroethoxy)-14-oxa-2,4,6,8,17,22,31-heptaazatetracyclo[22.2.2.2~10,13~.0.1~3,7~]hentriaconta-1(26),2,4,7(31),10,12,24,27,29-nonaen-23-one as white solid. The rest filtrate in ACN was used directly in the next step reaction without further purification. $^1$H NMR (400 MHz, METHANOL-$d_4$) δ 7.45 (d, J=9.0 Hz, 2H), 7.39 (d, J=9.0 Hz, 2H), 7.28 (d, J=8.8 Hz, 2H), 7.02 (d, J=8.8 Hz, 2H), 4.86 (m, 2H), 4.59 (s, 2H), 4.28 (t, 2H), 3.68 (m, 2H), 3.52 (m, 2H), 3.39 (m, 2H), 1.77-1.74 (m, 4H).

| (2E)-5-(2,2,2-trifluoroethoxy)-14-oxa-2,4,6,8,17,22,31-heptaazatetracyclo[22.2.2.2~10,13~.1~3,7~]hentriaconta-1(26),2,4,7(31),10,12,24,27,29-nonaen-23-one | |
|---|---|
| MS (M + H)+ Calcd. | 532.2 |
| MS (M + H)+ Observ. | 532.1 |
| Retention Time | 0.77 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 µm |

Example 4002

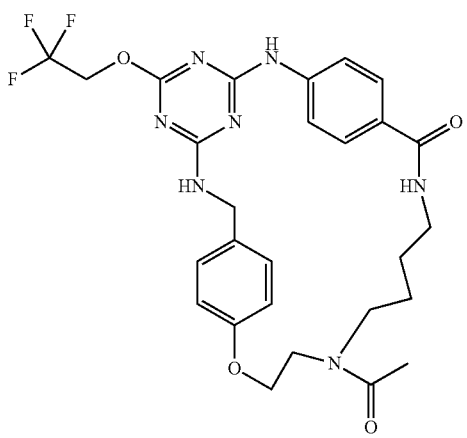 [SMILES: CC(=O)N1CCCCNC(=O)c2ccc(cc2)Nc2nc(nc(OCC(F)(F)F)n2)NCc2ccc(cc2)OCC1]

To a solution of Compound 4001 (20 mg, 0.038 mmol) in ACN (1 mL) was added acetyl chloride (8.9 mg, 0.11 mmol) and diisopropylethylamine (DIEA) (33 uL, 0.19 mmol) at room temperature. The resulting mixture was stirred at room temperature for 1 minute. The reaction mixture was quenched by MeOH then purified by preparative HPLC to afford 2.2 mg (10%) of the Compound 4002. LC-MS: 574.12 (M+H). $^1$H NMR (400 MHz, METHANOL-$d_4$) δ 7.51-7.23 (m, 6H), 6.97 (m, 2H), 4.86 (m, 2H), 4.55 (d, J=7.0 Hz, 2H), 4.20-4.02 (m, 2H), 3.82-3.66 (m, 2H), 3.59-3.38 (m, 2H), 3.35 (m, 2H), 2.18 (s, 3H), 1.85-1.57 (m, 4H).

Example 4003

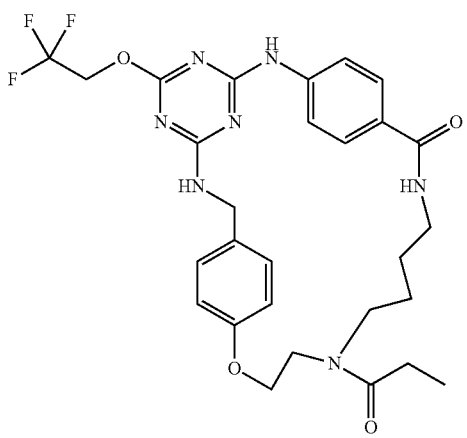 [SMILES: CCC(=O)N1CCCCNC(=O)c2ccc(cc2)Nc2nc(nc(OCC(F)(F)F)n2)NCc2ccc(cc2)OCC1]

The Example 4003 was prepared following the procedure reported in Example 4002. Propionyl chloride was used instead of acetyl chloride. LC-MS: 588.15 (M+H).

$^1$H NMR (400 MHz, METHANOL-$d_4$) δ 7.51-7.23 (m, 6H), 6.96 (dd, J=8.7, 4.9 Hz, 2H), 4.86 (m, 2H), 4.55 (d, J=5.5 Hz, 2H), 4.17-4.03 (m, 2H), 3.81-3.66 (m, 2H), 3.58-3.40 (m, 4H), 2.59-2.36 (m, 2H), 1.75-1.66 (m, 4H), 1.14 (td, J=7.4, 4.5 Hz, 3H).

Example 4004

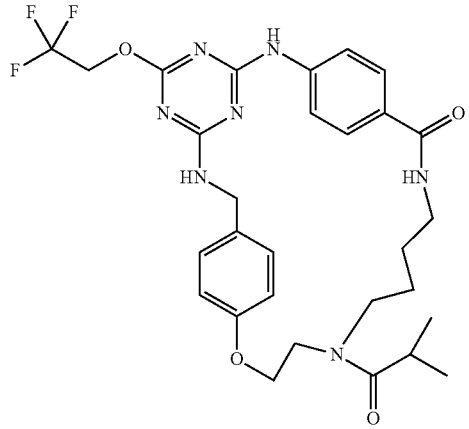 [SMILES: CC(C)C(=O)N1CCCCNC(=O)c2ccc(cc2)Nc2nc(nc(OCC(F)(F)F)n2)NCc2ccc(cc2)OCC1]

The Example 4004 was prepared following the procedure reported in Example 4002. Isobutyryl chloride was used instead of acetyl chloride. LC-MS: 602.19 (M+H).

$^1$H NMR (400 MHz, METHANOL-$d_4$) δ 7.52-7.23 (m, 6H), 6.96 (dd, J=8.5, 5.0 Hz, 2H), 4.86 (m, 2H), 4.55 (d, J=5.8 Hz, 2H), 4.09 (d, J=17.1 Hz, 2H), 3.81 (s, 1H), 3.69 (s, 1H), 3.58-3.41 (m, 2H), 3.35 (m, 2H), 3.12-2.93 (m, 1H), 1.12 (m, 4H), 1.14 (t, 6H).

Example 4005

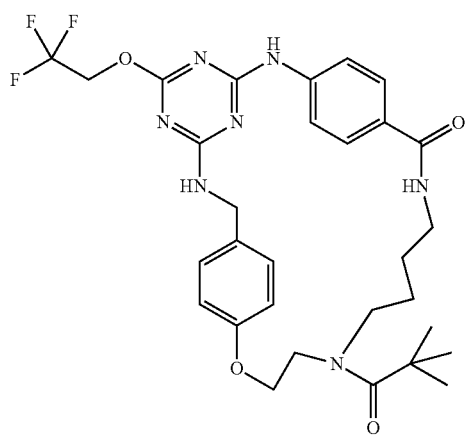 [SMILES: CC(C)(C)C(=O)N1CCCCNC(=O)c2ccc(cc2)Nc2nc(nc(OCC(F)(F)F)n2)NCc2ccc(cc2)OCC1]

The Example 4005 was prepared following the procedure reported in Example 4002. Pivaloyl chloride was used instead of acetyl chloride. LC-MS: 616.21 (M+H).

$^1$H NMR (400 MHz, METHANOL-$d_4$) δ 7.56-7.42 (m, 2H), 7.35 (d, J=8.5 Hz, 2H), 7.26 (d, J=8.8 Hz, 2H), 6.96 (d,

J=8.8 Hz, 2H), 4.86 (m, 2H), 4.55 (s, 2H), 4.13 (t, J=7.0 Hz, 2H), 3.73 (m, 2H), 3.62-3.46 (m, 4H), 1.76 (m, 2H), 1.66 (m, 2H), 1.32 (s, 9H).

Example 4006

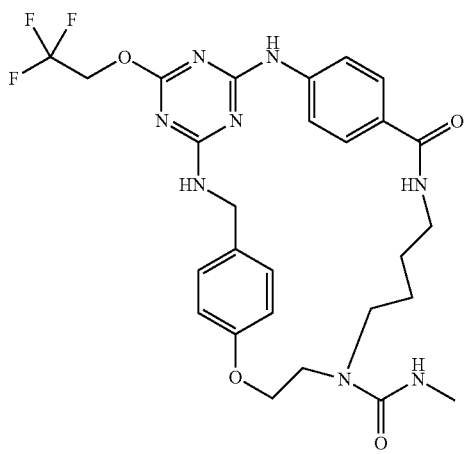 [SMILES: CNC(=O)N1CCCCNC(=O)c2ccc(cc2)Nc2nc(nc(OCC(F)(F)F)n2)NCc2ccc(cc2)OCC1]

To a solution of Compound 4001 (20 mg, 0.038 mmol) in ACN (1 mL) was added isocyanatomethane (4.3 mg, 0.075 mmol) at room temperature. The resulting mixture was stirred at room temperature for 30 minutes. The reaction mixture was quenched by MeOH then purified by preparative HPLC to afford 2.7 mg (12%) of the Compound 4006. LC-MS: 589.21 (M+H). $^1$H NMR (400 MHz, METHANOL-$d_4$) δ 7.52-7.41 (d, J=9.0 Hz, 2H), 7.39-7.31 (d, J=9.0 Hz, 2H), 7.29-7.22 (d, J=8.8 Hz, 2H), 7.02-6.90 (d, J=8.8 Hz, 2H), 4.86 (m, 2H), 4.54 (s, 2H), 4.06 (t, 2H), 3.64 (t, 2H), 3.57-3.44 (m, 4H), 2.75 (s, 3H), 1.64 (m, 4H).

Example 4007

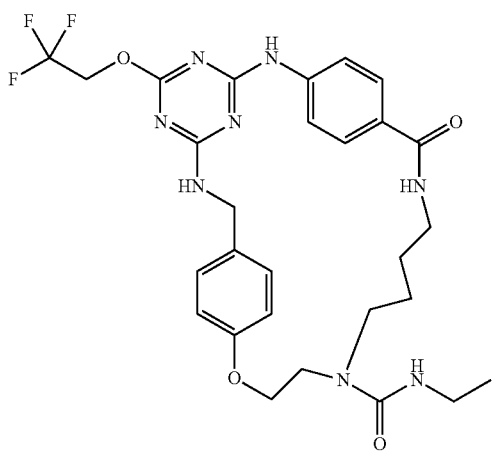 [SMILES: CCNC(=O)N1CCCCNC(=O)c2ccc(cc2)Nc2nc(nc(OCC(F)(F)F)n2)NCc2ccc(cc2)OCC1]

The Example 4007 was prepared following the procedure reported in Example 4006. Isocyanatoethane was used instead of isocyanatomethane. LC-MS: 603.21 (M+H).

$^1$H NMR (400 MHz, METHANOL-$d_4$) δ 7.52-7.42 (d, J=8.8 Hz, 2H), 7.40-7.33 (d, J=8.5 Hz, 2H), 7.29-7.21 (d, J=8.5 Hz, 2H), 7.01-6.92 (d, J=8.8 Hz, 2H), 4.86 (m, 2H), 4.55 (s, 2H), 4.07 (t, J=6.7 Hz, 2H), 3.64 (t, J=6.8 Hz, 2H), 3.55-3.45 (m, 2H), 3.32 (m, 2H), 3.22 (m, 2H), 1.68 (m, 4H), 1.13 (t, J=7.2 Hz, 3H).

Example 4008

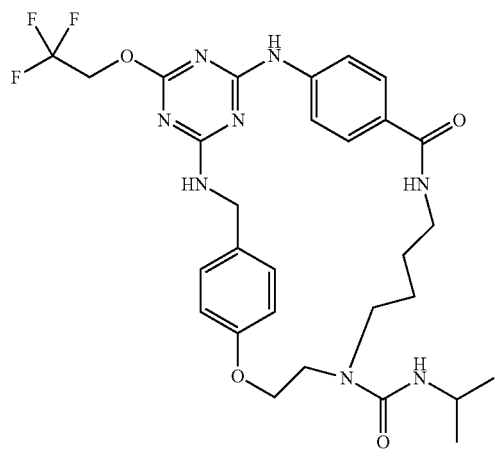 [SMILES: CC(C)NC(=O)N1CCCCNC(=O)c2ccc(cc2)Nc2nc(nc(OCC(F)(F)F)n2)NCc2ccc(cc2)OCC1]

The Example 4008 was prepared following the procedure reported in Example 4006. 2-Isocyanatopropane was used instead of isocyanatomethane. LC-MS: 617.23 (M+H). $^1$H NMR (400 MHz, METHANOL-$d_4$) δ 7.53-7.43 (d, J=8.8 Hz, 2H), 7.41-7.32 (d, J=9.0 Hz, 2H), 7.30-7.17 (d, J=8.8 Hz, 2H), 7.04-6.90 (d, J=8.8 Hz, 2H), 4.86 (m, 2H), 4.55 (s, 2H), 4.07 (t, J=6.5 Hz, 2H), 3.97-3.84 (m, 1H), 3.64 (t, J=6.7 Hz, 2H), 3.50 (d, J=5.0 Hz, 2H), 3.45-3.32 (m, 2H), 1.66 (m, 4H), 1.17 (d, J=6.8 Hz, 6H).

Example 4009

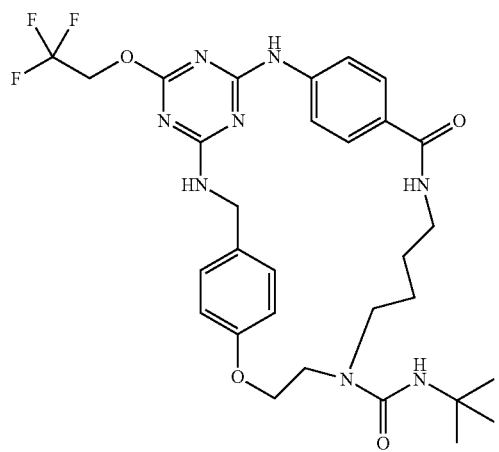 [SMILES: CC(C)(C)NC(=O)N1CCCCNC(=O)c2ccc(cc2)Nc2nc(nc(OCC(F)(F)F)n2)NCc2ccc(cc2)OCC1]

The Example 4009 was prepared following the procedure reported in Example 4006. 2-Isocyanato-2-methylpropane was used instead of isocyanatomethane. LC-MS: 631.30 (M+H). $^1$H NMR (400 MHz, METHANOL-$d_4$) δ 7.51-7.41 (d, J=8.8 Hz, 2H), 7.39-7.30 (d, J=9.0 Hz, 2H), 7.28-7.23 (d, J=8.8 Hz, 2H), 7.02-6.85 (d, J=8.5 Hz, 2H), 4.86 (m, 2H), 4.55 (s, 2H), 4.07 (t, J=6.1 Hz, 2H), 3.62 (t, J=6.1 Hz, 2H), 3.52-3.41 (m, 2H), 3.40-3.32 (m, 2H), 1.65 (m, 4H), 1.42-1.20 (s, 9H).

Example 4013

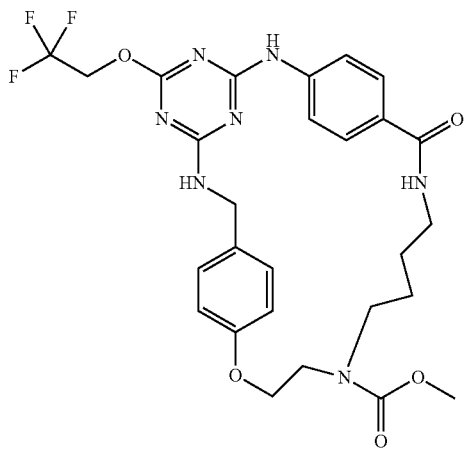 [SMILES: COC(=O)N1CCCCNC(=O)c2ccc(cc2)Nc2nc(nc(OCC(F)(F)F)n2)NCc2ccc(cc2)OCC1]

To a solution of Compound 4001 (20 mg, 0.038 mmol) in ACN (1 mL) was added methyl carbonochloridate (10.7 mg, 0.11 mmol) and diisopropylethylamine (DIEA) (33 uL, 0.19 mmol) at room temperature. The resulting mixture was stirred at room temperature for 2 minute. The reaction mixture was quenched by MeOH then purified by preparative HPLC to afford 1.1 mg (5%) of the Compound 4013. LC-MS: 590.16 (M+H). $^1$H NMR (400 MHz, METHANOL-$d_4$) δ 7.48 (d, J=8.8 Hz, 2H), 7.33 (d, J=8.8 Hz, 2H), 7.30-7.22 (d, J=9.0 Hz, 2H), 7.02-6.93 (d, J=8.5 Hz, 2H), 4.86 (m, 2H), 4.54 (s, 2H), 4.06 (t, 2H), 3.73 (s., 3H), 3.64 (m, 2H), 3.50 (m, 2H), 3.15 (m, 2H), 1.72 (m, 2H), 1.63 (m, 2H).

Example 4014

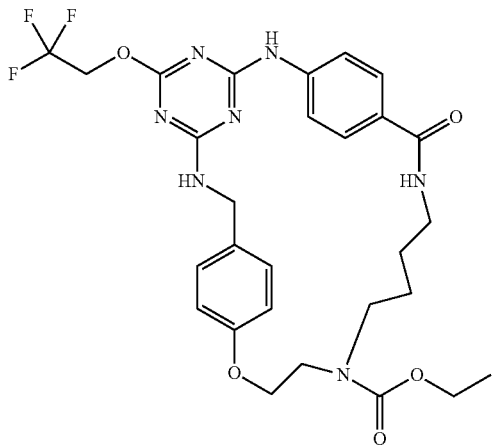 [SMILES: CCOC(=O)N1CCCCNC(=O)c2ccc(cc2)Nc2nc(nc(OCC(F)(F)F)n2)NCc2ccc(cc2)OCC1]

The Example 4014 was prepared following the procedure reported in Example 4013. Ethyl carbonochloridate was used instead of methyl carbonochloridate. LC-MS: 604.22 (M+H).

$^1$H NMR (400 MHz, METHANOL-$d_4$) δ 7.55-7.46 (d, J=8.8 Hz, 2H), 7.39-7.31 (d, J=8.8 Hz, 2H), 7.29-7.23 (d, J=8.3 Hz, 2H), 7.02-6.92 (d, J=8.3 Hz, 2H), 4.86 (m, 2H), 4.54 (s, 2H), 4.16 (m, 4H), 3.63 (t, J=6.9 Hz, 2H), 3.50 (m, 2H), 3.41 (m, 2H), 1.70 (m 2H), 1.64 (m, 2H), 1.29 (t, J=7.0 Hz, 3H).

Example 4015

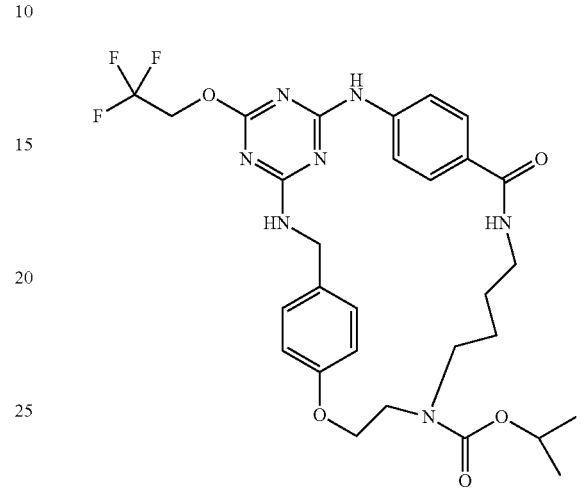

The Example 4015 was prepared following the procedure reported in Example 4013. Isopropyl carbonochloridate was used instead of methyl carbonochloridate. LC-MS: 618.21 (M+H). $^1$H NMR (400 MHz, METHANOL-$d_4$) δ 7.54-7.45 (d, J=8.8 Hz, 2H), 7.38-7.31 (d, J=8.8 Hz, 2H), 7.29-7.20 (d, J=7.8 Hz, 2H), 7.02-6.90 (d, J=7.0 Hz, 2H), 4.86 (m, 2H), 4.54 (s, 2H), 4.06 (t, J=6.9 Hz, 2H), 3.62 (m, 2H), 3.55-3.35 (m, 5H), 1.70 (m, 2H), 1.64 (m, 2H), 1.29 (d, J=6.3 Hz, 6H).

Example 4016

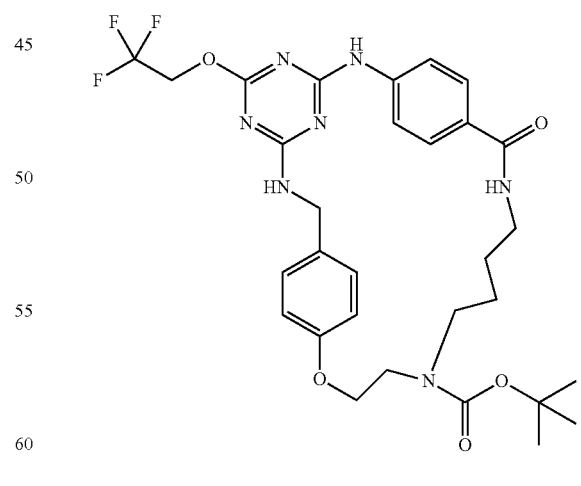

The Example 4016 was prepared following the procedure reported in Example 4013. Di-tert-butyl dicarbonate was used instead of methyl carbonochloridate. LC-MS: 632.3 (M+H). $^1$H NMR (400 MHz, METHANOL-$d_4$) δ 7.50 (d, J=8.5 Hz, 2H), 7.33 (d, J=8.8 Hz, 2H), 7.25 (d, J=7.0 Hz, 2H), 6.96 (d, J=8.5 Hz, 2H), 4.86 (m, 2H), 4.54 (s, 2H), 4.09-4.01 (m, 2H), 3.63-3.54 (m, 2H), 3.50 (m, 4H), 1.79-1.60 (m, 4H), 1.49 (m, 9H).

Example 4017

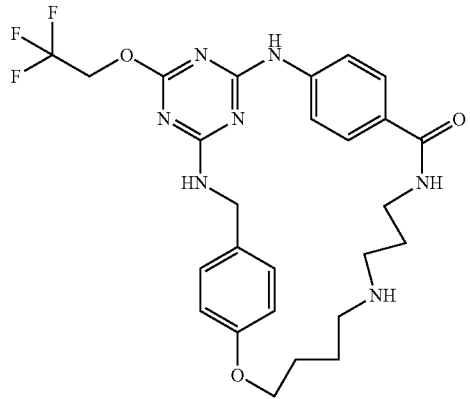 [SMILES: O=C1NCCCNCCCCOc2ccc(cc2)CNc2nc(nc(OCC(F)(F)F)n2)Nc2ccc1cc2]

The Example 4017 was prepared following the procedure reported in Example 4001. 1,4-diiodobutane and tert-butyl (3-aminopropyl)carbamate were used instead of 1,2-dibromoethane and tert-butyl (4-aminobutyl)carbamate as starting material in step 3 and step 5 of Example 4001. LC-MS: 546.13 (M+H). $^1$H NMR (400 MHz, METHANOL-$d_4$) δ 7.56-7.43 (d, J=9.0 Hz, 2H), 7.30-7.15 (m, 4H), 7.05-6.92 (d, J=8.5 Hz, 2H), 4.86 (m, 2H), 4.54 (s, 2H), 4.04 (t, J=5.3 Hz, 2H), 3.67-3.53 (m, 2H), 3.12-2.99 (m, 2H), 2.92 (t, J=6.3 Hz, 2H), 2.05-1.79 (m, 6H).

Example 4018

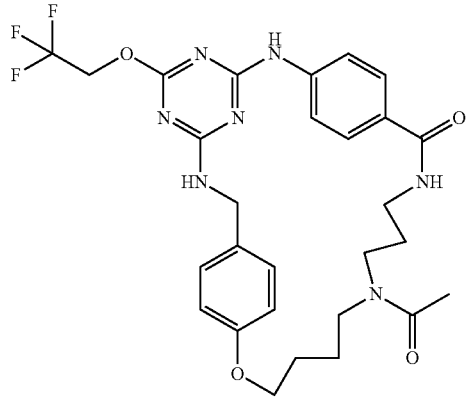 [SMILES: CC(=O)N1CCCCOc2ccc(cc2)CNc2nc(nc(OCC(F)(F)F)n2)Nc2ccc(cc2)C(=O)NCCC1]

The Example 4018 was prepared following the procedure reported in Example 4002. Compound 4017 was used instead of Compound 4001. LC-MS: 588.21 (M+H).

$^1$H NMR (400 MHz, METHANOL-$d_4$) δ 7.55-7.46 (m, 2H), 7.41-7.32 (m, 2H), 7.25 (d, J=8.8 Hz, 2H), 7.01-6.86 (m, 2H), 4.86 (m, 2H), 4.56 (s, 2H), 4.01 (m, 2H), 3.54-3.32 (m, 6H), 2.13 (s, 3H), 1.97-1.86 (m, 2H), 1.74 (m, 2H), 1.69 (m, 2H).

Example 4019

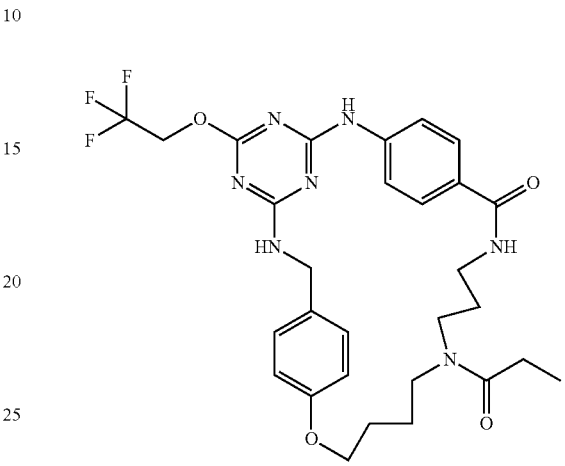

The Example 4019 was prepared following the procedure reported in Example 4018. propionic anhydride was used instead of acetyl chloride. LC-MS: 602.24 (M+H).

$^1$H NMR (400 MHz, METHANOL-$d_4$) δ 7.53-7.45 (m, 2H), 7.37 (m, 2H), 7.25 (d, J=8.8 Hz, 2H), 6.94 (dd, J=8.5, 1.5 Hz, 2H), 4.86 (m, 2H), 4.56 (s, 2H), 4.01 (d, J=6.8 Hz, 2H), 3.44-3.32 (m, 6H), 2.49-2.26 (m, 2H), 1.90 (m, 2H), 1.71 (m, 4H), 1.13 (dt, J=11.4, 7.5 Hz, 3H).

Example 4020

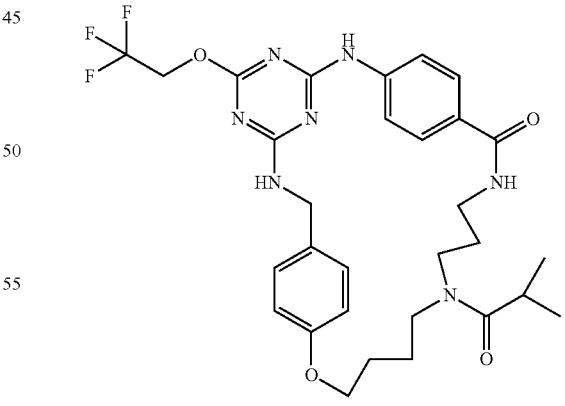

The Example 4020 was prepared following the procedure reported in Example 4018. isobutyric propionic anhydride was used instead of acetyl chloride. LC-MS: 616.24 (M+H).

$^1$H NMR (400 MHz, METHANOL-$d_4$) δ 7.54-7.45 (m, 2H), 7.42-7.33 (m, 2H), 7.25 (d, J=8.5 Hz, 2H), 6.94 (dd, J=8.8, 2.0 Hz, 2H), 4.86 (m, 2H), 4.56 (s, 2H), 4.09-3.96 (m, 2H), 3.54-3.36 (m, 6H), 2.87 (dt, J=13.7, 6.8 Hz, 1H), 1.89 (m, 2H), 1.74 (m 2H), 1.68 (m, 2H), 1.12 (t, J=6.5 Hz, 6H).

J=8.8 Hz, 2H), 4.86 (m, 2H), 4.56 (s, 2H), 3.99 (t, J=5.3 Hz, 2H), 3.69 (s, 3H), 3.43 (m 2H), 3.28 (m 4H), 1.89 (m, 2H), 1.70 (m, 4H).

Example 4022

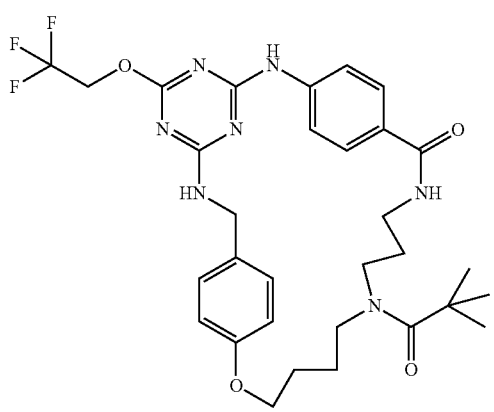 [SMILES: CC(C)(C)C(=O)N1CCCCOc2ccc(cc2)CNc2nc(nc(OCC(F)(F)F)n2)Nc2ccc(cc2)C(=O)NCCC1]

The Example 402 was prepared following the procedure reported in Example 4018. Pivalic anhydride was used instead of acetyl chloride. LC-MS: 630.27 (M+H).

¹H NMR (400 MHz, METHANOL-d₄) δ 7.48 (m, 2H), 7.40 (m, 2H), 7.26 (d, J=8.8 Hz, 2H), 6.94 (d, J=8.5 Hz, 2H), 4.86 (m, 2H), 4.55 (s, 2H), 4.00 (m, 2H), 3.57-3.32 (m, 6H), 1.99-1.86 (m, 2H), 1.70 (m, 4H), 1.30 (s, 9H).

Example 4024

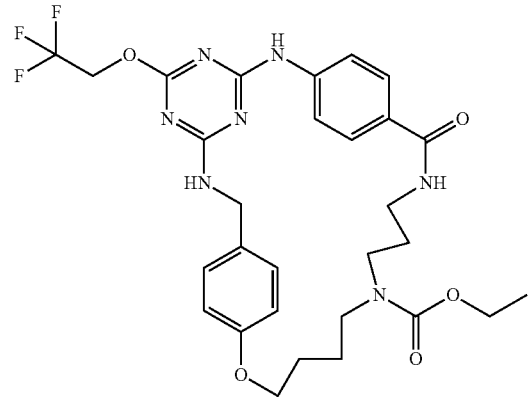

The Example 4024 was prepared following the procedure reported in Example 4023. Ethyl carbonochloridate was used instead of methyl carbonochloridate. LC-MS: 618.25 (M+H).

¹H NMR (400 MHz, METHANOL-d₄) δ 7.47 (d, J=8.8 Hz, 2H), 7.37 (d, J=8.8 Hz, 2H), 7.30-7.22 (d, J=9.0 Hz, 2H), 6.98-6.89 (d, J=8.8 Hz, 2H), 4.86 (m, 2H), 4.56 (s, 2H), 4.10 (m, 2H), 4.05-3.94 (m, 2H), 3.55-3.42 (m, 6H), 1.88 (m, 2H), 1.71 (m, 4H), 1.30 (t, 3H).

Example 4023

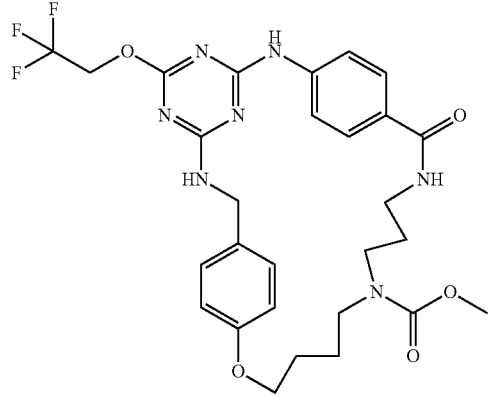 [SMILES: COC(=O)N1CCCCOc2ccc(cc2)CNc2nc(nc(OCC(F)(F)F)n2)Nc2ccc(cc2)C(=O)NCCC1]

The Example 4023 was prepared following the procedure reported in Example 4013. Compound 4017 was used instead of Compound 4001. LC-MS: 604.22 (M+H).

¹H NMR (400 MHz, METHANOL-d₄) δ 7.52-7.42 (d, 2H), 7.38 (d, 2H), 7.31-7.21 (d, J=8.8 Hz, 2H), 7.01-6.86 (d,

Example 4025

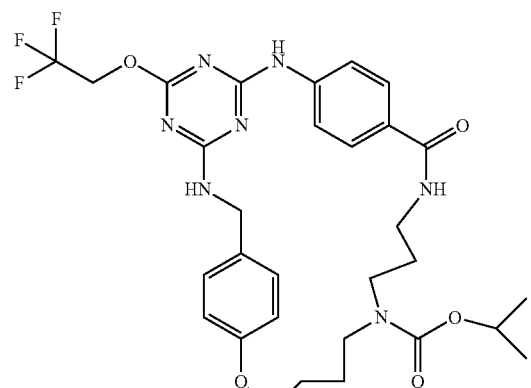

The Example 4025 was prepared following the procedure reported in Example 4023. Isopropyl carbonochloridate was used instead of methyl carbonochloridate. LC-MS: 632.28 (M+H). ¹H NMR (400 MHz, METHANOL-d₄) δ 7.52-7.43 (d, J=8.8 Hz, 2H), 7.41-7.33 (d, J=9.0 Hz, 2H), 7.28-7.17 (d, J=8.5 Hz, 2H), 7.00-6.87 (d, J=8.8 Hz, 2H), 4.86 (m, 2H), 4.56 (s, 2H), 4.00 (t, J=5.3 Hz, 2H), 3.43 (m., 2H), 3.31-3.23 (m, 5H), 1.89 (m, 2H), 1.71 (m, 4H), 1.25 (d, J=7.3 Hz, 6H).

Example 4026

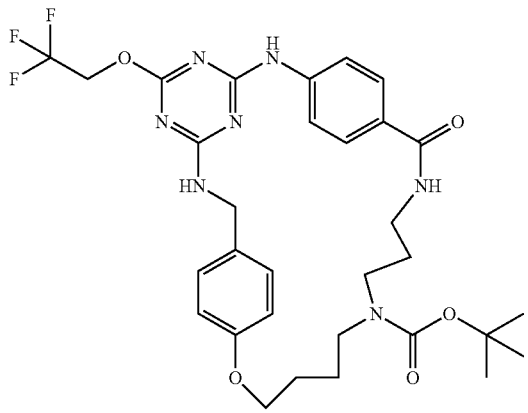 [SMILES: CC(C)(C)OC(=O)N1CCCCOc2ccc(cc2)CNc2nc(nc(OCC(F)(F)F)n2)Nc2ccc(cc2)C(=O)NCCC1]

The Example 4026 was prepared following the procedure reported in Example 4023. Di-tert-butyl dicarbonate was used instead of methyl carbonochloridate. LC-MS: 646.29 (M+H). $^1$H NMR (400 MHz, METHANOL-$d_4$) δ 7.51-7.42 (d, 2H), 7.38 (d, 2H), 7.24 (d, J=8.8 Hz, 2H), 6.99-6.89 (d, J=8.5 Hz, 2H), 4.86 (m, 2H), 4.55 (s, 2H), 4.00 (t, J=5.5 Hz, 2H), 3.47-3.39 (m, 2H), 3.28-3.19 (m, 4H), 1.88 (m, 2H), 1.70 (m, 4H), 1.47 (s, 9H).

Example 4030

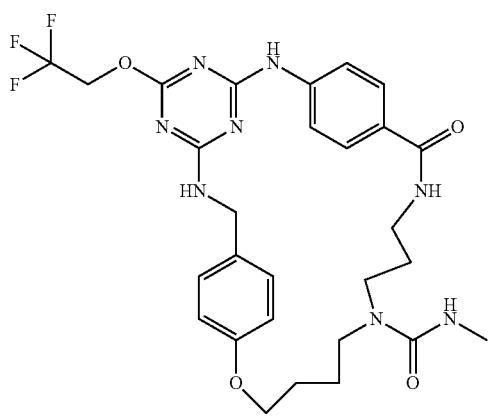 [SMILES: CNC(=O)N1CCCCOc2ccc(cc2)CNc2nc(nc(OCC(F)(F)F)n2)Nc2ccc(cc2)C(=O)NCCC1]

The Example 4030 was prepared following the procedure reported in Example 4006. Compound 4017 was used instead of Compound 4001. LC-MS: 603.24 (M+H).

$^1$H NMR (400 MHz, METHANOL-$d_4$) δ 7.52-7.43 (d, J=8.8 Hz, 2H), 7.41-7.34 (d, J=8.8 Hz, 2H), 7.29-7.20 (d, J=8.5 Hz, 2H), 7.01-6.90 (d, J=8.5 Hz, 2H), 4.86 (m, 2H), 4.56 (s, 2H), 4.00 (t, J=5.5 Hz, 2H), 3.48-3.38 (m, 2H), 3.28-3.18 (m, 4H), 2.73 (s, 3H), 1.86 (m, 2H), 1.71 (m, 4H).

Example 4031

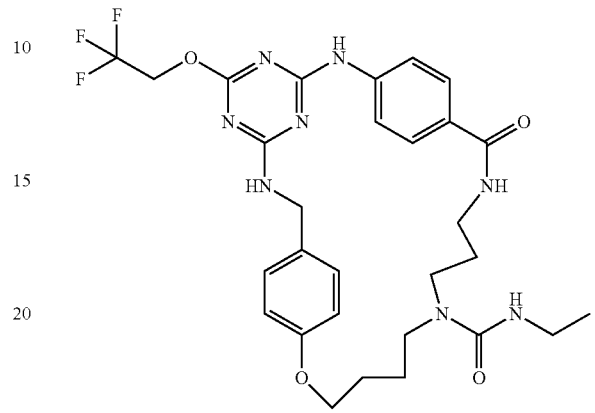

The Example 4031 was prepared following the procedure reported in Example 4030. Isocyanatoethane was used instead of isocyanatomethane. LC-MS: 617.26 (M+H).

$^1$H NMR (400 MHz, METHANOL-$d_4$) δ 7.48 (d, J=9.0 Hz, 2H), 7.37 (d, J=8.8 Hz, 2H), 7.25 (d, J=8.8 Hz, 2H), 6.93 (d, J=8.8 Hz, 2H), 4.86 (m, 2H), 4.56 (s, 2H), 4.00 (t, J=5.5 Hz, 2H), 3.51-3.39 (m, 2H), 3.30-3.15 (m, 6H), 1.86 (m, 2H), 1.75-1.58 (m, 4H), 1.12 (t, J=7.2 Hz, 3H).

Example 4032

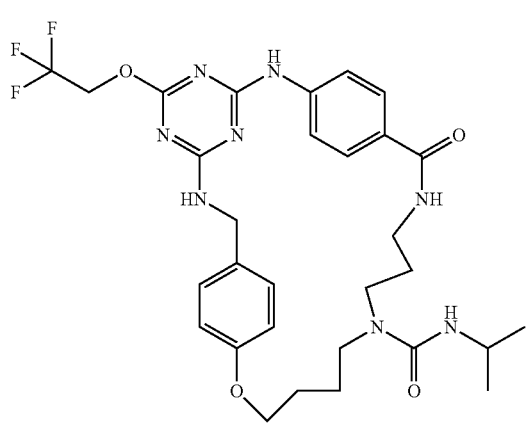 [SMILES: CC(C)NC(=O)N1CCCCOc2ccc(cc2)CNc2nc(nc(OCC(F)(F)F)n2)Nc2ccc(cc2)C(=O)NCCC1]

The Example 4032 was prepared following the procedure reported in Example 4030. 2-Isocyanatopropane was used instead of isocyanatomethane. LC-MS: 631.26 (M+H). $^1$H NMR (400 MHz, METHANOL-$d_4$) δ 7.48 (d, J=9.0 Hz, 2H), 7.37 (d, J=8.8 Hz, 2H), 7.29-7.18 (d, J=8.8 Hz, 2H), 6.99-6.88 (d, J=8.5 Hz, 2H), 4.86 (m, 2H), 4.56 (s, 2H), 4.00 (t, J=5.8

Hz, 2H), 3.95-3.86 (m, 1H), 3.50-3.38 (m, 2H), 3.30-3.18 (m, 4H), 1.86 (m, 2H), 1.76-1.61 (m, 4H), 1.15 (d, J=6.5 Hz, 6H).

4.18 (s, 1H), 4.13-4.04 (m, 2H), 3.77-3.64 (m, 2H), 3.59-3.37 (m, 4H), 3.42 (s, 3H), 1.75 (m, 2H), 1.65 (m, 2H).

Example 4034

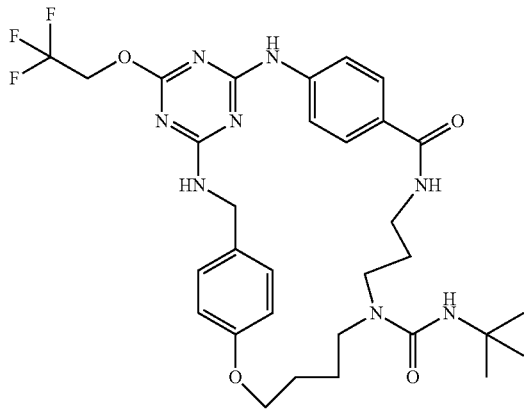 [SMILES: CC(C)(C)NC(=O)N1CCCCOc2ccc(cc2)CNc2nc(nc(OCC(F)(F)F)n2)Nc2ccc(cc2)C(=O)NCCC1]

The Example 4034 was prepared following the procedure reported in Example 4030. 2-2-Isocyanato-2-methylpropane was used instead of isocyanatomethane. LC-MS: 645.29 (M+H). $^1$H NMR (400 MHz, METHANOL-$d_4$) δ 7.53-7.43 (d, J=8.8 Hz, 2H), 7.41-7.34 (d, J=9.0 Hz, 2H), 7.28-7.20 (d, J=8.8 Hz, 2H), 7.00-6.87 (d, J=8.8 Hz, 2H), 4.86 (m, 2H), 4.56 (s, 2H), 4.07-3.94 (m, 2H), 3.47-3.37 (m, 2H), 3.24 (d, J=8.3 Hz, 4H), 1.86 (d, J=7.3 Hz, 2H), 1.76-1.62 (m, 4H), 1.41-1.29 (m, 9H).

Example 4037

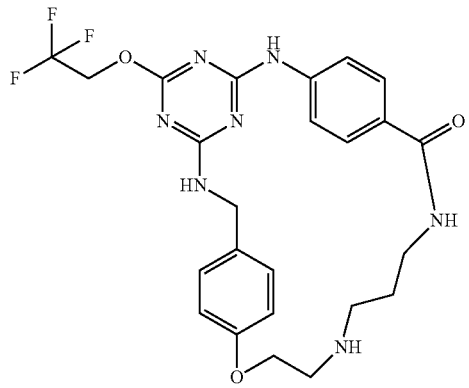

The Example 4037 was prepared following the procedure reported in Example 4001. N-t-Boc-propylenediamine was used instead of tert-butyl (4-aminobutyl)carbamate as starting material in step 5 of Example 4001. LC-MS: 518.12 (M+H).

$^1$H NMR (400 MHz, METHANOL-$d_4$) δ 7.42-7.28 (m, 4H), 7.25-7.18 (d, J=8.8 Hz, 2H), 6.97-6.89 (d, J=8.8 Hz, 2H), 4.86 (m, 2H), 4.61 (s, 2H), 4.32-4.22 (m, 2H), 3.61-3.44 (m, 4H), 3.18-3.09 (m, 2H), 1.97 (d, J=6.8 Hz, 2H).

Example 4035

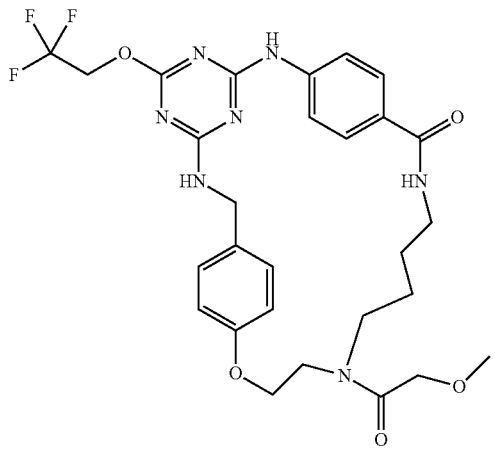 [SMILES: COCC(=O)N1CCCCNC(=O)c2ccc(cc2)Nc2nc(nc(OCC(F)(F)F)n2)NCc2ccc(cc2)OCC1]

The Example 4035 was prepared following the procedure reported in Example 4001. 2-Methoxyacetyl chloride was used instead of acetyl chloride. LC-MS: 604.22 (M+H). $^1$H NMR (400 MHz, METHANOL-$d_4$) δ 7.47 (d, J=8.8 Hz, 1H), 7.39 (q, J=9.0 Hz, 2H), 7.33-7.19 (m, 3H), 6.94 (dd, J=8.8, 3.0 Hz, 2H), 4.86 (m, 2H), 4.54 (d, J=5.8 Hz, 2H), 4.28 (s, 1H), Example 4038

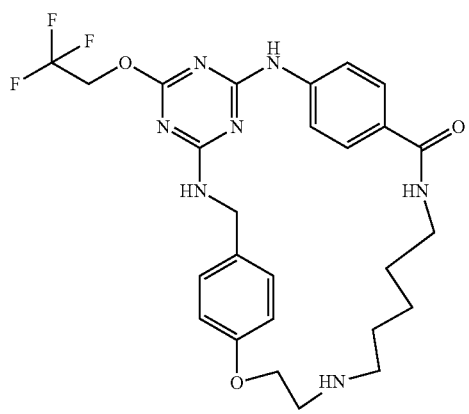 [SMILES: O=C1NCCCCCNCCOc2ccc(cc2)CNc2nc(nc(OCC(F)(F)F)n2)Nc2ccc1cc2]

The Example 4038 was prepared following the procedure reported in Example 4001. Tert-butyl (5-aminopentyl)carbamate was used instead of tert-butyl (4-aminobutyl)carbamate as starting material in step 5 of Example 4001. LC-MS: 546.16 (M+H). $^1$H NMR (400 MHz, METHANOL-$d_4$) δ 7.53-7.44 (d, J=9.0 Hz, 2H), 7.35-7.25 (m, 4H), 7.10-6.97 (d, J=8.8 Hz, 2H), 4.86 (m, 2H), 4.57 (s, 2H), 4.37-4.23 (m, 2H), 3.57-3.40 (m, 4H), 3.08 (t, J=6.4 Hz, 2H), 1.89-1.80 (m, 2H), 1.74-1.62 (m, 2H), 1.46-1.32 (m, 2H).

(d, J=8.8 Hz, 2H), 4.86 (m, 2H), 4.52 (s, 2H), 4.21-4.03 (m, 4H), 3.61-3.35 (m, 6H), 2.03-1.77 (m, 2H), 1.29 (t, J=7.0 Hz, 3H).

Example 4039

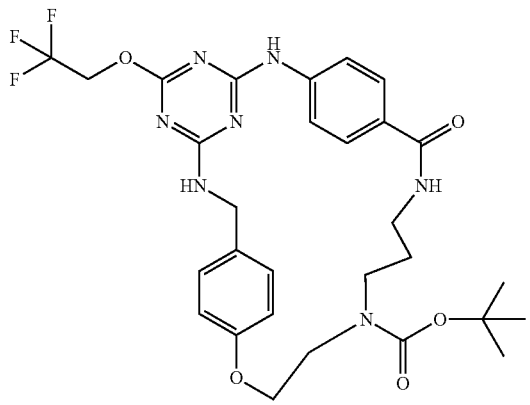 [SMILES: CC(C)(C)OC(=O)N1CCCNC(=O)c2ccc(cc2)Nc2nc(nc(OCC(F)(F)F)n2)NCc2ccc(cc2)OCC1]

The Example 4039 was prepared following the procedure reported in Example 4016. LC-MS: 618.25 (M+H). $^1$H NMR (400 MHz, METHANOL-$d_4$) δ 7.54-7.42 (d, J=8.8 Hz, 2H), 7.40-7.31 (d, J=8.5 Hz, 2H), 7.25-7.14 (d, J=8.8 Hz, 2H), 6.94-6.81 (d, J=8.5 Hz, 2H), 4.86 (m, 2H), 4.52 (s, 2H), 4.13 (t, J=6.9 Hz, 2H), 3.51 (t, J=6.4 Hz, 4H), 1.93 (d, J=7.3 Hz, 2H), 1.48 (s, 9H), 1.97 (d, J=6.8 Hz, 2H).

Example 4041

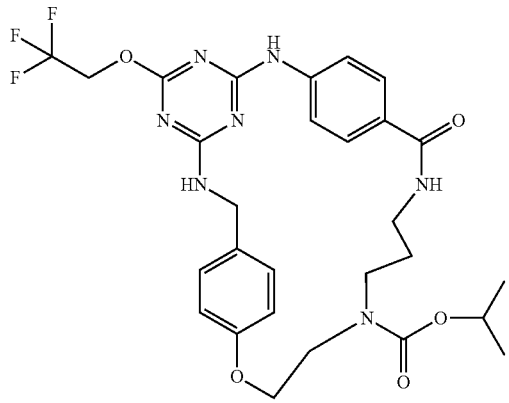

The Example 4041 was prepared following the procedure reported in Example 4015. LC-MS: 604.22 (M+H). $^1$H NMR (400 MHz, METHANOL-$d_4$) δ 7.50-7.43 (d, J=8.8 Hz, 2H), 7.40-7.30 (d, J=8.8 Hz, 2H), 7.23-7.16 (d, J=8.5 Hz, 2H), 6.93-6.84 (d, J=8.8 Hz, 2H), 4.86 (m, 2H), 4.52 (s, 2H), 4.14 (t, J=6.9 Hz, 2H), 3.55-3.49 (m, 1H), 3.47-3.34 (m, 6H), 2.02-1.82 (m, 2H), 1.28 (d, J=6.0 Hz, 6H).

Example 4040

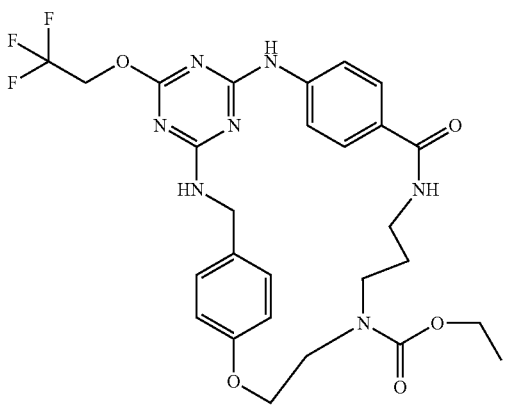 [SMILES: CCOC(=O)N1CCCNC(=O)c2ccc(cc2)Nc2nc(nc(OCC(F)(F)F)n2)NCc2ccc(cc2)OCC1]

The Example 4040 was prepared following the procedure reported in Example 4014. LC-MS: 590.19 (M+H). $^1$H NMR (400 MHz, METHANOL-$d_4$) δ 7.48 (d, J=8.8 Hz, 2H), 7.25-7.16 (d, J=8.8 Hz, 2H), 7.25-7.16 (d, J=8.8 Hz, 2H), 6.94-6.82

Example 4043

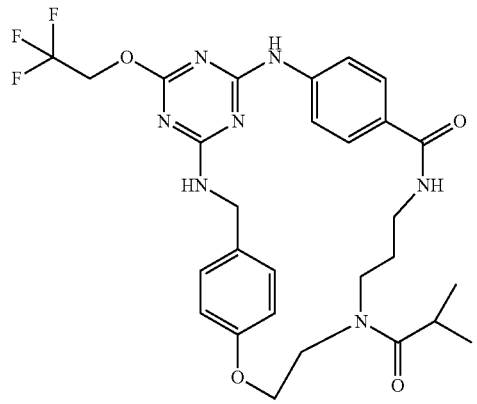 [SMILES: CC(C)C(=O)N1CCCNC(=O)c2ccc(cc2)Nc2nc(nc(OCC(F)(F)F)n2)NCc2ccc(cc2)OCC1]

The Example 4043 was prepared following the procedure reported in Example 4004. LC-MS: 588.21 (M+H). $^1$H NMR (400 MHz, METHANOL-$d_4$) δ 7.49 (dd, J=8.8, 6.0 Hz, 2H), 7.40-7.33 (m, 2H), 7.20 (t, J=9.3 Hz, 2H), 6.88 (t, J=9.2 Hz, 2H), 4.86 (m, 2H), 4.52 (d, J=5.8 Hz, 2H), 4.20-4.08 (m, 2H), 3.73-3.58 (m, 2H), 3.58-3.38 (m, 4H), 3.04-2.89 (m, 1H), 1.95 (m, 2H), 1.15 (t, J=6.4 Hz, 6H).

Example 4044

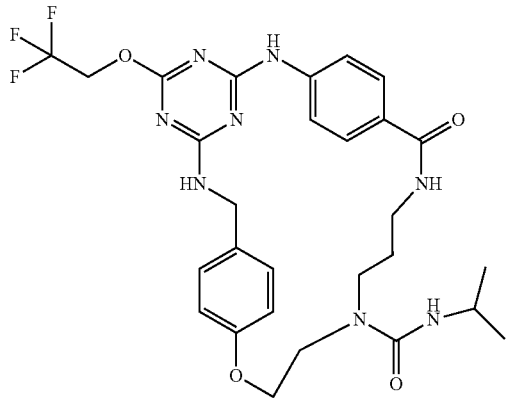 [SMILES: CC(C)NC(=O)N1CCCNC(=O)c2ccc(cc2)Nc2nc(nc(OCC(F)(F)F)n2)NCc2ccc(cc2)OCC1]

The Example 4044 was prepared following the procedure reported in Example 4008. LC-MS: 603.22 (M+H). $^1$H NMR (400 MHz, METHANOL-$d_4$) δ 7.52-7.43 (d, J=9.0 Hz, 2H), 7.37-7.27 (d, J=8.8 Hz, 2H), 7.24-7.16 (d, J=8.8 Hz, 2H), 6.95-6.82 (d, J=8.8 Hz, 2H), 4.86 (m, 2H), 4.52 (s, 2H), 4.13 (t, J=6.8 Hz, 2H), 3.96-3.82 (m, 1H), 3.56 (t, J=6.8 Hz, 2H), 3.50-3.35 (m, 4H), 1.90 (d, J=6.8 Hz, 2H), 1.14 (d, J=6.5 Hz, 6H).

Example 4045

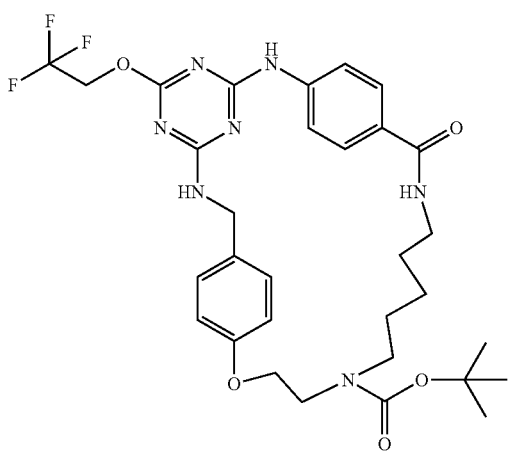 [SMILES: CC(C)(C)OC(=O)N1CCCCCNC(=O)c2ccc(cc2)Nc2nc(nc(OCC(F)(F)F)n2)NCc2ccc(cc2)OCC1]

The Example 4045 was prepared following the procedure reported in Example 4016. LC-MS: 646.29 (M+H). $^1$H NMR (400 MHz, METHANOL-$d_4$) δ 7.55 (d, J=8.5 Hz, 2H), 7.41 (d, J=8.8 Hz, 2H), 7.30-7.21 (d, J=8.5 Hz, 2H), 6.97-6.84 (d, J=8.8 Hz, 2H), 4.86 (m, 2H), 4.52 (s, 2H), 4.16-3.98 (m, 2H), 3.60-3.37 (m, 4H), 3.26 (m, 2H), 1.67 (m, 4H), 1.41 (m, 2H), 1.39 (s., 9H).

Example 4046

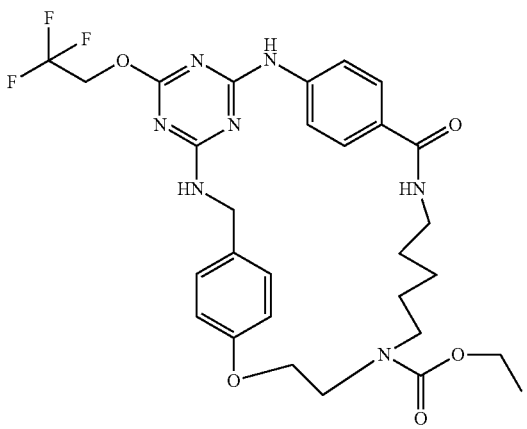 [SMILES: CCOC(=O)N1CCCCCNC(=O)c2ccc(cc2)Nc2nc(nc(OCC(F)(F)F)n2)NCc2ccc(cc2)OCC1]

The Example 4046 was prepared following the procedure reported in Example 4014. LC-MS: 618.25 (M+H). $^1$H NMR (400 MHz, METHANOL-$d_4$) δ 7.55 (d, J=8.3 Hz, 2H), 7.41 (d, J=8.8 Hz, 2H), 7.29-7.19 (d, J=8.5 Hz, 2H), 6.96-6.79 (d, J=8.5 Hz, 2H), 4.86 (m, 2H), 4.51 (s, 2H), 4.20-4.04 (m, 4H), 3.58-3.37 (m., 4H), 3.26 (m, 2H), 1.67 (m., 4H), 1.39 (m, 2H), 1.29 (t, J=7.0 Hz, 3H).

Example 4047

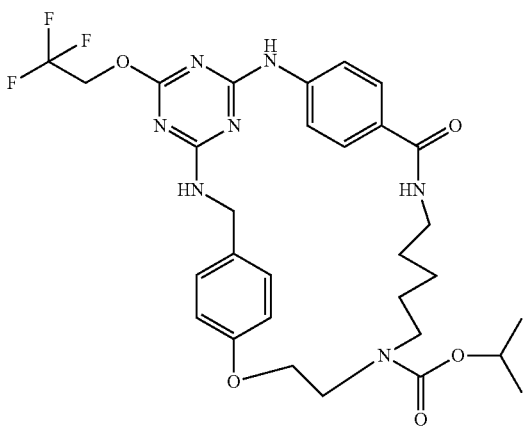 [SMILES: CC(C)OC(=O)N1CCCCCNC(=O)c2ccc(cc2)Nc2nc(nc(OCC(F)(F)F)n2)NCc2ccc(cc2)OCC1]

The Example 4047 was prepared following the procedure reported in Example 4015. LC-MS: 632.28 (M+H). $^1$H NMR (400 MHz, METHANOL-$d_4$) δ 7.55 (d, J=8.5 Hz, 2H), 7.41 (d, J=8.8 Hz, 2H), 7.24 (d, J=8.5 Hz, 2H), 6.90 (d, J=8.5 Hz, 2H), 4.86 (m, 2H), 4.51 (s, 2H), 4.11 (t, J=6.0 Hz, 2H), 3.57 (m, 5H), 3.26 (m, 2H), 1.67 (m, 4H), 1.40 (m, 2H), 1.26-1.09 (m, 6H).

2H), 3.68-3.55 (m, 4H), 2.96-2.74 (m, 1H), 1.63 (m, 4H), 1.48-1.38 (m, 2H), 1.01 (dd, J=18.8, 6.5 Hz, 6H).

Example 4049

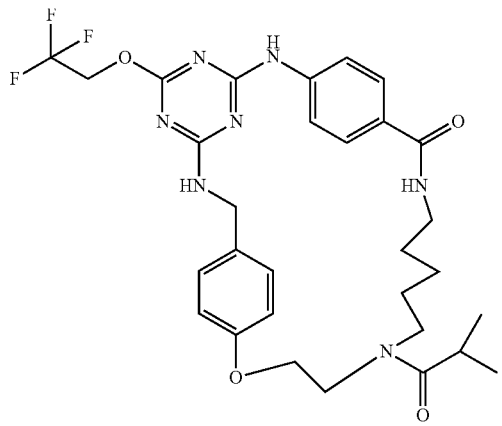 [SMILES: CC(C)C(=O)N1CCCCCNC(=O)c2ccc(cc2)Nc2nc(nc(OCC(F)(F)F)n2)NCc2ccc(cc2)OCC1]

Example 4050

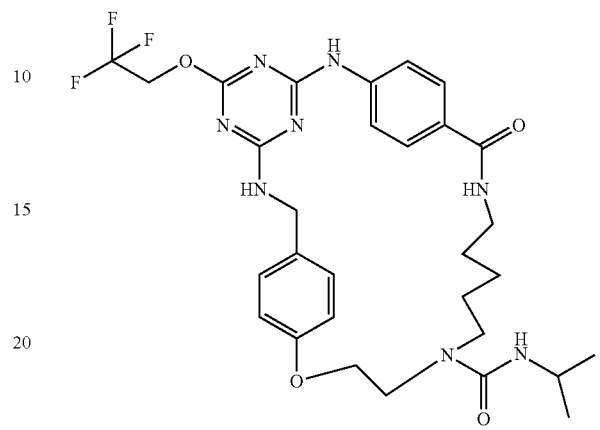

The Example 4049 was prepared following the procedure reported in Example 4004. LC-MS: 616.27 (M+H). $^1$H NMR (400 MHz, METHANOL-$d_4$) δ 7.55 (d, J=8.5 Hz, 2H), 7.45-7.37 (d, J=8.8 Hz, 2H), 7.30-7.19 (m, 2H), 6.95-6.75 (m, 2H), 4.85 (m, 2H), 4.53 (s, 2H), 4.25-4.07 (m, 2H), 3.73-3.62 (m, The Example 4050 was prepared following the procedure reported in Example 4008. LC-MS: 631.26 (M+H). $^1$H NMR (400 MHz, METHANOL-$d_4$) δ 7.59-7.43 (d, J=8.8 Hz, 2H), 7.43-7.30 (d, J=8.8 Hz, 2H), 7.25 (d, J=8.8 Hz, 2H), 6.91 (d, J=8.5 Hz, 2H), 4.85 (m, 2H), 4.53 (s, 2H), 4.13 (t, J=5.1 Hz, 2H), 3.88-3.76 (m, 1H), 3.60 (t, J=5.3 Hz, 2H), 3.52-3.40 (m, 2H), 3.36 (m, 2H), 1.64 (m, 4H), 1.41 (m, 2H), 1.05 (d, J=6.5 Hz, 6H).

Series 5000

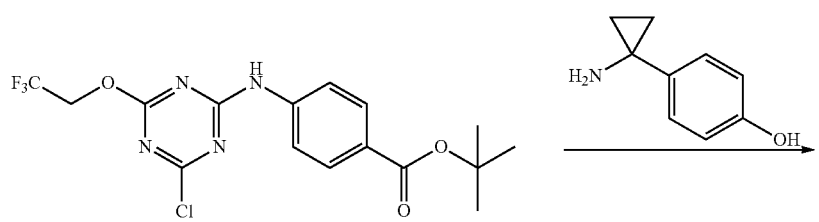

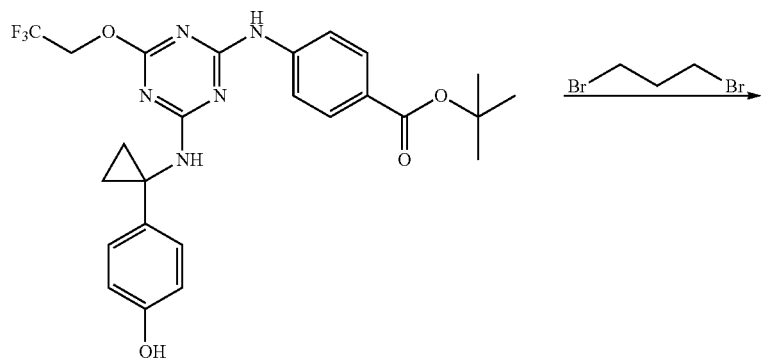

-continued
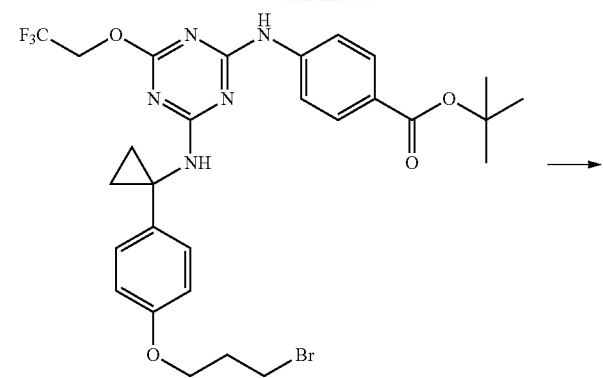
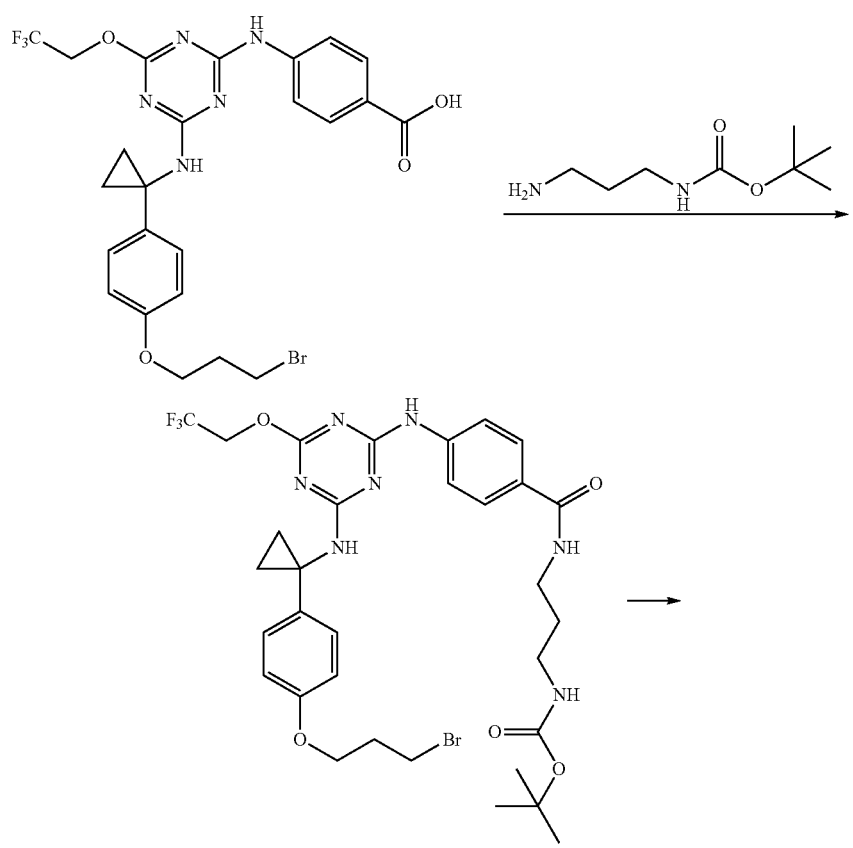
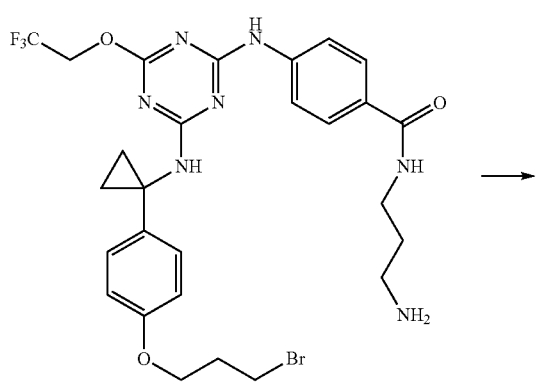

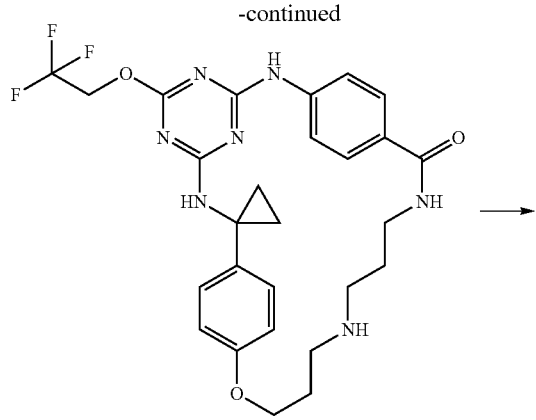

Example 5001

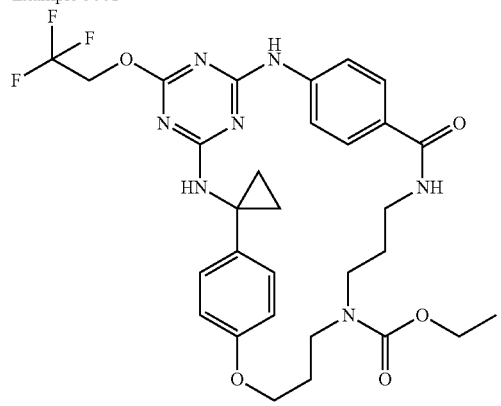

Example 5002

Step 1: tert-butyl 4-((4-((1-(4-hydroxyphenyl)cyclopropyl)amino)-6-(2,2,2-trifluoroethoxy)-1,3,5-triazin-2-yl)amino)benzoate was prepared following the procedure reported in Example 4001 step 2. 4-(1-aminocyclopropyl)phenol was used instead of 4-(aminomethyl)phenol as starting material.

| tert-butyl 4-((4-((1-(4-hydroxyphenyl)cyclopropyl)amino)-6-(2,2,2-trifluoroethoxy)-1,3,5-triazin-2-yl)amino)benzoate | |
|---|---|
| MS (M + H)+ Calcd. | 518.0 |
| MS (M + H)+ Observ. | 518.0 |
| Retention Time | 1.10 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 2: tert-butyl 4-((4-((1-(4-(3-bromopropoxy)phenyl)cyclopropyl)amino)-6-(2,2,2-trifluoroethoxy)-1,3,5-triazin-2-yl)amino)benzoate was prepared following the procedure reported in Example 4001 step 3. 1,3-dibromopropane was used instead of 1,2-dibromopropane as starting material.

| tert-butyl 4-((4-((1-(4-(3-bromopropoxy)phenyl)cyclopropyl)amino)-6-(2,2,2-trifluoroethoxy)-1,3,5-triazin-2-yl)amino)benzoate | |
|---|---|
| MS (M + H)+ Calcd. | 638.2 |
| MS (M + H)+ Observ. | 638.2 |
| Retention Time | 1.23 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: 4-((4-((1-(4-(3-bromopropoxy)phenyl)cyclopropyl)amino)-6-(2,2,2-trifluoroethoxy)-1,3,5-triazin-2-yl)amino)benzoic acid was prepared following the procedure reported in Example 4001 step 4.

| 4-((4-((1-(4-(3-bromopropoxy)phenyl)cyclopropyl)amino)-6-(2,2,2-trifluoroethoxy)-1,3,5-triazin-2-yl)amino)benzoic acid | |
|---|---|
| MS (M + H)+ Calcd. | 582.1 |
| MS (M + H)+ Observ. | 582.0 |
| Retention Time | 1.06 min |

-continued

| 4-((4-((1-(4-(3-bromopropoxy)phenyl)cyclopropyl)amino)-6-(2,2,2-trifluoroethoxy)-1,3,5-triazin-2-yl)amino)benzoic acid | |
|---|---|
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: tert-butyl (3-(4-((4-((1-(4-(3-bromopropoxy)phenyl)cyclopropyl)amino)-6-(2,2,2-trifluoroethoxy)-1,3,5-triazin-2-yl)amino)benzamido)propyl)carbamate was prepared following the procedure reported in Example 4001 step 5. tert-butyl (3-aminopropyl)carbamate was used instead of tert-butyl (4-aminobutyl)carbamate as starting material.

| tert-butyl (3-(4-((4-((1-(4-(3-bromopropoxy)phenyl)cyclopropyl)amino)-6-(2,2,2-trifluoroethoxy)-1,3,5-triazin-2-yl)amino)benzamido)propyl)carbamate | |
|---|---|
| MS (M + H)+ Calcd. | 738.2 |
| MS (M + H)+ Observ. | 738.3 |
| Retention Time | 1.12 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: N-(3-aminopropyl)-4-((4-((1-(4-(3-bromopropoxy)phenyl)cyclopropyl)amino)-6-(2,2,2-trifluoroethoxy)-1,3,5-triazin-2-yl)amino)benzamide TFA salt was prepared following the procedure reported in Example 4001 step 6.

Step 6: Example 5001 was prepared following the procedure reported in Example 4001 step 7.

| Example 5001 | |
|---|---|
| MS (M + H)+ Calcd. | 558.2 |
| MS (M + H)+ Observ. | 558.2 |
| Retention Time | 0.85 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 7: Example 5001 (10 mg, 0.018 mmol) and diethyl dicarbonate (5.82 mg, 0.036 mmol) were dissolved in DMF (1 mL) and Hunig's Base (9.40 μl, 0.054 mmol) was added. The reaction was stirred for 16 h. The crude product was purified by reverse phase prep-HPLC using a gradient of 40-100% ACN/Water w/0.1% TFA modifier. The product fraction was collected, diluted with EtOAc, washed with sat. sodium bicarbonate then brine. The organic layer was collected, dried over sodium sulfate, and concentrated under vacuum to give 6 mg (51%) of Example 5002 as a solid. $^1$H NMR (400 MHz, METHANOL-$d_4$) δ 7.50-7.42 (m, 2H), 7.35-7.28 (m, 2H), 7.13-7.06 (m, 2H), 6.91-6.84 (m, 2H), 4.94-4.84 (m, 2H), 4.19-4.07 (m, 2H), 3.99 (t, J=5.6 Hz, 2H), 3.46-3.34 (m, 4H), 2.03-1.91 (m, 2H), 1.90-1.79 (m, 2H), 1.43-1.18 (m, 9H).

| Example 5002 | |
|---|---|
| MS (M + H)+ Calcd. | 630.3 |
| MS (M + H)+ Observ. | 630.3 |
| Retention Time | 0.99 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 5003

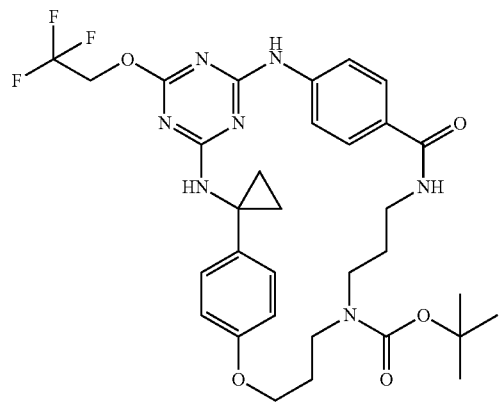 [SMILES: CC(C)(C)OC(=O)N1CCCNC(=O)c2ccc(cc2)Nc2nc(nc(OCC(F)(F)F)n2)NC2(CC2)c2ccc(cc2)OCCC1]

The Example 5003 was prepared following the procedure reported in Example 5001. di-tert-butyl dicarbonate was used instead of diethyl dicarbonate. LC-MS: 658.3 (M+H). $^1$H NMR (400 MHz, METHANOL-$d_4$) δ 7.54-7.40 (m, 2H), 7.35-7.28 (m, 2H), 7.12-7.06 (m, 2H), 6.92-6.83 (m, 2H), 4.94-4.85 (m, 2H), 3.99 (t, J=5.6 Hz, 2H), 3.45-3.38 (m, 2H), 1.99-1.90 (m, 2H), 1.89-1.79 (m, 2H), 1.48 (s, 9H), 1.38-1.27 (m, 8H).

2H), 3.49-3.45 (m, 2H), 3.30-3.25 (m, 4H), 2.72 (s, 3H), 2.01-1.91 (m, 2H), 1.69-1.59 (m, 4H), 1.41-1.34 (m, 2H), 1.33-1.27 (m, 2H).

Example 5003

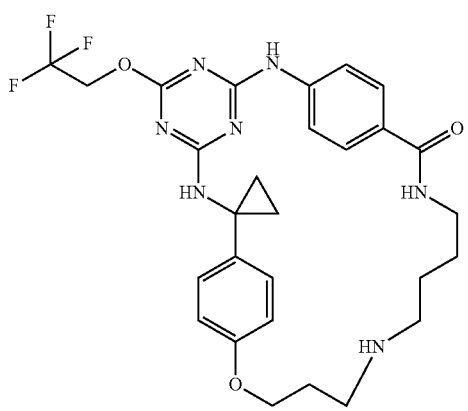 [SMILES: O=C1NCCCCNCCCOc2ccc(cc2)C2(CC2)Nc2nc(nc(OCC(F)(F)F)n2)Nc2ccc1cc2]

The Example 5003 was prepared following the procedure reported in Example 5001. tert-butyl 4-aminobutylcarbamate was used instead of tert-butyl (3-aminopropyl)carbamate as starting material in step 4 of Example 5001. LC-MS: 572.2 (M+H). $^1$H NMR (400 MHz, METHANOL-$d_4$) δ 7.51-7.35 (m, 4H), 7.22-7.15 (m, 2H), 6.96-6.89 (m, 2H), 4.93-4.84 (m, 2H), 4.09-4.02 (m, 2H), 3.54-3.50 (m, 2H), 3.16-3.06 (m, 4H), 2.15-2.05 (m, 2H), 1.75-1.59 (m, 4H), 1.42-1.33 (m, 2H), 1.33-1.26 (m, 2H).

Example 5004

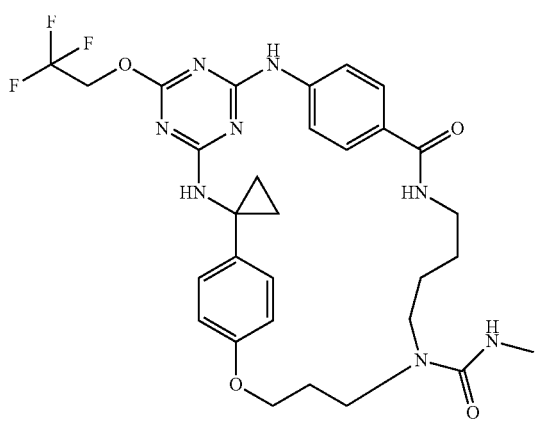 [SMILES: CNC(=O)N1CCCCNC(=O)c2ccc(cc2)Nc2nc(nc(OCC(F)(F)F)n2)NC2(CC2)c2ccc(cc2)OCCC1]

Example 5003 (20 mg, 0.035 mmol) was dissolved in DMF (1 mL) and isocyanatomethane (3.99 mg, 0.070 mmol) was added. The reaction was stirred for 2 minutes then quenched with a drop of water. The material was purified by reverse phase prep-HPLC using a gradient of 30-100% CAN/water w/0.1% TFA modifier. The product fraction was collected and concentrated by speedvac to give 5 mg (22%) of Example 5004 as a white solid. LC-MS: 629.3 (M+H). $^1$H NMR (400 MHz, METHANOL-$d_4$) δ 7.49-7.32 (m, 4H), 7.21-7.09 (m, 2H), 6.96-6.81 (m, 2H), 4.99-4.85 (m, 2H), 4.06-3.92 (m, Example 5005

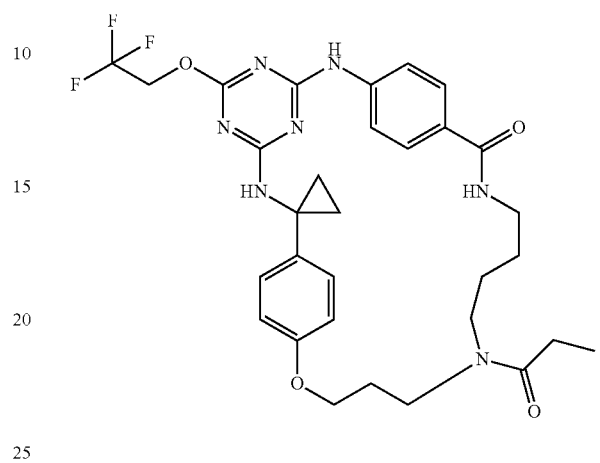

Example 5003 (20 mg, 0.035 mmol) was dissolved in DMF (1 mL) and Hunig's Base (0.018 mL, 0.105 mmol) was added followed by propionyl chloride (6.47 mg, 0.070 mmol). The reaction was stirred for 2 min. then quenched with a drop of water. The material was purified by reverse phase prep-HPLC using a gradient of 30-100% ACN/water w/0.1% TFA modifier. The product fraction was collected and concentrated by speedvac to give 5 mg (22%) of Example 5005 as a white solid. LC-MS: 629.2 (M+H). $^1$H NMR (400 MHz, METHANOL-$d_4$) δ 7.52-7.29 (m, 4H), 7.21-7.09 (m, 2H), 6.99-6.84 (m, 2H), 4.98-4.81 (m, 2H), 4.11-3.91 (m, 2H), 3.48-3.44 (m, 2H), 3.39-3.29 (m, 4H), 2.47-2.32 (m, 2H), 2.04-1.94 (m, 2H), 1.74-1.57 (m, 4H), 1.43-1.27 (m, 4H), 1.16-1.04 (m, 3H).

Example 5006

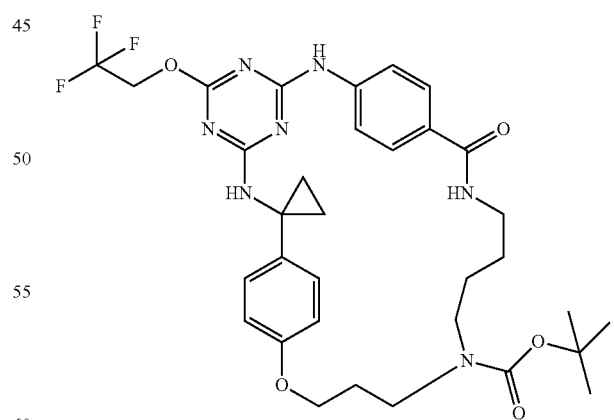

Example 5003 (20 mg, 0.035 mmol) was dissolved in DMF (1 mL) followed by the addition of di-tert-butyl dicarbonate (15.27 mg, 0.070 mmol) and Hunig's Base (0.018 mL, 0.105 mmol). The reaction was stirred for 16 h. The material was purified by reverse phase prep-HPLC using a gradient of 30-100% CAN/water w/0.1% TFA modifier. The product fraction was collected and diluted with EtOAc and water. The organic layer was collected and washed with brine, dried over sodium sulfate and concentrated under vacuum to give 6 mg (22%) of Example 5006 as a white solid. LC-MS: 672.3 (M+H). $^1$H NMR (400 MHz, METHANOL-$d_4$) δ 7.50-7.33 (m, 4H), 7.18-7.11 (m, 2H), 6.92-6.85 (m, 2H), 4.95-4.86 (m, 2H), 3.99 (t, J=6.4 Hz, 2H), 3.49-3.44 (m, 2H), 3.30-3.24 (m, 4H), 1.99-1.91 (m, 2H), 1.71-1.59 (m, 4H), 1.47 (s, 9H), 1.40-1.34 (m, 2H), 1.33-1.28 (m, 2H).

Procedures for the synthesis of 6000 series examples in Table 1.

Compounds in table 1 can be prepared similarly by either following method or above described methods.

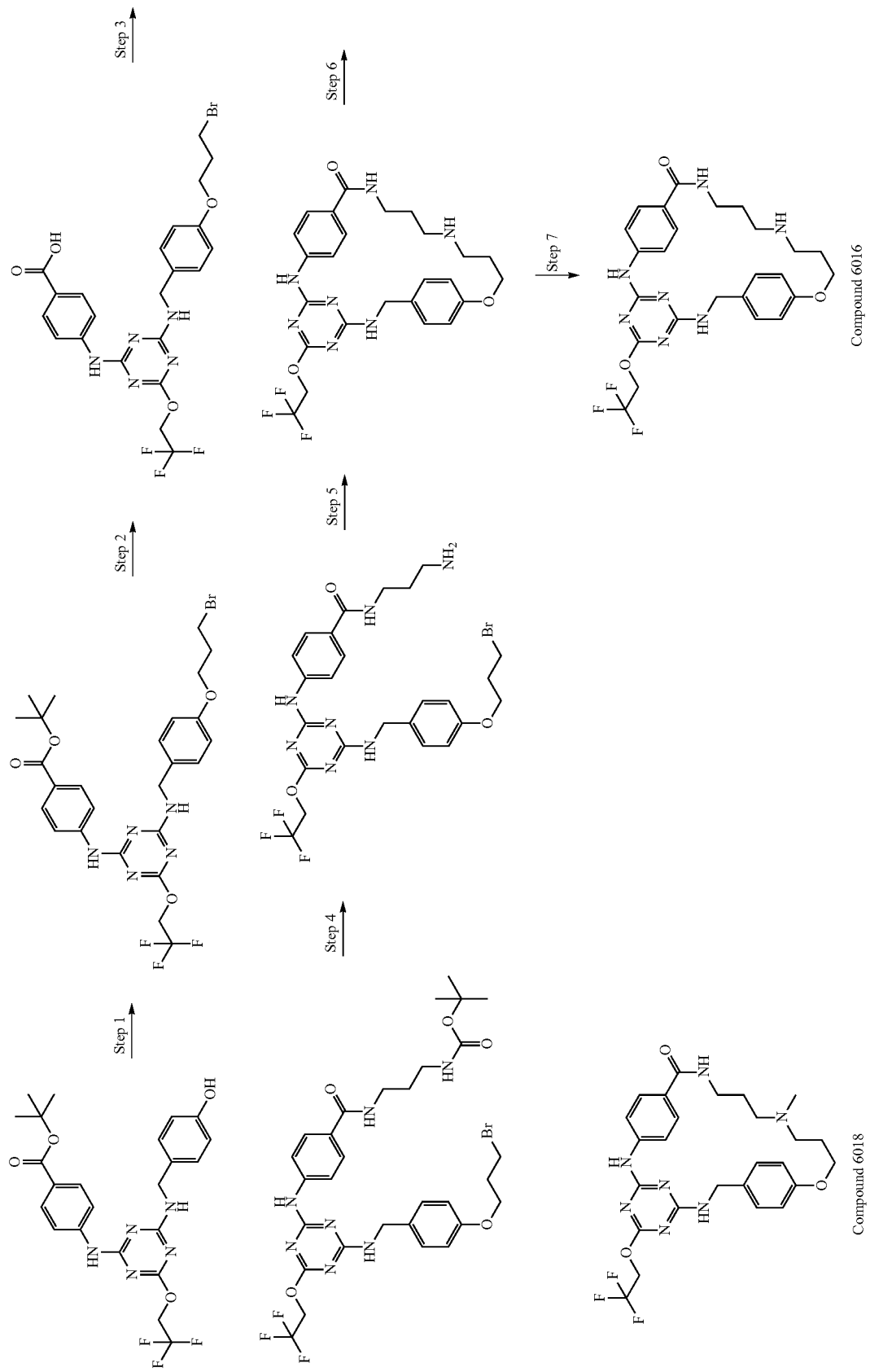

Step 1: To a solution of tert-butyl 4-((4-((4-hydroxybenzyl)amino)-6-(2,2,2-trifluoroethoxy)-1,3,5-triazin-2-yl)amino)benzoate (1966 mg, 4 mmol), 1,3-dibromopropane (1292 mg, 6.40 mmol), and 1,3-dibromopropane (1292 mg, 6.40 mmol) in acetone (50 mL) was added 1,3-dibromopropane (1292 mg, 6.40 mmol). The resulting solution was stirred for 6 h at reflux. After concentration, purification by Biotage eluting with 20-33% ethyl acetate in hexane to give 1500 mg of the desired product as a solid. MS m/z (M+H)$^+$ 614.11.

Step 2: A solution of tert-butyl 4-(4-(4-(3-bromopropoxy)benzylamino)-6-(2,2,2-trifluoroethoxy)-1,3,5-triazin-2-ylamino)benzoate (1.5 g, 2.449 mmol) in 4 M HCl in dioxane (3 mL, 12.00 mmol) was stirred for 16 h. Concentration gave 1360 mg of a solid product that will be used as it is. MS m/z (M+H)$^+$ 558.01.

Step 3: To solution of 4-((4-((4-(3-bromopropoxy)benzyl)amino)-6-(2,2,2-trifluoroethoxy)-1,3,5-triazin-2-yl)amino)benzoic acid (723 mg, 1.3 mmol), Hunig's Base (1.135 mL, 6.50 mmol) and tert-butyl (3-aminopropyl)carbamate (227 mg, 1.300 mmol) in CH$_2$Cl$_2$ (8 mL) was added HATU (741 mg, 1.950 mmol). After stirring for 2 h, the mixture was concentrate and purified by Biotage eluting with 50%-80% ethyl acetate in hexane to give 800 mg of product as a solid. MS m/z (M+H)$^+$ 714.11.

Step 4: To a solution of tert-butyl (3-(4-((4-((4-(3-bromopropoxy)benzyl)amino)-6-(2,2,2-trifluoroethoxy)-1,3,5-triazin-2-yl)amino)benzamido)propyl)carbamate (713 mg, 1 mmol) in CH$_2$Cl$_2$ (5 mL) was added TFA (1 ml, 12.98 mmol). The resulting solution was stirred for 1 h. The solvents were removed and the residue (726 mg) was used as it was without any further purification. MS m/z (M+H)$^+$ 614.15.

Step 5: To a solution of N-(3-aminopropyl)-4-((4-((4-(3-bromopropoxy)benzyl)amino)-6-(2,2,2-trifluoroethoxy)-1,3,5-triazin-2-yl)amino)benzamide (0.612 g, 1 mmol) in 7 mL microwave vial in MeCN (14 mL) was added POTASSIUM CARBONATE (0.276 g, 2.000 mmol). The resulting mixture was stirred in microwave at 130° C. for 0.5 h. The solvents were removed and the residue was purified by prep HPLC to give 300 mg of the product as TFA salt. MS m/z (M+H)$^+$ 532.16.

Step 6: To a solution of the Step 5 product (10.63 mg, 0.02 mmol), acetic acid (1.201 mg, 0.020 mmol), and 37% formaldehyde in water (3.25 mg, 0.040 mmol) in MeOH (1 mL) was added sodium cyanotrihydroborate (2.51 mg, 0.040 mmol). The resulting mixture was stirred for 3 h and purified by prep HPLC to give 3.4 mg the desired product Compound 6018. MS m/z (M+H)$^+$ 546.2.

Step 7: To a solution of the Step 5 product (10 mg, 0.019 mmol) and Hunig's Base (0.033 mL, 0.188 mmol) in MeCN (1 mL) was added propyl carbonochloridate (9.22 mg, 0.075 mmol). The resulting mixture was stirred at rt for 5 min and queched with MeOH. The solvents were removed and the residue was purified by prep HPLC to give 5 mg of the product Compound 6016 as solid. MS m/z (M+H)$^+$ 618.22.

Example 6001: $^1$H NMR (400 MHz, METHANOL-d$_4$) δ 7.42-7.32 (m, 2H), 7.27-7.15 (m, 4H), 6.95-6.86 (m, 2H), 4.90-4.81 (m, 2H), 4.54 (s, 2H), 3.99 (t, J=6.1 Hz, 2H), 3.55 (br. s., 4H), 3.39-3.28 (m, 2H), 2.06-1.96 (m, 2H), 1.32 (s, 9H).

Example 6002: $^1$H NMR (400 MHz, METHANOL-d$_4$) δ 7.43-7.34 (m, 2H), 7.33-7.24 (m, 2H), 7.23-7.17 (m, 2H), 6.97-6.86 (m, 2H), 4.92-4.80 (m, 2H), 4.56 (s, 2H), 4.00 (t, J=5.5 Hz, 2H), 3.65-3.58 (m, 2H), 3.51-3.44 (m, 2H), 3.37-3.25 (m, 2H), 2.02-1.91 (m, 2H), 1.51 (s, 9H).

Example 6011: $^1$H NMR (400 MHz, METHANOL-d$_4$) δ 7.48-7.41 (m, 2H), 7.35-7.29 (m, 2H), 7.28-7.21 (m, 2H), 6.99-6.92 (m, 2H), 4.81 (q, J=8.7 Hz, 2H), 4.60 (s, 2H), 4.34 (t, J=6.1 Hz, 2H), 3.62 (t, J=6.0 Hz, 2H), 3.15 (t, J=6.0 Hz, 2H), 2.90 (t, J=5.9 Hz, 2H), 2.21 (quin, J=6.0 Hz, 2H), 2.02-1.91 (m, 2H).

Example 6013: $^1$H NMR (METHANOL-d$_4$, 400 MHz): δ=7.36-7.43 (m, 2H), 7.29-7.35 (m, 2H), 7.17-7.23 (m, 2H), 6.86-6.93 (m, 2H), 4.83 (q, J=8.7 Hz, 2H), 4.53 (s, 2H), 4.03 (t, J=5.8 Hz, 2H), 3.41-3.48 (m, 2H), 3.30-3.39 (m, 2H), 1.92-2.02 (m, 2H), 1.80-1.90 (m, 2H), 1.31 ppm (s, 9H).

Example 6024: $^1$H NMR (400 MHz, METHANOL-d$_4$) δ 7.49 (d, J=9.0 Hz, 2H), 7.34 (d, J=9.0 Hz, 2H), 7.23 (d, J=8.8 Hz, 2H), 6.95 (d, J=8.8 Hz, 2H), 4.85 (m, 2H), 4.60 (s, 2H), 4.40 (t, J=5.8 Hz, 2H), 3.36 (s, 2H), 3.11 (t, J=6.0 Hz, 2H), 2.63 (s, 2H), 2.32-2.17 (t, J=6.0 Hz, 2H), 1.11 (s, 6H).

Example 6031: $^1$H NMR (500 MHz, DMSO-d$_6$) δ 9.85 (s, 1H), 8.40 (t, J=6.0 Hz, 1H), 8.21 (t, J=6.1 Hz, 1H), 7.97 (s, 1H), 7.29-7.11 (d, J=8.5 Hz, 2H), 7.02-6.86 (d, J=8.5 Hz, 2H), 4.99 (q, J=9.1 Hz, 2H), 4.42 (d, J=5.8 Hz, 2H), 3.97 (t, J=6.1 Hz, 2H), 3.12 (d, J=6.4 Hz, 2H), 2.90 (s, 2H), 2.75 (s, 2H), 1.85 (t, J=6.1 Hz, 2H), 1.28 (s, 9H), 0.84 (s, 6H).

Example 6040: $^1$H NMR (500 MHz, DMSO-d$_6$) δ 9.84 (s, 1H, NH), 8.51-8.32 (m, 2H, NH), 7.36-7.28 (d, J=8.5 Hz, 2H), 7.22-7.10 (m, 4H), 7.04-6.98 (d, J=8.9 Hz, 2H), 5.00 (q, J=9.0 Hz, 2H), 4.37 (d, J=5.5 Hz, 2H), 4.16 (t, J=6.6 Hz, 2H), 3.20 (d, J=5.2 Hz, 2H), 2.48 (d, J=7.6 Hz, 2H), 2.31 (s, 2H), 2.10 (s, 3H), 1.87-1.76 (m, 2H), 0.94 (s, 6H).

TABLE 2

| Example | Structure | Formula | MW | MS m/z (M + H)$^+$ |
|---|---|---|---|---|
| 6001 | 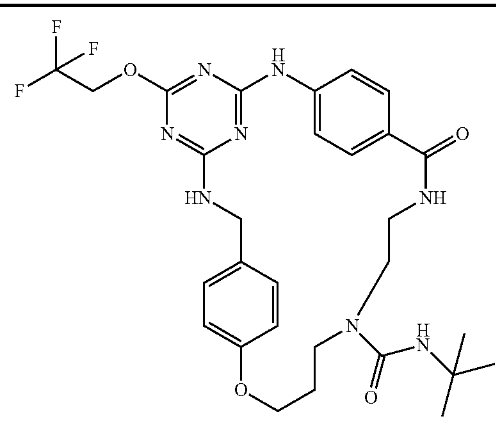 | C29 H35 F3 N8 O4 | 616.64 | 617.26 |

TABLE 2-continued
| Example | Structure | Formula | MW | MS m/z (M + H)+ |
|---------|-----------|---------|-----|-----------------|
| 6002 | 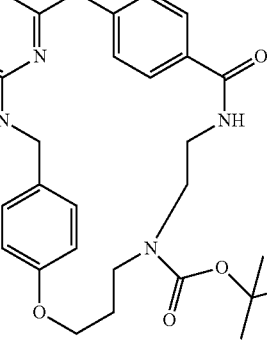 | C29 H34 F3 N7 O5 | 617.63 | 618.24 |
| 6003 | 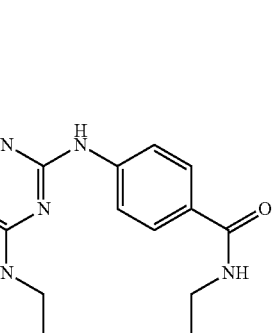 | C28 H33 F3 N8 O4 | 602.62 | 603.3 |
| 6004 | 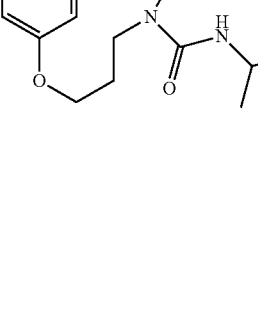 | C28 H32 F3 N7 O5 | 603.6 | 604.3 |

TABLE 2-continued

| Example | Structure | Formula | MW | MS m/z (M + H)+ |
|---------|-----------|---------|-----|-----------------|
| 6005 | 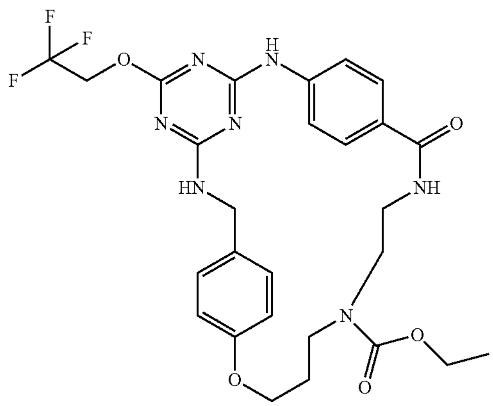 [SMILES: CCOC(=O)N1CCCOc2ccc(cc2)CNc2nc(nc(OCC(F)(F)F)n2)Nc2ccc(cc2)C(=O)NCC1] | C27 H30 F3 N7 O5 | 589.57 | 590.3 |
| 6006 | 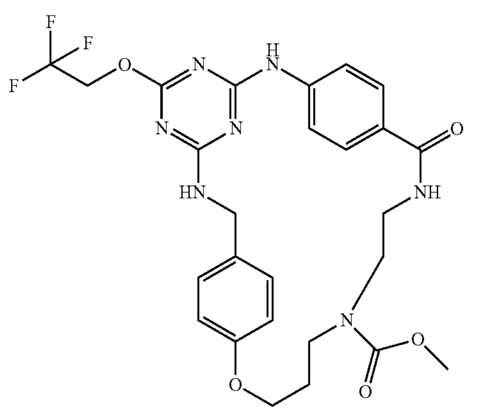 [SMILES: COC(=O)N1CCCOc2ccc(cc2)CNc2nc(nc(OCC(F)(F)F)n2)Nc2ccc(cc2)C(=O)NCC1] | C26 H28 F3 N7 O5 | 575.55 | 576.16 |
| 6007 | 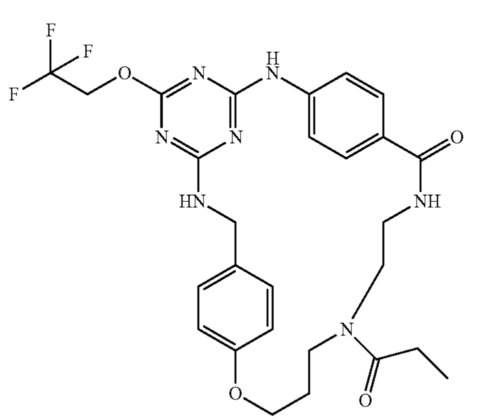 [SMILES: CCC(=O)N1CCCOc2ccc(cc2)CNc2nc(nc(OCC(F)(F)F)n2)Nc2ccc(cc2)C(=O)NCC1] | C27 H30 F3 N7 O4 | 573.57 | 574.18 |

TABLE 2-continued
| Example | Structure | Formula | MW | MS m/z (M + H)+ |
|---|---|---|---|---|
| 6008 | 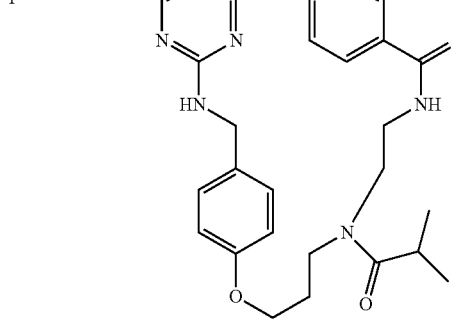 | C28 H32 F3 N7 O4 | 587.6 | 588.21 |
| 6011 | 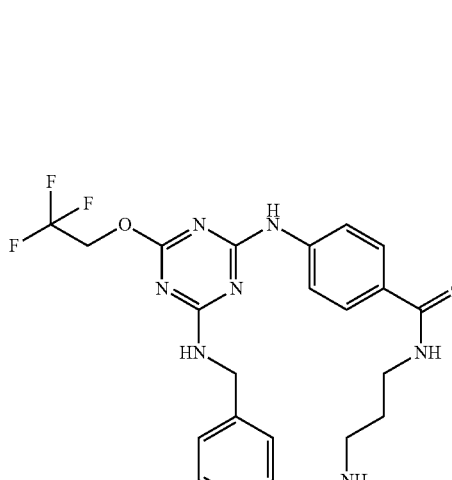 | C25 H28 F3 N7 O3 | 531.54 | 532.16 |
| 6012 | 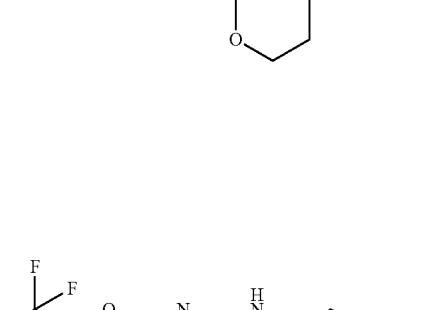 | C28 H33 F3 N8 O4 | 602.62 | 603.24 |

TABLE 2-continued

| Example | Structure | Formula | MW | MS m/z (M + H)+ |
|---|---|---|---|---|
| 6013 | 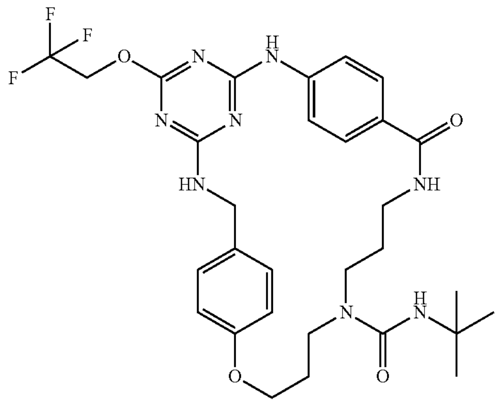 [SMILES: CC(C)(C)NC(=O)N1CCCNC(=O)c2ccc(cc2)Nc2nc(nc(OCC(F)(F)F)n2)NCc2ccc(cc2)OCCC1] | C30 H37 F3 N8 O4 | 630.67 | 631.28 |
| 6014 | 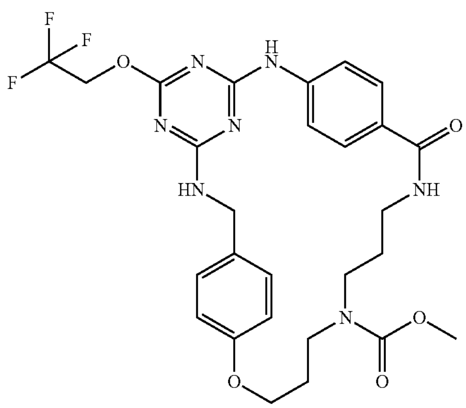 [SMILES: COC(=O)N1CCCNC(=O)c2ccc(cc2)Nc2nc(nc(OCC(F)(F)F)n2)NCc2ccc(cc2)OCCC1] | C27 H30 F3 N7 O5 | 589.57 | 590.17 |
| 6015 | 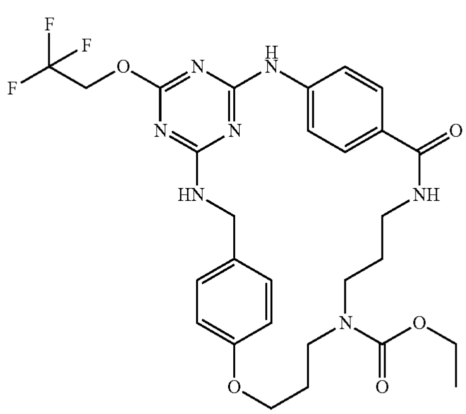 [SMILES: CCOC(=O)N1CCCNC(=O)c2ccc(cc2)Nc2nc(nc(OCC(F)(F)F)n2)NCc2ccc(cc2)OCCC1] | C28 H32 F3 N7 O5 | 603.6 | 604.22 |

TABLE 2-continued
| Example | Structure | Formula | MW | MS m/z (M + H)+ |
|---|---|---|---|---|
| 6016 | 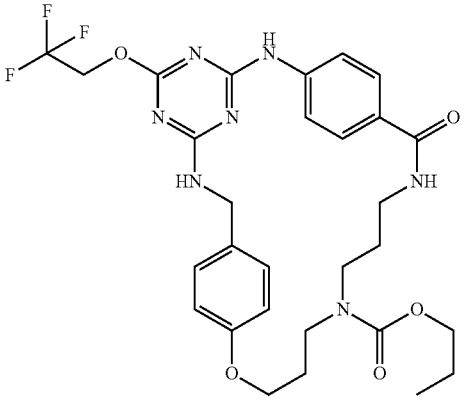 [SMILES: CCCOC(=O)N1CCCNC(=O)c2ccc(cc2)Nc2nc(nc(OCC(F)(F)F)n2)NCc2ccc(cc2)OCCC1] | C29 H34 F3 N7 O5 | 617.63 | 618.22 |
| 6017 | 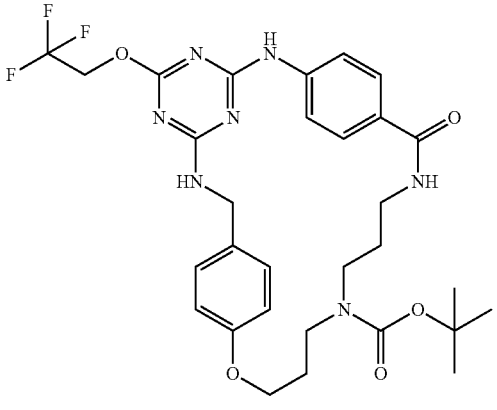 [SMILES: CC(C)(C)OC(=O)N1CCCNC(=O)c2ccc(cc2)Nc2nc(nc(OCC(F)(F)F)n2)NCc2ccc(cc2)OCCC1] | C30 H36 F3 N7 O5 | 631.65 | 632.26 |
| 6018 | 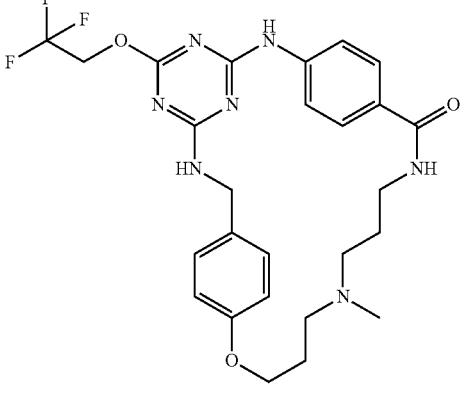 | C26 H30 F3 N7 O3 | 545.56 | 546.2 |

TABLE 2-continued
| Example | Structure | Formula | MW | MS m/z (M + H)+ |
|---|---|---|---|---|
| 6019 | 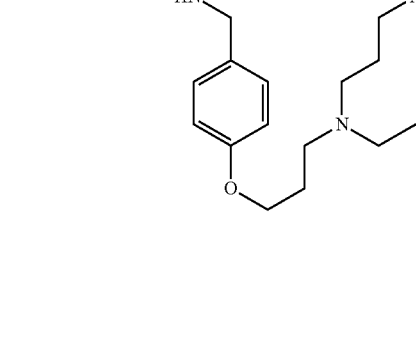 | C29 H36 F3 N7 O3 | 587.64 | 588.2 |
| 6020 | 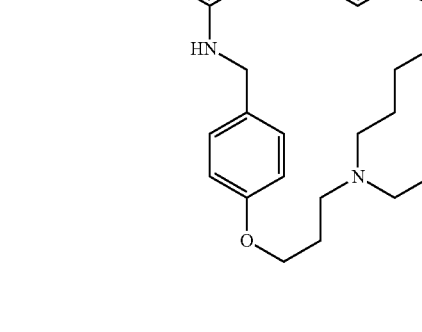 | C29 H36 F3 N7 O3 | 587.64 | 588.2 |
| 6021 | 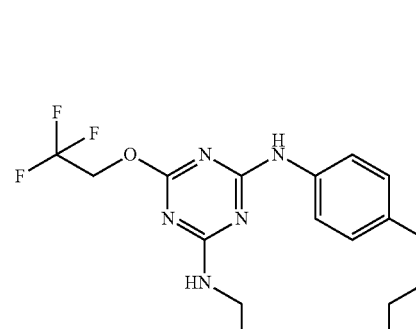 | C28 H33 F3 N8 O4 | 602.62 | 603.23 |

TABLE 2-continued
| Example | Structure | Formula | MW | MS m/z (M + H)+ |
|---|---|---|---|---|
| 6022 | 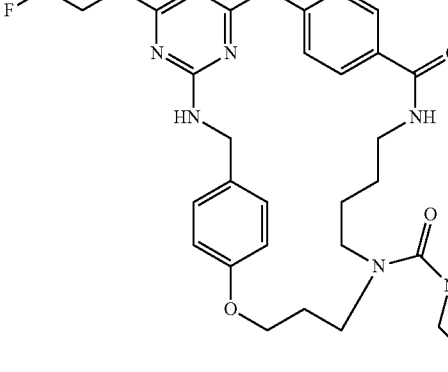 | C29 H35 F3 N8 O4 | 616.64 | 617.24 |
| 6023 | 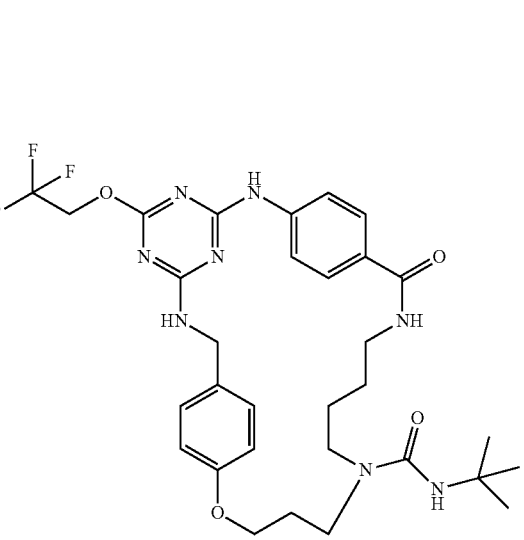 | C31 H39 F3 N8 O4 | 644.7 | 645.26 |
| 6024 | 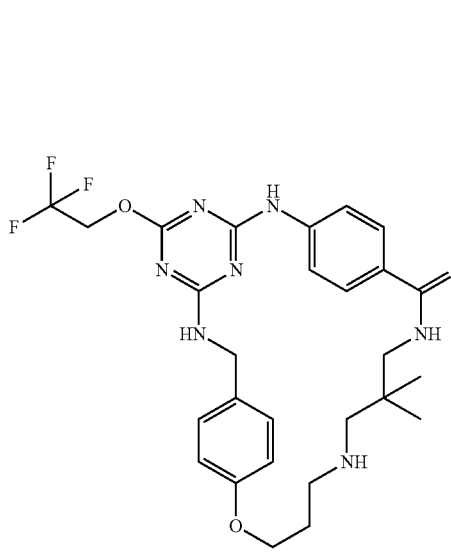 | C27 H32 F3 N7 O3 | 559.59 | 560.21 |

TABLE 2-continued
| Example | Structure | Formula | MW | MS m/z (M + H)+ |
|---|---|---|---|---|
| 6025 | 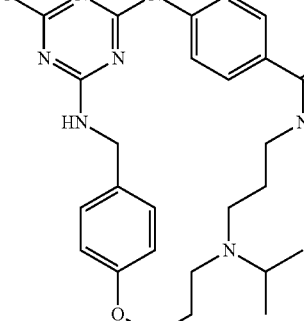 | C28 H34 F3 N7 O3 | 573.62 | 574.23 |
| 6026 | 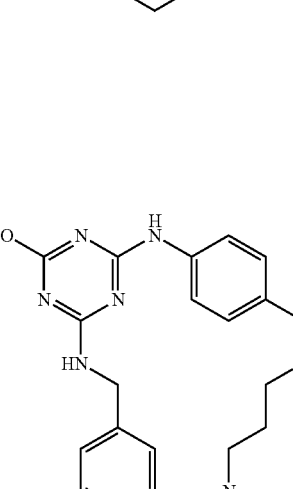 | C27 H32 F3 N7 O3 | 559.59 | 560.21 |
| 6027 | 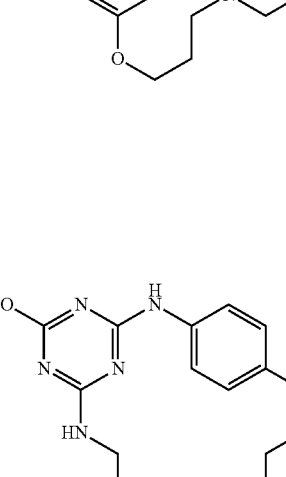 | C28 H34 F3 N7 O3 | 573.62 | 574.23 |

TABLE 2-continued
| Example | Structure | Formula | MW | MS m/z $(M + H)^+$ |
|---|---|---|---|---|
| 6028 | 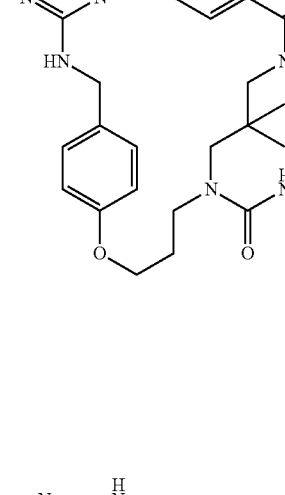 | C30 H37 F3 N8 O4 | 630.67 | 631.2 |
| 6030 | 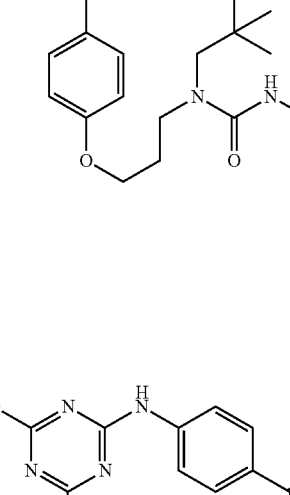 | C31 H39 F3 N8 O4 | 644.7 | 645.3 |
| 6031 | 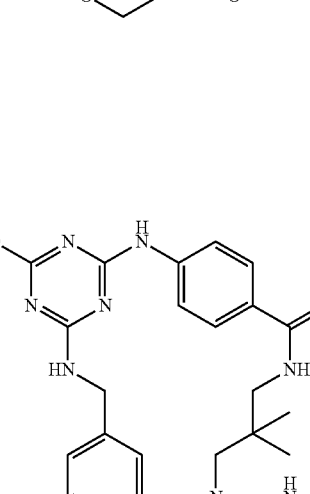 | C32 H41 F3 N8 O4 | 658.72 | 659.3 |

TABLE 2-continued

| Example | Structure | Formula | MW | MS m/z (M + H)+ |
|---------|-----------|---------|-----|------------------|
| 6032 | 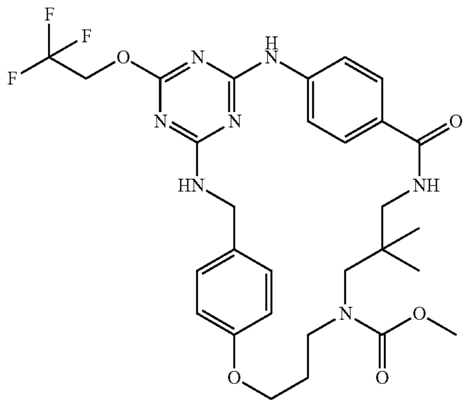 [SMILES: COC(=O)N1CCCOc2ccc(cc2)CNc2nc(nc(OCC(F)(F)F)n2)Nc2ccc(cc2)C(=O)NCC(C)(C)C1] | C29 H34 F3 N7 O5 | 617.63 | 618.2 |
| 6033 | 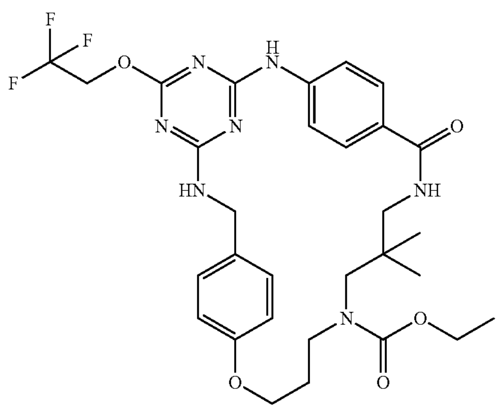 [SMILES: CCOC(=O)N1CCCOc2ccc(cc2)CNc2nc(nc(OCC(F)(F)F)n2)Nc2ccc(cc2)C(=O)NCC(C)(C)C1] | C30 H36 F3 N7 O5 | 631.65 | 637.2 |
| 6034 | 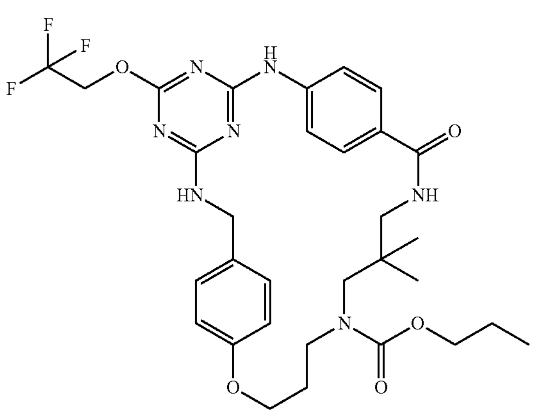 [SMILES: CCCOC(=O)N1CCCOc2ccc(cc2)CNc2nc(nc(OCC(F)(F)F)n2)Nc2ccc(cc2)C(=O)NCC(C)(C)C1] | C31 H38 F3 N7 O5 | 645.68 | 646.2 |

TABLE 2-continued
| Example | Structure | Formula | MW | MS m/z (M + H)+ |
|---|---|---|---|---|
| 6035 | 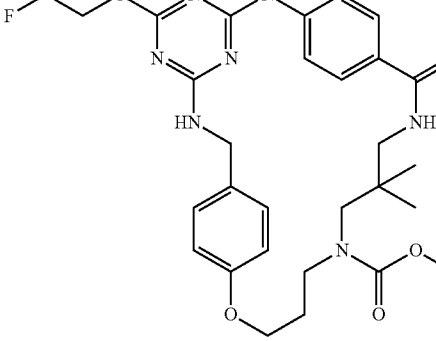 | C31 H38 F3 N7 O5 | 645.68 | 646.2 |
| 6036 | 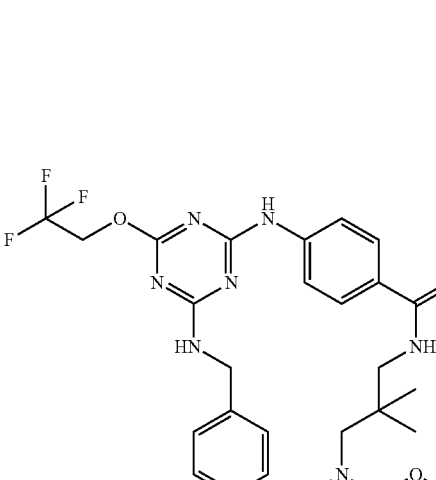 | C32 H40 F3 N7 O5 | 659.71 | 660.3 |
| 6037 | 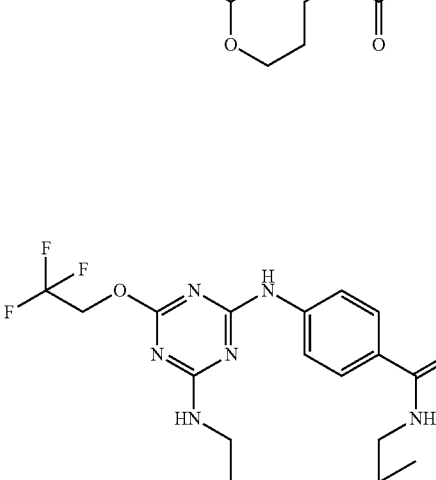 | C31 H39 F3 N8 O4 | 644.7 | 645.2 |

TABLE 2-continued
| Example | Structure | Formula | MW | MS m/z (M + H)+ |
|---|---|---|---|---|
| 6038 | 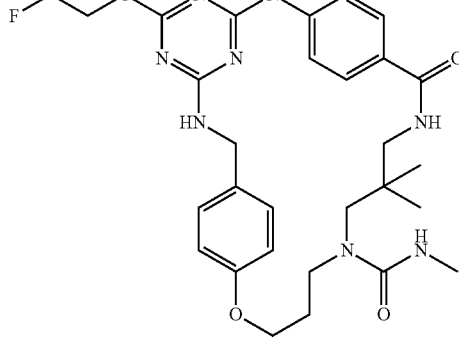 | C29 H35 F3 N8 O4 | 616.64 | 617.2 |
| 6039 | 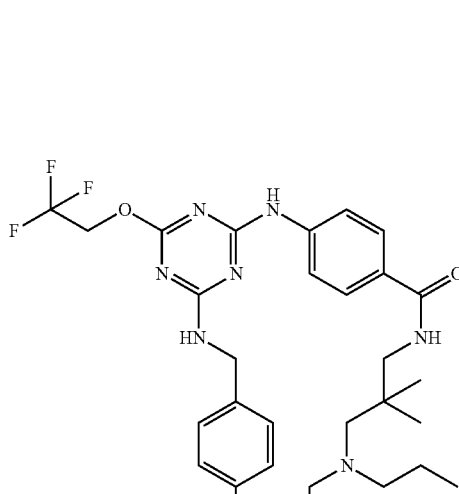 | C30 H38 F3 N7 O3 | 601.67 | 600.2 |
| 6040 | 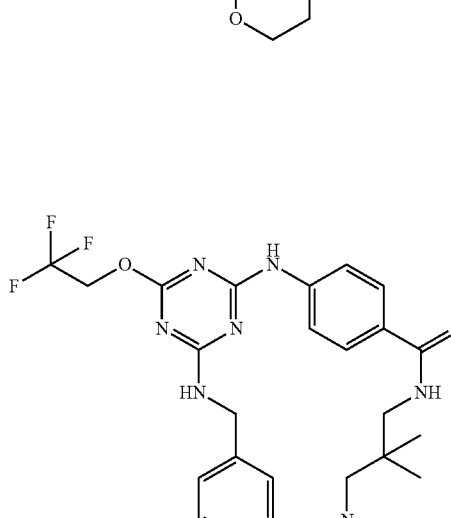 | C28 H34 F3 N7 O3 | 573.62 | 574.2 |

| Example | Structure | Formula | MW | MS m/z (M + H)+ |
|---|---|---|---|---|
| 6041 | 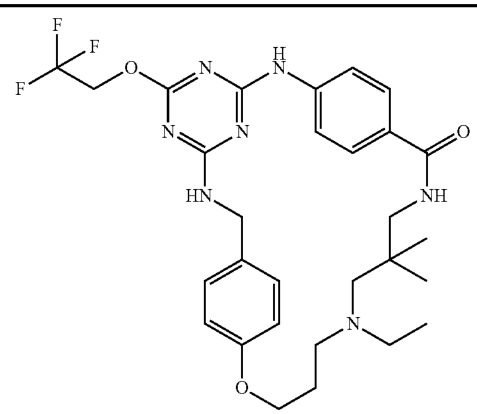 | C29 H36 F3 N7 O3 | 587.64 | 588.2 |
Series 7000
Example 7001
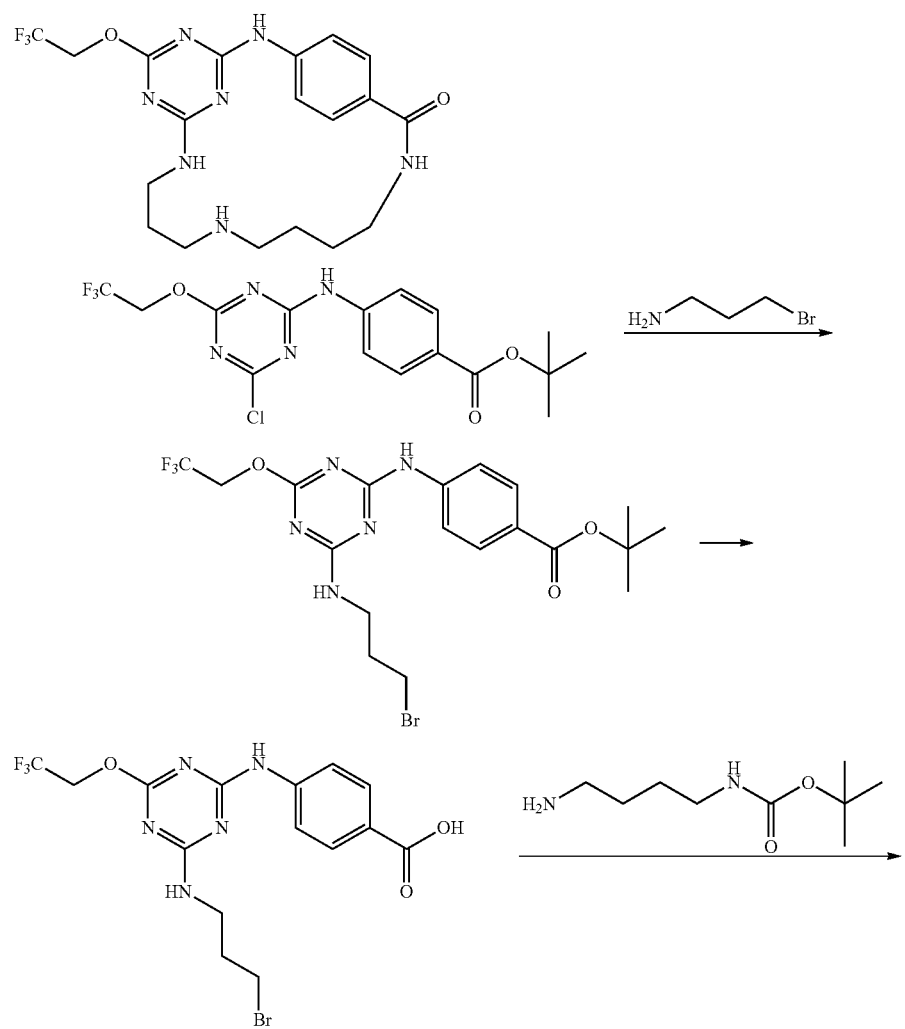

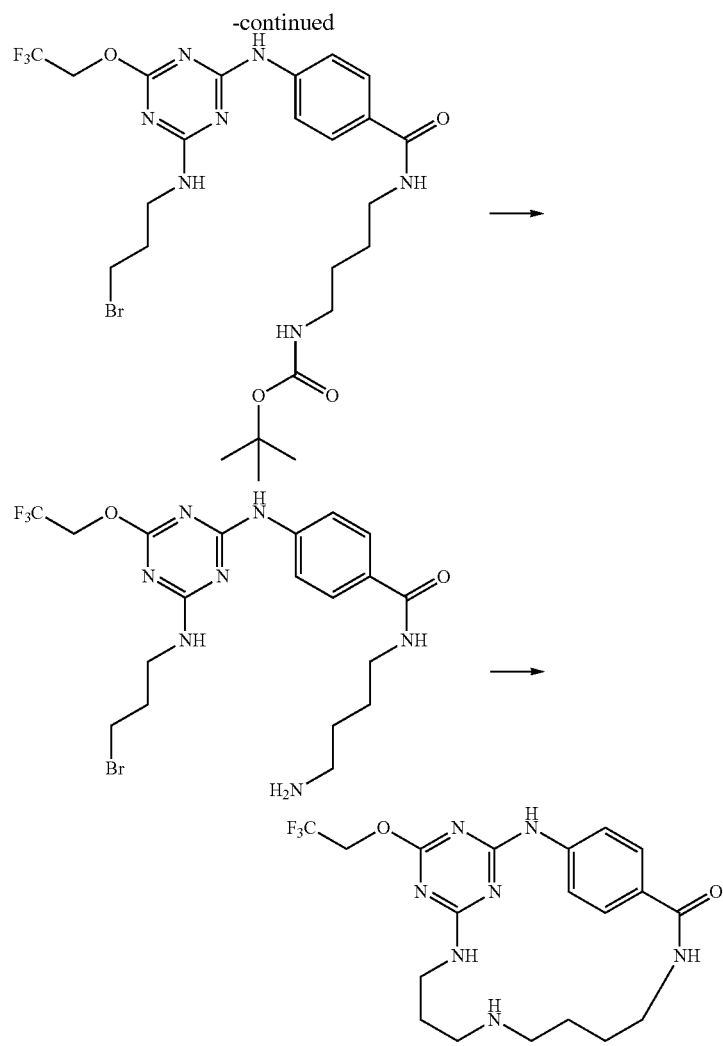

Step 1: tert-butyl 4-(4-(3-bromopropylamino)-6-(2,2,2-trifluoroethoxy)-1,3,5-triazin-2-ylamino)benzoate was prepared following the procedure reported in Example 4001 step 2.

3-bromopropan-1-amine HBr salt was used instead of 4-(aminomethyl)phenol as starting material.

| tert-butyl 4-(4-(3-bromopropylamino)-6-(2,2,2-trifluoroethoxy)-1,3,5-triazin-2-ylamino)benzoate | |
|---|---|
| MS (M + H)+ Calcd. | 506.1 |
| MS (M + H)+ Observ. | 506.0 |
| Retention Time | 1.16 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 2: 4-(4-(3-bromopropylamino)-6-(2,2,2-trifluoroethoxy)-1,3,5-triazin-2-ylamino)benzoic acid was prepared following the procedure reported in Example 4001 step 4.

| 4-(4-(3-bromopropylamino)-6-(2,2,2-trifluoroethoxy)-1,3,5-triazin-2-ylamino)benzoic acid | |
|---|---|
| MS (M + H)+ Calcd. | 450.0 |
| MS (M + H)+ Observ. | 449.9 |
| Retention Time | 0.95 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: tert-butyl 4-(4-(4-(3-bromopropylamino)-6-(2,2,2-trifluoroethoxy)-1,3,5-triazin-2-ylamino)benzamido)butylcarbamate was prepared following the procedure reported in Example 4001 step 5.

| tert-butyl 4-(4-(4-(3-bromopropylamino)-6-(2,2,2-trifluoroethoxy)-1,3,5-triazin-2-ylamino)benzamido)butylcarbamate | |
|---|---|
| MS (M + H)+ Calcd. | 620.2 |
| MS (M + H)+ Observ. | 620.2 |
| Retention Time | 1.02 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: N-(4-aminobutyl)-4-(4-(3-bromopropylamino)-6-(2,2,2-trifluoroethoxy)-1,3,5-triazin-2-ylamino)benzamide TFA salt was prepared following the procedure reported in Example 4001 step 6.

| N-(4-aminobutyl)-4-(4-(3-bromopropylamino)-6-(2,2,2-trifluoroethoxy)-1,3,5-triazin-2-ylamino)benzamide TFA salt | |
|---|---|
| MS (M + H)+ Calcd. | 520.1 |
| MS (M + H)+ Observ. | 520.0 |
| Retention Time | 0.82 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: Example 7001 was prepared following the procedure reported in Example 4001 step 7. $^1$H NMR (400 MHz, METHANOL-$d_4$) δ 7.98-7.88 (m, 2H), 7.65-7.55 (m, 2H), 4.81 (q, J=8.5 Hz, 2H), 4.13 (t, J=6.0 Hz, 2H), 3.56 (t, J=5.6 Hz, 2H), 3.48-3.42 (m, 2H), 3.04-2.95 (m, 2H), 2.35-2.24 (m, 2H), 1.80-1.67 (m, 4H).

| Example 7001 | |
|---|---|
| MS (M + H)+ Calcd. | 520.1 |
| MS (M + H)+ Observ. | 520.0 |
| Retention Time | 0.82 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Series 8000

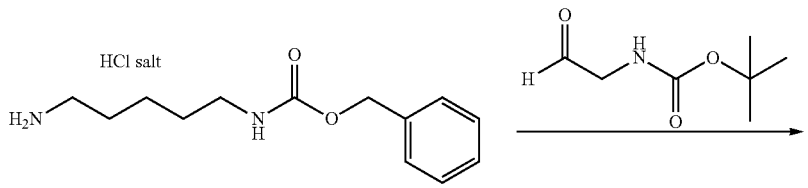

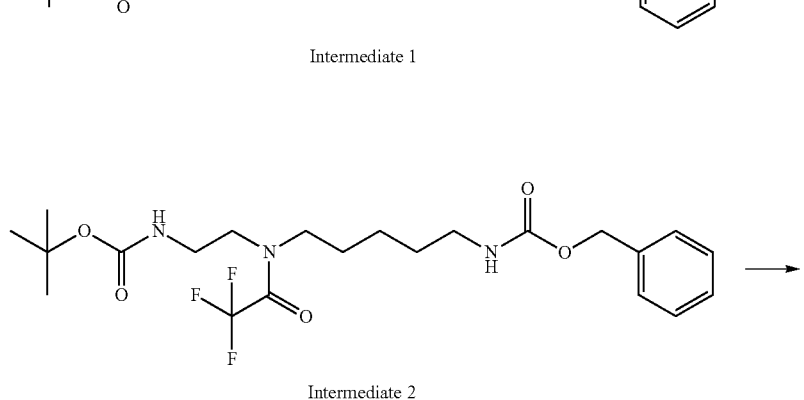

Intermediate 1

Intermediate 2

183 184
-continued
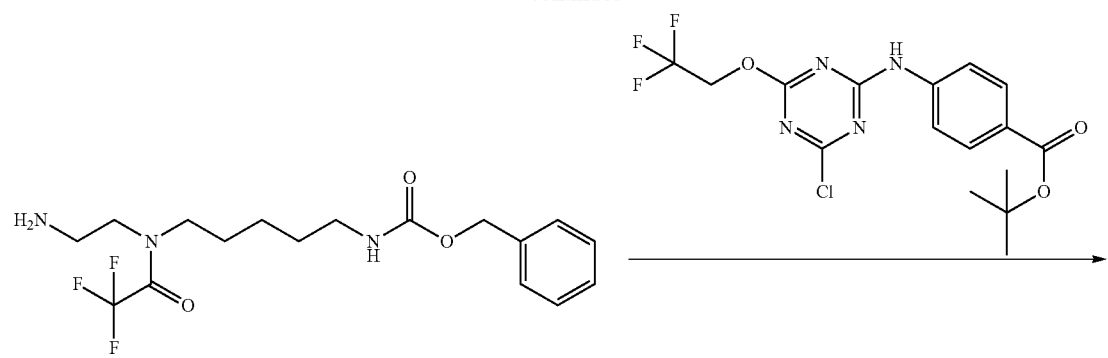
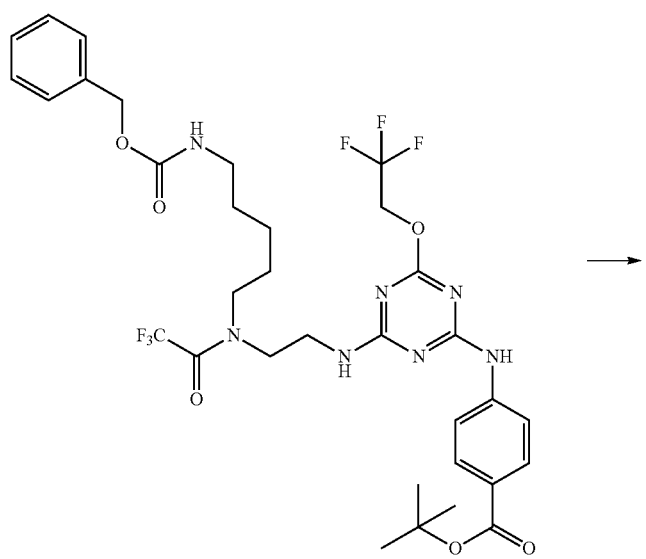
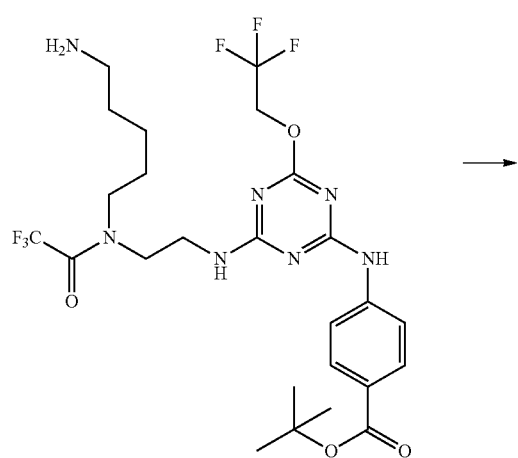

-continued

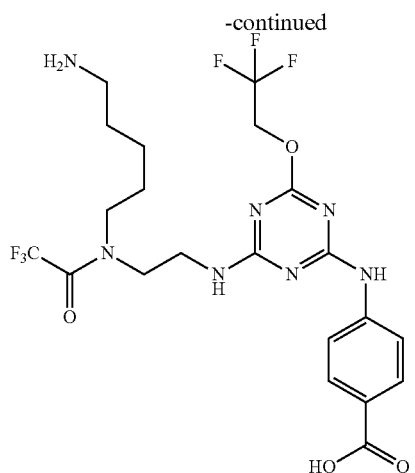

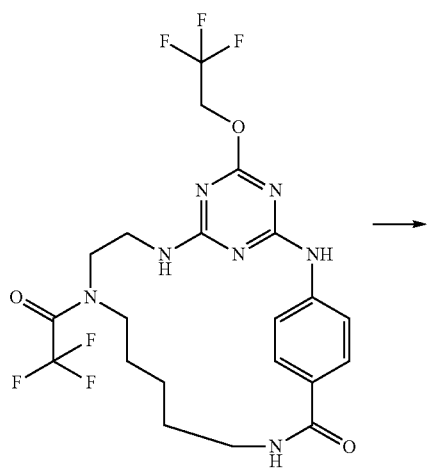

Example 8001

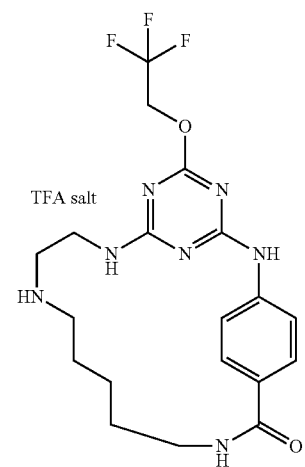

Example 8002

Step 1: benzyl 5-aminopentylcarbamate, HCl (1401 mg, 5.14 mmol), tert-butyl 2-oxoethylcarbamate (545 mg, 3.42 mmol), AcOH (0.196 mL, 3.42 mmol) were dissolved in DCM (Volume: 2 mL) and stirred for 16 h followed by the addition of Sodium triacetoxyborohydride (1016 mg, 4.79 mmol). The reaction was stirred for 4 h. The solvent was removed under vacuum and the crude product was purified silica gel chromatography using a gradient of 5-10% MeOH/ DCM with 2% Et3N. The product fractions were collected and concentrated under vacuum to give 470 mg (36%) of intermediate 1 as an oil.

| Intermediate 1 | |
|---|---|
| MS (M + H)+ Calcd. | 380.3 |
| MS (M + H)+ Observ. | 380.2 |
| Retention Time | 0.81 min |

-continued

| Intermediate 1 | |
|---|---|
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 2: Intermediate 1 (470 mg, 1.238 mmol) and Hunig's Base (0.433 mL, 2.477 mmol) were dissolved in DCM (10 mL) and cooled to 0° C. Trifluoroacetic anhydride (0.210 mL, 1.486 mmol) was added to the reaction and stirring was continued for 1 h. The reaction was diluted with water and DCM. The organic layer was collected, dried over sodium sulfate, and concentrated under vacuum to give 617 mg (105%) intermediate 2.

| Intermediate 2 | |
|---|---|
| MS (M + H)$^+$ Calcd. | 476.2 |
| MS (M + H)$^+$ Observ. | 476.2 |
| Retention Time | 1.05 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: Intermediate 2 (617 mg, 1.298 mmol) was dissolved in DCM (2 mL) and Trifluoroacetic acid (500 μl) was added. The reaction was allowed to stir for 30 min. The solvent was removed under vacuum to give 635 mg (100%) benzyl 5-(N-(2-aminoethyl)-2,2,2-trifluoroacetamido)pentylcarbamate which was carried to the next step without further purification.

| benzyl 5-(N-(2-aminoethyl)-2,2,2-trifluoroacetamido)pentylcarbamate | |
|---|---|
| MS (M + H)$^+$ Calcd. | 376.2 |
| MS (M + H)$^+$ Observ. | 376.1 |
| Retention Time | 0.77 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: tert-butyl 4-(4-(2-(N-(5-(benzyloxycarbonylamino)pentyl)-2,2,2-trifluoroacetamido)ethylamino)-6-(2,2,2-trifluoroethoxy)-1,3,5-triazin-2-ylamino)benzoate was prepared following the procedure reported in Example 4001 step 2. Benzyl 5-(N-(2-aminoethyl)-2,2,2-trifluoroacetamido)pentylcarbamate was used instead of 4-(aminomethyl)phenol as starting material.

| tert-butyl 4-(4-(2-(N-(5-(benzyloxycarbonylamino)pentyl)-2,2,2-trifluoroacetamido)ethylamino)-6-(2,2,2-trifluoroethoxy)-1,3,5-triazin-2-ylamino)benzoate | |
|---|---|
| MS (M + H)$^+$ Calcd. | 744.3 |
| MS (M + H)$^+$ Observ. | 744.3 |
| Retention Time | 1.20 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: tert-butyl 44442-(N-(5-(((benzyloxy)carbonyl)amino)pentyl)-2,2,2-trifluoroacetamido)ethyl)amino)-6-(2,2,2-trifluoroethoxy)-1,3,5-triazin-2-yl)amino)benzoate (135 mg, 0.181 mmol) was dissolved in MeOH (20 mL) and Palladium on carbon (60 mg, 0.056 mmol) was added under $N_2$ atmosphere. The flask was purged with $H_2$ (g) and stirred for 16 h. The reaction was filtered through celite and the solvent was removed under vacuum to give 110 mg (100%) tert-butyl 4-(4-(2-(N-(5-aminopentyl)-2,2,2-trifluoroacetamido)ethylamino)-6-(2,2,2-trifluoroethoxy)-1,3,5-triazin-2-ylamino)benzoate.

| tert-butyl 4-(4-(2-(N-(5-aminopentyl)-2,2,2-trifluoroacetamido)ethylamino)-6-(2,2,2-trifluoroethoxy)-1,3,5-triazin-2-ylamino)benzoate | |
|---|---|
| MS (M + H)$^+$ Calcd. | 610.3 |
| MS (M + H)$^+$ Observ. | 610.2 |
| Retention Time | 0.96 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 6: 4-(4-(2-(N-(5-aminopentyl)-2,2,2-trifluoroacetamido)ethylamino)-6-(2,2,2-trifluoroethoxy)-1,3,5-triazin-2-ylamino)benzoic acid was prepared following the procedure reported in Example 4001 step 4.

| 4-(4-(2-(N-(5-aminopentyl)-2,2,2-trifluoroacetamido)ethylamino)-6-(2,2,2-trifluoroethoxy)-1,3,5-triazin-2-ylamino)benzoic acid | |
|---|---|
| MS (M + H)$^+$ Calcd. | 554.2 |
| MS (M + H)$^+$ Observ. | 554.1 |
| Retention Time | 0.81 min |
| LC Condition | |
| Solvent A | 100% Water:0.05% TFA |
| Solvent B | 100% ACN:0.05% TFA |

-continued 4-(4-(2-(N-(5-aminopentyl)-2,2,2-trifluoroacetamido)ethylamino)-6-(2,2,2-trifluoroethoxy)-1,3,5-triazin-2-ylamino)benzoic acid

| | |
|---|---|
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 7: 4-(4-(2-(N-(5-aminopentyl)-2,2,2-trifluoroacetamido)ethylamino)-6-(2,2,2-trifluoroethoxy)-1,3,5-triazin-2-ylamino)benzoic acid (100 mg, 0.181 mmol), HATU (103 mg, 0.271 mmol), and Hunig's Base (0.158 ml, 0.903 mmol) were dissolved in DMF (36 ml) and stirred for 16 h. The solvent was removed under vacuum and the crude material was purified by rev. phase prep-HPLC using a gradient of 20-80% ACN/Water with 0.1% TFA modifier. The product fractions were collected and the solvent removed by speed vacuum to give 25 mg (25%) Example 8001 as a white solid.

4-(4-(2-(N-(5-aminopentyl)-2,2,2-trifluoroacetamido)ethylamino)-6-(2,2,2-trifluoroethoxy)-1,3,5-triazin-2-ylamino)benzoic acid

| | |
|---|---|
| MS (M + H)$^+$ Calcd. | 536.2 |
| MS (M + H)$^+$ Observ. | 536.1 |
| Retention Time | 0.91 min |
| | LC Condition |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 8: Example 8001 (25 mg, 0.047 mmol) was dissolved in MeOH (1 mL) followed by the addition of Water (0.2 mL) and K$_2$CO$_3$ (32.3 mg, 0.233 mmol). The reaction was warmed to 65° C. for 16 h. The reaction mixture was filtered and injected on a rev. phase prep-HPLC using a gradient of 10-40% ACN/Water w/0.1% TFA modifier. The product fraction was collected and the solvent removed by speed vac to give 3 mg (11%) Example 8002 as a white solid.

Series 9000

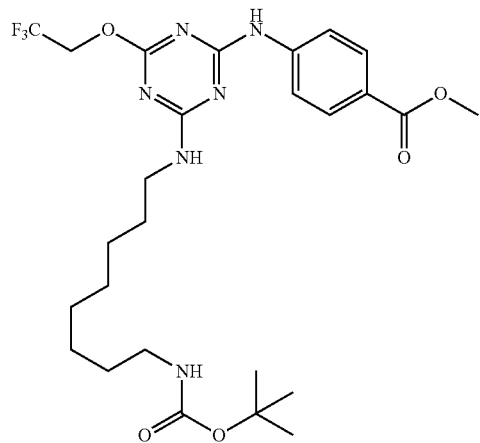

-continued

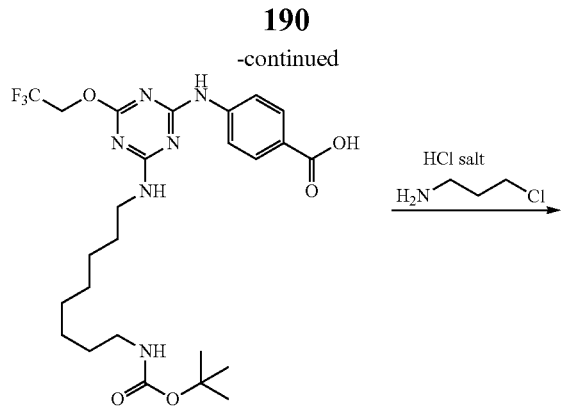

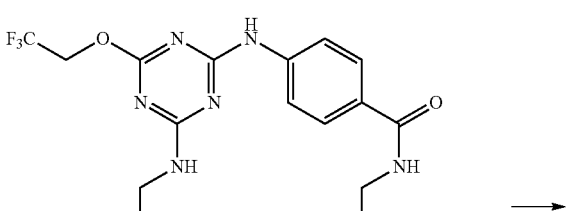

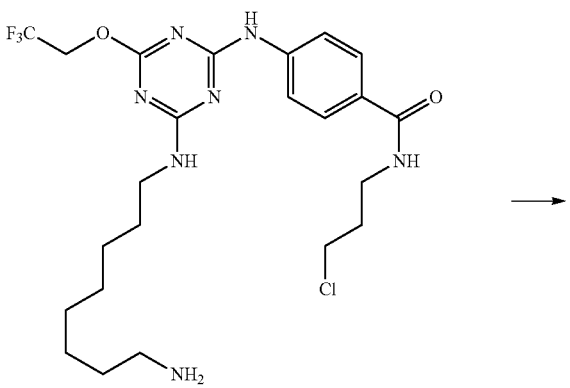

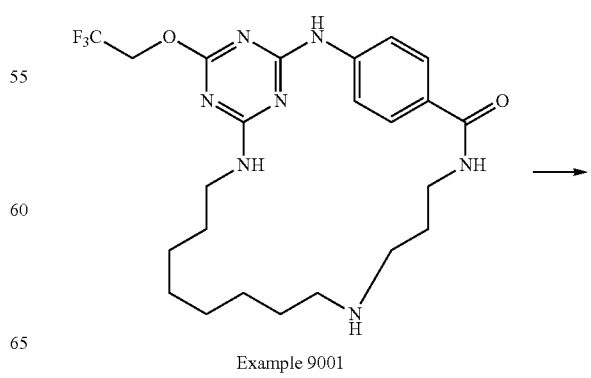

Example 9001

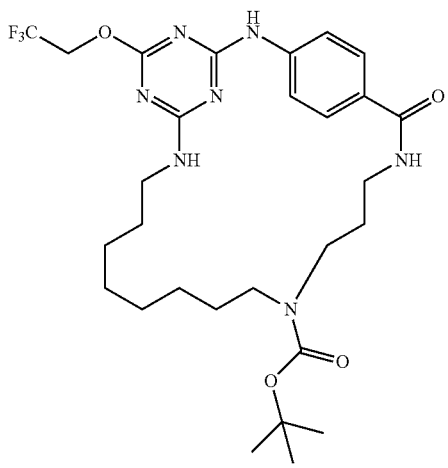

Example 9002

Step 1: methyl 444-((8-((tert-butoxycarbonyl)amino)octyl)amino)-6-(2,2,2-trifluoroethoxy)-1,3,5-triazin-2-yl)amino)benzoate (1.5 g, 2.63 mmol), was dissolved in THF (5 mL) followed by the addition of LiOH (0.315 g, 13.14 mmol) and Water (5 mL). The reaction was headed to 65° C. for 6 h. The reaction was concentrated under vacuum and diluted 1N HCl. The solid that precipitated out was collected and washed with water then dried to give 1.2 g (82%) 4-(4-(8-(tert-butoxycarbonylamino)octylamino)-6-(2,2,2-trifluoroethoxy)-1,3,5-triazin-2-ylamino)benzoic acid as a white solid.

| 4-(4-(8-(tert-butoxycarbonylamino)octylamino)-6-(2,2,2-trifluoroethoxy)-1,3,5-triazin-2-ylamino)benzoic acid | |
|---|---|
| MS (M + H)$^+$ Calcd. | 557.3 |
| MS (M + H)$^+$ Observ. | 557.2 |
| Retention Time | 1.09 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 2: 4-((4-((8-((tert-butoxycarbonyl)amino)octyl)amino)-6-(2,2,2-trifluoroethoxy)-1,3,5-triazin-2-yl)amino)benzoic acid (650 mg, 1.168 mmol), 3-chloropropan-1-amine, HCl (182 mg, 1.401 mmol), HATU (666 mg, 1.752 mmol), and Hunig's Base (1.020 mL, 5.84 mmol) were stirred in DMF (1 mL) for 16 h. The solvent was removed and the crude material was purified by silica gel chromatography using a gradient of 20-40% EtOAc/Hexanes. The product fraction was collected and the solvent removed under vacuum to give 264 (36%) tert-butyl 8-(4-(4-(4-(3-chloropropylcarbamoyl)phenylamino)-6-(2,2,2-trifluoroethoxy)-1,3,5-triazin-2-ylamino)octylcarbamate.

| tert-butyl 8-(4-(4-(3-chloropropylcarbamoyl)phenylamino)-6-(2,2,2-trifluoroethoxy)-1,3,5-triazin-2-ylamino)octylcarbamate | |
|---|---|
| MS (M + H)$^+$ Calcd. | 632.3 |
| MS (M + H)$^+$ Observ. | 632.3 |
| Retention Time | 1.13 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 3: tert-butyl (8-((4-((4-((3-chloropropyl)carbamoyl)phenyl)amino)-6-(2,2,2-trifluoroethoxy)-1,3,5-triazin-2-yl)amino)octyl)carbamate (264 mg, 0.418 mmol) was dissolved in a 1:1 TFA (1 ml, 12.98 mmol)/DCM (1 mL). The reaction was stirred for 1 h. The solvent was removed under vacuum and the residue was dissolved in EtOAc and washed with saturated sodium bicarbonate solution, then brine. The organic layer was collected and dried over sodium sulfate, and concentrated under vacuum to give 222 mg (100%) 4-(4-(8-aminooctylamino)-6-(2,2,2-trifluoroethoxy)-1,3,5-triazin-2-ylamino)-N-(3-chloropropyl)benzamide as a white solid.

| 4-(4-(8-aminooctylamino)-6-(2,2,2-trifluoroethoxy)-1,3,5-triazin-2-ylamino)-N-(3-chloropropyl)benzamide | |
|---|---|
| MS (M + H)$^+$ Calcd. | 532.2 |
| MS (M + H)$^+$ Observ. | 532.2 |
| Retention Time | 0.86 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 4: Example 9001 was prepared following the procedure reported in Example 4001 step 7 except that the microwave conditions for heating was 150° C. for 30 minutes instead of 130° C. for 1 h. (rotomers) $^1$H NMR (400 MHz, METHANOL-d$_4$) δ 8.13-7.79 (m, 4H), 5.07-4.81 (m, 2H), 3.82-3.73 (m, 1.5H), 3.72-3.64 (m, 0.5H), 3.62-3.39 (m, 4H), 2.98-2.86 (m, 2H), 2.44-2.32 (m, 1.5H), 2.16-2.06 (m, 0.5H), 1.67 (br. s., 4H), 1.42 (br. s., 8H).

| Example 9001 | |
|---|---|
| MS (M + H)$^+$ Calcd. | 496.3 |
| MS (M + H)$^+$ Observ. | 496.2 |
| Retention Time | 0.76 min |
| LC Condition | |
| Solvent A | 100% Water:0.05% TFA |
| Solvent B | 100% ACN:0.05% TFA |
| Start % B | 2 |

-continued

| Example 9001 | |
|---|---|
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Step 5: Example 9001 (20 mg, 0.040 mmol) and di-tert-butyl dicarbonate (17.62 mg, 0.081 mmol) were dissolved in DMF (1 mL) and Hunig's Base (0.021 mL, 0.121 mmol) was added. The reaction was stirred for 3 h. TLC showed no more starting material. The solvent was purified by rev. phase prep-HPLC using a gradient of 40-100% ACN/Water w/0.1% TFA modifier. The product fraction was collected, diluted with EtOAc, washed with saturated sodium bicarbonate and brine. The organic layer was collected, dried over sodium sulfate, and concentrated under vacuum to give Example 9002 as a solid. $^1$H NMR (400 MHz, METHANOL-$d_4$) δ 7.78 (s, 4H), 4.90-4.82 (m, 2H), 4.47-4.39 (m, 2H), 3.56 (t, J=5.8 Hz, 2H), 3.49-3.36 (m, 4H), 3.07-2.98 (m, 2H), 2.03 (quin, J=5.6 Hz, 2H), 1.72-1.57 (m, 2H), 1.53-1.27 (m, 19H).

| Example 9002 | |
|---|---|
| MS (M + H)$^+$ Calcd. | 596.3 |
| MS (M + H)$^+$ Observ. | 596.3 |
| Retention Time | 1.00 min |
| LC Condition | |
| Solvent A | 100% Water:0.05% TFA |
| Solvent B | 100% ACN:0.05% TFA |
| Start % B | 2 |
| Final % B | 98 |
| Gradient Time | 2.2 min |
| Flow Rate | 0.8 mL/min |
| Wavelength | 220 |
| Solvent Pair | ACN:Water:TFA |
| Column | Acquity UPLC BEH C18 1.7 μm |

Example 9003

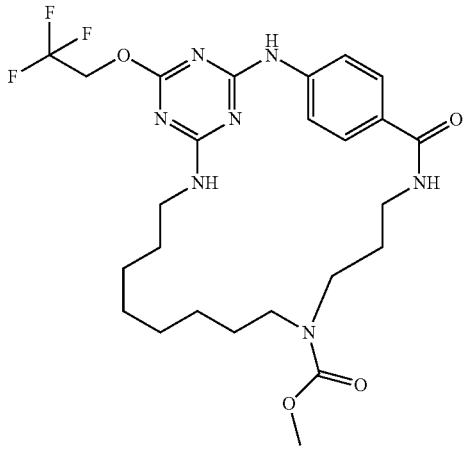 [SMILES: COC(=O)N1CCCCCCCCNc2nc(nc(OCC(F)(F)F)n2)Nc2ccc(cc2)C(=O)NCCC1]

Example 9003 was prepared following the procedure reported in Example 9002. Dimethyl dicarbonate was used instead of di-tertbutyl dicarbonate as starting material. LC-MS: 554.2 (M+H). $^1$H NMR (500 MHz, DMSO-$d_6$) δ 7.85-7.67 (m, 4H), 5.06-4.91 (m, 2H), 4.32 (t, J=5.2 Hz, 2H), 3.51 (s, 3H), 3.48 (t, J=5.8 Hz, 2H), 3.33-3.24 (m, 2H), 2.99-2.92 (m, 2H), 1.93-1.84 (m, 2H), 1.61-1.48 (m, 2H), 1.44-1.19 (m, 10H).

Example 9004

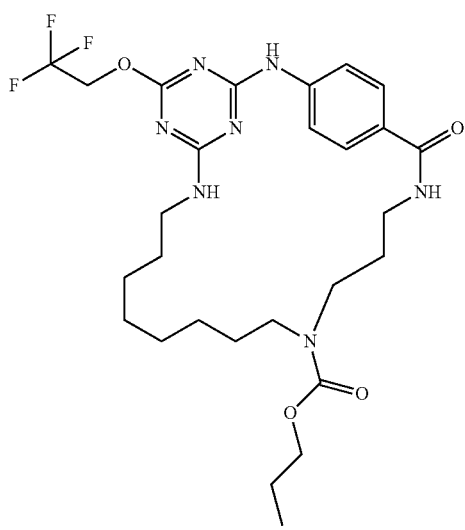 [SMILES: CCCOC(=O)N1CCCCCCCCNc2nc(nc(OCC(F)(F)F)n2)Nc2ccc(cc2)C(=O)NCCC1]

Example 9004 was prepared following the procedure reported in Example 9002. Propyl chloroformate was used instead of di-tertbutyl dicarbonate as starting material. LC-MS: 582.3 (M+H). $^1$H NMR (500 MHz, DMSO-$d_6$) δ 7.87-7.68 (m, 4H), 5.04-4.90 (m, 2H), 4.32 (t, J=4.7 Hz, 2H), 3.87 (t, J=6.6 Hz, 2H), 3.48 (t, J=5.8 Hz, 2H), 3.34-3.24 (m, 2H), 2.99-2.91 (m, 2H), 1.94-1.83 (m, 2H), 1.60-1.48 (m, 4H), 1.43-1.20 (m, 10H), 0.87 (t, J=7.3 Hz, 3H).

Example 9006

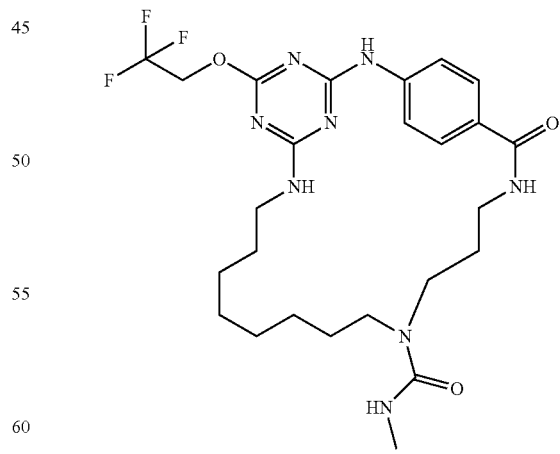

Example 9006 was prepared following the procedure reported in Example 9002. Methyl isocyanate was used instead of di-tertbutyl dicarbonate as starting material. LC-MS: 553.2 (M+H). $^1$H NMR (400 MHz, DMSO-$d_6$) δ 7.76 (s, 4H), 5.86-5.75 (m, 1H), 5.69-5.59 (m, 1H), 5.05-4.89 (m, 2H), 4.32 (t, J=5.3 Hz, 2H), 3.48 (t, J=5.8 Hz, 2H), 2.96 (q, J=6.4 Hz, 2H), 2.54 (s, 3H), 1.89 (quin, J=5.6 Hz, 2H), 1.60-1.48 (m, 2H), 1.43-1.15 (m, 10H).

Example 9008

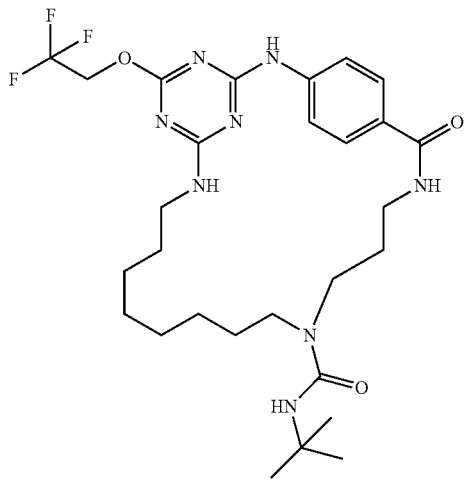 [SMILES: CC(C)(C)NC(=O)N1CCCCCCCCNc2nc(nc(OCC(F)(F)F)n2)Nc2ccc(cc2)C(=O)NCCC1]

Example 9008 was prepared following the procedure reported in Example 9002. Tert-Butyl isocyanate was used instead of di-tertbutyl dicarbonate as starting material. LC-MS: 595.3 (M+H). $^1$H NMR (400 MHz, DMSO-$d_6$) δ 7.83-7.69 (m, 4H), 5.60-5.54 (m, 1H), 5.52 (s, 1H), 5.04-4.90 (m, 2H), 4.32 (t, J=5.3 Hz, 2H), 3.49 (t, J=5.8 Hz, 2H), 2.97-2.87 (m, 2H), 1.94-1.84 (m, 2H), 1.63-1.48 (m, 2H), 1.38-1.23 (m, 10H), 1.21 (s, 9H).

Example 9009

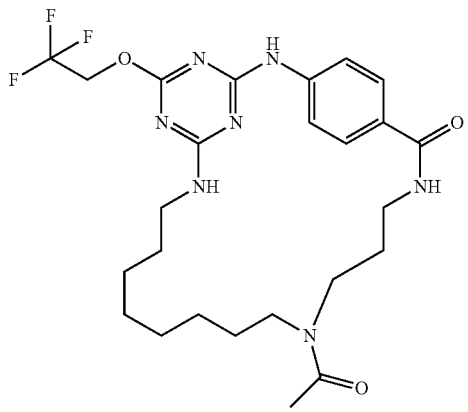 [SMILES: CC(=O)N1CCCCCCCCNc2nc(nc(OCC(F)(F)F)n2)Nc2ccc(cc2)C(=O)NCCC1]

Example 9009 was prepared following the procedure reported in Example 9002. Acetic anhydride was used instead of di-tertbutyl dicarbonate as starting material. LC-MS: 538.2 (M+H). $^1$H NMR (400 MHz, DMSO-$d_6$) δ 7.84-7.69 (m, 4H), 5.06-4.90 (m, 2H), 4.32 (t, J=5.3 Hz, 2H), 3.48 (t, J=5.8 Hz, 2H), 3.01 (q, J=6.5 Hz, 2H), 1.89 (quin, J=5.6 Hz, 2H), 1.78 (s, 3H), 1.64-1.48 (m, 2H), 1.45-1.15 (m, 10H).

| Example 3012 | |
|---|---|
| MS (M + H)$^+$ Calcd. | 636.6 |
| MS (M + H)$^+$ Observ. | 636.2 |
| Retention Time | 2.58 min |
| LC Condition | |
| Solvent A | 10% MeOH:90% Water:0.1% TFA |
| Solvent B | 90% MeOH:10% Water:0.1% TFA |
| Start % B | 0 |
| Final % B | 100 |
| Gradient Time | 3 min |
| Flow Rate | 1 mL/min |
| Wavelength | 220 |
| Solvent Pair | MeOH:Water:TFA |
| Column | Phenomenex 2.0 × 30 mm, 3 uM |

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of formula I

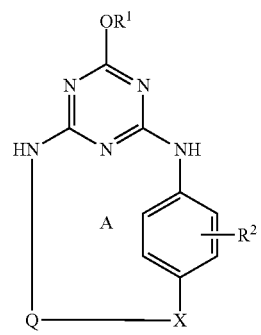

where
R$^1$ is alkyl, hydroxyalkyl, alkoxyalkyl, haloalkyl, cycloalkyl, hydroxycycloalkyl, alkoxycycloalkyl, halocycloalkyl, cycloalkenyl, benzyl, indanyl, or alkylcarbonyl;
R$^2$ is cyano, hydrogen, halo, alkyl, haloalkyl, alkoxy, or haloalkoxy;
R$^3$ is hydrogen, alkyl, (amino)alkyl, (alkylamino)alkyl, (dialkylamino)alkyl ((alkylcarbonyl)amino)alkyl, ((haloalkylcarbonyl)amino)alkyl, ((alkoxycarbonyl)amino) alkyl, ((benzyloxycarbonyl)amino)alkyl, alkylcarbonyl, alkoxycarbonyl, benzyloxycarbonyl, aminocarbonyl, alkylaminocarbonyl, or dialkyaminocarbonyl;
R$^4$ is hydrogen, alkyl, (amino)alkyl, (alkylamino)alkyl, or (dialkylamino)alkyl;
R$^5$ is hydrogen, alkyl, (amino)alkyl, (alkylamino)alkyl, or (dialkylamino)alkyl;
R$^6$ is pyrollidinyl, piperidinyl, or piperazinyl and is substituted with 0-3 substituents selected from alkyl, alkylcarbonyl, alkoxycarbonyl, and benzyloxycarbonyl;
Q is an alkylene or alkenylene chain containing 0-6 groups selected from the group consisting of O, NR$^3$, S, S(O), S(O₂), C(O)O, C(O)NR⁴, OC(O)NR⁴, NR⁴C(O)NR⁴, and Z, provided that any O or S atom does not directly bond to another O or S atom, such that ring A is 13-24 membered; and where the alkylene or alkenylene chain is substituted with 0-6 substituents selected from the group consisting of alkyl, hydroxy, alkoxy, R⁶, (R⁶)alkyl, and phenyl where the phenyl substituent is further substituted with 0-4 cyano, halo, alkyl, haloalkyl, alkoxy, or haloalkoxy substituents;

X is O, CH₂, CO, CO₂, or C(O)NR⁵; and

Z is C$_{3-7}$ cycloalkylene, phenylene, pyrrolidindiyl, piperidindiyl, or piperazindiyl;

wherein the compound is selected from the group consisting of

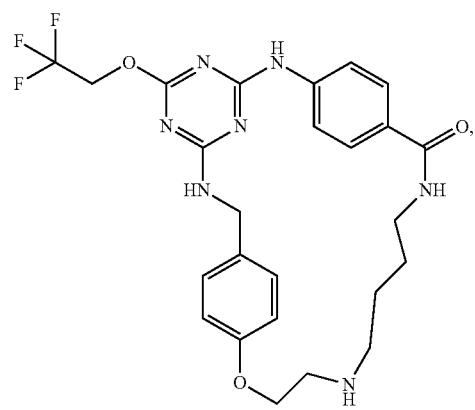

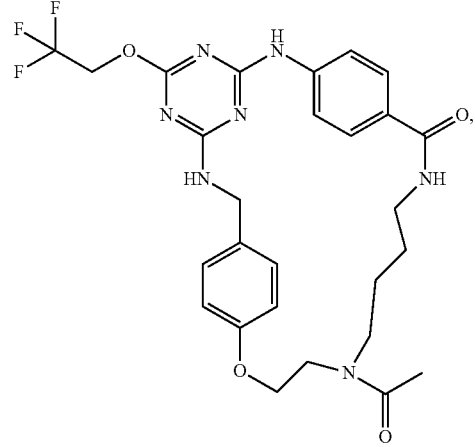

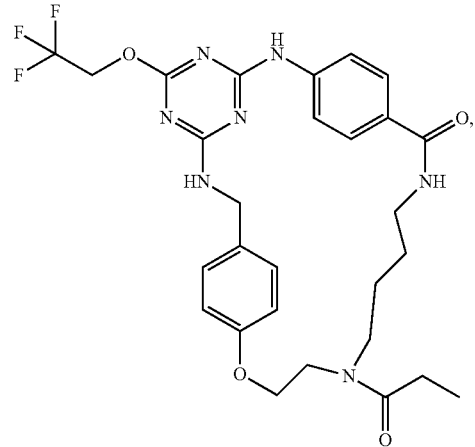

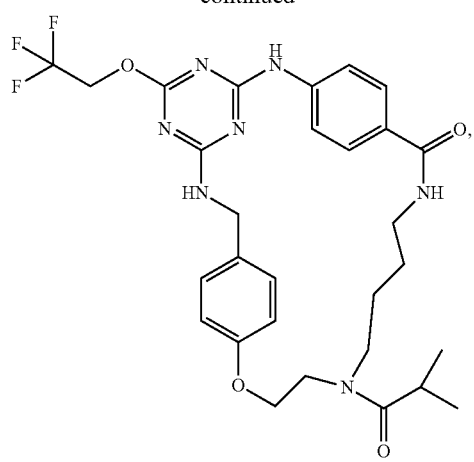

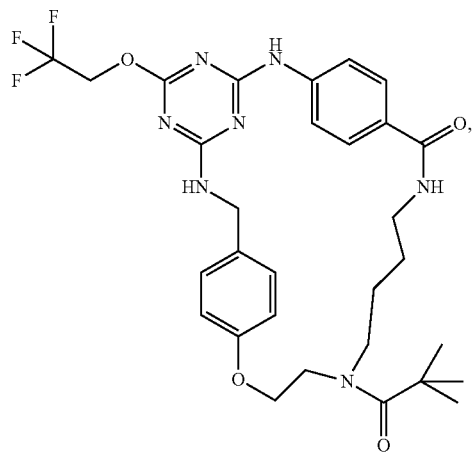

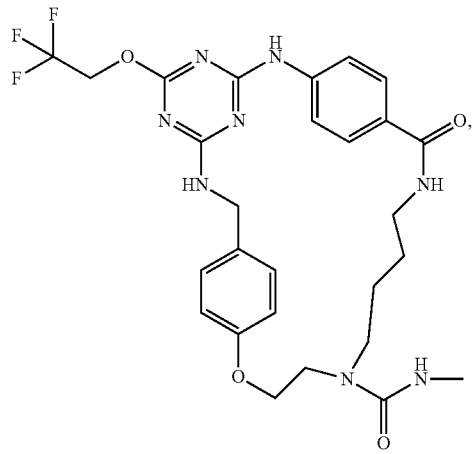

199
-continued
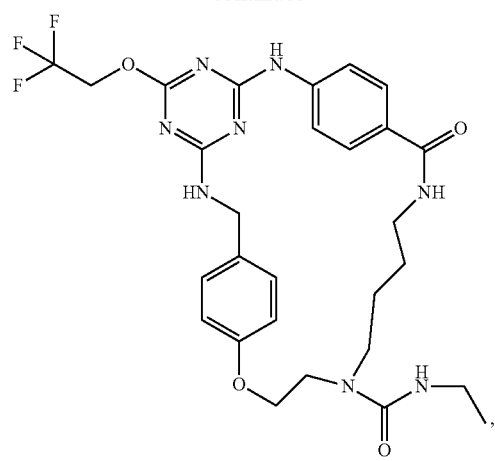
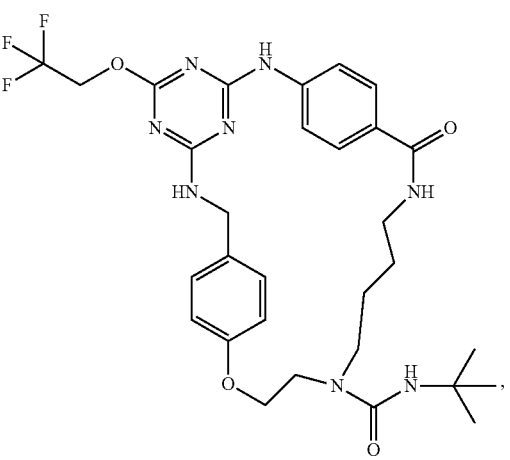
200
-continued
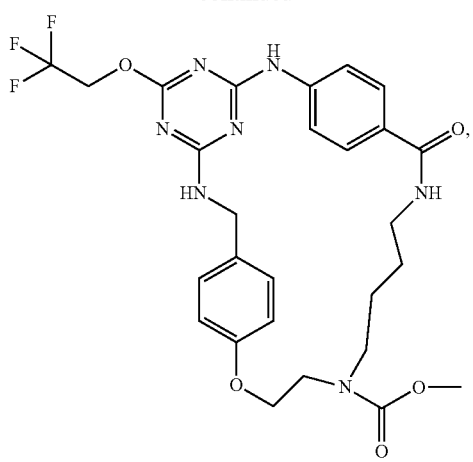
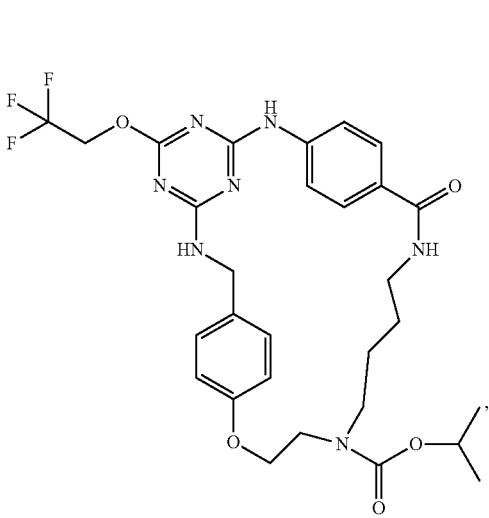

201
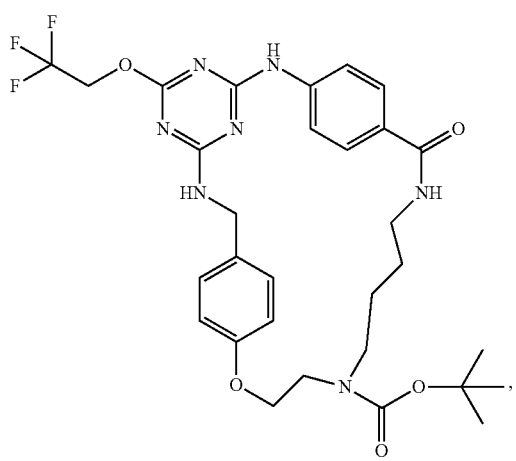
202
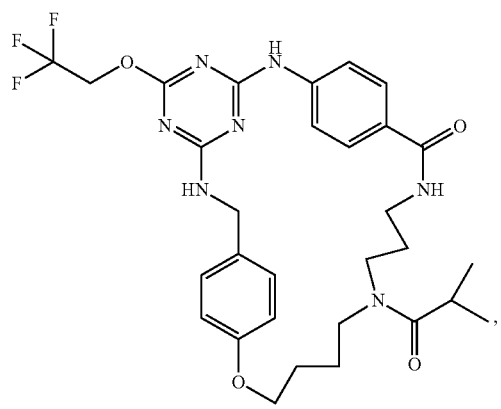

203
-continued
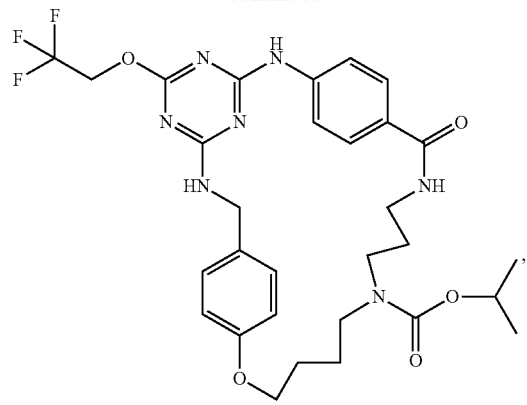
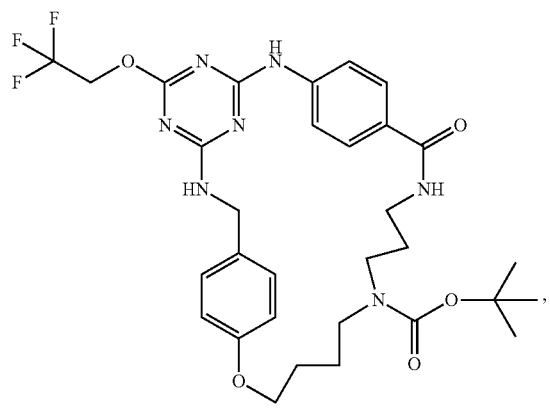
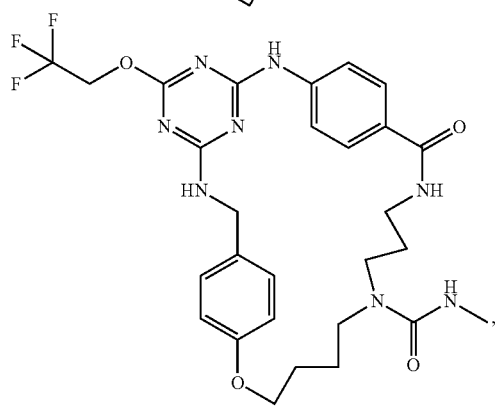
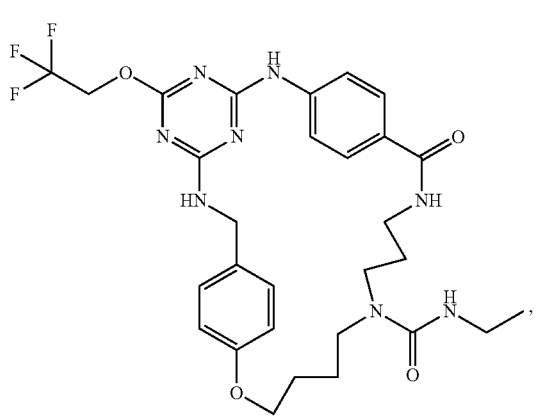
204
-continued
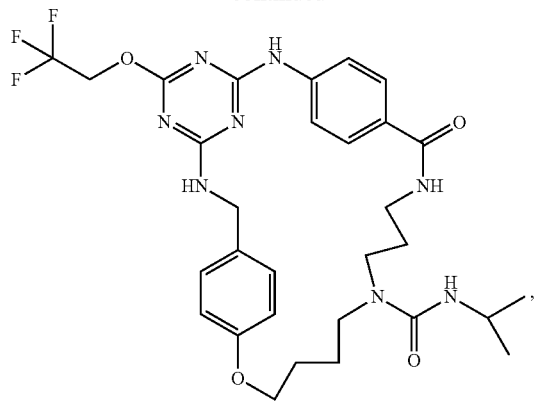
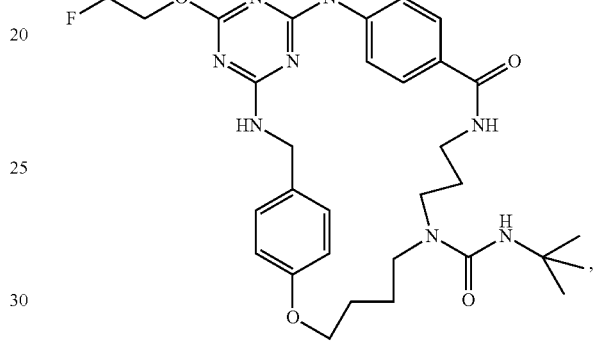
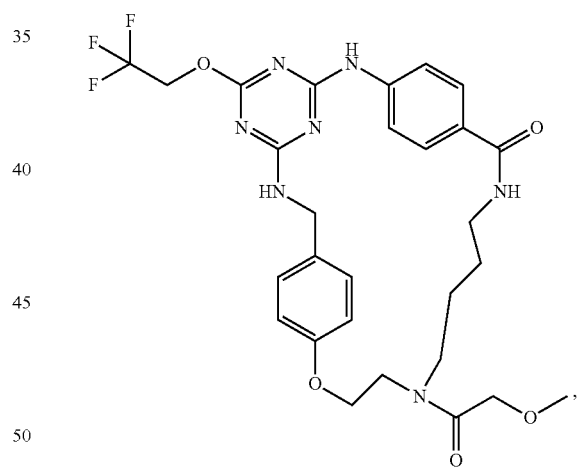
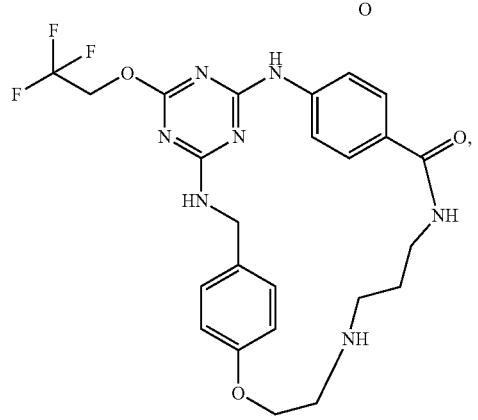

205
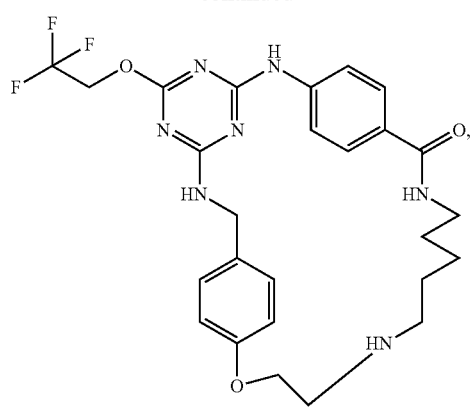
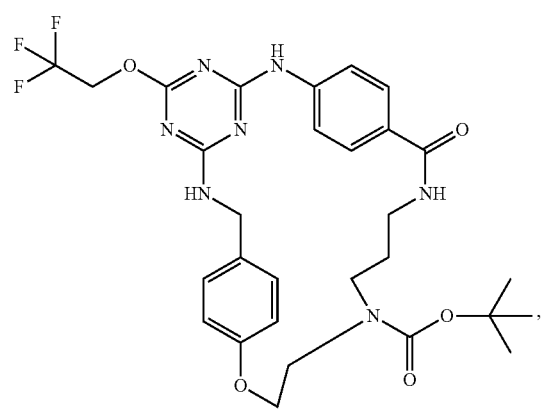
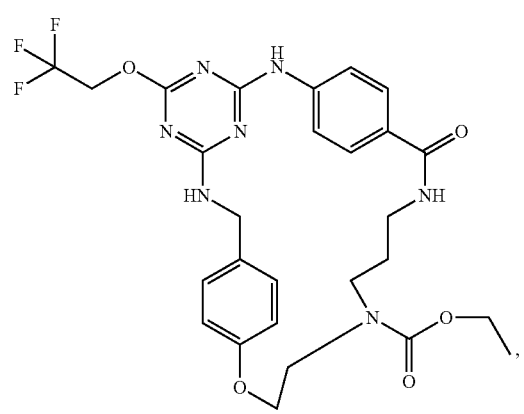
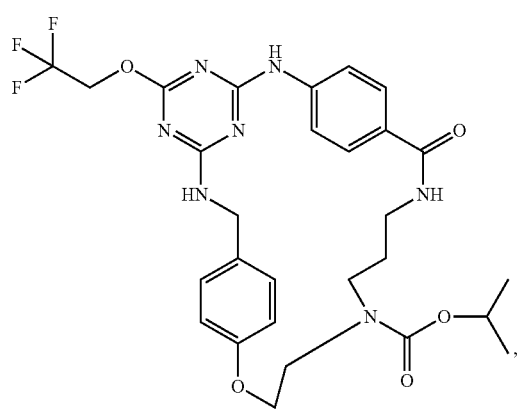
206
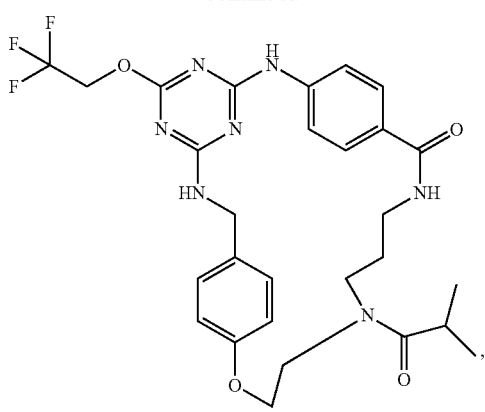
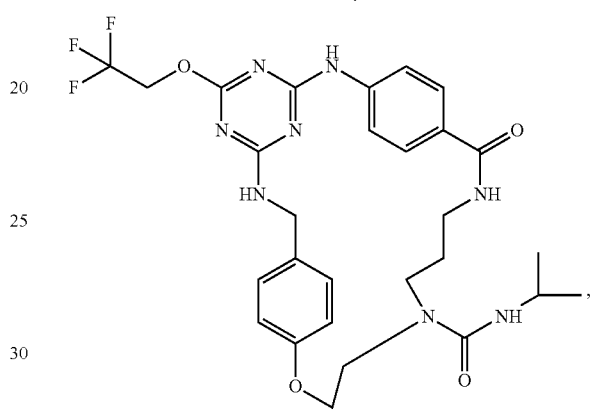
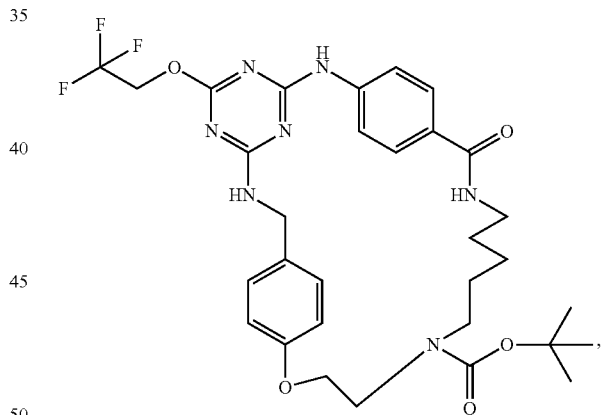
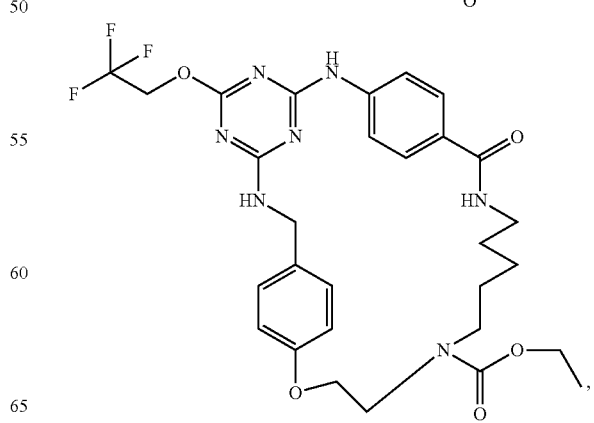

207
-continued
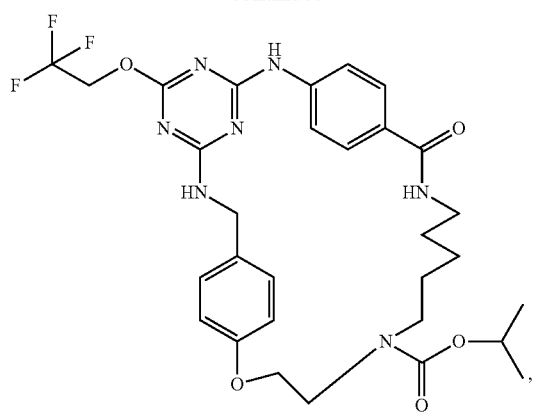
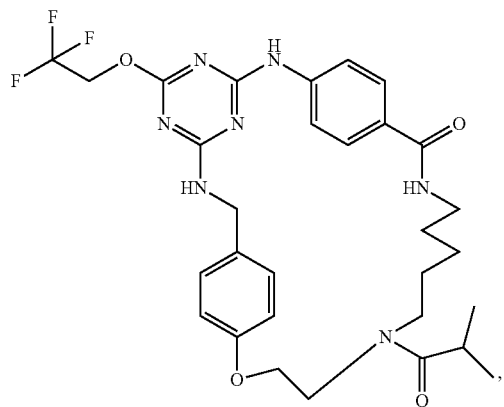
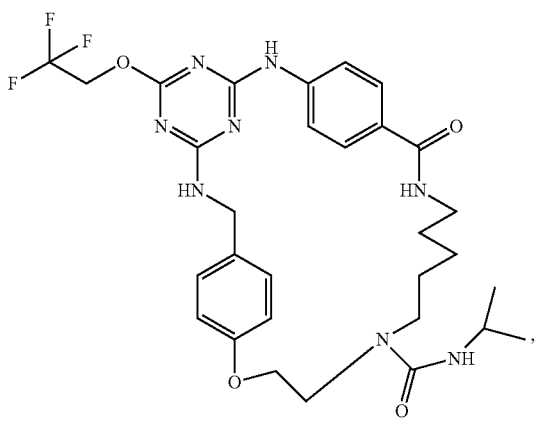
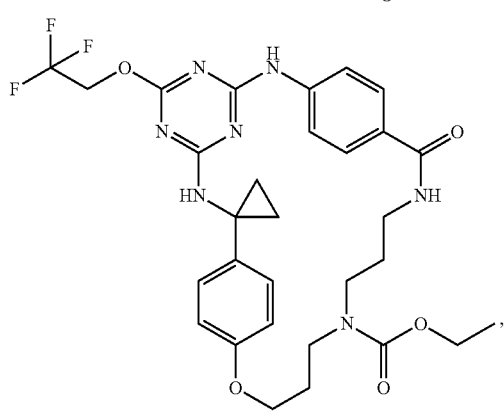
208
-continued
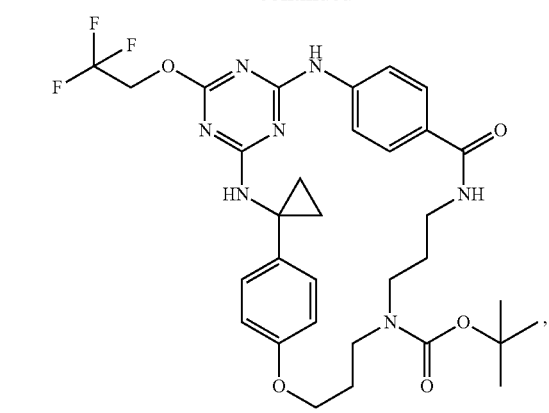
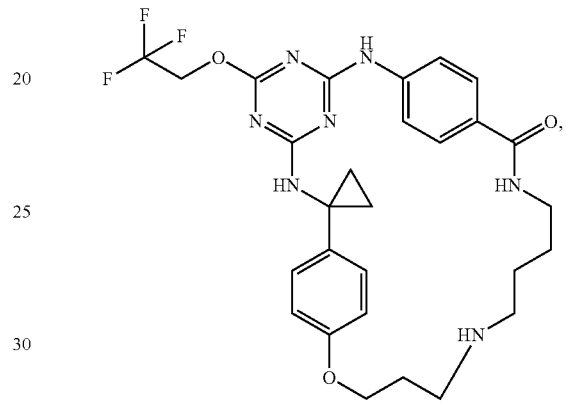
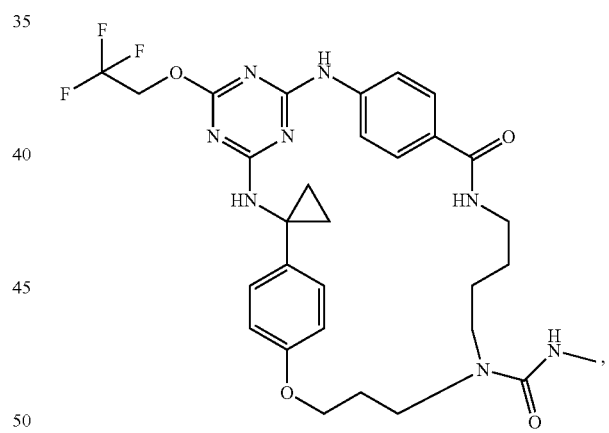
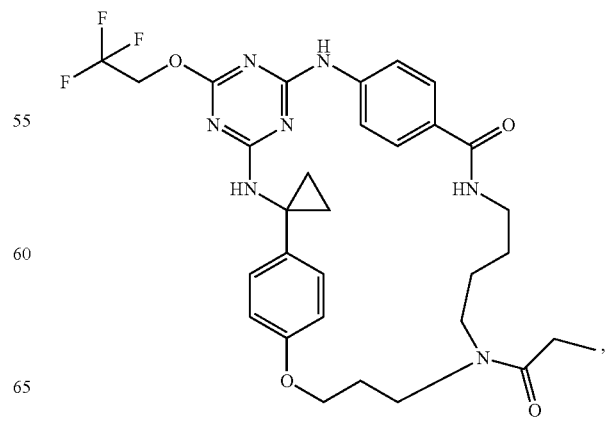

-continued

211
-continued
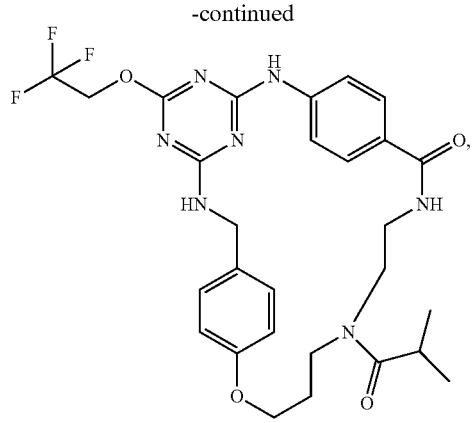
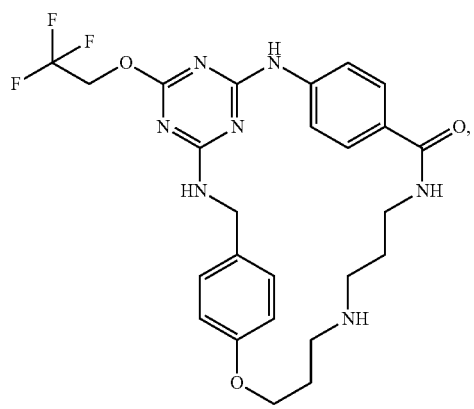
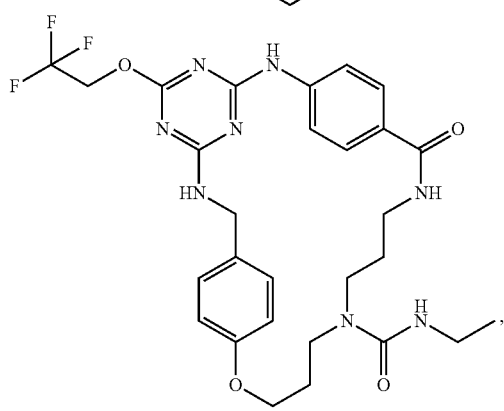
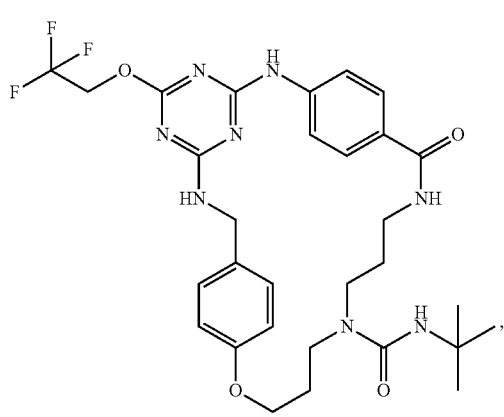
212
-continued
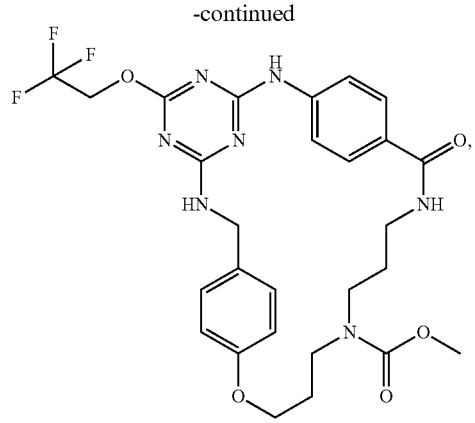
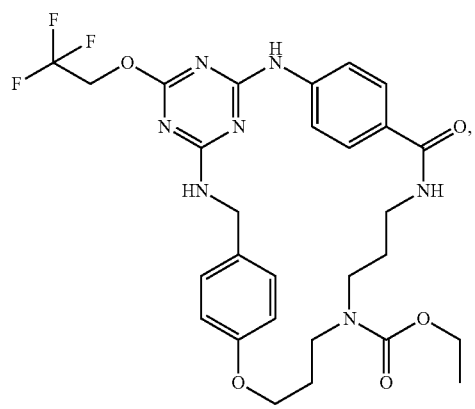
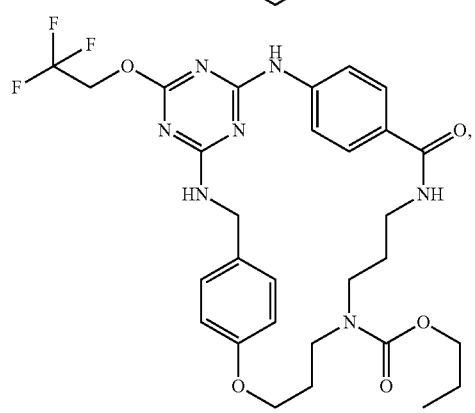
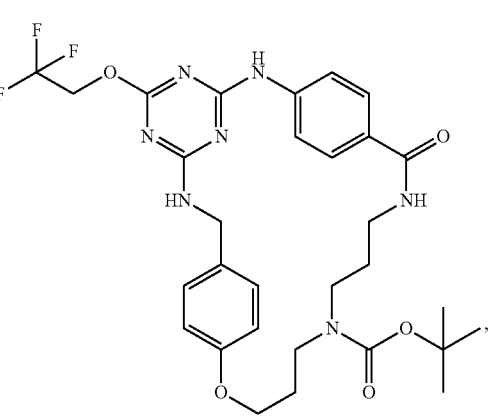

213
-continued
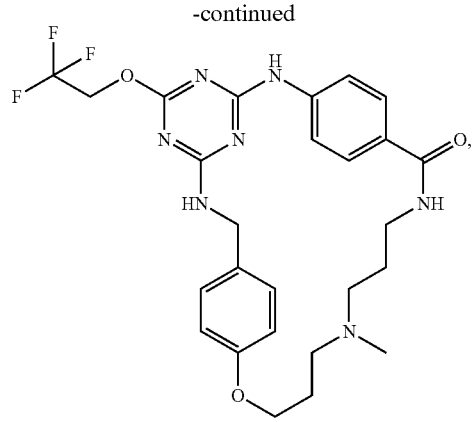
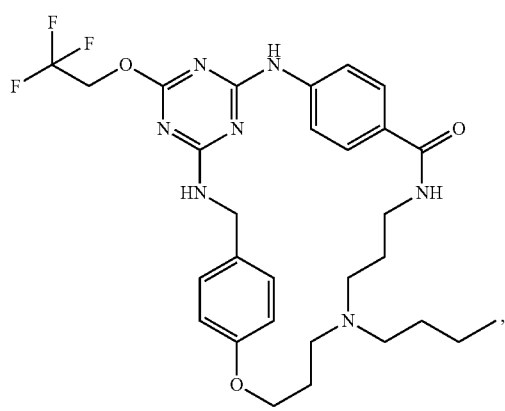
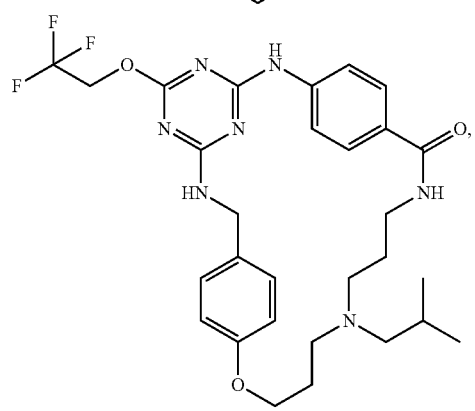
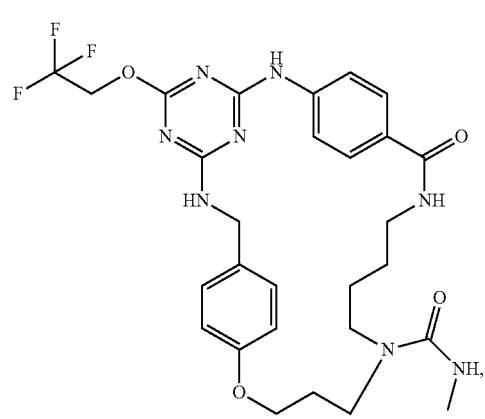
214
-continued
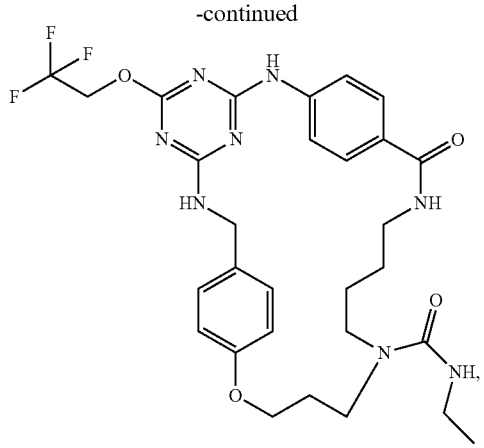
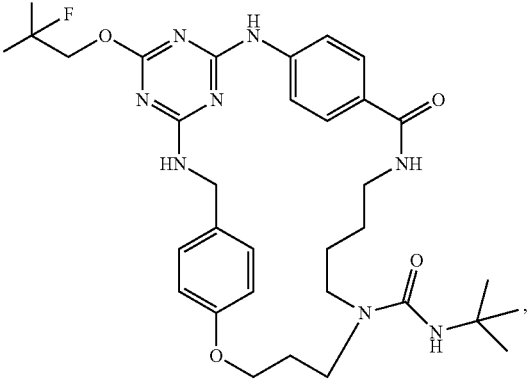
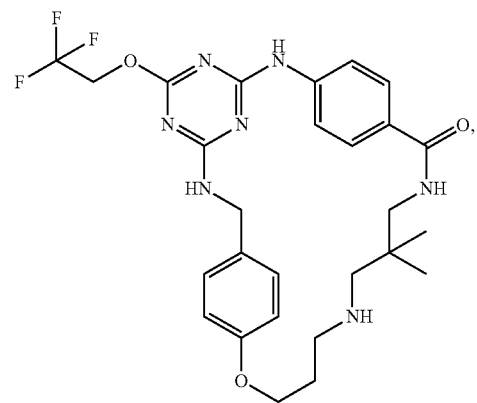
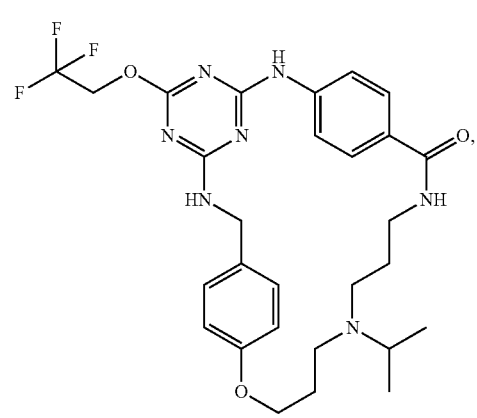

215
-continued
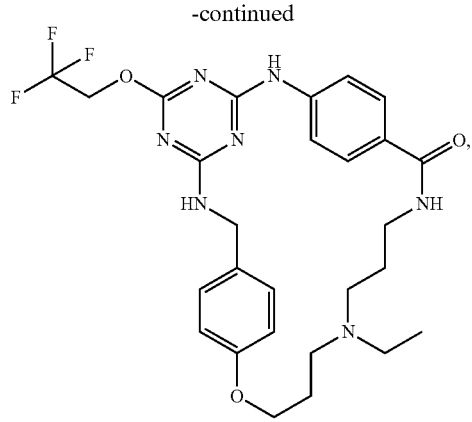
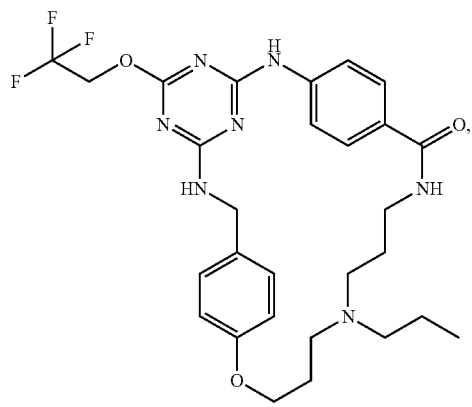
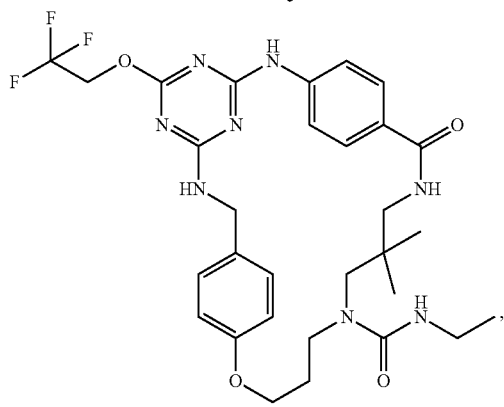
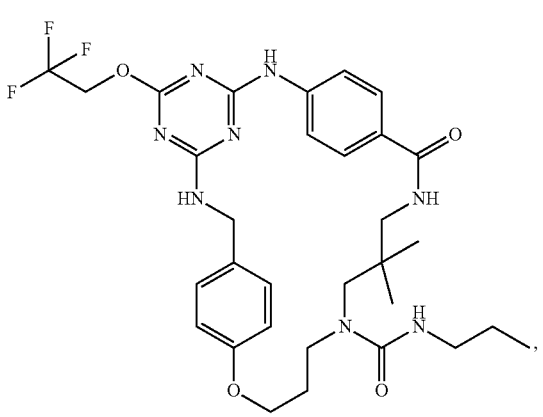
216
-continued
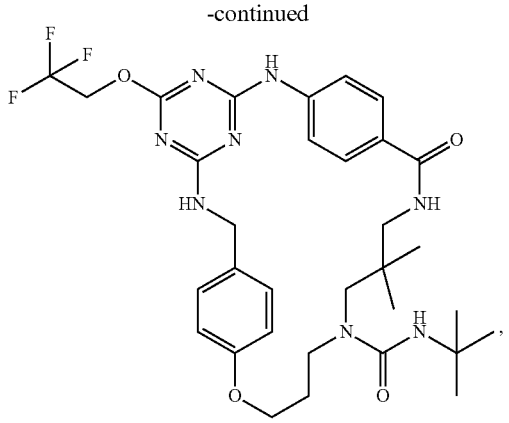
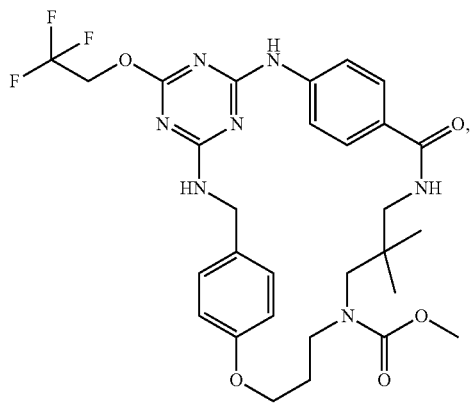
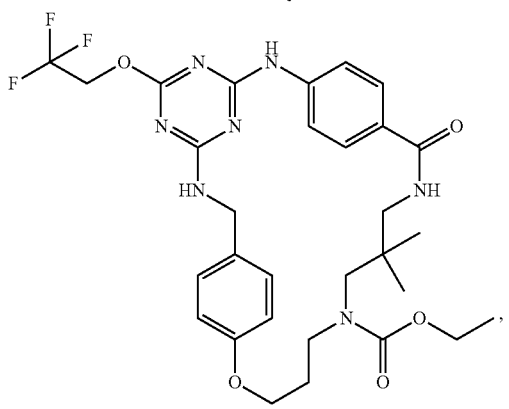
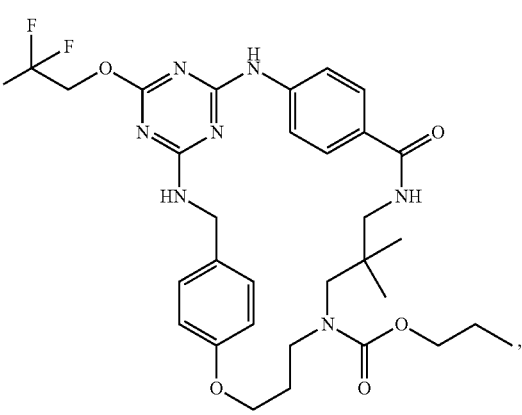

217
-continued
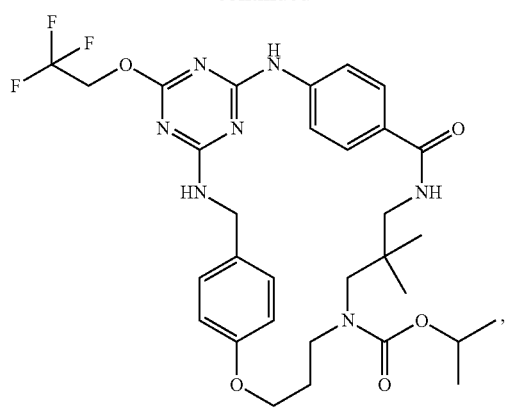
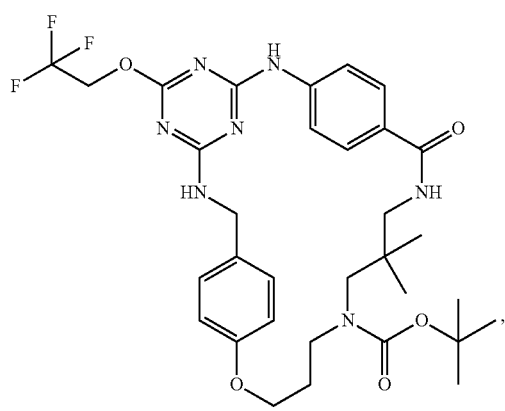
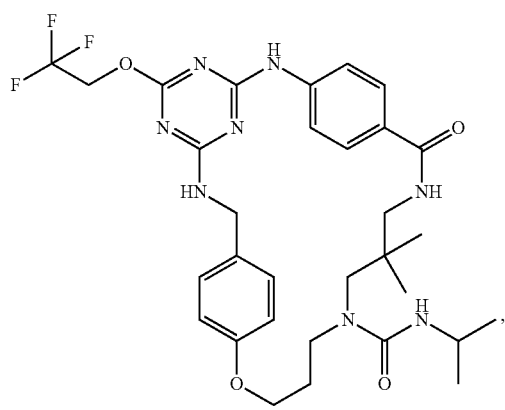
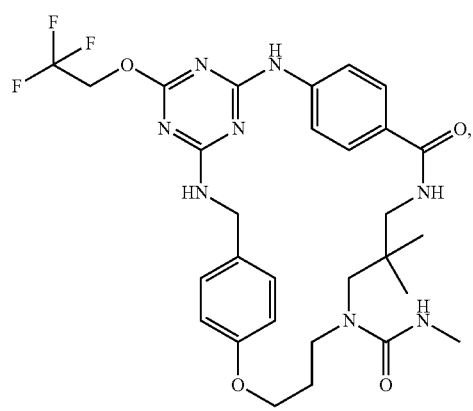
218
-continued
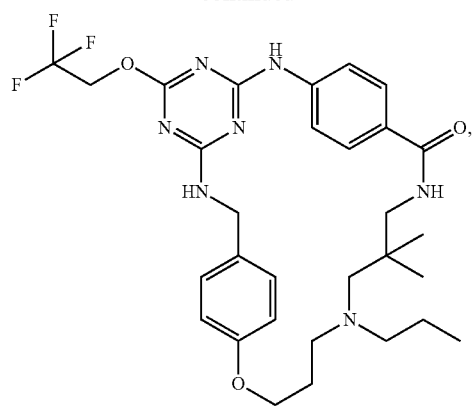
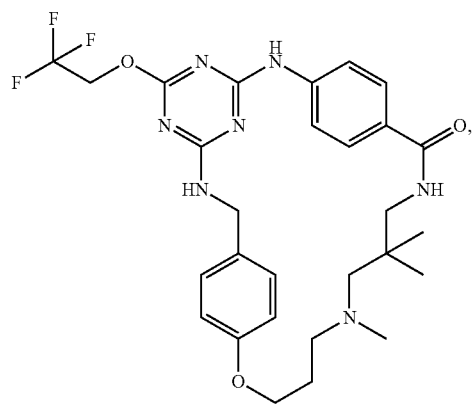
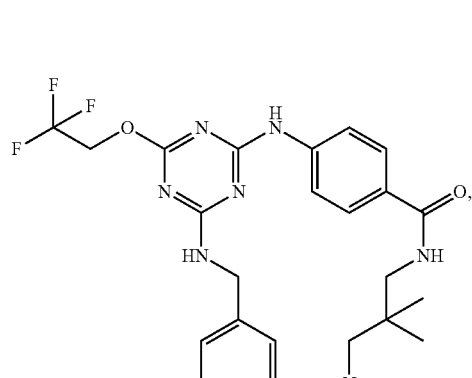
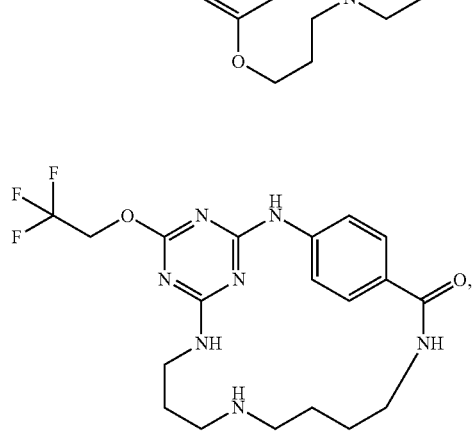

219
-continued
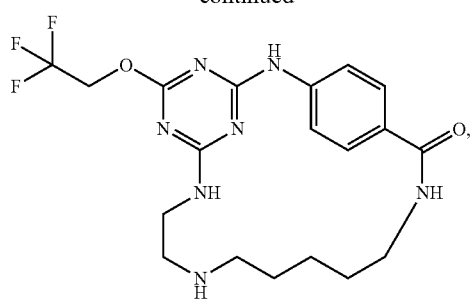
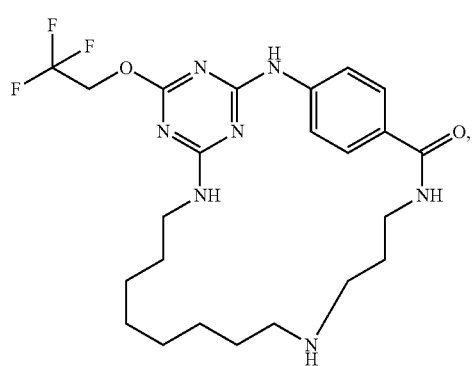
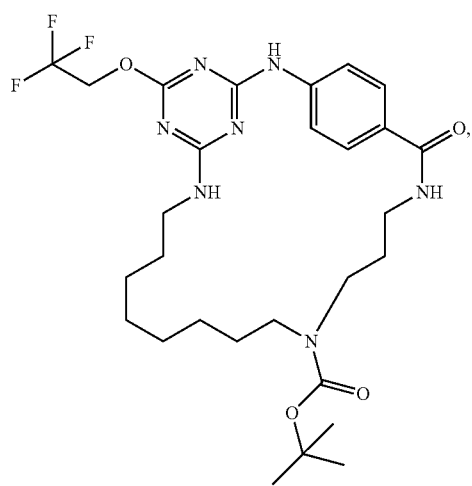
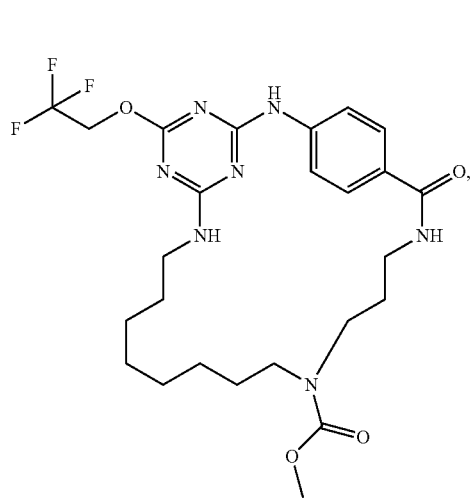
220
-continued
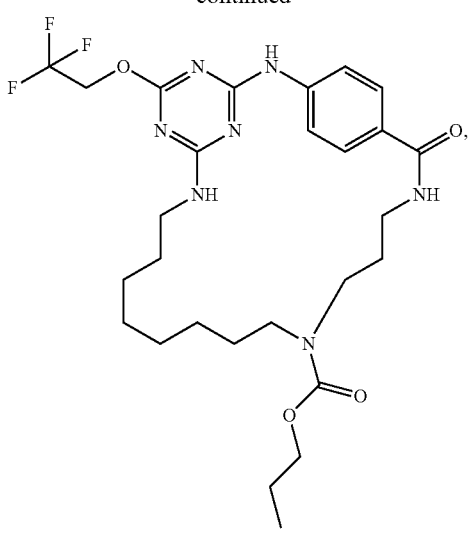
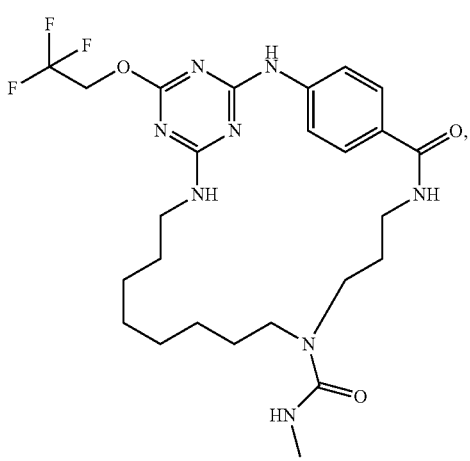
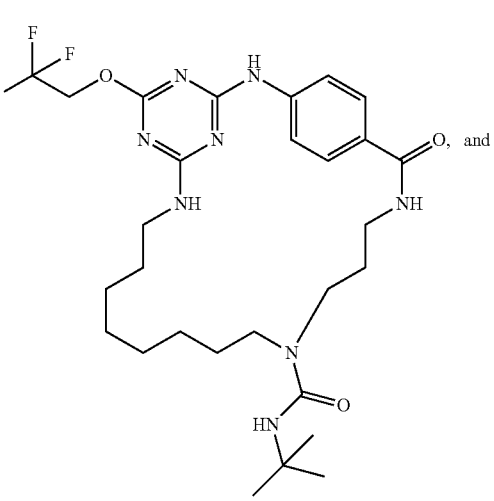

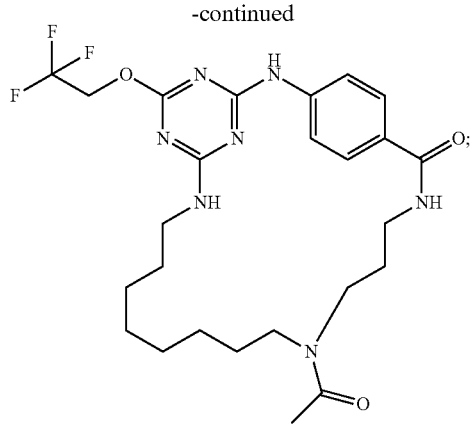
or a pharmaceutically acceptable salt thereof.
2. A composition comprising a compound of claim 1, or a pharmaceutically acceptable salt thereof, and a pharmaceutically acceptable carrier.
* * * * *

UNITED STATES PATENT AND TRADEMARK OFFICE
CERTIFICATE OF CORRECTION

PATENT NO. : 8,445,490 B2  
APPLICATION NO. : 13/086036  
DATED : May 21, 2013  
INVENTOR(S) : Tao Wang et al.

Page 1 of 1

It is certified that error appears in the above-identified patent and that said Letters Patent is hereby corrected as shown below:

In the Specification:

Column 3, line 41, change "dialkyaminocarbonyl;" to -- dialkylaminocarbonyl; --.

Column 3, line 46, change "pyrollidinyl" to -- pyrrolidinyl --.

Column 3, lines 60 and 61, change "pyrrolidindiyl, piperidindiyl, or piperazindiyl;" to -- pyrrolidinyl, piperidinyl, or piperazinyl; --.

Column 4, line 4, change "dialkyaminocarbonyl;" to -- dialkylaminocarbonyl; --.

Column 5, line 6, change "pyrrolidindiyl or piperazindiyl." to -- pyrrolidinyl or piperazinyl. --.

In the Claims:

Claim 1:

Column 196, line 58, change "dialkyaminocarbonyl;" to -- dialkylaminocarbonyl; --.

Column 196, line 63, change "pyrollidinyl" to -- pyrrolidinyl --.

Column 197, lines 12 and 13, change "pyrrolidindiyl, piperidindiyl, or piperazindiyl;" to -- pyrrolidinyl, piperidinyl, or piperazinyl; --.

Signed and Sealed this  
Sixth Day of May, 2014

Michelle K. Lee  
*Deputy Director of the United States Patent and Trademark Office*